US006608027B1

(12) United States Patent
Tsantrizos et al.

(10) Patent No.: US 6,608,027 B1
(45) Date of Patent: Aug. 19, 2003

(54) MACROCYCLIC PEPTIDES ACTIVE AGAINST THE HEPATITIS C VIRUS

(75) Inventors: Youla S. Tsantrizos, Saint-Laurent (CA); Dale R. Cameron, Rosemere (CA); Anne-Marie Faucher, Oka (CA); Elise Ghiro, Laval (CA); Nathalie Goudreau, Mont-Royal (CA); Teddy Halmos, Laval (CA); Montse Llinas-Brunet, Dollard-des-Ormeaux (CA)

(73) Assignee: Boehringer Ingelheim (Canada) Ltd, Laval (CA)

( * ) Notice: Subject to any disclaimer, the term of this patent is extended or adjusted under 35 U.S.C. 154(b) by 0 days.

(21) Appl. No.: 09/760,946

(22) Filed: Jan. 16, 2001

Related U.S. Application Data

(63) Continuation-in-part of application No. 09/542,675, filed on Apr. 3, 2000, now abandoned.

(60) Provisional application No. 60/128,011, filed on Apr. 6, 1999.

(51) Int. Cl.[7] ........................ A61K 38/05; A61K 38/06; A61K 38/12; C07K 5/08; C07K 5/12

(52) U.S. Cl. ............................... 514/9; 514/10; 514/11; 514/18; 514/19; 530/317; 530/321; 530/331; 540/454; 540/455; 540/460; 548/536; 548/537

(58) Field of Search ................................ 514/9, 10, 11, 514/18, 19; 530/317, 321, 331; 540/444, 460, 454, 455; 548/536, 537

(56) References Cited

U.S. PATENT DOCUMENTS

| | | | |
|---|---|---|---|
| 3,139,421 A | 6/1964 | Elslager et al. | 534/581 |
| 5,114,918 A | 5/1992 | Ishikawa et al. | 514/11 |
| 5,192,746 A | 3/1993 | Seiyaku | 514/11 |
| 5,633,388 A | 5/1997 | Diana et al. | 548/305.7 |
| 5,721,210 A | 2/1998 | Lobl et al. | 514/11 |
| 5,830,888 A | 11/1998 | Getman et al. | 514/183 |
| 5,866,684 A | 2/1999 | Attwood et al. | 530/329 |
| 5,869,253 A | 2/1999 | Draper et al. | 435/6 |
| 6,018,020 A | 1/2000 | Attwood et al. | 530/329 |
| 6,323,180 B1 | 11/2001 | Llinas-Brunet et al. | 514/118 |

FOREIGN PATENT DOCUMENTS

| | | |
|---|---|---|
| CA | 2087021 | 1/1992 |
| CA | 2222524 | 1/1997 |
| EP | 0 937 459 | 8/1999 |
| WO | WO 92 00995 | 1/1992 |
| WO | WO 94 15958 | 7/1994 |
| WO | WO 95 33764 | 12/1995 |
| WO | WO 97 01579 | 1/1997 |
| WO | WO 97 06804 | 2/1997 |
| WO | WO 97 43310 | 11/1997 |
| WO | WO 98 17679 | 3/1998 |
| WO | WO 98 22496 | 5/1998 |
| WO | WO 98 46597 | 10/1998 |
| WO | WO 98 46630 | 10/1998 |
| WO | WO 98/53814 A1 | 12/1998 |
| WO | WO 99 07733 A2 | 2/1999 |
| WO | WO 99 07733 | 2/1999 |
| WO | WO 99 07734 | 2/1999 |
| WO | WO 99 38888 | 8/1999 |
| WO | WO 99 50230 | 10/1999 |
| WO | WO 99 64442 | 12/1999 |
| WO | WO 00 09543 A2 | 2/2000 |
| WO | WO 00 09543 | 2/2000 |
| WO | WO 00 09558 | 2/2000 |
| WO | WO 00 09558 A1 | 2/2000 |
| WO | WO 01 77113 | 10/2001 |
| WO | WO 01 81325 | 11/2001 |
| WO | WO 02 08244 A2 | 1/2002 |
| WO | WO 02 08256 A2 | 1/2002 |
| WO | WO 02 18369 A2 | 3/2002 |

OTHER PUBLICATIONS

Wieland, et al; "Amanita Toxins. XVII. Attempted syntheses of phalloine-like cyclopeptides"; Ann. 1959, 626: 154–73.

Jackson, et al; "Potent alpha 4 beta 1 Peptide Antagonists as Potential Anti-Inflammatory Agents"; J. Med. Chem. 1997, 40, 3359–3368.

Chemical Abstracts–CA 54:2190d HCA, Wieland, et al, Ann. (1959), 626: 154–173.

US Patent Application No. 10/091,293; filed Mar. 05, 2002; Llinas–Brunet, M. et al; Attorney Docket No. 13/068-7-C1.

US Application No. 09/368,670, filed on Aug. 5, 1999, Llinas–Brunet, M. et al. (Attorney Docket No. 13/063-2-C2).

(List continued on next page.)

*Primary Examiner*—Jeffrey E. Russel

(74) *Attorney, Agent, or Firm*—Robert P. Raymond; Philip I. Datlow; Alan R. Stempel

(57) ABSTRACT

The present invention covers macrocyclic compounds of formula I active in-vitro and in cellular assays against the NS3 protease of the hepatitis C virus.

(I)

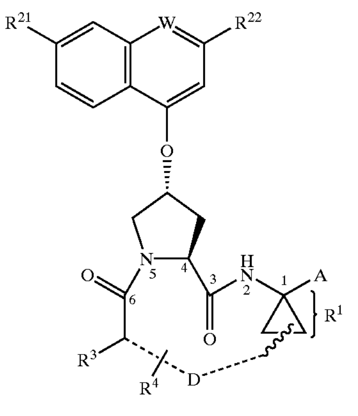

wherein W, $R^{21}$, $R^{22}$, $R^3$, $R^4$, D and A are as defined herein, or a pharmaceutically acceptable salts or ester thereof.

145 Claims, No Drawings

OTHER PUBLICATIONS

Steinkuhler, C. et al; "Product Inhibition of the Hepatitis C Virus NS3 Protease"; Biochemistry, 1998, 8899–8905, 37.

Ingallinella, P. et al; "Potent Peptide Inhibitors of Human Hepatitis C Virus NS3 Protease Are Obtained by Optimizing the Cleavage Products"; Biochemistry, 1998, 8906–8914, 37.

Chu, M. et al; "Structure of Sch 68631: A New Hepatitis C Virus Proteinase Inhibitor from Streptomyces sp."; Tetrahedron Letters, 1996, 7229–7232, vol. 37, No. 40.

Matsumoto, Y. et al; "3D Modeling of HCV Protease and Computer Screening of its Inhibitors", Antiviral Research, 1996, A 23, 30, 1, Abstract 19.

Llinas–Brunet, et al; "Peptide–Based Inhibitors of the Hepatitis C. Virus Serine Protease"; Bioorganic & Med. Chem. Ltrs. 8; 1998, pp. 1713–1718.

Llinas–Brunet, et al; "Studies on the C–Terminal of Hexapeptide Inhibitors of the Hepatitis C Virus Serine Protease"; Bioorganic & Med. Chem. Ltrs. 8; 1998; pp. 2719–2724.

SEQUENCE LISTING

```
<160> NUMBER OF SEQ ID NOS: 5

<210> SEQ ID NO 1
<211> LENGTH: 11
<212> TYPE: PRT
<213> ORGANISM: Artificial Sequence
<220> FEATURE:
<223> OTHER INFORMATION: Substrate for NS3-NS4A heterodimer protein
      fluorogenic assay
<221> NAME/KEY: MOD_RES
<222> LOCATION: (1)
<223> OTHER INFORMATION: Asp is derivatized with anthranilyl
<221> NAME/KEY: MOD_RES
<222> LOCATION: (6)
<223> OTHER INFORMATION: Xaa at position 6 is amino butyric acid (Abu)
<221> NAME/KEY: SITE
<222> LOCATION: (6)..(7)
<223> OTHER INFORMATION: Peptide linkage is replaced by -C(O)-O-
<221> NAME/KEY: MOD_RES
<222> LOCATION: (9)
<223> OTHER INFORMATION: Tyr at position 9 is labeled with 3-NO2

<400> SEQUENCE: 1

Asp Asp Ile Val Pro Xaa Ala Met Tyr Thr Trp
1               5                   10


<210> SEQ ID NO 2
<211> LENGTH: 12
<212> TYPE: PRT
<213> ORGANISM: Artificial Sequence
<220> FEATURE:
<223> OTHER INFORMATION: Substrate for recombinant HCV NS3 protease
      radiometric assay

<400> SEQUENCE: 2

Asp Asp Ile Val Pro Cys Ser Met Ser Tyr Thr Trp
1               5                   10


<210> SEQ ID NO 3
<211> LENGTH: 12
<212> TYPE: PRT
<213> ORGANISM: Artificial Sequence
<220> FEATURE:
<223> OTHER INFORMATION: Tracer for NS3 protease assay
<221> NAME/KEY: MOD_RES
<222> LOCATION: (1)
<223> OTHER INFORMATION: Asp at position 1 is biotinylated
<221> NAME/KEY: MOD_RES
<222> LOCATION: (10)
<223> OTHER INFORMATION: Tyr at position 10 is iodinated with I-125

<400> SEQUENCE: 3

Asp Asp Ile Val Pro Cys Ser Met Ser Tyr Thr Trp
1               5                   10


<210> SEQ ID NO 4
<211> LENGTH: 6
<212> TYPE: PRT
<213> ORGANISM: Artificial Sequence
<220> FEATURE:
<223> OTHER INFORMATION: NS3 protease C-cleavage product
<221> NAME/KEY: MOD_RES
<222> LOCATION: (4)
<223> OTHER INFORMATION: Tyr at position 4 is iodinated with I-125

<400> SEQUENCE: 4

Ser Met Ser Tyr Thr Trp
1               5
```

-continued

```
<210> SEQ ID NO 5
<211> LENGTH: 4
<212> TYPE: PRT
<213> ORGANISM: Artificial Sequence
<220> FEATURE:
<223> OTHER INFORMATION: Artificial substrate for chymotrypsin assay
<221> NAME/KEY: MOD_RES
<222> LOCATION: (1)
<223> OTHER INFORMATION: Ala at position 1 is succinylated
<221> NAME/KEY: MOD_RES
<222> LOCATION: (4)
<223> OTHER INFORMATION: Phe at position 4 is labeled at C-terminal with
      para-nitro aniline (pNA)

<400> SEQUENCE: 5

Ala Ala Pro Phe
1
```

MACROCYCLIC PEPTIDES ACTIVE AGAINST THE HEPATITIS C VIRUS

This application is a continuation-in-part of U.S. patent application Ser. No. 09/542,675 filed Apr. 3, 2000, now abandoned, which claims the benefit of U.S. provisional application No. 60/128,011 filed Apr. 6, 1999, both of which are herein incorporated by reference in their entirety.

FIELD OF THE INVENTION

The present invention relates to compounds, compositions, the preparation of such compounds and methods for the treatment of hepatitis C virus (HCV) infection. In particular, the present invention provides novel peptide analogues, pharmaceutical compositions containing such analogues and methods for using these analogues in the treatment of HCV infection.

BACKGROUND OF THE INVENTION

Hepatitis C virus (HCV) is the major etiological agent of post-transfusion and community-acquired non-A non-B hepatitis worldwide. It is estimated that over 170 million people worldwide are infected by the virus. A high percentage of carriers become chronically infected and many progress to chronic liver disease, so-called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established. Immunoglobulins have been reported for prophylaxis of transfusion-associated viral hepatitis, however, the Center for Disease Control does not presently recommend immunoglobulins treatment for this purpose. The lack of an effective protective immune response is hampering the development of a vaccine or adequate post-exposure prophylaxis measures, so in the near-term, hopes are firmly pinned on antiviral interventions. Various clinical studies have been conducted with the goal of identifying pharmaceutical agents capable of effectively treating HCV infection in patients afflicted with chronic hepatitis C. These studies have involved the use of interferon-alpha, alone and in combination with other antiviral agents. Such studies have shown that a substantial number of the participants do not respond to these therapies, and of those that do respond favorably, a large proportion were found to relapse after termination of treatment.

Until a few years ago, interferon (IFN) was the only available therapy of proven benefit approved in the clinic for patients with chronic hepatitis C. However the sustained response rate is low, and interferon treatment also induces severe side-effects (i.e. retinopathy, thyroiditis, acute pancreatitis, depression) that diminish the quality of life of treated patients. Interferon in combination with ribavirin was originally approved for patients non-responsive to IFN alone. It has now been approved for naive patients and presently constitutes the gold standard in HCV therapy. However, the side effects caused by IFN are not alleviated with this combination therapy.

Therefore, a need exists for the development of effective antiviral agents for treatment of HCV infection that overcomes the limitations of existing pharmaceutical therapies.

HCV is an enveloped positive strand RNA virus in the Flaviviridae family. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature nonstructural proteins (NS2, NS3, NS4A, NS4B, NS5A, and NS5B) is effected by two viral proteases. The first one, as yet poorly characterized, cleaves at the NS2–NS3 junction; the second one is a serine protease contained within the N-terminal region of NS3 (henceforth referred to as NS3 protease) and mediates all the subsequent cleavages downstream of NS3, both in cis, at the NS3–NS4A cleavage site, and in trans, for the remaining NS4A–NS4B, NS4B–NS5A, NS5A–NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

Patent application WO 97/06804 describes the (−) enantiomer of the nucleoside analogue cytosine-1,3-oxathiolane (also known as 3TC) as active against HCV. This compound, although reported as safe in previous clinical trials against HIV and HBV, has yet to be clinically proven active against HCV and its mechanism of action against the virus has yet to be reported.

A general strategy for the development of antiviral agents is to inactivate virally encoded enzymes that are essential for the replication of the virus.

In this vein, intense efforts to discover compounds which inhibit the NS3 protease or RNA helicase of HCV have led to the following disclosures:

U.S. Pat. No. 5,633,388 describes heterocyclic-substituted carboxamides and analogues as being active against HCV. These compounds are directed against the helicase activity of the NS3 protein of the virus but clinical tests have not yet been reported. A phenanthrenequinone has been reported by Chu et al., (Tet. Lett., (1996), 7229–7232) to have activity against the HCV NS3 protease in vitro. No further development on this compound has been reported.

A paper presented at the Ninth International Conference on Antiviral Research, Urabandai, Fukyshima, Japan (1996) (Antiviral Research, (1996), 30, 1, A23 (abstract 19)) reports thiazolidine derivatives to be inhibitory to the HCV protease.

Several studies have reported compounds inhibitory to other serine proteases, such as human leukocyte elastase. One family of these compounds is reported in WO 95/33764 (Hoechst Marion Roussel, 1995). The peptides disclosed in that application are morpholinylcarbonyl-benzoyl-peptide analogues that are structurally different from the peptides of the present invention.

WO 98/17679 from Vertex Pharmaceuticals Inc. discloses inhibitors of serine protease, particularly, Hepatitis C virus NS3 protease Hoffman LaRoche (WO 98/22496; U.S. Pat. Nos. 5,866,684 & 6,018,020) has also reported hexapeptides that are proteinase inhibitors useful as antiviral agents for the treatment of HCV infection.

Steinkühler et al. and Ingallinella et al. have published on NS4A-4B product inhibition (Biochemistry (1998), 37, 8899–8905 and 8906–8914).

WO 97/43310 by Schering Corporation discloses 20 and 21 amino acid peptide sequences active against the HCV NS3 protease.

WO 98/46597 by Emory University discloses peptides and peptidomimetics active in vitro against serine proteases.

WO 98/46630 by Peptide Therapeutics Limited discloses depsipeptide substrate inhibiting the HCV NS3 protease.

Finally, U.S. Pat. No. 5,869,253 discloses enzymatic RNA molecules that inhibit the HCV NS3 protease.

None of the prior patent applications described above disclose suggest cyclic peptides active and selective against the Hepatitis C virus NS3 protease.

WO 99/07733, WO 99/07734, WO 00/09543 and WO00/09558 disclose hexa to tetra-peptides and tripeptide analogs that inhibit the NS3 protease. However, these disclosures do not suggest or lead to the design of macrocyclic analogs of the present invention.

WO 99/38888 published Aug. 5, 1999 by the Institute de Richerche di Biologia Moleculare (IRBM) discloses small peptides inhibitors of the HCV NS3 protease. Nothing in this disclosure suggest or indicates the cyclic nature of the peptides of the present invention. In addition, this PCT application was published after the priority date of the present application.

WO 99/64442 by IRBM, also published after the priority date of this application, discloses oligopeptides with ketoacids at P1.

WO 99/50230 from Vertex Pharmaceuticals (published on Oct. 7, 1999) was also published after the priority date of the present application. Even then, the publication does not remotely suggest any cyclic peptides of the present invention.

One advantage of the present invention is that it provides macrocyclic peptides that are inhibitory to the NS3 protease of the hepatitis C virus.

A further advantage of one aspect of the present invention resides in the fact that these peptides specifically inhibit the NS3 protease and do not show significant inhibitory activity against other serine proteases such as human leukocyte elastase (HLE), porcine pancreatic elastase (PPE), or bovine pancreatic chymotrypsin, or cysteine proteases such as human liver cathepsin B (Cat B).

A further advantage of the present invention is that it provides small peptides of low molecular weight that are capable of penetrating cell membranes and inhibit the NS3 protease activity in cell culture.

Still, a further advantage of the compounds of the present invention resides in the fact that they are active in both major genotypes found in clinical isolates (1*a* & 1*b*), strongly suggesting that these compound will be active against all presently known genotypes of HCV.

SUMMARY OF THE INVENTION

Included in the scope of the invention are compounds of formula (I):

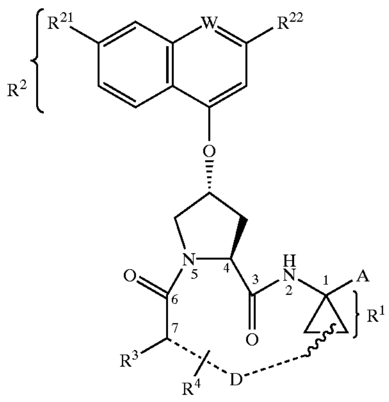

(I)

wherein

W is CH or N, $R^{21}$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^{23})_2$, wherein each $R^{23}$ is independently H, $C_{1-6}$ alkyl or $C_{3-6}$ cycloalkyl; and $R^{22}$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{3-6}$ cycloalkyl, $C_{6\ or\ 10}$ aryl or Het, wherein Het is a five-, six-, or seven-membered, saturated or unsaturated heterocycle, containing from one to four heteroatoms selected from nitrogen, oxygen and sulfur;

said cycloalkyl, aryl or Het being substituted with $R^{24}$, wherein $R^{24}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{25})_2$; NH—C(O)—$R^{25}$, or NH—C(O)—NH—$R^{25}$, wherein each $R^{25}$ is independently: H, $C_{1-6}$ alkyl or $C_{3-6}$ cycloalkyl;

or $R^{24}$ is NH—C(O)—O$R^{26}$ wherein $R^{26}$ is $C_{1-6}$ alkyl or $C_{3-6}$ cycloalkyl;

$R^3$ is hydroxy, $NH_2$, or a group of formula —NH—$R^{31}$, wherein $R^{31}$ is $C_{6\ or\ 10}$ aryl, heteroaryl, —C(O)—$R^{32}$, —C(O)—O$R^{32}$, or —C(O)—NH$R^{32}$, wherein $R^{32}$ is: $C_{1-6}$ alkyl or $C_{3-6}$ cycloalkyl;

D is a 5 to 10-atom saturated or unsaturated alkylene chain optionally containing one to three heteroatoms independently selected from: O, S, or N—$R^{41}$, wherein $R^{41}$ is H, $C_{1-6}$ alkyl, $C_{3-6}$ cycloalkyl, or —C(O)—$R^{42}$, wherein $R^{42}$ is $C_{1-6}$ alkyl, $C_{3-6}$ cycloalkyl or $C_{6\ or\ 10}$ aryl; and wherein the atoms of the D chain that form part of the macrocyclic ring in structural formula (I) are numbered from left to right in structural formula (I) starting with position number 8.

$R^4$ is H or from one to three substituents at any carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio, or $C_{1-6}$ thioalkyl and A is an amide of formula —C(O)—NH—$R^5$, wherein $R^5$ is selected from the group consisting of: $C_{1-8}$ alkyl, $C_{3-6}$ cycloalkyl, $C_{6\ or\ 10}$ aryl or $C_{7-16}$ aralkyl;

or A is a carboxylic acid or a pharmaceutically acceptable salt or ester thereof.

Included within the scope of this invention is a pharmaceutical composition comprising an anti-hepatitis C virally effective amount of a compound of formula I, or a therapeutically acceptable salt or ester thereof, in admixture with a pharmaceutically acceptable carrier medium or auxiliary agent.

An important aspect of the invention involves a method of treating a hepatitis C viral infection in a mammal by administering to the mammal an anti-hepatitis C virally effective amount of the compound of formula I, or a therapeutically acceptable salt or ester thereof or a composition as described above.

Another important aspect involves a method of inhibiting the replication of hepatitis C virus by exposing the virus to a hepatitis C NS3 protease-inhibiting amount of the compound of formula I, or a therapeutically acceptable salt or ester thereof or a composition as described above.

Still another aspect involves a method of treating a hepatitis C viral infection in a mammal by administering thereto an anti-hepatitis C virally effective amount of a combination of the compound of formula I, or a therapeutically acceptable salt or ester thereof. According to one embodiment, the pharmaceutical compositions of this invention comprise an additional immunomodulatory agent. Examples of additional immunomodulatory agents include but are not limited to, α-, β-, and δ-interferons.

According to an alternate embodiment, the pharmaceutical compositions of this invention may additionally comprise an antiviral agent. Examples of antiviral agents include, ribavirin and amantadine.

According to another alternate embodiment, the pharmaceutical compositions of this invention may additionally comprise other inhibitors of HCV protease.

According to yet another alternate embodiment, the pharmaceutical compositions of this invention may additionally comprise an inhibitor of other targets in the HCV life cycle, such as helicase, polymerase, metalloprotease or IRES.

DETAILED DESCRIPTION OF PREFERRED EMBODIMENTS

Definitions

As used herein, the following definitions apply unless otherwise noted:

The designation herein of a position within the D chain by position number(s), e.g. "position 10 of said D chain" or "D chain is substituted at position 8" or "double bond at position 13, 14 of said D chain" or "D chain contains one double bond at position 11,12", or similar language, means the position or positions within the D chain when the atoms of the D chain are numbered as set forth previously, i.e., the atoms of the D chain that form part of the macrocyclic ring in structural formula (I) are numbered from left to right in structural formula (I) starting with position number 8.

With reference to the instances where (R) or (S) is used to designate the absolute configuration of a substituent, e.g. $R^4$ of the compound of formula I, the designation is done in the context of the whole compound and not in the context of the substituent alone.

The designation "P1, P2, and P3" as used herein refer to the position of the amino acid residues starting from the C-terminus end of the peptide analogs and extending towards the N-terminus (i.e. P1 refers to position 1 from the C-terminus, P2: second position from the C-terminus, etc.) (see Berger A. & Schechter I., Transactions of the Royal Society London series B257, 249–264 (1970)).

As used herein the term "1-aminocyclopropyl-carboxylic acid" (ACCA) refers to a compound of formula:

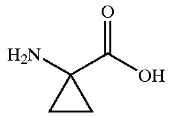

As used herein the term "vinyl-ACCA" refers to a compound of formula:

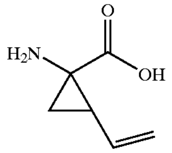

As used herein the term "homo-allyl-ACCA" refers to a compound of formula:

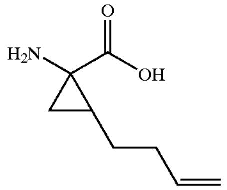

The term "halo" as used herein means a halogen substituent selected from bromo, chloro, fluoro or iodo.

The term "$C_{1-6}$ haloalkyl" as used herein means as used herein, either alone or in combination with another substituent, means acyclic, straight or branched chain alkyl substituents containing from 1 to six carbon atoms having one or more hydrogen substituted for a halogen selected from bromo, chloro, fluoro or iodo.

The term "$C_{1-6}$ thioalkyl" as used herein means as used herein, either alone or in combination with another substituent, means acyclic, straight or branched chain alkyl substituents containing a thiol group such a thiopropyl.

The term "$C_{1-6}$ alkyl" or "(lower)alkyl" as used herein, either alone or in combination with another substituent, means acyclic, straight or branched chain alkyl substituents containing from 1 to six carbon atoms and includes, for example, methyl, ethyl, propyl, butyl, hexyl, 1-methylethyl, 1-methylpropyl, 2-methylpropyl, 1,1-dimethylethyl.

The term "$C_{3-6}$ cycloalkyl" as used herein, either alone or in combination with another substituent, means a cycloalkyl substituent containing from three to six carbon atoms and includes cyclopropyl, cyclobutyl, cyclopentyl, and cyclohexyl.

The term "unsaturated cycloalkyl" includes, for example, the substituent cyclohexenyl:

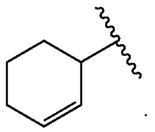

The term "saturated or unsaturated alkylene" as used herein means a divalent alkyl substituent derived by the removal of one hydrogen atom from each end of a saturated or unsaturated straight or branched chain aliphatic hydrocarbon and includes, for example, $—CH_2CH_2C(CH_3)_2CH_2CH_2—$, $—CH_2CH_2CH{=}CHCH_2CH_2—$ or —$CH_2C$≡—$CCH_2CH_2$—. This alkyl chain may optionally contain a heteroatom such as oxygen (for example: $CH_3$—$CH_2$—O—$CH_2$—).

The term "$C_{1-6}$ alkoxy" as used herein, either alone or in combination with another substituent, means the substituent —O—$C_{1-6}$ alkyl wherein alkyl is as defined above containing up to six carbon atoms. Alkoxy includes methoxy, ethoxy, propoxy, 1-methylethoxy, butoxy and 1,1-dimethylethoxy. The latter substituent is known commonly as tert-butoxy.

The term "$C_{3-6}$ cycloalkoxy" as used herein, either alone or in combination with another substituent, means the substituent —O—$C_{3-6}$ cycloalkyl containing from three to 6 carbon atoms.

The term "$C_{1-6}$ alkoxyalkyl" as used herein, means the substituent $C_{1-6}$ alkyl-O—$C_{1-6}$ alkyl wherein alkyl is as defined above containing up to six carbon atoms. For example, methoxymethyl means —$CH_2$—O—$CH_3$.

The term "$C_{2-7}$ acyl" as used herein, either alone or in combination with another substituent, means an $C_{1-6}$ alkyl group linked through a carbonyl group such as —C(O)—$C_{1-6}$ alkyl.

The term "$C_6$ or $C_{10}$ aryl" as used herein, either alone or in combination with another substituent, means either an aromatic monocyclic system containing 6 carbon atoms or an aromatic bicyclic system containing 10 carbon atoms. For example, aryl includes a phenyl or a naphthyl—ring system.

The term "$C_{7-16}$ aralkyl" as used herein, either alone or in combination with another substituent, means an aryl as defined above linked through an alkyl group, wherein alkyl is as defined above containing from 1 to 6 carbon atoms. Aralkyl includes for example benzyl, and butylphenyl.

The term "Het" as used herein, either alone or in combination with another substituent, means a monovalent substituent derived by removal of a hydrogen from a five-, six-, or seven-membered saturated or unsaturated (including aromatic) heterocycle containing from one to four heteroatoms selected from nitrogen, oxygen and sulfur. Examples of suitable heterocycles include: tetrahydrofuran, thiophene, diazepine, isoxazole, piperidine, dioxane, morpholine, pyrimidine or

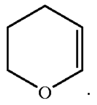
.

The term "Het" also includes a heterocycle as defined above fused to one or more other cycle be it a heterocycle or any other cycle. One such examples includes thiazolo[4,5-b]-pyridine.

Although generally covered under the term "Het", the term "heteroaryl" as used herein precisely defines an unsaturated heterocycle which is an aromatic system. Suitable example of heteroaromatic system include: quinoline, indole, pyridine,

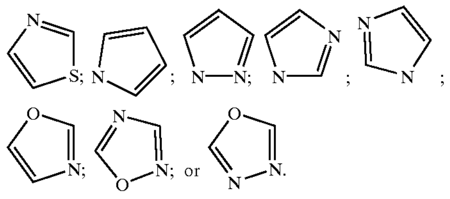

The term "pharmaceutically acceptable ester" as used herein, either alone or in combination with another substituent, means esters of the compound of formula I in which any of the carboxyl functions of the molecule, but preferably the carboxy terminus, is replaced by an alkoxycarbonyl function:

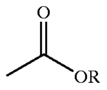

in which the R moiety of the ester is selected from alkyl (e.g. methyl, ethyl, n-propyl, t-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, $C_{1-4}$ alkyl or $C_{1-4}$ alkoxy. Other suitable prodrug esters are found in Design of prodrugs, Bundgaard, H. Ed. Elsevier (1985) incorporated herewith by reference. Such pharmaceutically acceptable esters are usually hydrolyzed in vivo when injected in a mammal and transformed into the acid form of the compound of formula I.

With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group.

In particular the esters may be a $C_{1-16}$ alkyl ester, an unsubstituted benzyl ester or a benzyl ester substituted with at least one halogen, $C_{1-6}$ alkyl, $C_{1-6}$ alkoxy, nitro or trifluoromethyl.

The term "pharmaceutically acceptable salt" as used herein includes those derived from pharmaceutically acceptable bases. Examples of suitable bases include choline, ethanolamine and ethylenediamine. $Na^+$, $K^+$, and $Ca^{++}$ salts are also contemplated to be within the scope of the invention (also see Pharmaceutical salts, Birge, S. M. et al., J. Pharm. Sci., (1977), 66, 1–19, incorporated herein by reference).

Preferred Embodiments $R^1$

Preferred embodiments of the present invention include compounds of formula I as described above, wherein the $R^1$ moiety is selected from the 2 different diastereoisomers where the 1-carbon center has the R configuration as represented by structures (i) and (ii):

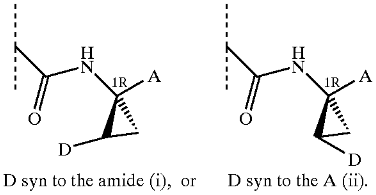

D syn to the amide (i), or D syn to the A (ii).

More preferably, the linker D is linked to $R^1$ in the configuration syn to A as represented by structure (ii).

$R^2$

Preferred embodiments of the present invention include compounds of formula I as described above, wherein the $R^2$ moiety is

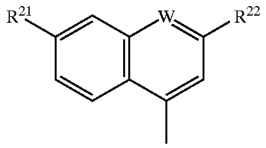

wherein W is preferably N.

Preferably, $R^{21}$ is H, $C_{1-6}$ alkyl, $C_{1-6}$ alkoxy, hydroxy, chloro, or $N(R^{23})_2$ wherein $R^{23}$ is preferably H or $C_{1-6}$ alkyl. More preferably, $R^{21}$ is H or $C_{1-6}$ alkoxy. Most preferably, $R^{21}$ is methoxy.

Preferably $R^{22}$ is H, $C_{1-6}$ thioalkyl, $C_{1-6}$ alkoxy, phenyl or Het selected from the group consisting of:

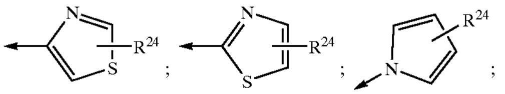

; ; ;

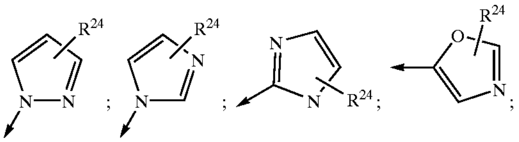

; ; ; ;

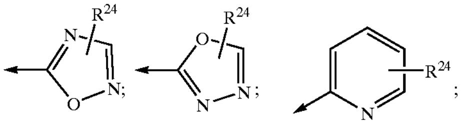

; ; and

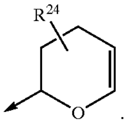

.

Preferably, $R^{24}$ is H, $C_{1-6}$ alkyl, NH—$R^{25}$, NH—C(O)—$R^{25}$; or NH—C(O)—NH—$R^{25}$ or NH—C(O)—$OR^{26}$.

More preferably $R^{22}$ is $C_{1-4}$ alkoxy, phenyl or Het selected from the group consisting of:

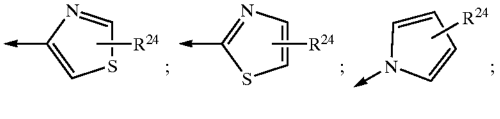

; ; ;

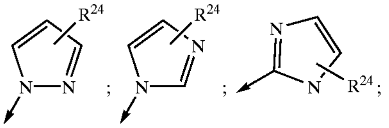

; ; and

-continued

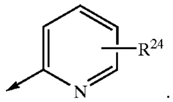

.

More preferably, $R^{24}$ is H, $C_{1-6}$ alkyl, NH—$R^{25}$, NH—C(O)—$R^{25}$; or NH—C(O)—$OR^{26}$.

Most preferably $R^{22}$ is ethoxy, or Het selected from the group consisting of:

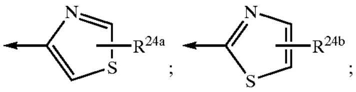

; ; and

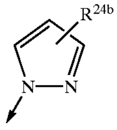

.

Most preferably, $R^{24a}$ is NH—$R^{25}$, NH—C(O)—$R^{25}$, or NH—C(O)—$OR^{26}$. Most preferably, $R^{24b}$ is H or $C_{1-6}$ alkyl.

Preferably, each $R^{25}$ is independently: H, $C_{1-6}$ alkyl, or $C_{3-6}$ cycloalkyl. More preferably, $R^{25}$ is $C_{1-6}$ alkyl or $C_{3-6}$ cycloalkyl. More preferably, $R^{25}$ is $C_{1-6}$ alkyl.

Preferably, $R^{26}$ is $C_{1-6}$ alkyl.

$R^3$

Preferred embodiments of the present invention include compounds of formula I as described above, wherein the $R^3$ moiety is preferably an amide of formula NH—C(O)—$R^{32}$, a urea of formula NH—C(O)—NH—$R^{32}$, or a carbamate of formula NH—C(O)—$OR^{32}$. More preferably, $R^3$ is a carbamate or a urea. Most preferably, $R^3$ is a carbamate.

Preferably, $R^{32}$ is $C_{1-6}$ alkyl, or $C_{3-6}$ cycloalkyl. More preferably, $R^{32}$ is $C_{1-6}$ alkyl, or $C_{4-6}$ cycloalkyl. Most preferably, $R^{32}$ is tert-butyl, cyclobutyl or cyclopentyl.

D

Preferred embodiments of the present invention include compounds of formula I, wherein linker D is a 6 to 8 atom saturated or unsaturated alkylene chain. More preferably, linker D is 7 atom chain.

Preferably, the D chain contains one or two heteroatoms selected from: O, S, NH, N—$C_{1-6}$ alkyl or N—$C_{2-7}$ acyl. More preferably, the D chain optionally contains one heteroatom selected from: NH, or N—$C_{2-7}$ acyl, most preferably N(Ac), and is positioned at atom 10 of the chain. Most preferably, the chain containing a nitrogen atom is saturated.

Alternatively, D contains one heteroatom selected from: O, or S. Preferably, when D is 7 atom in length, the O or S atom is at position 9 of the chain. Preferably, this chain is substituted with $R^4$, wherein $R^4$ is H or $C_{1-6}$ alkyl. More preferably, $R^4$ is H or methyl. Most preferably, $R^4$ is H or 8-(S)—Me. Even most preferably, D is saturated. Alternatively, D contains one double bond at position 11,12. Preferably, this double bond is trans.

Alternatively, D is an all carbon saturated or unsaturated alkylene chain. In this case, D is preferably saturated and is 7 atom in length. More preferably, D is substituted with $R^4$, wherein $R^4$ is H, oxo, thio, hydroxy, thioalkyl, alkoxy or alkyl. More preferably, $R^4$ is H or $C_{1-6}$ alkyl. Most preferably, $R^4$ is H or methyl. Most preferably, $R^4$ is H or 10-(S)—Me.

Alternatively, D is an all carbon alkylene chain containing preferably one double bond and is 7 atom in length. More preferably, this double bond is at position 13,14 of the chain. Most preferably, this double bond is cis. Preferably, this D chain is substituted with $R^4$, wherein $R^4$ is H, oxo, hydroxy, alkoxy or alkyl. More preferably, $R^4$ is H or $C_{1-6}$ alkyl. Even more preferably, $R^4$ is H or methyl. Most preferably, $R^4$ is H or 10-(S)—Me.

A

Preferred embodiments of the present invention include compounds of formula I as described above, wherein A is a carboxylic acid.

Specific Embodiments

Preferred embodiments of the present invention include compounds of formula I as described above, wherein $R^2$ is a quinoline substituent (i.e. W is N);

$R^3$ is a group of formula —NH—C(O)—$NHR^{32}$ or —NH—C(O)—$OR^{32}$,
wherein $R^{32}$ is: $C_{1-4}$ alkyl or $C_{4-6}$ cycloalkyl;

D is a 6 to 8 atom saturated or unsaturated alkylene chain linked to $R^1$ in configuration syn to A, optionally containing one or two heteroatoms independently selected from: O, S or N—$R^{41}$, wherein $R^{41}$ is $C_{2-7}$ acyl;

$R^4$ is H, or from one to three substituents independently selected from hydroxy or $C_{1-6}$ alkyl; and A is a carboxylic acid, or a pharmaceutically acceptable salt or ester thereof.

More preferably are compounds of formula I wherein $R^1$ is as defined above; $R^{21}$ is H or methoxy;

$R^{22}$ is $C_{1-6}$ alkoxy, or Het selected from the group consisting of:

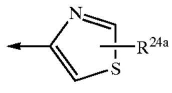
;
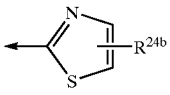
; and

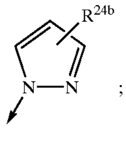
;

wherein $R^{24a}$ is H, $C_{1-6}$ alkyl, NH—$R^{25}$, NH—C(O)—$R^{25}$, NH—C(O)—NH—$R^{25}$,
wherein $R^{25}$ is: H, $C_{1-6}$ alkyl or $C_{3-6}$ cycloalkyl;
or $R^{24a}$ is NH—C(O)—$OR^{26}$, wherein $R^{26}$ is $C_{1-6}$ alkyl or $C_{3-6}$ cycloalkyl;
and $R^{24b}$ is H or $C_{1-6}$ alkyl;

$R^3$ is a urea of the formula NH—C(O)—$NHR^{32}$ or a carbamate of formula NH—C(O)—$OR^{32}$, wherein $R^{32}$ is $C_{1-6}$ alkyl or $C_{3-6}$ cycloalkyl;

D is a C7-atom saturated or unsaturated alkylene chain optionally containing one double bond at position 11,12 or 13,14;

said D chain optionally containing one heteroatom independently selected from: O, S, NH, N(Me), or N(Ac); and $R^4$ is H or $C_{1-6}$ alkyl.

Most preferably, are compounds of formula I wherein $R^{21}$ is methoxy, and $R^{22}$ is ethoxy or:

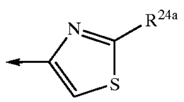

wherein $R^{24a}$ is NH—($C_{1-4}$ alkyl), NH—C(O)—($C_{1-4}$ alkyl); or NH—C(O)—O—($C_{1-4}$ alkyl),; and D is saturated or contains one cis double bond at position 13,14.

Finally, included within the scope of this invention are all compounds of formula I as presented in Tables 1 to 9.

The pharmaceutical compositions of this invention may be administered orally, parenterally or via an implanted reservoir. Oral administration or administration by injection are preferred. The pharmaceutical compositions of this invention may contain any conventional non-toxic pharmaceutically-acceptable carriers or auxiliary agents such as adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example. Tween 80) and suspending agents.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

Other suitable vehicles or carriers for the above noted formulations and compositions can be found in standard pharmaceutical texts, e.g. in "Remington's Pharmaceutical Sciences", $19^{th}$ ed., Mack Publishing Company, Easton, Pa., 1995. Dosage levels of between about 0.01 and about 100 mg/kg body weight per day, preferably between about 0.5 and about 75 mg/kg body weight per day of the protease inhibitor compounds described herein are useful in a monotherapy for the prevention and treatment of HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this invention comprise a combination of a compound of formula I and one or more additional therapeutic or prophylactic agent, both the compound and the additional agent should be present at dosage levels of between about 10 to 100%, and more preferably between about 10 and 80% of the dosage normally administered in a monotherapy regimen.

When these compounds or their pharmaceutically acceptable salts are formulated together with a pharmaceutically acceptable carrier, the resulting composition may be administered in vivo to mammals, such as man, to inhibit HCV NS3 protease or to treat or prevent HCV virus infection. Such treatment may also be achieved using the compounds of this invention in combination with agents which include, but are not limited to: immunomodulatory agents, such as α-, β-, or γ-interferons; other antiviral agents such as ribavirin, amantadine; other inhibitors of HCV NS3 protease; inhibitors of other targets in the HCV life cycle such as helicase, polymerase, metalloprotease, or internal ribosome entry site (IRES); or combinations thereof. The additional agents may be combined with the compounds of this invention to create a single dosage form. Alternatively these additional agents may be separately administered to a mammal as part of a multiple dosage form.

Accordingly, another embodiment of this invention provides methods of inhibiting HVC NS3 protease activity in mammals by administering a compound of the formula I, wherein the substituents are as defined above.

In a preferred embodiment, these methods are useful in decreasing HCV NS3 protease activity in a mammal. If the pharmaceutical composition comprises only a compound of this invention as the active component, such methods may additionally comprise the step of administering to said mammal an agent selected from an immunomodulatory agent, an antiviral agent, a HCV protease inhibitor, or an inhibitor of other targets in the HCV life cycle such as helicase, polymerase, or metalloprotease. Such additional agent may be administered to the mammal prior to, concurrently with, or following the administration of the compositions of this invention.

In an alternate preferred embodiment, these methods are useful for inhibiting viral replication in a mammal. Such methods are useful in treating or preventing HCV disease. If the pharmaceutical composition comprises only a compound of this invention as the active component, such methods may additionally comprise the step of administering to said mammal an agent selected from an immunomodulatory agent, an antiviral agent, a HCV protease inhibitor, or an inhibitor of other targets in the HCV life cycle. Such additional agent may be administered to the mammal prior to, concurrently with, or following the administration of the composition according to this invention.

The compounds set forth herein may also be used as laboratory reagents. The Applicant provides for the first time compounds with a low molecular weight, that are highly active and specific against the HCV NS3 protease. Some of the present compounds may be instrumental in providing research tools for designing of viral replication assays, validation of animal assay systems and structural biology studies to further enhance knowledge of the HCV disease mechanisms.

The compounds of this invention may also be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection or transfusion apparatuses and materials).

Methodology

Several ways of carrying the synthesis of acyclic intermediates of compounds of formula I are disclosed in WO 00/09543 and WO 00/09558 incorporated herein by reference.

The compounds of the present invention are synthesized according to the general process illustrated in Schemes I, II and III (wherein PG is an appropriate protecting groups. [In all schemes presented below, D' has the same definition as D but is 2 to 5 atom shorter].

When the invention covers compounds of formula I wherein A is a N-substituted amide, vinyl-ACCA or homoallyl ACCA ($R^1$) is coupled to an appropriate amine prior to the coupling to P2. Such coupling will be readily recognized by persons skilled in the art. As will be recognized by persons skilled in the art, such amide (A) is not protected but bears any relevant substituent $R^5$ as defined above.

The ring-closing reaction (macrocyclization) is carried out by either olefin metathesis (Scheme I) or when the linker contains a nitrogen atom, by reductive amination (Scheme II), or by peptide bond formation Scheme III.

Details of these processes are presented below:

A. Macrocyclisation via Olefin Metathesis

Scheme I

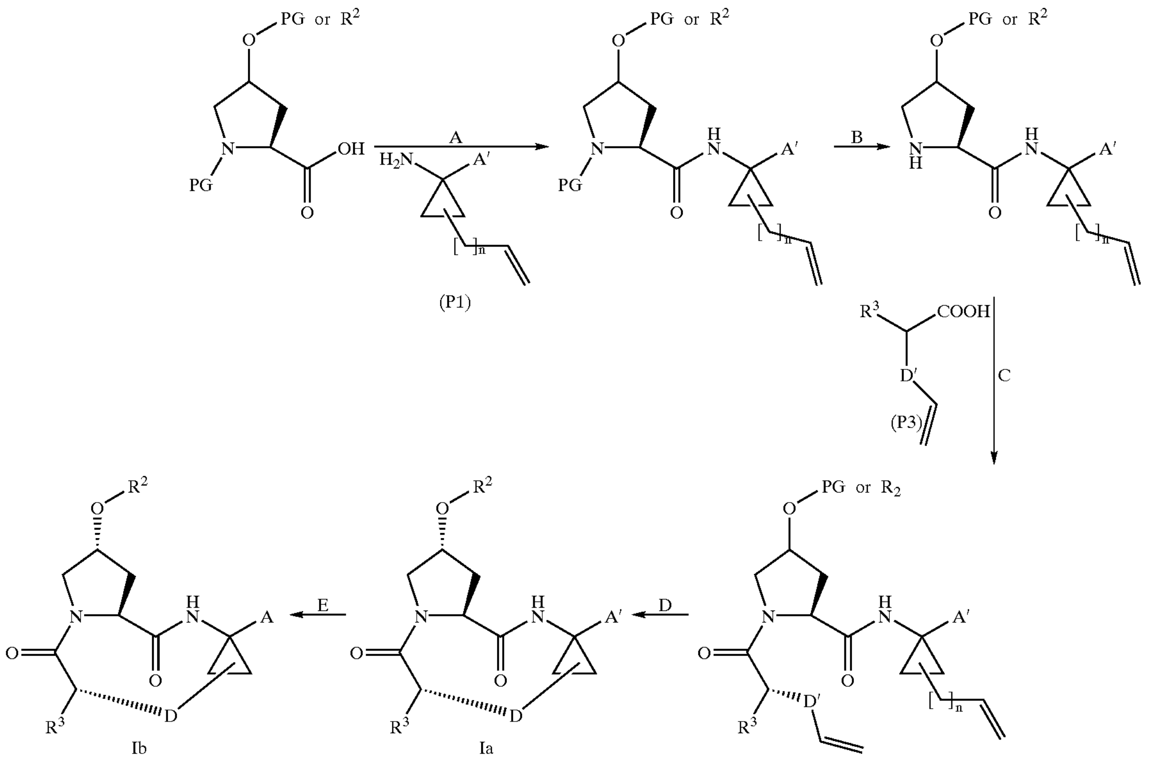

Ib
D = saturated

Ia
D = unsaturated

A' = protected carboxylic acid or N-substituted amide.
n = 0 or 2

Scheme I

There are several ways in which the coupling sequence can be carried out which can be easily recognized by persons skilled in the art. Starting with 4-(S)-hydroxyproline, the substituent at the 4-hydroxy can be incorporated via a Mitsunobu reaction (as described in Mitsunobu *Synthesis* 1981, January, 1–28; Rano et al. *Tet. Lett.* 1994, 36, 3779–3792; Krchnak et al. *Tet. Lett.* 1995, 36, 6193–6196) before or after the macrocyclization. Alternatively the assembly can be done with the required 4-(R)-hydroxy-substituted proline as disclosed in the general processes of WO 00/09543 & WO 00/09558 (see below for specific examples of these fragments).

Steps A, B, C: Briefly, the P1, P2, and P3 moieties can be linked by well known peptide coupling techniques and generally disclosed in WO 00/09543 & WO 00/09558.

Step D: The formation of the macrocycle can be carried out via an olefin metathesis using a Ru-based catalyst such as the one reported by Miller, S. J.; Blackwell, H. E.; Grubbs, R. H. *J. Am. Chem. Soc.* 1996, 118, 9606–9614 (a); Kingsbury, J. S.; Harrity, J. P. A.; Bonitatebus, P. J.; Hoveyda, A. H. *J. Am. Chem. Soc.* 1999, 121, 791–799 (b) and Huang, J.; Stevens, E. D.; Nolan, S. P.; Petersen, J. L.; *J. Am. Chem. Soc.* 1999, 121, 2674–2678 (c). It will also be recognized that catalysts containing other transition metals such as Mo can be used for this reaction.

(a)

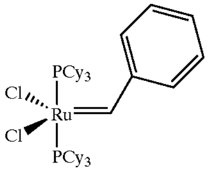

Grubb's catalyst (b)

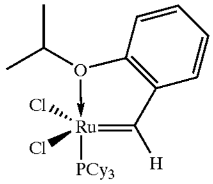

Hoveyda's catalyst (c)

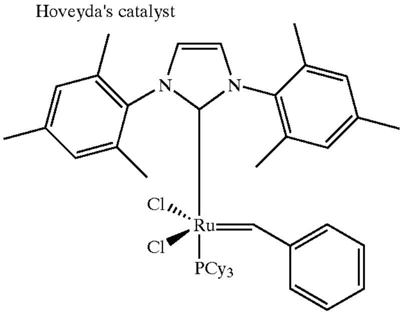

Nolan's catalyst

Step E: Optionally, the double bond is reduced by standard hydrogenation methods well known in the art. When A' is a protected carboxylic acid, it is also deprotected appropriately.

B. Macrocyclization via Reductive Amination (for Linkers Containing N)

When the linker contains a nitrogen atom, macrocyclization is achieved by reductive amination as shown in Scheme II to obtain inhibitors of general structure II.

Scheme II

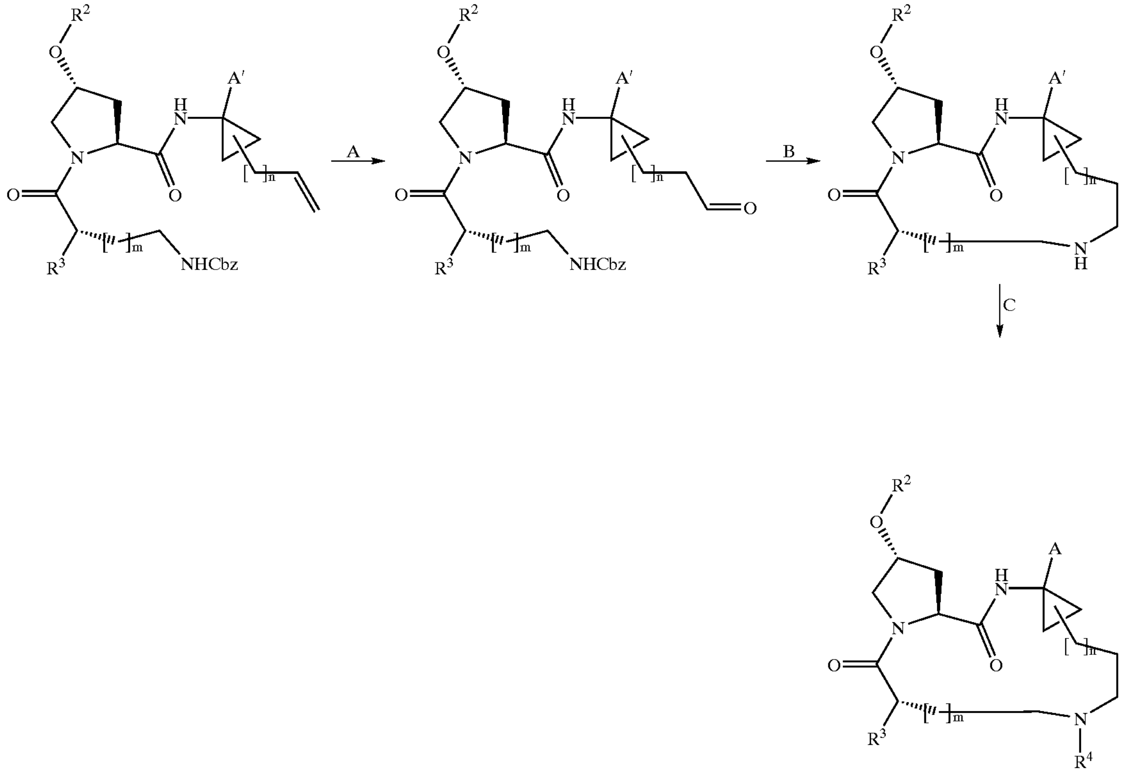

II

A' = protected carboxylic acid or N-substituted amide.
n = 1 to 5
m = 1 to 5

Step A: Hydroboration of the double bond following Brown's procedure (H. C. Brown and B. C. Subba Rao, *J. Am. Che. Soc.* 1959, 81, 6434–6437) followed by oxidation of the resulting alcohol (for example via Dess-Martin periodinate, *J. Am. Chem. Soc.* 1991, 113, 7277–7287) affords the corresponding aldehyde.

Step B: Hydrogenation in the presence of acid leads to the removal of the amino protecting group followed by macrocyclization via reductive amination. The P3 unit used in this synthesis is easily obtained from a variety of amino acids, such as lysine, ornithine, glutamine (after a Hofmann reaction: Ber. 1881, 14, 2725) and others; these synthetic modifications are methods well known in the art.

Step C: Optionally, the secondary amine in the linker D (formed after step D) is alkylated with alkyl halides or acetylated with alkyl or aryl acid chlorides using methodologies well known in the art to obtain inhibitors of general structure II. When A' is a protected carboxylic acid, it is also deprotected appropriately.

C. Macrocyclization via Lactam Formation

Alternatively, it is understood that these macrocyclic compounds with general structure I and II can be synthesized in other ways. For example P1 and P3 can be first connected to the linker D, then coupled to P2 and the macrocyclization reaction can be a lactam formation in two possible ways as will be recognized by persons skilled in the art and as shown in Scheme III.

Scheme III

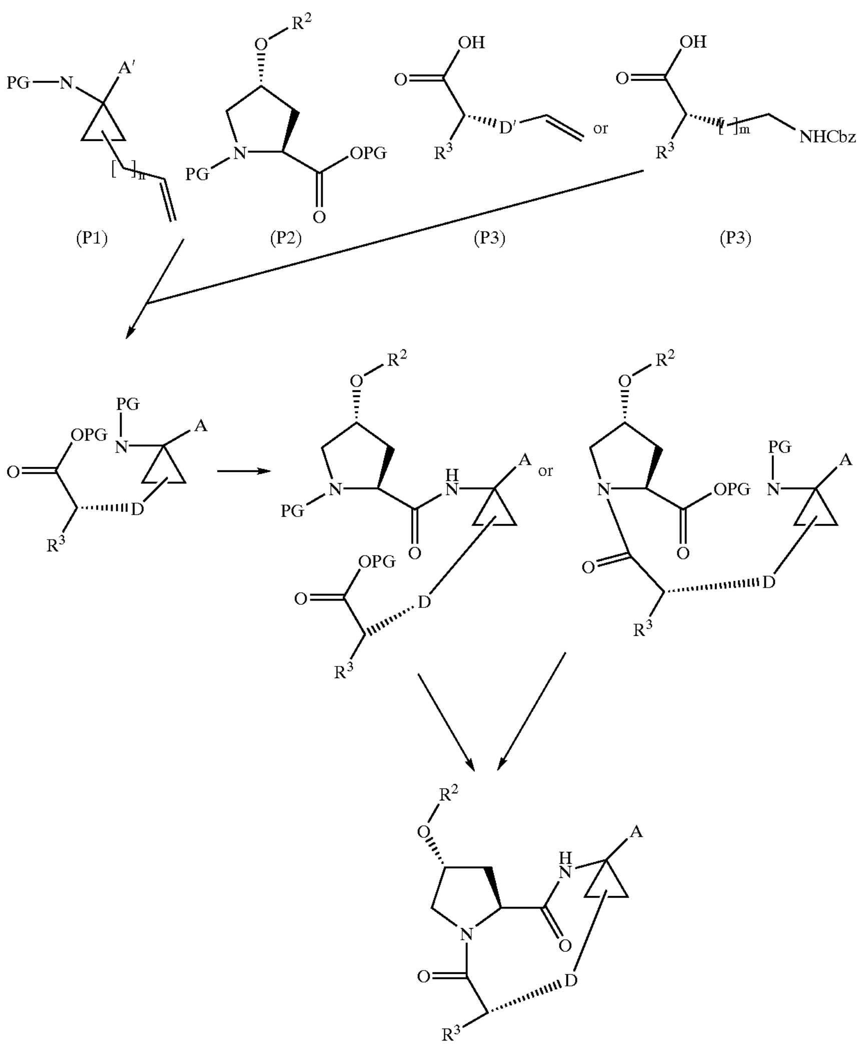

(P1) (P2) (P3) (P3)

A' = protected carboxylic acid or N-substituted amide.
n = 0 or 2
m = 1 to 7

Synthesis of P1

The synthesis of inhibitors with general structure I and II requires the same P1 fragments:

a) vinyl ACCA, the synthesis and resolution of which is described in WO 00/09543 & WO 00/09558 and co-pending applications Ser. No. 09/368,866 incorporated herein by reference in its entirety) or b) homoallyl ACCA (Example 1, compound 1f).

Synthesis of P2

Some of the P2 fragments used for the synthesis of compounds of formula I are described in WO 00/09543 & WO 00/09558 and co-pending applications Ser. No. 09/368,866 incorporated herein by reference in its entirety.

Other P2 fragments are synthesized as follows:

a. Synthesis of 2-“Het”-4-hydroxy-7-methoxyquinoline Derivative (i) Approach from the Corresponding “Het” Carboxylic Acid IVb Scheme IV

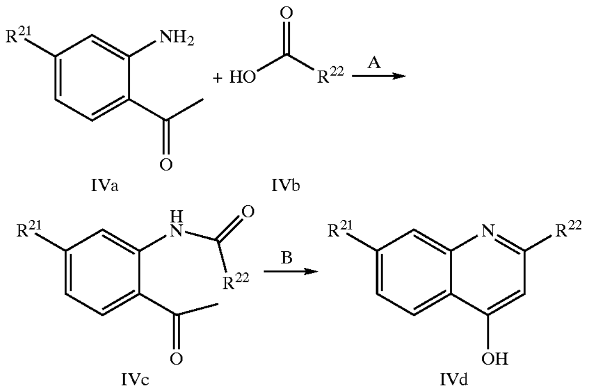

IVa IVb IVc IVd

The synthesis is carried out according to a modified procedure in Li et al. *J. Med. Chem.* 1994, 34, 3400–3407. Intermediate IVa where $R^{21}$=OMe (Example 7, compound 7b) is prepared as described by Brown et al. *J. Med. Chem.* 1989, 32, 807–826.

Step A: Intermediate IVa is coupled with heterocyclic carboxylic acids IVb under basic conditions with $POCl_3$ to activate the carboxylate group. A variety of carboxylic acids with general structure IVb are used for the preparation of inhibitors; these are either commercially available, synthesized as shown in scheme V, VI and VII, or synthesized individually using methods described in the specific examples.

Step B: Ring-closure, followed by dehydration is achieved under basic conditions to obtain quinolines of general structure IVd.

(i.a). Synthesis of "Het"-carboxylic Acids of General Formula IVb

Synthesis of 2-(substituted)-amino-4-carboxy-aminothiazole Derivatives (Vc)

A modification of the procedure described by Berdikhina el al. *Chem. Heterocycl. Compd.* (Engl. Transl.) 1991, 4, 427–433 is used.

Scheme V

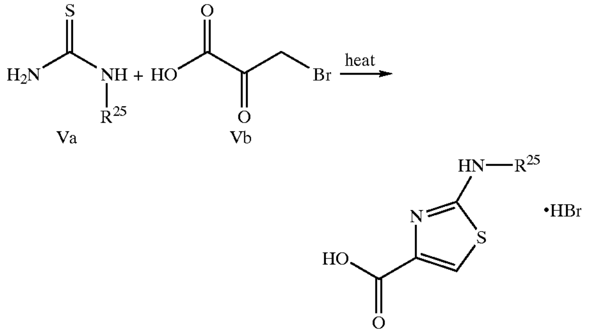

Va Vb

Vc

A variety of 2-alkylaminothiazolyl-4-carboxylic acids, compounds of general structure Vc, are made using the general synthetic methodology outlined in Scheme V using thioureas (Va) with different alkyl substituents ($R^{25}$=alkyl group) and 3-bromopyruvic acid. This type of condensation reaction is well known in the art. Alternatively, the P2 fragment containing the 2-amino-substituted-thiazole derivatives are synthesized from the corresponding 2-carboxyl derivative as shown in scheme VI according to the procedure of: Unangst, P. C.; Connor, D. T. *J. Heterocyc. Chem.* 29, 5, 1992, 1097–1100.

Scheme VI

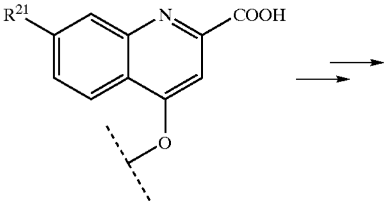

(VIa)

-continued

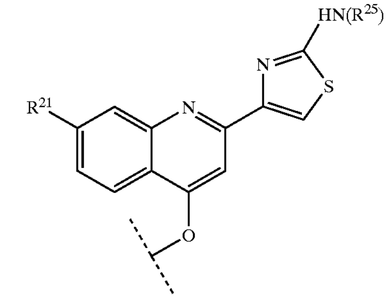

(VIb)

Examples of this process are disclosed in WO 00/09543 & WO 00/09558.

Synthesis of 2-carboxy-4-substituted Aminothiazole Derivatives VIId

A variety of 4-alkylthiazolyl-2-carboxylic acids, compounds of general structure VIId, is made using the general synthetic methodology outlined in Scheme VII.

Scheme VII

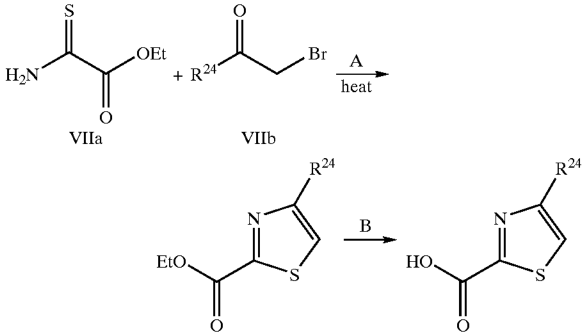

VIIa VIIb

VIIc VIId

The procedure described by Janusz et al. *J. Med. Chem.* 1998, 41, 3515–3529 is used with modifications as described as follows: Ethyl thiooxamate (VIIa) is reacted with different β-bromoketones of general structure VIIb ($R^{24}$=alkyl group) to form thiazolyl carboxylic acids of general structure VIId. This type of condensation reaction is well known in the art.

Synthesis of 2-carboxy-(substituted)-imidazole Derivative (VIIIb)

A variety of alkylimidazolyl-2-carboxylic acids, compounds of general structure VIIIb, are made using the general synthetic methodology outlined in Scheme VIII.

Scheme VIII

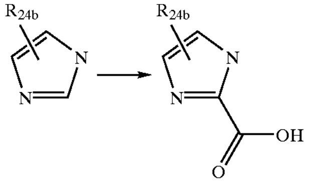

VIIIa VIIIb

The procedure described by Baird et al. *J. Amer. Chem. Soc.* 1996, 118, 6141–6146. was used: an alkyl imidazole is deprotonated with a strong base (e.g. nBuLi) and then reacted with $CO_2$ to form the carboxylic acid VIIIb. This type of condensation reaction is well known in the art.

b. Synthesis of 4-hydroxy-7-methoxy-2-(imidazolyl or pyrazolyl)quinolines

4-Hydroxy-7-$R^{21}$ quinolines having an imidazolyl or pyrazolyl moiety at C2 are generally prepared using the methodology outlined in Scheme IX.

Scheme IX

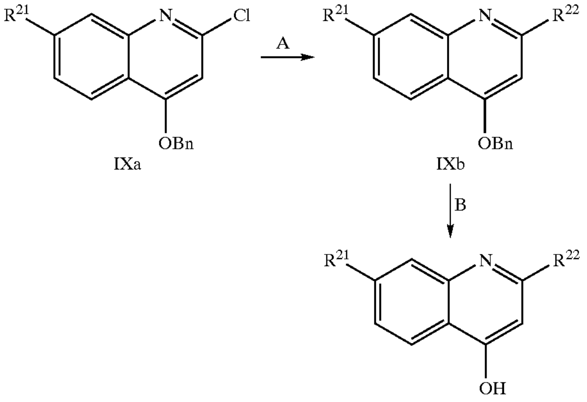

IXa IXb IXc $R^{22}$ = imidazole or pyrazole derivatives

The synthesis of the key intermediate, (wherein $R^{21}$= OMe) 4-benzyloxy-2-chloro-7-methoxyquinoline IXa is described in detail in Example 6 (compound 6e).

Step A: At high temperatures, a variety of imidazoles, alkyl substituted imidazoles, pyrazoles or alkyl substituted pyrazoles can be used to displace the 2-chloro moiety of compound IXa giving compounds of general structure IXb.

Step B: Upon removal of the benzyl protecting group from the 4-hydroxy moiety of the quinoline by standard hydrogenation methods, quinoline derivatives of general structure IXc are obtained.

Synthesis of P3

A variety of P3 fragments are synthesized containing the appropriate D linker extension for macrocyclization by olefin metathesis. In general P3 units containing a terminal olefin for metathesis are synthesized following the general schemes shown below (Schemes X, XI & XII).

Synthesis of Linkers in Class A

This general synthesis is used to make linkers that are all carbon based (no heteroatom) (Scheme X).

Scheme X

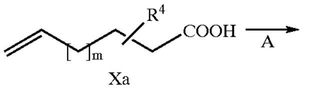

Xa

-continued

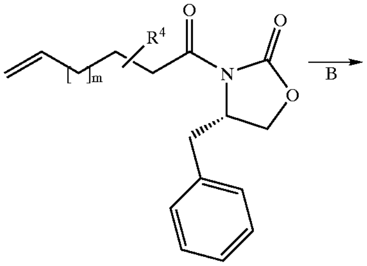

Xb

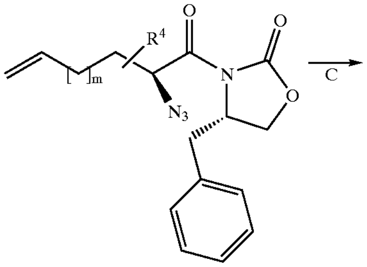

Xc

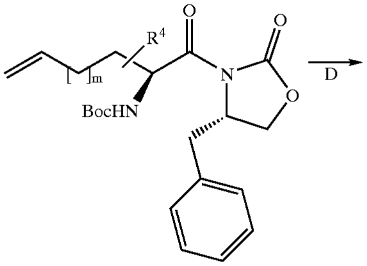

Xd

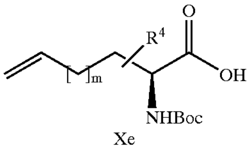

Xe m = 1 to 5

$R^4$ = H or alkyl

The synthesis is performed according to the procedure of Evans et al. *J. Am. Chem. Soc.* 1990, 112, 4011–4030.

The starting carboxylic acids (Xa) is commercially available or is prepared by know literature procedures familiar to those skilled in the art.

Step A: The carboxylic acid Xa is activated with pivaloyl chloride and then reacted with the anion of Evans'chiral auxiliary 4(S)-4-(phenylmethyl)-2-oxazolidinone following well known chemistry (Review: D. J. Ager et al. *Aldrichimica Acta* 1997, 30, 3–11, and references therein) to obtain compounds of general structure Xb.

Step B: Stereoselective α-azidation with trizylazide, of a chiral imide enolate such as those which would form from compounds with general structure Xb in the presence of a base like KHMDS, is also well known in the art (Review: D. J. Ager et al. *Aldrichimica Acta* 1997, 30, 3–11, and references therein).

Step C: Reduction of the α-azide, catalyzed by $SnCl_2$, is followed by protection of the amine formed as its t-butyl carbamate gives intermediates of general structure Xc. These reactions are also well known in the art.

Step D: Finally, the chiral auxiliary is hydrolyzed under basic conditions, such as a mixture of $H_2O_2$ with LiOH, to produce the amino acid-type linkers of general structure Xe.

Alternatively, P3 moieties having the same general structure Xe are synthesized following de procedure described by M. J. Burk et al. *J. Am. Chem. Soc* 1998, 120, 657–663 illustrated in Scheme XI. These compounds varied in the number of methylene units ($—CH_2—$) along the linker (m=1 to 5) and the substitution of alkyl groups at $R_4$, but did not contain a heteroatom.

Scheme XI

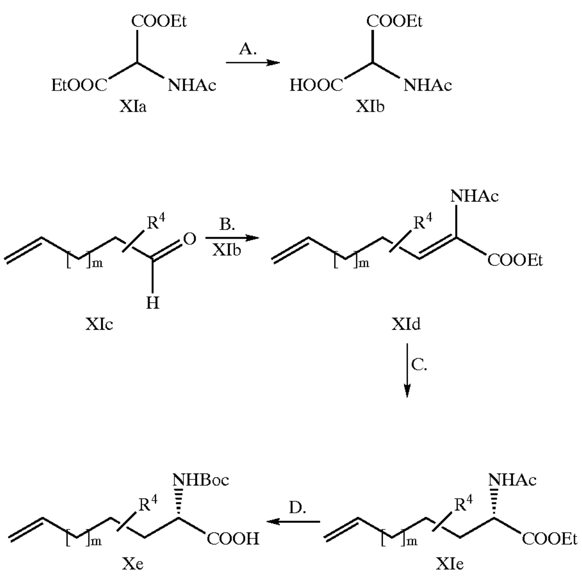

XIa XIb XIc XId XIe Xe m = 1–5, $R^4$ = H or alkyl

Step A: The monoacid compound XIb is prepared from commercially available diethyl 2-acetamidomalonate by standard ester hydrolysis under basic conditions.

Step B: Knoevenagel-type condensation between an aldehyde of general structure XIc and compound XIb in the presence of a base, such as pyridine, and acetic anhydride leads to the formation of enamide intermediate XId having the Z stereochemistry around the newly formed double bond as shown.

Step C: Regioselective and enantioselective catalytic hydrogenation of the enamide intermediate XId to the amino acid intermediate XIe is achieved using Burk's method.

Step D: The nitrogen of the acetamido derivative XIe is then di-protected with the addition of a t-butyl carbamate substituent before the acetate group, as well as the ethyl ester, are hydrolyzed under standard basic condition to obtain P3 moieties of general structure XIf.

Synthesis of Linkers in Class B

General Structure of Linkers in Class B

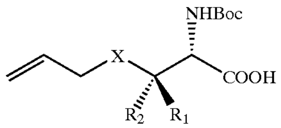

X = O or S
$R_1$ = H or $CH_3$
$R_2$ = H or $CH_3$

This general synthesis is used to make linkers containing oxygen or sulfur.

Scheme XII

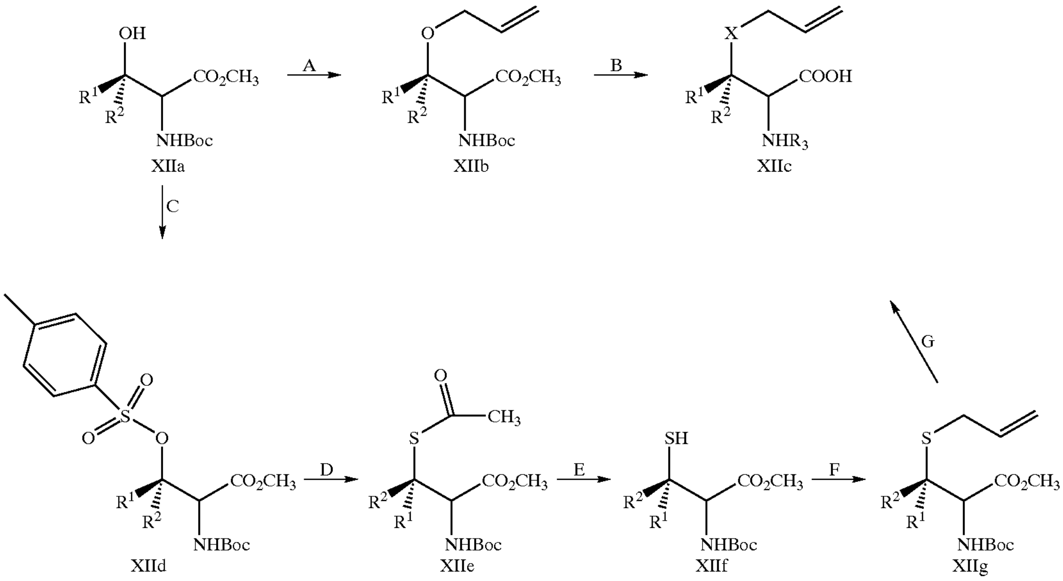

XIIa XIIb XIIc XIId XIIe XIIf XIIg

X = O or S
$R^1$ = H or $CH_3$
$R^2$ = H or $CH_3$ but not both $R^1$ = $R^2$ = $CH_3$ Step A: Suitably protected amino acids, such Boc-(L)-serine methyl ester, Boc-(L)-threonine methyl ester or Boc-(L)-allothreonine methyl ester, are alkylated with allyl iodide in the presence of $Ag_2O$ to give the methyl ester XIIb.

Step B: Hydrolysis of the methyl ester under standard basic conditions yields the ether-type linkers of general structure XIIc (X═O).

Step C: The sulfur analog is prepared from the same starting amino acid XIIa (appropriately protected as before) and its hydroxyl group is converted to a good leaving group (such as the tosylate intermediate XId) using standard methodology well known in the art.

Step D: The tosyl moiety is subsequently displaced with the anion of thioacetate leading to the formation of the thioester intermediate XIIe by inversion of the chiral center at the β-carbon.

Step E: Hydrolysis of the thioester moiety under mild basic conditions yields the free thiol XIIf.

Step F: Alkylation of the thiol moiety is easily achieved under basic conditions with allyl iodide.

Step G: Finally, the sulfide analog XIIc (X=S) are obtained after hydrolysis of the methyl ester using standard procedures.

Synthesis of R3 Fragment

Examples of synthesis of fragments wherein $R^3$ is NH—$R^{31}$ are disclosed in WO 00/09543.

EXAMPLES

The present invention is illustrated in further detail by the following non-limiting examples. Other specific ways of synthesis or resolution can be found in WO 00/09543 & WO 00/09558 and in co-pending applications Ser. No. 09/368,670 and 09/368,866, all of which are hereby incorporated by reference.

Temperatures are given in degrees Celsius. Solution percentages express a weight to volume relationship, and solution ratios express a volume to volume relationship, unless stated otherwise. Nuclear magnetic resonance (NMR) spectra were recorded on a Bruker 400 MHz spectrometer; the chemical shifts (δ) are reported in parts per million and are referenced to the internal deuterated solvent unless otherwise indicated. The NMR spectra of all final compounds (inhibitors) was recorded in DMSO-$d_6$ of their TFA salt unless otherwise indicated. Flash column chromatography was carried out on silica gel ($SiO_2$) according to Still's flash chromatography technique (W. C. Still et al., *J. Org. Chem.,* 1978, 43, 2923).

Abbreviations used in the examples include Bn: benzyl; Boc: tert-butyloxycarbonyl [$Me_3COC(O)$]; BSA: bovine serum albumin; Cbz: benzyloxycarbonyl; CHAPS: 3-[(3-cholamidopropyl)-dimethylammonio]-1-propanesulfonate; DBU: 1,8-diazabicyclo[5.4.0]undec-7-ene; $CH_2Cl_2$=DCM: methylene chloride; DEAD: diethylazodicarboxylate; DIAD: diisopropylazodicarboxylate; DIPEA: diisopropylethylamine; DMAP: dimethylaminopyridine; DCC: 1,3-dicyclohexylcarbodiimide; DME: 1,2-dimethyoxyethane; DMF: dimethylformamide; DMSO: dimethylsulfoxide; DTT: dithiothreitol or threo-1,4-dimercapto-2,3-butanediol; DPPA: diphenylphosphoryl azide; EDTA: ethylenediaminetetraacetic acid; Et: ethyl; EtOH: ethanol; EtOAc: ethyl acetate; $Et_2O$: diethyl ether; ESMS: electrospray mass spectrometry; HATU: O-(7-azabenzotriazol-1-yl)-1,1,3,3-tetramethyluronium hexafluorophosphate; HPLC: high performance liquid chromatography; MS: mass spectrometry; MALDI-TOF: Matrix Assisted Laser Disorption Ionization-Time of Flight, FAB: Fast Atom Bombardment; LAH: lithium aluminum hydride; Me: methyl; MeOH: methanol; MES: (2-[N-morpholino]ethane-sulfonic acid); NaHMDS: sodium bis(trimethylsilyl)amide; NMM: N-methylmorpholine; NMMO: N-methylmorpholine oxide; NMP: N-methylpyrrolidine; Pr: propyl; Succ: 3-carboxypropanoyl; PNA: 4-nitrophenylamino or p-nitroanilide; TBAF: tetra-n-butylammonium fluoride; TBME: tert-butyl-methyl ether; tBuOK: potassium tert-butoxide; TBTU: 2-(1H-benzotriazole-1-yl)-1,1,3,3-tetramethyluronium tetrafluoroborate; TCEP: tris(2-carboxyethyl) phosphine hydrochloride; TFA: trifluoroacetic acid; THF: tetrahydrofuran; TIS: triisopropylsilane; TLC: thin layer chromatography; TMSE: trimethylsilylethyl; Tris/HCl: tris(hydroxymethyl) aminomethane hydrochloride.

P1 Moieties

Example 1

Synthesis of t-butyl-(1R,2R)/(1S,2S)-1-amino-2-homoallylcyclopropyl Carboxylate (1f)

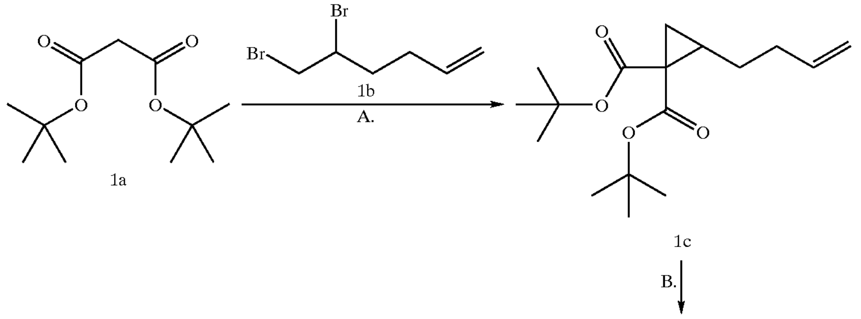

1a

1c

-continued

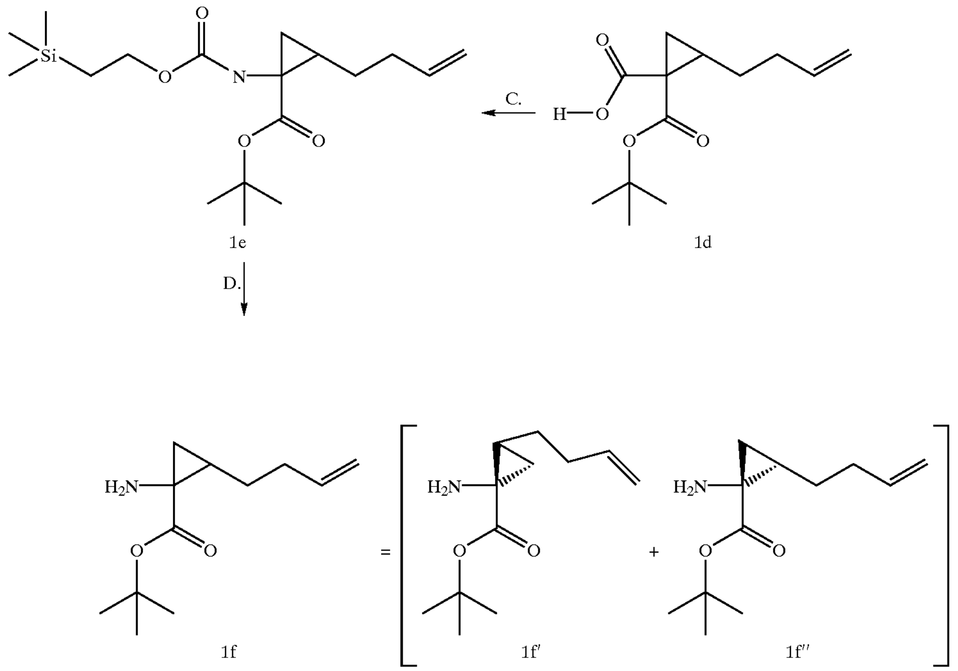

1e 1d

1f = [1f' + 1f'']

A. To a suspension of benzyltriethylammonium chloride (5.08 g, 22.3 mmol.) in 50% aqueous NaOH (50 mL), 1,2-dibromo-5-hexene (1b, 8.10 g, 33.46 mmol) and di-t-butylmalonate (1a, 4.82 g, 22.30 mmol) were added in succession. The mixture was stirred vigorously at RT for 16 h, then diluted with $H_2O$ and extracted with $CH_2Cl_2$ (3x50 mL). The organic layer was further washed with $H_2O$ (2x50 mL), brine/$H_2O$ (2/1, 2x50 mL, dried over $MgSO_4$ and evaporated. The crude residue was purified by flash column chromatography on silica gel, using 3 to 5% EtOAc in hexane as the eluent, to obtain compound 1c in 38% yield (2.48 g).

$^1$H NMR ($CDCl_3$, 400 MHz): δ 1.19 (bd, J=7.9 Hz, 2H), 1.25–1.33 (m, 1H), 1.46 (s, 9H), 1.48 (s, 9H), 1.47–1.60 (m, 1H), 1.75–1.82 (m, 1H), 2.14–2.22 (m, 2H), 4.93–5.50 (m, 2H), 4.96 (dm, J=10.2 Hz, 1H), 5.18 (dm, J=17.2 Hz, 1H). ES(+)MS m/z 297 $(M+H)^+$.

B. To a suspension of potassium t-butoxide (5.75 g, 51.25 mmol) in anhydrous diethyl ether (150 mL) at 0°, $H_2O$ was added (203 μL, 11.27 mmol) and the reaction mixture was stirred at 0° for 10 min. An ether solution of compound 1c (2.48 g in 10 mL diethyl ether, 10.25 mmol) was added and the mixture was stirred at RT for 5 h. The mixture was diluted with ice-cold $H_2O$ and extracted with diethyl ether (3x200 mL). The aqueous layer was acidified to pH 3.5–4 with ice-cold 10% aqueous citric acid and re-extracted with EtOAc (3x200 mL). The EtOAc layer was washed with $H_2O$ (2x100 mL), brine (100 mL), dried over $MgSO_4$ and evaporated to give compound 1d in 85% yield based on the amount of recovered starting material.

$^1$H NMR ($CDCl_3$, 400 MHz): δ 1.51 (s, 9H), 1.64–1.68 (m, 1H), 1.68–1.75 (m, 1H), 1.77–1.88 (m, 1H), 1.96–2.01 (m, 1H), 2.03–2.22 (m, 3H), 5.01 (dm, J=6.4 Hz, 1H), 5.03 (dm, J=14.9 Hz, 1H), 5.72–5.83 (m, 1H).

ES(+)MS: m/z 241 $(M+H)^+$.

C. To a solution of the acid ld in anhydrous benzene (1.14 g in 25 mL benzene, 4.74 mmol), $Et_3N$ (800 μL, 5.68 mmol) was added, followed by the addition of diphenylphosphoryl azide (1.13 mL, 5.21 mmol) and the mixture was heated to reflux for 3.5 h. Subsequently, trimethylsilylethanol (1.36 mL, 9.48 mmol.) was added and stirring at reflux was continued for an additional 4 h. The mixture was then cooled to RT, evaporated to half of its original volume, diluted with diethyl ether (30 mL) and washed with 5% aqueous $NaHCO_3$ (2x30 mL), brine (50 mL), dried over $MgSO_4$ and evaporated. The residual oil was chromatographed on silica gel using 10% EtOAc in hexane as the eluent to obtain pure compound 1e in 88% yield (1.49 g).

$^1$H NMR ($CDCl_3$, 400 MHz) δ 0.03 (s, 9H), 0.91–0.99 (m, 2H), 1.18–1.29 (m, 2H), 1.45 (bs, 11H), 1.56–1.72 (m, 2H), 2.02–2.18 (m, 2H), 4.12 (t, J=8.3 Hz, 2H), 4.93 (dm, J=10.2 Hz, 1H), 4.98 (dm, J=17.2 Hz, 1H), 5.07 (bs, 1H), 5.71–5.83 (m, 1H).

D. To a solution of the cyclopropyl derivative 1e (1.19 g, 3.35 mmol, in 30 mL THF), t-$Bu_4NF$ (6.7 mL of 1M in THF, 6.7 mmol.) was added and the mixture was first stirred at RT for 16 h and subsequently heated to reflux for 15 min. The solvent was carefully evaporated under low pressure (due to the high volatility of the free amine 1f, caution should be exercised during the evaporation of the solvent). The crude residue was re-dissolved in EtOAc (100 mL) and washed with $H_2O$ (2x50 mL), brine (50 mL), dried over $MgSO_4$ and again the solvent was carefully evaporated. The crude product 1f (as a mixture of two enantiomers 1f' and 1f'') was used for coupling with the P2 proline derivatives without further purification. Isolation of the P1P2 fragment having the desired stereochemistry at P1 was easily achieved at this stage using flash chromatography (example 21, fragment 21b).

P2 Moieties

Example 2

Synthesis of Boc-4(R)-[(7-methoxy-4-quinolinyl) oxy]proline (2c)

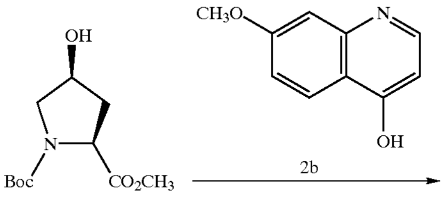

2a 2b

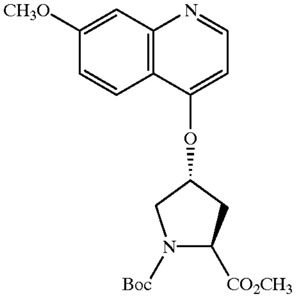

2c

4-Hydroxy-7-methoxyquinoline (2b) was prepared according to the method described by Chun, M. W.; Olmstead, K. K.; Choi, Y. S.; Lee, C. O.; Lee, C.-K.; Kim, J. H.; Lee, *J. Bioorg. Med. Chem. Lett.* 1997, 7, 789. A solution of compound 2b (1.88 g, 10.73 mmol) and DEAD (3.4 mL, 21.46 mmol) in anhydrous THF were added to a stirring solution of protected cis-hydroxyproline 2a (2.63 g, 10.73 mmol) and triphenylphosphine (5.63 g, 21.46 mmol) in anhydrous THF (160 mL) at 0° under $N_2$.

The reaction mixture was allowed to warm-up to RT and stir for 14 h. The THF was then evaporated and the pure product 2c was isolated after flash column chromatography using 5% MeOH in EtOAc as the eluent, in 35% yield (1.5 g).

$^1$H NMR ($CDCl_3$, 400 MHz): δ 1.44 (s, 9H), 1.65 (bs, 1H), 2.34–2.43 (m, 1H), 2.63–2.76 (m, 1H), 3.78 (s, 3H), 3.75–3.85 & 3.89–3.99 (2m, 1H, 2 rotamers), 3.95 (s, 3H), 4.51 & 4.60 (2t, J=8 Hz, 1H, 2 rotamers), 5.15 (bs, 1H), 6.53–6.59 (m, 1H), 7.12–7.18 (dd, J=8.9 & 2.2 Hz, 1H), 7.36 (d, J=2.6 Hz, 1H), 8.03 (bd, J=9.2 Hz, 1H), 8.65 (bd, J=5.1 Hz, 1H).

Example 3

Synthesis of 2-ethoxy-4-hydroxy-7-methoxy Quinoline (3c)

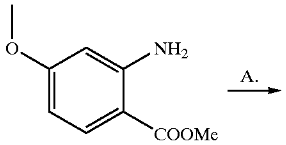

3a

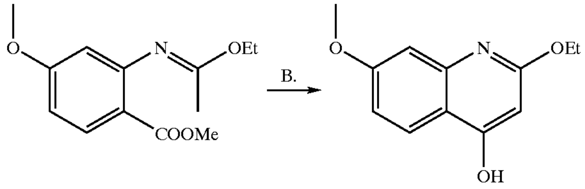

3b 3c

The synthesis of Methyl-p-methoxyantranylate 3a was done as described in Katz et al. *J. Org. Chem.,* 1953, 18, 1380–1400.

The general synthesis for the quinoline derivative 3c is a modification of the procedure of Baccar et al. *Indian Journal of Chemistry,* 1995, Sat. B, 330–332.

A. Methyl-p-methoxyantranylate 3a (3.069 g, 16.96 mmol) was dissolved in triethylorthoacetate (4.7 mL, 25.4 mmol), then a solution of anhydrous HCl (4 N/Dioxane, 50 μL, 0.6 mmol) was added. The resulting mixture was heated at reflux for 19 hours. The volatiles were then evaporated under vacuum to give product 3b (4.92 g, amber oil, quantitative yield) that was used as such for the next step.

B. To a solution of the substrate 3b (assumed 16.96 mmol) in THF (34 mL) at −78° C. under nitrogen, was added LiHMDS (1 M/THF, 22 mL, 1.3 eq.). Shortly after the addition, the cold temperature bath was removed and the mixture was left to stir at ambient temperature for 1 hour, after which time, another portion of LiHMDS (16 mL) was added. The resulting mixture was stirred until complete disappearance of starting material (1 hour) by TLC (100% EtOAc, imidate $R_f$=0.7, product $R_f$=0.2). HCl (4 N/dioxane, 10 mL) was then added and the mixture was concentrated under vacuum. The resulting paste was triturated from a mixture of EtOAc (10 mL) and aqueous $NaH_2PO_4$ (1 M, 10 mL) and sonicated. An abundant precipitate was formed, collected by filtration, washed with water and dried to afford the desired product 3c as a beige solid (3.117 g, 84% yield for 2 steps, >99% purity by HPLC).

$^1$H NMR (400 MHz, DMSO-d) δ (ppm): 7.88 (d, J=8.9 Hz, 1H), 6.98 (br. s, 1H), 6.89 (br. d, J=8.6 Hz, 1H), 5.94 (br. s, 1H), 4.30 (br. s, 2H), 3.84 (s, 3H), 1.34 (t, J=7.0 Hz, 3H).

Example 4

Synthesis of 4-hydroxy-7-methoxy-2(3-methyl-1,2,4-oxadiazol-5-yl) Quinoline (4d)

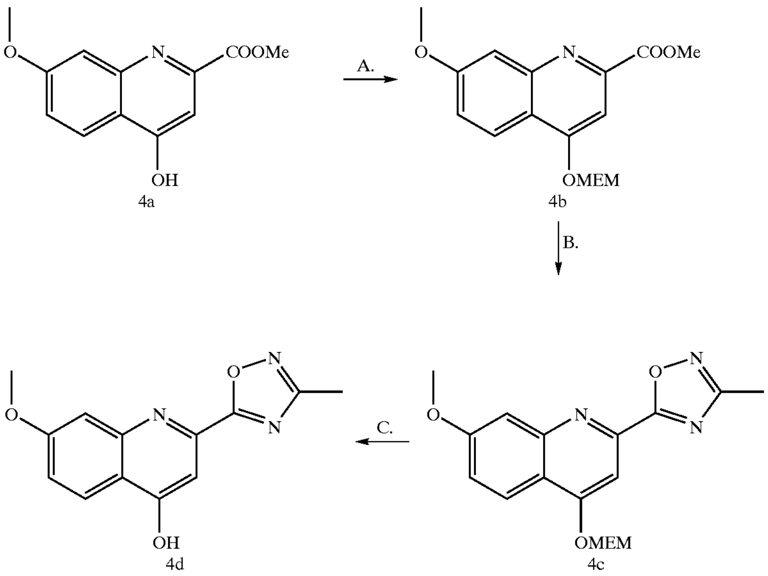

A. To a solution of 2-carbomethoxy-4-hydroxy-7-methoxyquinoline 4a (the preparation of which is described in WO 00/09543 and WO 00/09558) (1 g, 4.29 mmol) in DMF (10 mL) under nitrogen was added NaH (60% in mineral oil, 190 mg, 4.98 mmol). The resulting mixture was stirred at ambient temperature for 1 hour, MEM chloride (455 μL, 4.98 mmol) was then added dropwise and the resulting mixture was stirred at ambient temperature for an extra 19.5 hours. The reaction mixture was diluted with EtOAc (100 mL), washed with $H_2O$ (50 mL), brine (50 mL), dried with $MgSO_4$, concentrated under vacuum to afford the crude reaction isolate (1.37 g). The latter was purified by flash column chromatography to afford product 4b (1.04 g, 75% yield) as a colorless oil.

B. To a mixture of freshly activated 4Å molecular sieve (500 mg) and acetamidoxime (248 mg, 3.35 mmol) was added THF (3mL). The resulting mixture was stirred for 15 min. under nitrogen at ambient temperature, then NaH (60% in mineral oil, 124 mg, 3.24 mmol) was added by portions. The resulting suspension was stirred at ambient temperature for 1 hour, then ester 4b (500 mg, 1.56 mmol) was added in solution in THF (5 mL). The resulting mixture was heated at reflux for 1 hour then filtered over Celite, rinsing with EtOAc (3 portions of 20 mL) and concentrated under vacuum. The resulting crude mixture was purified by flash column chromatography (100% EtOAc) to afford product 4c (352 mg, 65% yield) as a white solid.

C. To the MEM ether 4c (170 mg, 0.493 mmol) in THF (4 mL) was added aqueous HCl (1 N, 1 mL). The resulting mixture was stirred at ambient temperature for 1 hour then diluted with aqueous $NaH_2PO_4$ (1 M, 50 mL). The solid formed was filtered, triturated with EtOAc, filtered and dried to afford the desired product (4d) (90 mg, 71% yield) as a white solid. MS (ES+) 258 (M+1), (ES−) 256 (M−1).

$^1H$ NMR (400 MHz, DMSO-d) δ (ppm): 8.03 (d, J=9.2 Hz, 1H), 7.38 (d, J=2.2 Hz, 1H), 7.06 (d, J=8.6 Hz, 1H), 6.85 (br. s, 1H), 3.88 (s, 3H), 2.64 (s, 3H).

Example 5

Synthesis of 4-hydroxy-7-methoxy-2(5-methyl-1,3,4-oxadiazol-2-yl) quinoline (5e)

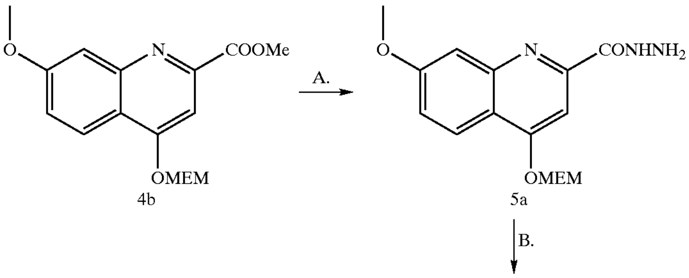

-continued

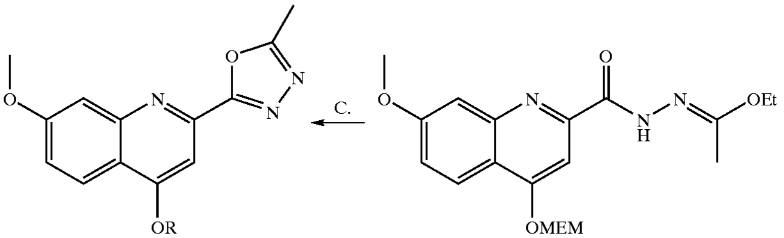

5c R = MEM
5d R = H

5b

A. To substrate 4b (465 mg, 1.45 mmol) in ethanol (5 mL) was added anhydrous hydrazine (57 μL, 1.8 mmoL). The resulting solution was heated at reflux for 4 h, then concentrated under vacuum to afford product 5a (704 mg, quantitative crude yield) as a yellow solid which was used as such in the next step.

B. Compound 5a (assumed 1.45 mmol) in triethylorthoacetate (5 mL) was heated at 100–110 ° C. under nitrogen. The resulting mixture was then diluted with EtOAc (100 mL), washed with aqueous saturated $NaHCO_3$ (50 mL), brine (50 mL), dried with $MgSO_4$, concentrated under vacuum and purified by flash column chromatography (100% EtOAc). Compound 5b (359 mg, 61% yield for two steps) was obtained as a yellow oil. MS (ES+) 392 (m+1), (ES−) 390 (m−1).

C. Compound 5b (333 mg, 0.852 mmol) was heated at 140° C. under high vacuum for 8.5 h and purified by flash column chromatography (100% EtOAc) to afford a mixture of 5b (116 mg, 35%, $R_f$ 0.5) and compound 5c (138 mg, 72% corrected yield, $R_f$ 0.3). To a THF (4 mL) solution of compound 5c (138 mg, 0.4 mmol) was added aqueous HCl (1 N, 1 mL) and the resulting mixture was stirred until completion (30 min.). THF was evaporated under vacuum and aqueous $NaH_2PO_4$ (1 M, 2 mL) was added. The resulting suspension was sonicated, filtered and the solid was dried under high vacuum to afford the desired product 5d, (75 mg, 73% yield) as a beige solid. MS (ES+) 258 (m+1), (ES−) 256 (m−1). $^1$H NMR (400 MHz, DMSO-d): δ 8.03 (d, J=9.2 Hz, 1H), 7.39 (d, J=2.2 Hz, 1H), 7.06 (br. d, J=8.6 Hz, 1H), 6.85 (br. s, 1H), 3.88 (s, 3H), 2.64 (s, 3H).

Example 6

Synthesis of 4-benzyloxy-2-(chloro)-7-methoxyquinoline (6e)

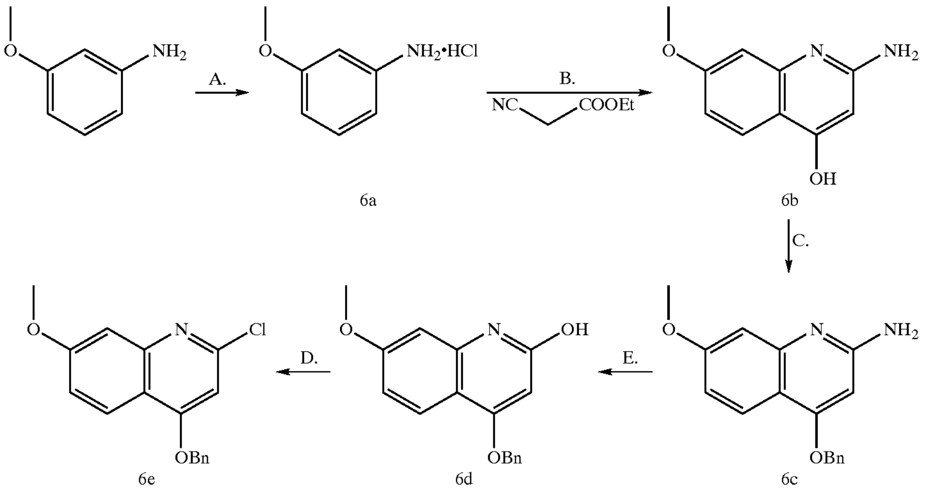

6a 6b 6c 6d 6e

A. Commercially available Meta-anisidine (25 g, 0.20 mol) in dioxane (80 mL) was cooled down to 0° C. and anhydrous HCl (4 N/dioxane, 75 mL, 0.30 mol) was added. Then $Et_2O$ (500 mL) was added and stirring was maintained for 1 hour. The beige solid was then filtered and dried under vacuum to afford salt 6a (31.88 g, 98% yield).

B. To this salt was added ethylcyanoacetate (21.3 mL, 0.20 mol) and the mixture, in a flask equipped with a distillation head and a collecting flask, was heated to 280–300° C. Ethanol produced was collected to monitor the evolution of the reaction. At 9 mL of collected ethanol (theoretical amount 11.7 mL), heating was stopped, the reaction mixture cooled down to RT, diluted with water (200 mL)-EtOAc (200 mL) then stirred and aqueous $NaH_2PO_4$ (300 mL) was added. After additional stirring for 1 h, filtration and drying, 6b was obtained (19.06 g, 84.5% purity, ~50% yield) as a yellow solid and was used as such in the next reaction.

C. Compound 6b (11.0 g, 57.8 mmol) in DMF (100 mL) at 0° C. was added to NaH (60% in mineral oil, 2.78 g, 115.6 mmol). The ice bath was then removed and the mixture was stirred at ambient temperature for 1 h, benzyl bromide (7.6 mL, 63.6 mmol) was then added and the reaction mixture was stirred for 16 hours. The solution was then diluted with EtOAc (220 mL)-hexane (220 mL) and the solid formed was filtered, triturated with aqueous saturated $NaHCO_3$ (110 mL), washed with water, hexane-EtOAc (1:1 ratio, 100 mL) and dried under high vacuum. Product 6c (5.6 g, 91% purity, 35% yield) was thus obtained as a yellow solid. To compound 6c (2.67 g, 9.52 mmol) in acetic acid (21 mL) was added iso-amyl nitrite (3.8 mL, 28.6 mmol) and the resulting mixture was stirred at ambient temperature and monitored by HPLC. More iso-amyl nitrite (1.3 mL, 9.52 mmol) was added after 2 hours and the mixture was left to stir over 90 hours (HPLC 81% product, 3% substrate). Water (100 mL) was added to the resulting suspension, which was then filtered. The brown solid collected was dried under high vacuum giving product 6d (2.35 g, 92% purity, 72% yield).

D. To compound 6d (1.5 g, 4.39 mmol) was added phosphorous oxychloride (13 mL, 141 mmol) and the resulting mixture was heated at reflux for 1 hour then diluted with EtOAc (150 mL) and quenched at 0° C. slowly with aqueous NaOH (1 N, 150 mL) to pH 9. The two layers were separated and the organic layer was dried with $MgSO_4$ and concentrated under vacuum to afford a brown solid which was purified by flash column chromatography (15% EtOAc/hexane). Product 6e (819 mg, purity >99%, 62% yield) was obtained as a yellow solid.

$^1H$ NMR (400 MHz, $CDCl_3$): δ 8.07 (d, J=9.2 Hz, 1H), 7.50–7.40 (m, 5H), 7.29 (d, J=2.5 Hz, 1H), 7.12 (dd, J=9.2, 2.5 Hz, 1H), 6.73 (s, 1H), 5.26 (s, 2H), 3.92 (s, 3H).

Example 7

Synthesis of 4-hydroxy-2-(1-imidazolyl)-7-methoxyquinoline (7b); 4-hydroxy-2-(4-methyl-1-imidazolyl)-7-methoxyquinoline (7d); 4-hydroxy-7-methoxy-2-(1-pyrazolyl)quinoline (7f); and 4-hydroxy-2-(3-methyl-1-pyrazolyl)-7-methoxyquinoline (7h)

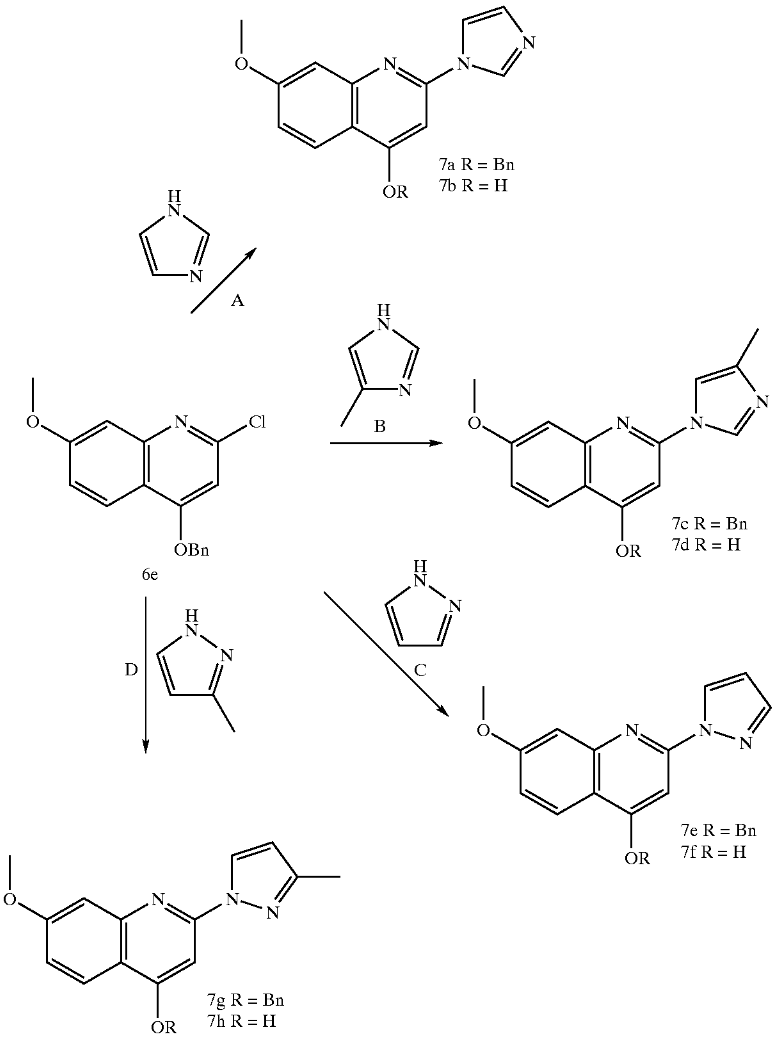

7a R = Bn
7b R = H

6e

7c R = Bn
7d R = H

7e R = Bn
7f R = H

7g R = Bn
7h R = H

A. Compound 6e (423 mg, 1.41 mmol) and imidazole (400 mg, 5.88 mmol.) were heated at 110° C. for 20 h. The mixture was then diluted with EtOAc and washed with water and brine, dried with $MgSO_4$, concentrated under reduced pressure to afford compound 7a (422 mg, 96% purity, 90% yield) as a yellow solid. Compound 7a (319 mg, 0.963 mmol) with Pd (5%/C, 64 mg) in a mixture of ethanol (5 mL) and THF (5 mL) was purged and placed under one ATM. of hydrogen. After 7.5 h of stirring at ambient temperature, the reaction mixture was filtered, rinsed with a chloroform-methanol mixture, and concentrated to afford 7b (130 mg, 97.7% purity, 56% yield) as a yellow solid. MS (ES+) 242 (m+1), (ES−) 240 (m−1).

$^1$H NMR (400 MHz, DMSO-d): δ 8.51 (s, 1H), 8.03 (d, J=8.9 Hz, 1H), 7.93 (s, 1H), 7.23 (d, J=1.9 Hz, 1H), 7.15 (s, 1H), 7.12 (dd, J=9.2, 2.2 Hz, 1H), 6.92 (br. s, 1H), 3.91 (s, 3H).

B. Compound 6e (251 mg, 0.837 mmol) and 4-methylimidazole (344 mg, 4.19 mmol.) were heated at 110° C. for 20 h. The mixture was then diluted with EtOAc, washed with water and brine, dried with $MgSO_4$, and concentrated under reduced pressure to afford a crude containing a 10:1 mixture of 4-methyl and 5-methylimidazolyl isomer respectively. The major assumed desired isomer 11c, a white solid, (166 mg, 99% purity, 57% yield) was separated from a second more polar fraction (76 mg, 23% yield) containing a mixture of 4- and 5-methyl imidazolyl isomer by flash column chromatography (100% EtOAc). Compound 7c (163 mg, 0.472 mmol) with Pd (5%/C, 33 mg) in a mixture of ethanol (2.4 mL) and THF (5 mL) was purged and placed under one ATM. of hydrogen. After 18 h of stirring at ambient temperature, the reaction mixture was filtered, rinsed with a chloroform-methanol mixture, and concentrated to afford 7d (118 mg, 99% purity, 98% yield) as a white solid.

$^1$H NMR (400 MHz, DMSO-d): δ 8.42 (br. s, 1H), 8.01 (d, J=9.2 Hz, 1H), 7.64 (br. s, 1H), 7.21 (br. s, 1H), 7.10 (d, J=8.9 Hz, 1H), 6.89 (br. s, 1H), 3.90 (s, 3H), 2.20 (s, 3H).

C. Compound 6e (184 mg, 0.614 mmol) and pyrazole (209 mg, 3.07 mmol.) were heated at 110° C. for 17 h. The mixture was then diluted with EtOAc and washed with aqueous NaOH (1 N) and brine, dried with $MgSO_4$, concentrated under reduced pressure to afford a crude product which was purified by flash column chromatography (2:1 hexane-EtOAc) to afford 7e (103 mg, 50% yield) as a pale yellow solid. Compound 7e (103 mg, 0.311 mmol) with Pd (5%/C, 20 mg) in a mixture of ethanol (2 mL) and THF (2 mL) was purged and placed under one atm. of hydrogen. After 5.5 h of stirring at ambient temperature, the reaction mixture was filtered, rinsed with a chloroform-methanol mixture, and concentrated to afford 7f (77 mg, 99% purity, 99% yield) as a yellow solid. MS (ES+) 242 (m+1), (ES−) 240 (m−1).

$^1$H NMR (400 MHz, DMSO-d): δ 8.72 (d, J=2.5 Hz, 1H), 8.31 (s, 1H), 8.00 (d, J=8.9 Hz, 1H), 7.83 (br. s, 1H), 7.43 (br. s, 1H), 7.24 (br. s, 1H), 7.10 (d, J=8.6 Hz, 1H), 6.59 (br. s, 1H), 3.90 (s, 3H).

D. Compound 6e (217 mg, 0.724 mmol) and 4-methypyrazole (594 mg, 7.24 mmol.) were heated at 110° C. for 23 h. The mixture showing a 1:1 mixture of debenzylated compound 7h and benzylated product 7g was then diluted with EtOAc (2–3 mL) and filtered to afford the pure debenzylated product 7h (111 mg, 95% purity, 54% yield) as a white solid.

$^1$H NMR (400 MHz, DMSO-d): δ 8.58 (d, J=2.6 Hz, 1H), 7.98 (d, J=9.2 Hz, 1H), 7.25 (br. s, 1H), 7.20 (s, 1H), 7.04 (br. d, J=9.2 Hz, 1H), 6.38 (s, 1H), 3.89 (s, 3H), 2.30 (s, 3H).

Example 8

Synthesis of 4-hydroxy-7-methoxy-2[4(2-isopropylaminothiazolyl)] Quinoline (8f)

Note: [A variety of 2-alkylaminothiazolyl substituents were made using the same synthetic scheme where compound 8b was replaced by other alkyl thioureas.]

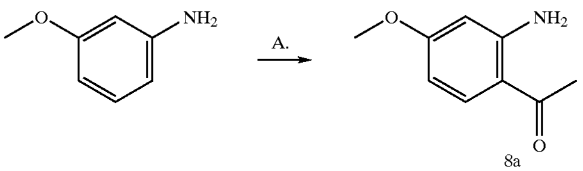

8a

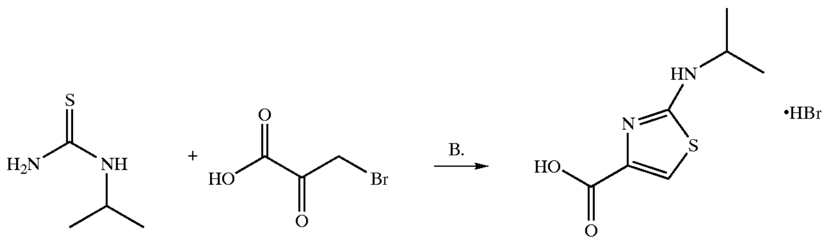

8b 8c 8d

-continued

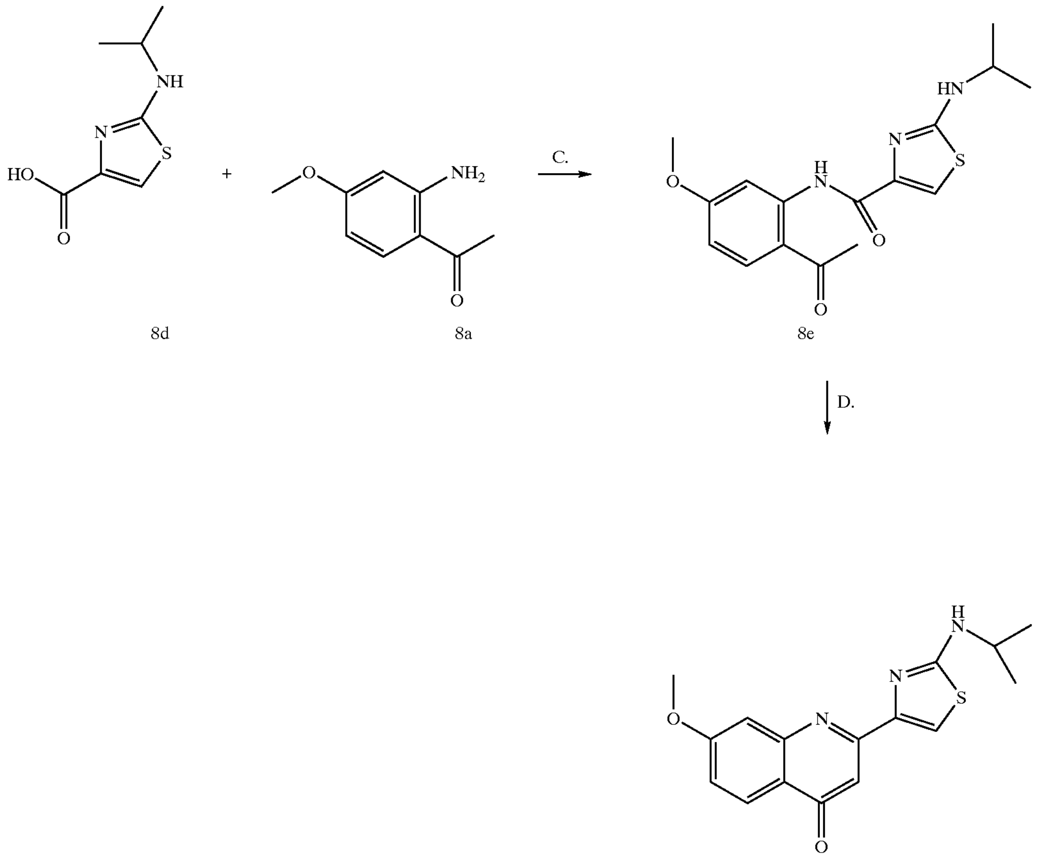

8d 8a 8e

8f

A. The protocol used for the conversion of m-anisidine to 8a was identical to that described in the literature: F. J. Brown et al. *J. Med. Chem.* 1989, 32, 807–826. However, the purification procedure was modified to avoid purification by chromatography. The EtOAc phase containing the desired product was treated with a mixture of $MgSO_4$, charcoal and 5% w/w (based on expected mass) silica gel. After filtration on celite, the product was triturated with ether. Compound 8a was obtained as a pale brown solid in >99% purity (as confirmed by HPLC).

B. A suspension of isopropyl thiourea (8b, 3.55 g, 30 mmol) and 3-bromopyruvic acid (8c, 5 g, 1 eq.) in dioxane (300 mL, 0.1 M) was heated to 80° C. Upon reaching 80° C. the solution became clear and soon after the product precipitated as a white solid. After 2 hours of heating, the solution was cooled to RT and the white precipitate was filtered to obtain compound 8d in high purity (>98% purity as confirmed by NMR) and 94% yield (7.51 g).

C. A mixture of the carboxylic acid 8d (4.85 g, 18.2 mmol) and the aniline derivative 8a (3 g, 1eq.) in pyridine (150 mL, 0.12 M) was cooled to −30° C. (upon cooling, the clear solution became partially a suspension). Phosphorus oxychloride (3.56 ml, 2.1 eq.) was then added slowly over a 5 min period. The reaction was stirred at −30° C. for 1 h, the bath was removed and the reaction mixture was allowed to warm-up to RT. After 1.5 h the reaction mixture was poured into ice, the pH was adjusted to 11 with aqueous 3N NaOH, extracted with $CH_2Cl_2$, dried over anhydrous $MgSO_4$, filtered and concentrated under vacuum. The beige solid was then purified by flash chromatography (45% EtOAc in hexane) to give compound 8e as a pale yellow solid in 73% yield (6.07 g).

D. A solution of tBuOK (2.42 g, 21.6 mmol) in anhydrous tBuOH (40 ml, 0.14 M, distilled from Mg metal) was heated to reflux. Compound 8e (1.8 g, 5.4 mmol) was added portion-wise over 5 min and the dark red solution formed was stirred at reflux for an additional 20 min (completion of the reaction was monitored by HPLC). The mixture was cooled to RT and HCl was added (4 N in dioxane, 1.5 eq.). The mixture was then concentrated under vacuum, in order to assure that all of the HCl and dioxane were removed, the product was re-dissolved twice in $CH_2Cl_2$ and dried under vacuum to finally obtain the HCl salt of compound 8f as a beige solid (1.62 g, 93% pure by HPLC). The product was then poured into a phosphate buffer (1N $NaH_2PO_4$, pH=~4.5) and sonicated. The beige solid was filtered and dried under vacuum to give compound 8f (1.38 g, 81% yield) as a beige solid (91% pure by HPLC).

$^1H$ NMR (400 MHz, DMSO) δ 8.27 (s, 1H), 8.12 (d, 1H, J=9.2 Hz), 7.97 (br.s, 1H), 7.94 (s, 1H), 7.43 (s, 1H), 7.24 (dd, 1H, J=9.2, 2.2 Hz), 3.97 (m, 1H), 3.94 (s, 3H), 1.24 (d, 2H, J=6.4 Hz).

Example 9

Synthesis of 4-hydroxy-7-methoxy-2[2(4-isopropylthiazolyl)]quinoline (9f)

Note: A variety of 2-(4-alkyl)-thiazolyl substituents were made using the same synthetic scheme where compound 9b was replaced by other α-bromoketones.

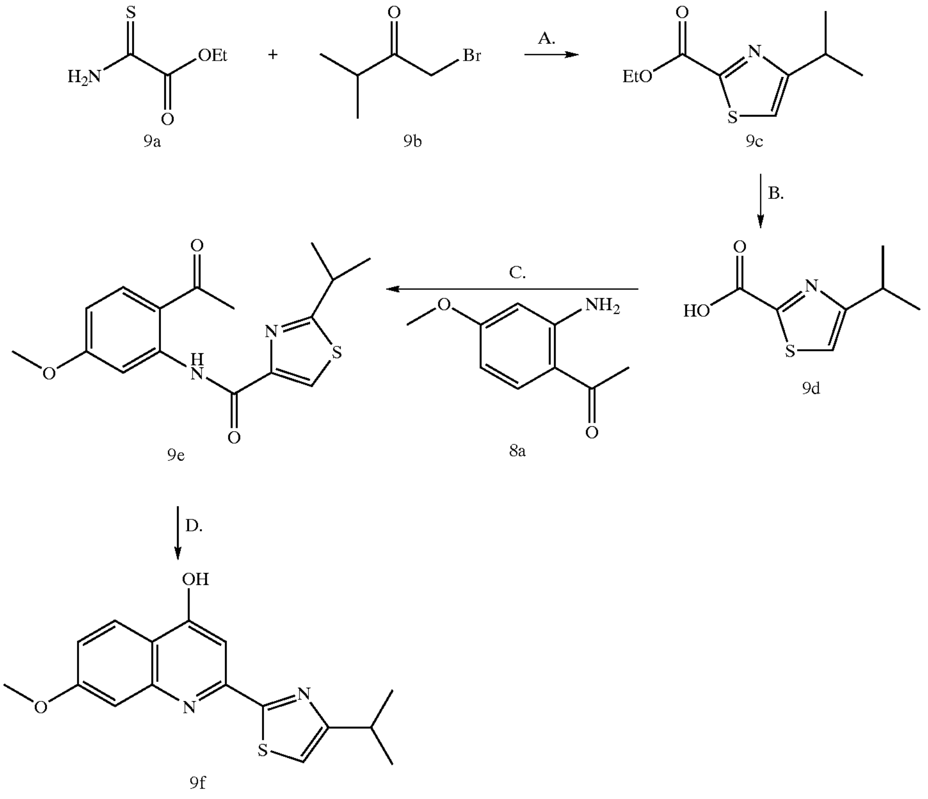

A. To a solution of 3-methyl-butan-2-one (8 g, 93 mmol) in MeOH (100 mL) at −30° C., $Br_2$ (4.79 ml, 93 mmol, 1 eq.) was added dropwise over a period of 45 min. The resulting mixture was then stirred at RT for 90 min. Pentane was added and the solution washed with 5% aqueous $NaHCO_3$, the organic layer was dried over anhydrous $Na_2SO_4$, filtered and concentrated under vacuum. The resulting crude yellow oil, compound 9b, was used without further purification. A solution of ethyl thiooxamate (9a, 1.8 g, 13.5 mmol) and bromoketone derivative 9b (13.5 mmol.) in ethanol was stirred at 70° C. for 15 h. The mixture was then concentrated under vacuum and subsequently purified by flash column chromatography, using 15% EtOAc in hexane as the eluent, to obtain compound 9c (740 mg, 28% yield).

B. A solution of compound 9c (700 mg, 3.5 mmol) in THF/MeOH/$H_2O$ (3:1:1 ratio, 13 mL) was treated with LiOH.$H_2O$ (148 mg, 3.5 mmol, 1eq.) at RT for 5 h. The pH was then adjusted to 6 with 0.1N HCl and the mixture was concentrated to dryness under vacuum to obtain the acid 9d, which was used directly in the next step without further purification.

C. A solution of 4-methoxy-2-amino-acetophenone (intermediate 8a, 570 mg, 3.45 mmol) and carboxylic acid derivative 9d (590 mg, 3.45 mmol, 1eq.) in pyridine (30 mL) was cooled to −20° C. $POCl_3$ (0.35 ml, 3.79 mmol, 1.1 eq.) was then added dropwise over a period of 5 min. The resulting solution was stirred at −10° C. for 2 h. The reaction was quenched with the addition of $H_2O$ and the mixture was concentrated under vacuum. The residue was poured in a saturated aqueous solution of $NaHCO_3$ and extracted with EtOAc. The organic layer was dried over anhydrous $MgSO_4$, filtered and concentrated under vacuum. The crude product was purified by flash column chromatography, using 25% EtOAc in hexane as the eluent, to give compound 9e as a white solid (740 mg, 67% yield).

D. tBuOK (518 mg, 2.1 eq.) was added to a suspension of compound 9e (700 mg, 2.2 mmol) in anhydrous tBuOH (11 mL). The resulting mixture was heated to 75° C. for 7.5 h, the solution was then cooled to RT and acidified with the addition of HCl (4N HCl in dioxane, 2.5 mL). The mixture was concentrated under vacuum and the residue obtained was poured into a solution of 1N $NaH_2PO_4$ and filtered. The solid material was then triturated with a small amount of EtOAc, filtered and dried under vacuum to obtain compound 9f as a pale beige solid (270 mg, 41% yield).

$^1H$ NMR (400 MHz, DMSO-$d_6$) δ 8.00 (br. s, 1h), 7.60 (br. s, 1H), 7.51 (br. s, 1H), 7.43 (br. s, 1H), 7.29 (br. s, 1H), 7.14 (br. s. 1H), 6.95 (br. a, 1H), 3.90 (s, 3H), 3.15 (m, 1H), 1.33 (d, J=5.4 Hz, 6H).

Example 10

Synthesis of 4-hydroxy-2(1-methyl-2-imidazolyl)-7-methoxyquinoline (10d)

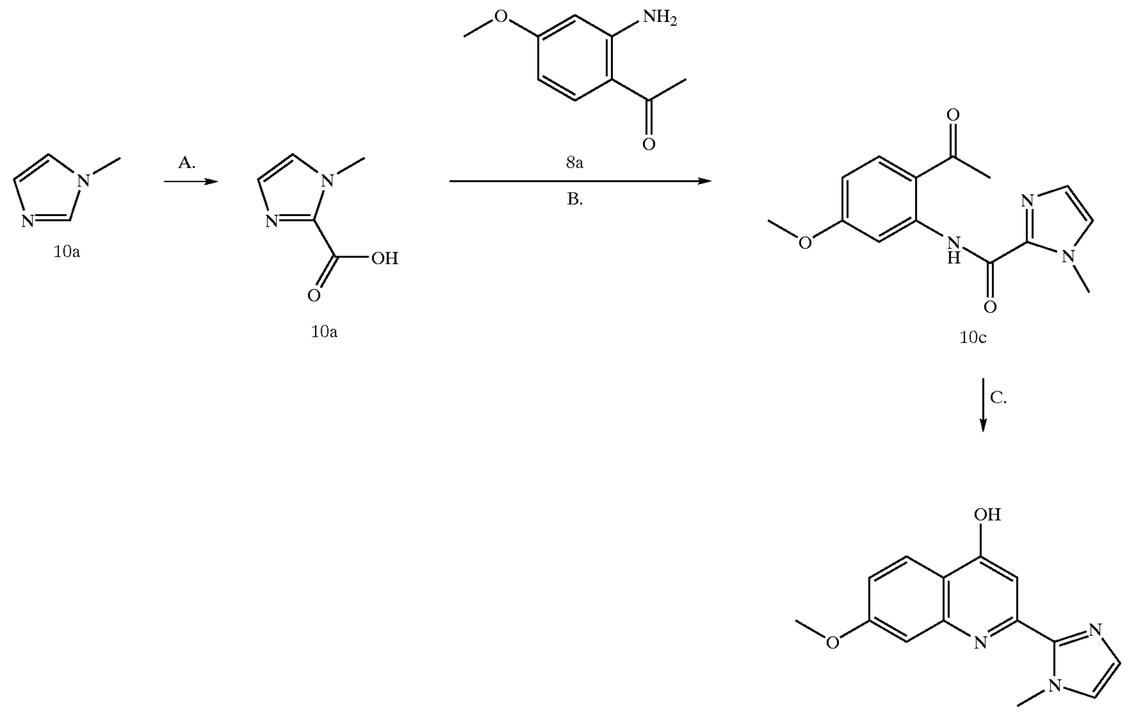

10a 10a 10c 10d

A. A solution of N-methylimidazole 10a (5 g, 61 mmol) in 100 mL THF was cooled at −78° C. n-BuLi (24.4 ml of a 2.5M/$Et_2O$ solution, 1 eq.) was added dropwise over 15 min. The resulting mixture was stirred 90 min. at −78° C. then poured portionwise over excess solid $CO_2$. The heterogeneous mixture was stirred 2 h and allowed to reach RT. 1N HCl was added to pH 5, the aqueous layer is separated and lyophilized. The residue thus obtained was extracted with EtOAc (to remove salts), dried ($Na_2SO_4$), filtered and concentrated under reduced pressure. 6.2 g (80% yield) of a white solid 10b was obtained.

B. A solution of 4-methoxy-2-amino-acetophenone 8a (394 mg, 2.39 mmol) and the carboxylic acid derivative 10b (301 mg, 1eq.) in pyridine (10 ml) was cooled to −20° C. $POCl_3$ (244 μl, 1.1 eq.) was then added dropwise over 5 min. The resulting solution was stirred at −10° C. for 2.5 h. Water was then added and the mixture was concentrated under reduced pressure. The residue was poured in a saturated solution of $NaHCO_3$ and extracted with EtOAc. The organic phase was dried ($MgSO_4$), filtered and concentrated under reduced pressure. The product was purified by chromatography using silica gel (25% EtOAc/Hex) affording 530 mg (81% yield) of a pale yellow solid 10c.

C. tBuOK (431 mg 2.1 eq.) was added to a suspension of the substrate 10c (500 mg, 1.8 mmol) in 8 ml of tBuOH. The resulting mixture was then heated to 75° C. for 7 h. The solution was allowed to reach room temperature overnight and 2.5 ml of HCl (4N/dioxane) was added. The mixture was concentrated under reduced pressure and the residue obtained was diluted with EtOAc. NaOH 1N was added until a pH of 7 was obtained. The organic phase was separated and dried ($MgSO_4$), filtered, and concentrated under reduce pressure to afford 145 mg of 10d (31% yield) as a pale beige solid. $^1H$ NMR (400 MHz, DMSO-d): δ 7.99 (d, J=8.9 Hz, 1H), 7.49 (s, 1H), 7.37 (s, 1H), 7.18 (s, 1H), 6.92 (d, J=8.9 Hz, 1H), 6.31 (s, 1H), 3.87 (s, 3H), 3.84 (s, 3H).

Example 11

Synthesis of 4-hydroxy-2(1-pyrrolyl)-7-methoxyquinoline (11b)

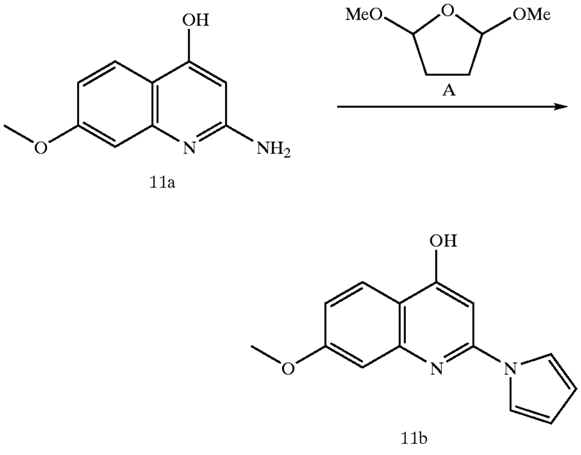

11a 11b

A. A solution of the substrate 11a (obtained from compound 6c after hydrogenolysis of the benzyl group with 5% Pd/C in ethanol-THF) (1 g, 5.25 mmol) and 2,5-dimethoxytetrahydro furan (0.68 ml, 1 eq.) in glacial acetic acid was refluxed for 4.5 h and allowed to reach RT. The mixture was then concentrated under reduced pressure. The residue was diluted with methanol and NaOH(aq.) 1N was added until pH 7 is reached. The product was purified by chromatography using silica gel (3% MeOH/$CH_2Cl_2$, the residue was pre-adsorbed on silica gel). 140 mg (13% yield) of 11b as a white solid was obtained.

$^1$H NMR (400 MHz, DMSO-d): δ 7.98 (d, J=9.2 Hz, 1H), 7.64 (s, 2H), 7.18 (d, J=2.5 Hz, 1H), 7.05 (br. d, J=7.9 Hz, 1H), 6.88 (br. s, 1H), 6.32 (s, 2H), 3.90 (s, 3H).

Example 12

Synthesis of 4-hydroxy-7-methoxy-2-(6-methyl-2-pyridyl)quinoline (12d)

B. To a solution of the crude acid chloride 12b in $CH_2Cl_2$ (5 mL) at 0° C., a solution of the aniline 8a (344 mg, 2.08 mmol), DIPEA (1.45 mL, 8.35 mmol) and DMAP (61 mg, 0.5 mmol) in $CH_2Cl_2$ (10 mL) was added. The reaction mixture was stirred a RT for 16 h. The volatile components were removed under vacuum, the residue was dissolved in EtOAc and the solution was washed with 5% $NaHCO_3$ (2×), $H_2O$ and brine. The organic layer was then dried over $MgSO_4$ and concentrated under vacuum. The mixture was purified by flash column chromatography, using EtOAc/hexane (1:2) as the eluent, to obtain the amide 12c (490 mg, 82%).

C. To a suspension of amide 12c (490 mg, 1.71 mmol) in t-BuOH (10 mL), tBuOK (410 mg, 3.43 mmol) was added and the mixture was stirred at 75° C. for 6 h and then at RT for 16 h. The mixture was then poured in phosphate buffer (175 mL, pH=7) and stirred for 30 min. The solid was triturated twice with ethyl acetate.

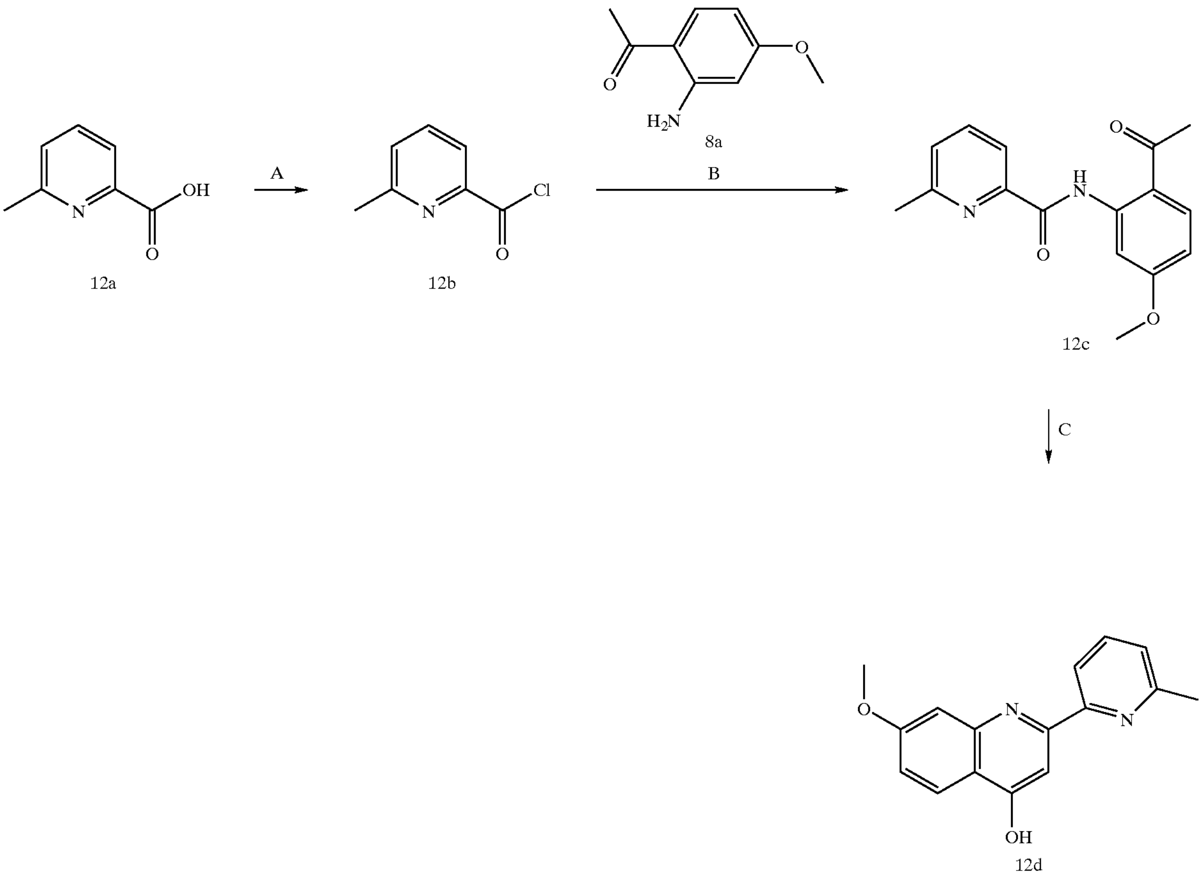

A. 6-Methylpicolinic acid 12a (411 mg, 3.0 mmol) and $SOC_2$ (0.520 mL, 7.2 mmol, 2.4 eq.) were refluxed in benzene (5 mL) for 2 h. The solvent and excess $SOCl_2$ were removed from the reaction mixture under vacuum and the residue was triturated with pentane. The solid material formed was filtered off and the filtrate concentrated to give the acid chloride 12b (500 mg, 2.6 mmol).

The organic phase was washed with brine, dried over $MgSO_4$ and concentrated under vacuum. The solid obtained was triturated with EtOAc to give the quinoline derivative 12d (263 mg, 58%). $^1$H NMR: ($CDCl_3$, 400 MHz): δ 2.68 (s, 3 H), 3,94 (s, 3H), 6.85–6.88 (2d, J=8.68 & 9.5 Hz, 2 H), 6.94 (dd, J=8.9 & 2.2 Hz, 1 H), 7.27 (dd, J=6.7 & 1.9 Hz, 1 H), 7.73–7.79 (m, 2 H), 8.28 (d, J=8.9 Hz, 1 H), 10.3 (br s, 1 H).

Example 13

Synthesis of 4-hydroxy-7-methoxy-2-(5-methoxy-2-pyridyl)quinoline (13d)

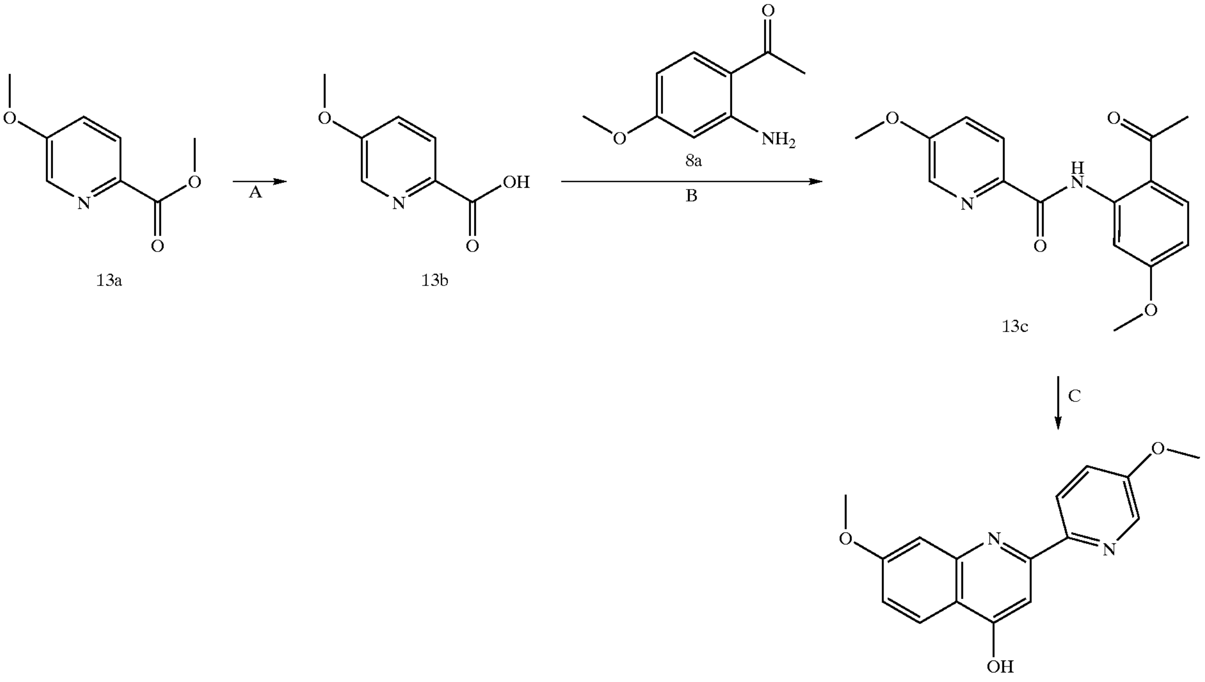

13a 13b 13c 13d

A. To a solution of compound 13a (623 mg, 3.73 mmol) in MeOH, NaOH (2M, 4.70 mL) was added and the reaction mixture was stirred at RT for 2 h. The solution was then acidified with HCl (6N, 2.2 mL) and concentrated to obtain compound 13b, which was used in the following step without purification.

B. To a solution of the crude compound 13b (~3.73 mmol) in pyridine (25 mL), the aniline 8a (500 mg, 3.03 mmol) was added and the solution was cooled to −25° C. before $POCl_3$ (0.35 mL, 3.73 mmol) was added. The reaction mixture was stirred at −10° C. for 1 h and then at 0° C. for 2 h. The mixture was then poured onto $H_2O$ and extracted with EtOAc (2–3x). The combined organic layers were washed with 5% $NaHCO_3$ and brine, dried over $MgSO_4$ and concentrated under vacuum. The crude material was purified by flash column chromatography, using EtOAc/hexane (1:2) as the eluent, to give the amide 13c (617 mg, 55%).

C. To a suspension of the amide 13c (617 mg, 2.05 mmol) in anhydrous t-BuOH (10 mL), tBuOK (490 mg, 4.11 mmol) was added and the mixture was stirred at 75° C. for 6 h and then at RT for 16 h. The reaction mixture was poured in phosphate buffer (175 mL, pH=7) and stirred for 30 min. The solid material formed was filtered and triturated with EtOAc to give the quinoline derivative 13d (250 mg, 43%). $^1H$ NMR: (DMSO, 400 MHz): δ 3.86 (s, 3 H), 3.94 (s, 3 H), 6.72 (bs, 1 H), 6.91 (dd, J=8.9 & 1.9 Hz, 1 H), 7.54 (d, J=1.9 Hz, 1 H), 7.60 (dd, J=8.9 & 2.9 Hz, 1 H), 7.97 (d, J=8.9 Hz, 1 H), 8.21 (d, J=8.6 Hz, 1 H), 8.48 (d, J=1.9 Hz, 1 H).

Example 14

Synthesis of 4-hydroxy-7-methoxy-2-(oxazol-5-yl) Quinoline (14c)

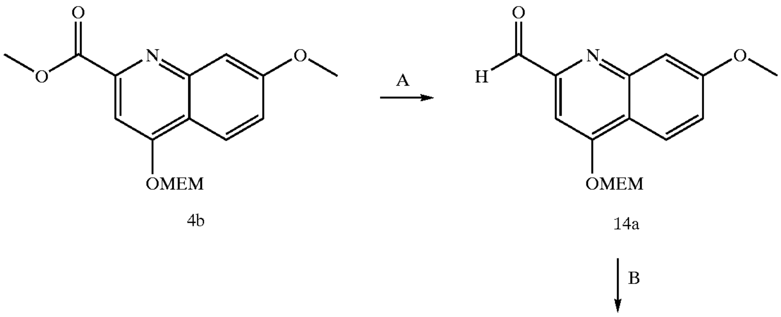

4b 14a

-continued

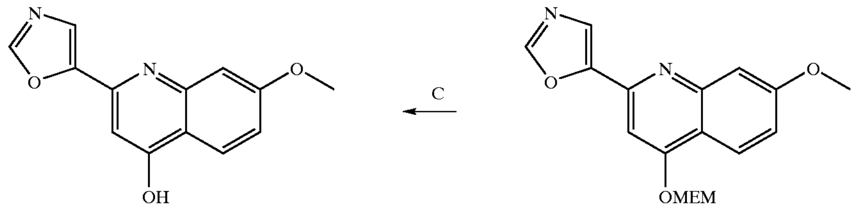

14c 14b

A. The protected quinoline derivative 4b from Example 4 (3.8 g, 11.8 mmol) was dissolved in $CH_2Cl_2$ (60 mL) and cooled to −78° C. before diisobutylaluminum hydride (7.9 mL, 1 equiv., 1.5M in toluene) was added very slowly over 15 min. After stirring for 80 min, an additional amount of DIBAL was added (5.5 mL, 0.7 equiv., 1.5 M in toluene). After stirring at −78° C. a further 2 h, the reaction was carefully quenched with methanol (4 mL) at −78° C. and then poured into aqueous solution of Rochelle salt (1N K—Na tartrate). The thick paste was stirred with $CH_2Cl_2$ (300 mL) for 2 h until clear. The phases were separated and the organic phase dried ($MgSO_4$), filtered and concentrated to give a white solid. Purification by flash chromatography ($SiO_2$, 230–400 mesh) with 50% EtOAc/hexane gave aldehyde 14a as a white solid (2.5 g, 73%).

B. To a stirred suspension of $K_2CO_3$ (48 mg, 0.34 mmol) in MeOH (7 mL) was added toluenesulphonylmethylisocyanide (66 mg, 0.34 mmol). The reaction was heated to 45° C. and aldehyde 14a (0.10 g, 0.34 mmol) was added. The reaction mixture was heated to 80° C. for 16 h and then concentrated to dryness under vacuum. Purification was performed by flash chromatography ($SiO_2$, 230–400 mesh) to afford the desired oxazole 14b (0.089 g, 80%). MS: 331.0 $(M+H)^+$.

C. The MEM protected hydroxyquinoline 14b was dissolved in THF (3 mL) and treated with aqueous HCl (1N, 1 mL). The reaction was stirred for 30 min at RT before being concentrated to dryness under vacuum. The residue was treated with phosphate buffer (3 mL, 1 N solution, pH 4.5) and stirred before the product was filtered out, washed with distilled water and dried overnight under high vacuum (60° C., 16 h). The desired hydroxy quinoline 14c was obtained as a tan colored solid (0.065 g, 100%). MS: 242.9 $(M+H)^+$.

$^1H$ NMR (DMSO-$d_6$): δ 8.65 (s, 1H), 8.02 (bs, 1H), 7.97 (d, J=8.9 Hz, 1H), 7.19 (s, 1H), 6.93 (d, J=7.9 Hz, 1H), 6.42 (bs, 1H), 3.87 (s, 3H). ES (+) MS: m/z 242.9 $(M+H)^+$.

Peptide Linker Moieties (P3)

Example 15

Synthesis of (2S)-N-Boc-amino-non-8-enoic Acid (15g)

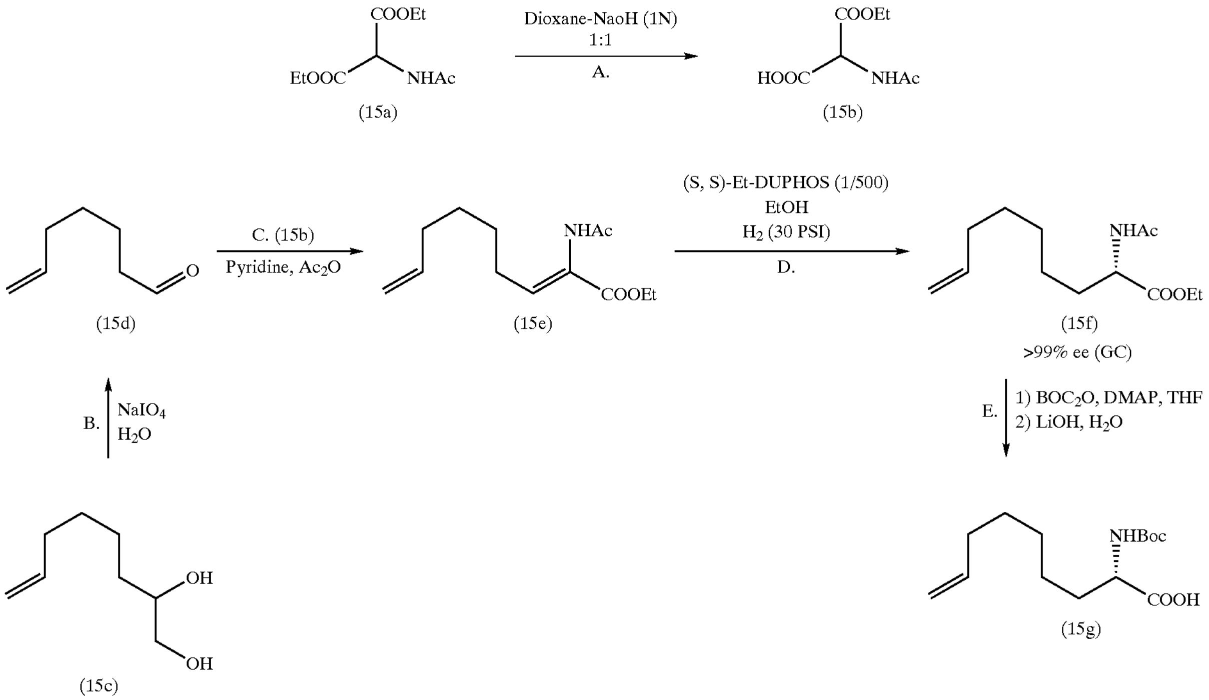

(15a) (15b) (15d) (15e) (15f) (15c) (15g)

A. To a solution of commercially available diethyl 2-acetamidomalonate 15a (100 g, 0.46 mole) in dioxane (500 mL) was added aqueous sodium hydroxide (1 M, 1 eq., 460 mL) dropwise over 30 to 45 min. The resulting mixture was left to stir for 16.5 h, then dioxane was evaporated in vacuo, the aqueous solution was extracted with three portions of 300 mL of ethyl acetate and acidified to pH 1 with concentrated HCl. This solution was left to crystallize in an ice-water bath. After the appearance of a few crystals, the mixture was sonicated and an abundant precipitate appeared. Filtration and drying under vacuum afforded compound 15b, (62.52 g, 72% yield) as a white solid.

B. To a magnetically stirred emulsion of commercially available 7-octene-1,2-diol 15c (25 g, 0.173 mole) and $H_2O$ (100 mL), in a 1 L round bottom flask, an aqueous solution of sodium periodate (40.7 g, 0.190 moles, 1.1 eq., in 475 mL $H_2O$) was added over a period of 20 min (slightly exothermic). The resulting mixture was stirred at room temperature for an additional 1 h (completion of reaction confirmed by TLC). The mixture was then decanted in a separatory funnel and the aqueous layer was separated from the organic layer. The aqueous solution was saturated with NaCl, decanted and separated from the organic fraction once more. The two organic fractions were combined, dried with sodium sulfate and filtered over a cotton plug (in a Pasteur pipette) to give compound 15d (15.135 g, colorless oil, 78% yield). The aqueous solution was extracted with $CH_2Cl_2$, dried with anhydrous $MgSO_4$, and concentrated under vacuum (without heating, heptanal b.p.153° C.) to obtain an additional amount of compound 15d (1.957 g, colorless oil, 10% yield). Total yield 88%.

C. To solid ethyl 2-acetamidomalonate 15b (7.57 g, 40 mmol.) was added 6-heptenal 15d (4.48 g, 40 mmol) in solution in pyridine (32 mL, 10 eq) over 1 min. The resulting solution was cooled in a 10° C. bath and acetic anhydride (12 mL, 3.2 eq.) was added over 4 min. The resulting orange solution was stirred for 3 h at RT and another portion of ethyl 2-acetamidomalonate 15b (2.27 g) was added. The resulting mixture was stirred at room temperature for an extra 11 h. Ice (60 mL) was then added and the solution was stirred for 1.5 h, then the mixture was diluted with 250 mL of water and extracted with two portions of ether. The etheral solution was washed with 1N HCl, sat. $NaHCO_3$, dried $Na_2SO_4$, concentrated and purified by flash chromatography (EtOAc 40%/hexane) to give compound 15e (4.8 g, 50% yield) as a pale yellow oil.

D. To a degassed (argon bubbling for 30 min.) solution of Z-ethyl 2-acetamido-2,8-nonadienoate 15e (8.38 g, 35 mmol) in dry ethanol (70 mL) was added (S,S)-Et-DUPHOS Rh(COD)OTf (51 mg, S/C=496). The mixture was put under 30 psi of hydrogen (after 4 vacuum-$H_2$ cycles) and stirred on a Parr shaker for 2 h. The resulting mixture was evaporated to dryness to obtain the crude compound 15f, which was used in the subsequent step without purification.

E. To a solution of crude (S)-ethyl 2-acetamido-8-nonenoate 15f (7.3 g, 30.3 mmol) in THF (100 mL), $Boc_2O$ (13.2 g, 2 eq.) and DMAP (740 mg, 0.2 eq) were added, and the reaction mixture was heated at reflux for 2.5 h. Subsequently, most of the THF solvent was evaporated, the crude mixture was diluted with $CH_2Cl_2$ and washed with 1 N HCl in order to remove the DMAP. The organic layer was further extracted with saturated aqueous $NaHCO_3$, dried with anhydrous $Na_2SO_4$ and concentrated under vacuum. The crude product was then diluted with THF (50 mL) and water (30 mL), $LiOH.H_2O$ (2.54 g, 2 eq.) was added and the resulting mixture was stirred at RT for 25 h (completion of the hydrolysis was confirmed by TLC). The reaction mixture was concentrated under vacuum to remove most of the THF solvent and diluted with $CH_2Cl_2$. The resulting solution was washed with 1 N HCl, dried with anhydrous $Na_2SO_4$ and concentrated under vacuum. In order to remove minor impurities and excess $Boc_2O$, the crude product was purified by flash chromatography (using a solvent gradient from 100% hexane–100% EtOAc as the eluent). The titled compound 15g was obtained in high purity as a pale yellow oil (5.82 g, 71% yield).

$^1H$ NMR (DMSO, 400 MHz): δ 7.01 (d, J=8 Hz, 1H), 5.79 (tdd, Jt=6.7 Hz, Jd=17.0, 10.2 Hz, 1H), 5.00 (md, Jd=17.0 Hz, 1H), 4.93 (md, Jd=10.2 Hz, 1H), 3.83 (m, 1H), 2.00 (q, J=6.9 Hz, 2H), 1.65–1.5 (m, 2H), 1.38 (s, 9H), 1.35–1.21 (m, 6H).

Example 15A

Alternative Synthesis of (2S)-N-Boc-amino non-8-enoic Acid (a5g)

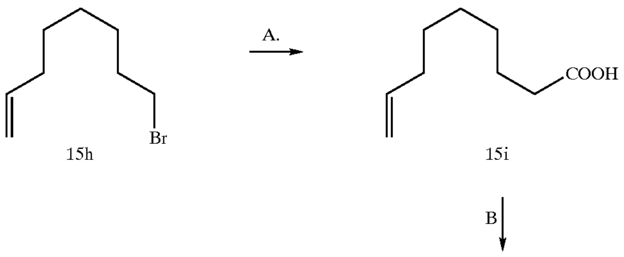

15h

15i

-continued

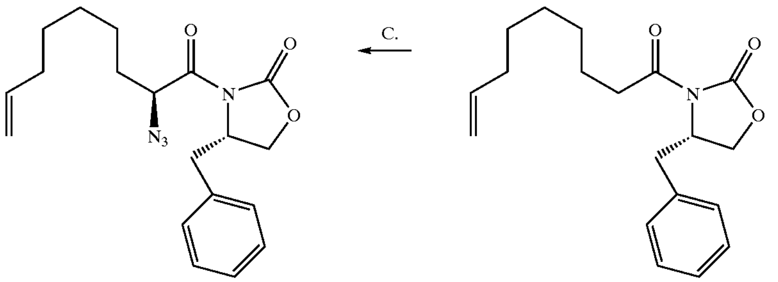

15k 15j

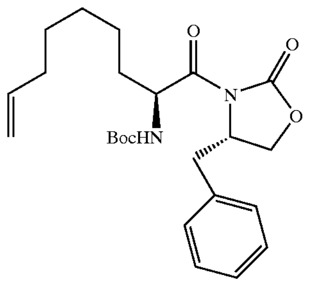

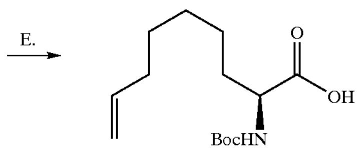

15g

15l

A. To a stirred suspension of finely cut Mg ribbons (0.55 g, 22.5 mmol) in dry THF (30 mL) containing dibromoethane (0.1 mL), 8-bromo-1-octene (15h, 2.52 mL, 15 mmol) was added dropwise over a period of 15 min, [the reaction is slightly exothermic]. After 30 min, the mixture was heated to 38° for 1 h and then cooled to −78° before it was added via a cannula onto an excess amount of solid $C_2$. The mixture was diluted with diethyl ether (100 mL) and the solution was washed with brine (2x50 mL), dried over $MgSO_4$ and evaporated. A crude oil was obtained which was purified by chromatography on silica gel using 15% EtOAc in hexanes as the eluent to give compound 15i in 62% yield(1.44 g).

$^1$H NMR ($CDCl_3$, 400 MHz) δ 1.31–1.42 (m, 6H), 1.60–1.69 (m, 2H), 2.02–2.09 (m, 2H), 2.35 (t, J=8.3 Hz, 2H), 4.99 (dm, J=10.0 Hz, 1H), 5.04 (dm, J=17.0 Hz, 1H), 5.75–5.86 (m, 1H).

B. To a vigorously stirring solution of the carboxylic acid 15i (1.36 g, 8.7 mmol) in anhydrous THF (70 mL) at −78°, freshly distilled $Et_3N$ (1.6 mL; 11.3 mmol) and pivaloyl chloride (1.18 mL, 9.58 mmol) were added via a syringe under anhydrous conditions. The mixture was stirred at −78° for 15 min and then at 0° for 45 min. The mixture was cooled again to −78° and then transferred via a cannula into an anhydrous solution of 4(S)-4-(phenylmethyl)-2-oxazolidinone lithium salt in THF at −78°; the lithium salt of the oxazolidinone reagent had been previously prepared by the slow addition of n-BuLi (2.00 M in hexanes, 7.85 mL, 15.7 mmol) into a THF (20 mL) solution of the oxazolidinone (2.78 g, 15.7 mmol) in THF at −78°. The reaction mixture was stirred at −78° for 15 min then at RT for 1.5 h. Finally, it was quenched with an aqueous solution of sodium bisulfate (100 mL of 1 M) and the THF evaporated to ¾ of its initial volume. The residue was extracted with EtOAc (2x150 mL) and the mixed organic layers were washed with 5% $NaHCO_3$ (3x50 mL), brined (2x50 mL), dried over $MgSO_4$ and evaporated. The resulting crude oil was chromatographed on silica gel, using 15% EtOAc in Hexanes to obtain compound 15j in 68% yield (1.88 g).

$^1$H NMR ($CDCl_3$, 400 MHz) δ 1.35–1.47 (m, 6H), 1.67–1.74 (m, 2H), 2.02–2.09 (m, 2H), 2.65 (dd, J=13.4 & 9.9 Hz, 1H), 2.84–3.02 (m, 2H), 3.31 (dd, J=13.4 & 3.2 Hz, 1H), 4.13–4.22 (m, 2H), 4.62–4.71 (m, 1H), 4.93 (d, J=10.2 Hz, 1H), 5.00 (dd, J=17.2 & 1.6 Hz, 1H), 5.75–5.84 (m, 1H), 7.18–7.38 (m, 5H).

C. To a stirred solution of KHMDS (0.8 M THF, 22 mL, 17.5 mmol) in dry THF (50 mL) at −78° was cannulated a solution of the acid derivative 15j (3.25 g, 10.30 mmol) in dry THF (40 mL) at −78°. The mixture was stirred at −78° for 45 min. To this mixture, a solution of trisylazide (3.67 g, 11.85 mmol) in dry THF (40 mL) at −78° was added. The mixture was stirred at −78° for 3 min then quenched with acetic acid (5 mL). Subsequently, it was stirred at RT for 1 h and 45 min and finally at 40° for 15 min. Most of the THF was evaporated. The residue was taken into EtOAc (100 mL) and the organic solution washed with $H_2O$ (50 mL), 5% $NaHCO_3$ (3x50 mL) and brine (50 mL), ($MgSO_4$) and evaporated. The oil obtained was chromatographed on silica gel using Hexane/$CH_2Cl_2$ (1/1) as the eluent to give compound 15k (2.47 g, yield 67%).

$^1$H NMR ($CDCl_3$, 400 MHz) δ 1.32–1.45 (m, 6H), 1.45-1.6 (m, 1H), 1.75–1.88 (2, 2H, rotamers), 2.01–2.11 (m, 2H), 2.82–2.87 (m, 1H), 3.33 (dd, J=13.4 & 3.2 Hz, 1H), 4.10–4.28 (m, 2H), 4.62–4.72 (m, 1H), 4.90–5.05 (m, 3H), 5.73–5.88 (m, 1H), 7.17–7.38 (m, 5H).

D. To a stirred solution of anhydrous $SnCl_2$ (2.61 g, 13.8 mmol) in anhydrous MeOH (80 mL), a solution of the azide 15k (2.45 g, 6.9 mmol) was cannulated at 0° in anhydrous MeOH (20 mL). The mixture was stirred at RT for 4 h. The MeOH was evaporated and the foamy material obtained was taken into dioxane/$H_2O$ (100 $\mu$L/20 $\mu$L) and treated with $Boc_2O$ (3.0 g, 13.8 mmol) and $NaHCO_3$ (2.89 g, 34.5 mmol) (pH adjusted to 8 with more $NaHCO_3$ if needed) and the mixture was stirred at RT for 16 h. Part of the dioxane was evaporated (~50%) and the residue was extracted twice with EtOAc. The organic solution was washed with brine (2×50 mL), dried and evaporated. The residue obtained was chromatographed on silica gel using 20–25% EtOAc in hexane as eluent to give the compound 151 (1.75 g, yield 60%). $^1H$ NMR ($CDCl_3$, 400 MHz) δ 1.27–1.53 (m, 6H), 1.46 (s, 9H), 1.80 (m, 1H), 2.00–2.08 (m, 1H), 2.80 (t, J=12.1 Hz, 1H), 3.34 (d, 14.3 Hz, 1H), 4.17–4.23 (m, 2H), 4.60–4.66 (m, 1H), 4.93 (d, J=10.2 Hz, 1H), 5.05 (dd, J=17.2 & 1.9 Hz, 1H), 5.13 (bs, 1H), 5.38–5.43 (m, 1H), 5.74–5.84 (m, 1H), 7.22–7.36 (m, 5H).

E. To a stirred solution at 90° of the N-Boc derivative 151 (1.74 g, 4.04 mmol) in THF/$H_2O$ (75 mL/15 mL), $H_2O_2$ (30% v/w, 2.05 mL, 16.2 mmol) and $LiOH.H_2O$ (0.34 g, 8.1 mmol) were added and the solution was stirred at 0° for 1 h. The reaction was quenched with $Na_2SO_3$ (2.24 g in $H_2O$, 15 mL, 17.8 mmol). The pH was adjusted to 4–5 with 10% aqueous citric acid and the mixture diluted with EtOAc. The aqueous fraction was extracted once more with EtOAc and the organic solution was washed twice with brine, dried and evaporated. The residue was chromatographed on silica gel using 20% hexane in EtOAc as the eluent to give the free carboxylic acid 15g (0.76 g, yield 70%). This compound was identical in all respects to the one obtained in example 15.

Example 16

Synthesis of (2S)-N-Boc-amino-5-oxo-non-8-enoic Acid Methyl Ester (16d)

This synthesis is based on methodology by T. Tsuda et al., *J. Am. Chem. Soc.,* 1980, 102, 6381–6384.

A. To a well stirred solution of the monoallyl ester of malonic acid (1.50 g, 10.4 mmol) in dry THF under $N_2$ (20 mL) at −78° n-$Bu_2Mg$ (0.9M/hexane, 5.8 mL, 5.2 mmol) was added dropwise over a period of 5 min. The heavy suspension was then stirred at RT for 1 h and evaporated to dryness (vacuum release under $N_2$). The solid Mg salt 16b, was dried under vacuum for 1 h.

Glutamic acid derivative 16a was first mixed with 1,1'-carbonylidiimidazole (1.65 g, 10.21 mmol) in anhydrous THF and the mixture was stirred at RT for 1 h in order to activate the free acid moiety. Subsequently, the activated glutamic acid derivative was cannulated into a solution of the Mg salt 16b and the reaction mixture obtained was stirred at RT for 16 h. It was then diluted with EtOAc and the organic solution was washed with 0.5 N ice-cold HCl, brined, dried and evaporated. The residue obtained was chromatographed on silica gel using 35–40% EtOAc in hexane as eluent to give compound 16c (1.85 g, yield 53%).

$^1H$ NMR ($CDCl_3$, 400 MHz) δ 1.44 (s, 9H), 1.85–1.95 (m, 1H), 2.12–2.22 (m, 1H), 2.58–2.74 (m, 2H), 3.48 (s, 2H), 3.74 (s, 3H), 4.24–4.34 (m, 1H), 4.52 (dm, J=5.7 Hz, 2H), 5.09 (m, 1H), 5.25 (dm, J=10.2 Hz, 1H), 5.34 (dm, J=17.2 Hz, 1H), 5.91 (m, 1H).

B. To a stirred solution of tetrakis (triphenylphosphine) Pd (0) (0.116 g, 5 mol %, 0.1 mmole) in dry DMF (7 mL) was added (via a siring and under a $N_2$ atmosphere) the diester 16c (0.687 g, 2 mmol) in dry DMF (3 mL). The mixture was stirred at RT for 3.5 h. The DMF was evaporated under reduced pressure and the residue diluted with EtOAc (20 mL). The EtOAc solution was washed with 0.5 N ice-cold HCl (5 mL), brine (10 mL), dried and evaporated. The residue was chromatographed on silica gel using 15–20% EtOAc in hexane as eluent to give compound 16d (0.253 g, yield 42%).

$^1H$ NMR ($CDCl_3$, 400 MHz) δ 1.44 (s, 9H), 1.84–1.94 (m, 1H), 2.08–2.22 (m, 1H), 2.33 (dd, J=14.0 & 7.3 Hz, 2H), 2.45–2.55 (m, 4H), 3.74 (s, 3H), 4.28 (bm, 1H), 4.98 (dm, J=10.2 Hz, 1H), 5.03 (dm, J=17.2 Hz, 1H), 5.00–5.10 (m, 1H), 5.74–5.85 (m, 1H).

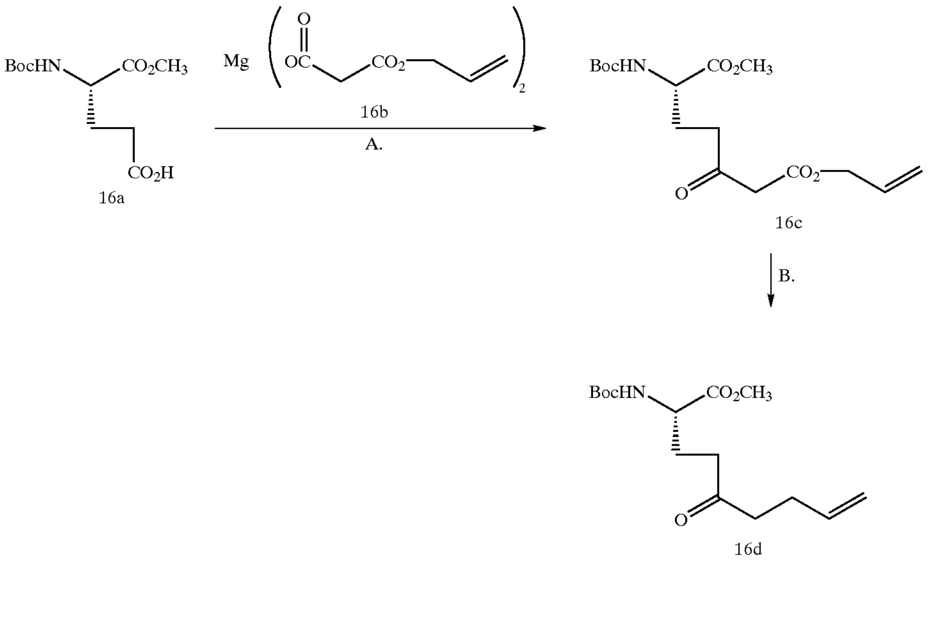

16a
16c
16d

Example 17

Synthesis of (2S,5R)-N-Boc-2-amino-5-methyl-non-8-enoic Acid (17f)

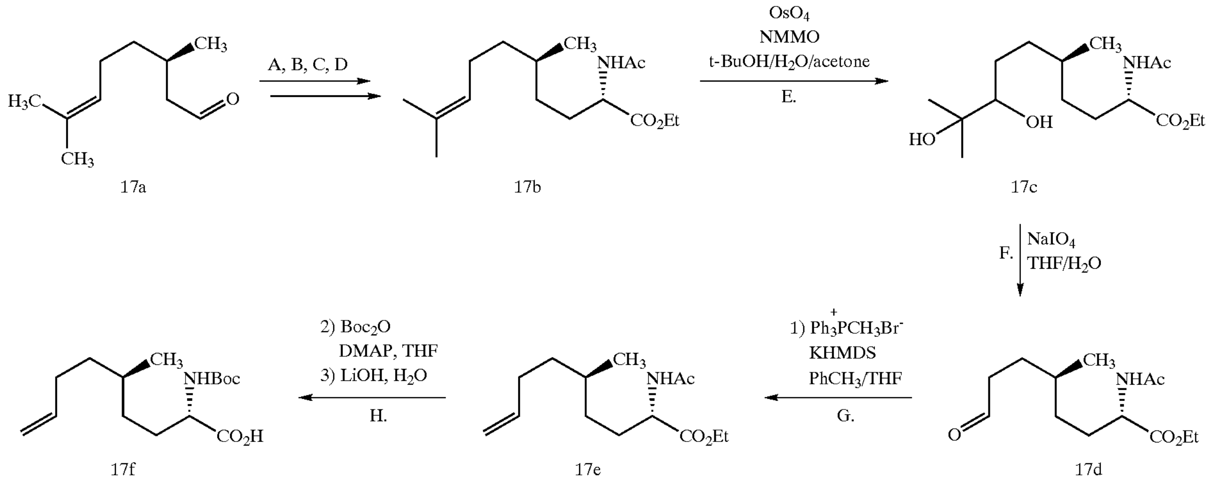

A,B,C,D. Commercially available (R)-(+)-citronellal 17a was first converted to the amino acid derivative 17b following the same synthetic steps as those previously described in Example 15 for the conversion of aldehyde 15d to amino acid intermediate 15f.

E. Compound 17b (0.675 g, 5.6 mmol) was dissolved in a mixture of tBuOH/acetone/$H_2O$ (1:1:1, 18 mL) and placed in an ice bath (0° C.). NMMO (0.789 g, 6.74 mmol, 1.2 eq.) and $OsO_4$ (2.5% w/w in tBuOH, 0.7 mL, 0.067 mmol., 0.012 eq) were added consecutively and the reaction mixture was stirred at RT for 4 h. Most of the acetone was removed by evaporation under vacuum and then the mixture was extracted with EtOAc. The organic layer was further washed with $H_2O$ and brine, dried over anhydrous $MgSO_4$ and evaporated to dryness. The diol 17c was obtained in high purity after flash column chromatography using 1% EtOH in EtOAc as the eluent in 77% yield (0.575 g).

F. To a solution of diol 17c (0.575 g, 1.73 mmol) in THF/$H_2O$ (1:1, 20 mL) at 0° C., $NaIO_4$ (0.48 g, 2.25 mmol, 1.3 eq.) was added and the reaction mixture was stirred at RT for 3.5 h. Most of the THF solvent was subsequently removed by evaporation under vacuum and the remaining mixture was extracted with EtOAc (2×100 mL). The combined organic layers were further washed with 5% aqueous citric acid solution (2×20 mL), 5% aqueous $NaHCO_3$ (20 mL) and brine (2×50 mL), then the EtOAc solution was dried over anhydrous $MgSO_4$ and evaporated to dryness under vacuum. The aldehyde intermediate 17d (0.47 g of crude product) was used in the next step without further purification.

G. To a solution of $Ph_3PCH_3Br$ (925 mg, 2.6 mmol) in anhydrous toluene (15 mL), KHMDS (0.5M in toluene, 5.2 mL, 2.6 mmol) was added and the yellow suspension formed was stirred at RT for 30 min under $N_2$. After that period, the suspension was first cooled to 0° C., a solution of the aldehyde 17d (0.47 g 1.73 mmol, dissolved in 15 mL of anhydrous THF) was added via a syringe and the mixture was allowed to warm-up to RT. After stirring at RT for 1 h, most of the THF was removed by evaporation under vacuum, EtOAc (100 mL) was added to the mixture and the organic layer was washed with $H_2O$ (30 mL), 5% aqueous $NaHCO_3$ (30 mL) and brine (30 mL). The EtOAc solution was then dried over anhydrous $MgSO_4$ and evaporated to dryness under vacuum. Pure compound 17e was isolated after purification by flash column chromatography on silica gel, using hexane:EtOAc (3:2) as the eluent, in 63% yield (0.29 g) for the two last steps. The hydrolysis of the ethyl ester and simultaneous exchange of the N-acetyl protecting group for a Boc in intermediate 17e to obtain compound 17f was carried out using the same procedure as that reported for the conversion of compound 15f to 15g (17f, 310 mg, quantitative). $^1H$ NMR ($CDCl_3$, 400 MHz): δ 0.88 (d, J=6.4 Hz, 3H), 1.18–1.28 (m, 2H), 1.35–1.48 (m, 3H), 1.45 (s, 9H), 1.64–1.74 (m, 1H), 1.81–1.89 (m, 1H), 1.94–2.12 (m, 2H), 4.28 (bd, J=~3.2 Hz, 1H), 4.93 (dm, J=11.1 Hz, 1H), 5.00 (dm, J=16.8 Hz, 1H), 5.74–5.84 (m, 1H).

Example 18

Synthesis of N-Boc-O-allyl-(L)-threonine (18d)

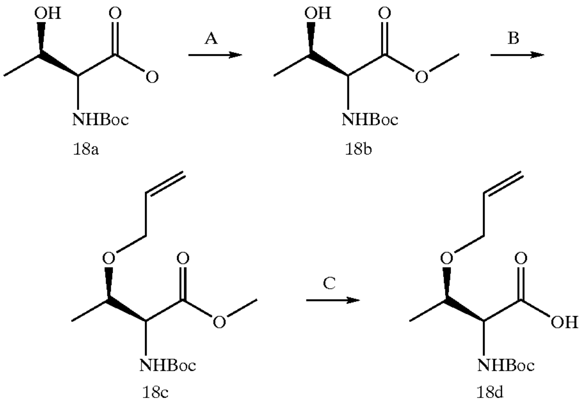

A. Boc-(L)-threonine 18a (500 mg, 2.28 mmol) was partially dissolved in $CH_2Cl_2$/MeOH (8 mL/0.5 mL, respectively) at 0° C. A solution of diazomethane in diethyl ether was slowly added until the yellow color persisted, indicating the presence of excess diazomethane. Upon evaporation of the solvents, crude methyl ester 18b was obtained as a cloudy white oil (0.534 g).

B. Intermediate 18b (311 mg, 1.33 mmol) was then dissolved in anhydrous diethyl ether (8 mL), $Ag_2O$ was added (341 mg, 1.47 mmol) and freshly activated 4 Å molecular sieves (1 g). Finally, allyl iodide (134 μL, 1.47 mmol) was added to the reaction flask and the mixture was stirred at reflux. Two more portions of allyl iodide (45 μL, 0.50 mmol, each time) were added after a period of 20 h and 30 h, and stirring was continued for a total of 36 hours. Then the mixture was filtered through celite and purified by flash column chromatography on silica gel, using EtOAc/hexane (1:4) as the eluent, to give 73 mg (27% yield) of compound 18c as a clear oil.

$^1H$ NMR ($CDCl_3$, 400 MHz): δ 1.21 (d, J=6.0 Hz, 3H), 1.45 (s, 9H), 3.75 (s, 3H), 3.82–3.87 (m, 1H), 3.99–4.07 (m, 2H), 4.29 (dd, J=9.5 & 2.5 Hz, 1H), 5.14 (dm, J=10.5 Hz, 1H), 5.21 (dm, J=17.2 Hz, 1H), 5.75–5.84 (m, 1H).

C. The ester compound 18c (99 mg, 0.362 mmol) was dissolved in a mixture of THF/MeOH/$H_2O$ (2:1:1, 4 mL) and LiOH.$H_2O$ (61 mg, 1.45 mmol) was added. The solution was stirred at RT for 2 h, and was then acidified with 1N HCl to pH ~3 before the solvents were removed under vacuum. The resulting oil, compound 18d was used as such for the synthesis of macrocyclic inhibitors.

Example 19

Synthesis of (2S, 3S)-N-Boc-2-amino-3 (Mercaptoallyl)butanoic Acid (19e)

B. To solution of intermediate 19b (775 mg, 2 mmol) in anhydrous DMF (2.5 mL), potassium thioacetate (365 mg, 3.2 mmol, 1.6 eq.) was added and the reaction mixture was stirred at RT for 24 h. Most of the DMF was then evaporated under vacuum and the remaining mixture was partitioned between EtOAc and $H_2O$. The aqueous layer was re-extracted with EtOAc, the combined organic layers were washed with brine, dried over anhydrous $MgSO_4$ and evaporated to dryness. Purification of the crude material by flash column chromatography using hexane/EtOAc (4:1 ratio) as the eluent, led to the isolation of compound 19c in 80% yield (465 mg).

C. To a solution of thioester 19c (465 mg) in $H_2O$/EtOH (3:5 ratio, 8 mL), an aqueous solution of 0.2M NaOH (2.4 mL) was added and the mixture was stirred at RT for 1.5 h. Allyl iodide (0.292 mL, 3.2 mmol, 2 eq.) was then added and stirring was continued at RT for an additional 30 min. The reaction mixture was concentrated to half of its original volume and then extracted with EtOAc. The aqueous layer was acidified to pH=~3 with cold aqueous 0.5N HCl and re-extracted with EtOAc. The combined organic layers were washed with brine, dried over anhydrous $MgSO_4$ and evaporated to dryness under vacuum. The crude reaction mixture contained at least four products; all of the products were isolated after flash column chromatography on silica gel, using hexane/EtOAc (gradient from 9:1 to 3:1 ratio). The structure of the least polar compound (TLC $R_f$=0.68 in hex/EtOAc 4:1) corresponded to the desired product 19d (83 mg, 18% yield).

$^1H$ NMR ($CDCl_3$, 400 MHz): δ 1.24 (d, J=7.0 Hz, 3H), 1.46 (s, 9H), 3.13–3.19 (m, 2H), 3.24–3.29 (m, 1H), 3.77 (s, 3H), 4.50 (dd, J=8.6 & 3.8 Hz, 1H), 5.12 (d, J=12.4 Hz, 1H), 5.15 (dd, J=18.4 & 1.3 Hz, 1H), 5.22 (bd, J=7.6 Hz, 1H), 5.75–5.85 (m, 1H).

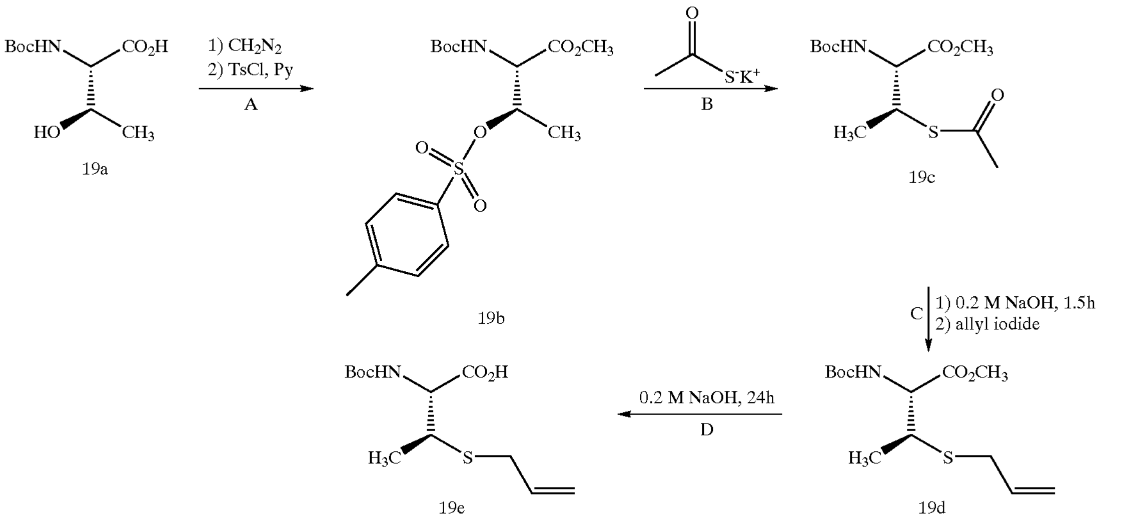

A. Compound 19a (9.1 mmol) was dissolved in pyridine (5 mL) and the solution was cooled to 0° C. in an ice bath, tosyl chloride (2.3 g, 11.8 mmol, 1.3 eq.) was added in small portions and the reaction mixture was stirred at RT for 24 h. After that period, the reaction mixture was partitioned between diethyl ether (300 mL) and $H_2O$ (100 mL). The ether layer was further washed with 0.2N HCl (6×100 mL) and brine (100 mL), dried over anhydrous $MgSO_4$, filtered and concentrated to dryness under vacuum. Purification of the crude material by flash column chromatography, using hexane/EtOAc (gradient from 8:2 to 7:3 ratio) as the eluent, led to the isolation of tosyl derivative 19b in 85% yield (3.05 g).

D. A solution of the methyl ester 19d (83 mg, 0.287 mmol) in MeOH/$H_2O$ (3:1, 4 mL) was mixed with aqueous NaOH (0.2 N, 1.3 mL, 0.26 mmol) for 24 h at RT and for 1 h at 40° C. The reaction mixture was acidified with cold aqueous HCl (0.5 N HCl, at 0° C., pH=4–5), the MeOH was removed under vacuum and the remaining aqueous mixture was extracted with EtOAc. The organic solution was dried over $MgSO_4$ and evaporated to dryness in order to obtain compound 19e. Compound 19e was used for the final synthesis of inhibitors without any further purification.

Example 20

Synthesis of (S)-N-Boc-2-amino-3-methyl-3(1-mercapto-4-butenyl)butanoic Acid (20c)

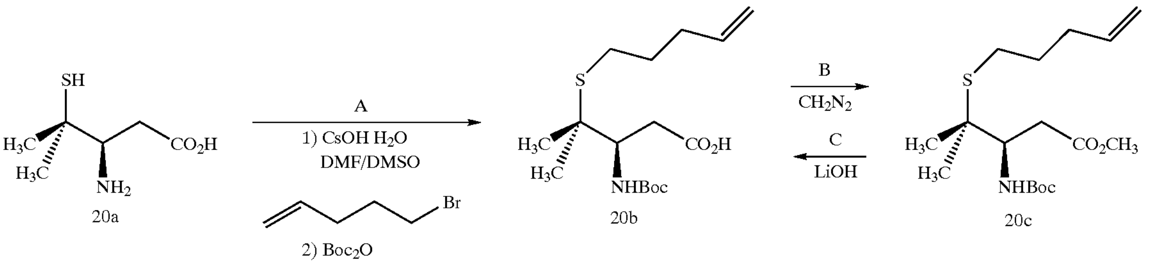

20a 20b 20c

A. L-Penicillamine 20a (448 mg, 3 mmol) was dissolved in DMF/DMSO (5:1 ratio, 6 mL), 4-bromopentene (0.46 mL, 4.5 mmol, 1.5 eq.) and $CsOH.H_2O$ (1.0 g, 6 mL, 2 eq.) were added and the reaction mixture was stirred at RT. After 24 h, $Boc_2O$ (820 mg, 3.75 mmol, 1.25 eq.) was added to the mixture and stirring was continued for an additional 12 h. The DMF was subsequently removed under vacuum, the remaining mixture was diluted with cold aqueous 0.5N HCl adjusting the pH=~4–5 and then extracted with EtOAc (2×50 mL). The organic layer was washed with brine (2×), dried over anhydrous $MgSO_4$ and evaporated to dryness to give the crude carboxylic acid 20b.

B. Purification of 20b turned out to be difficult, thus the crude product was first treated with diazomethane to form the corresponding methyl ester 20c, and then purified by flash column chromatography, using hexane/EtOAc (9:1) as the eluent, to obtain 190 mg (20% yield) of the pure methyl ester 20c.

$^1$H NMR (400 MHz, $CDCl_3$): δ 1.35 (s, 3H), 1.37 (s, 3H), 1.44 (s, 9H), 1.59–1.67 (m, 2H), 2.11–2.17 (m, 2H), 2.51–2.60 (m, 2H), 3.74 (s, 3H), 4.29 (d, J=8.6 Hz, 1H), 4.98 (dm, J=10.5 Hz, 1H), 5.03 (dm, J=19 Hz, 1H), 5.35 (bd, J=7 Hz, 1H), 5.72–5.83 (m, 1H).

C. The ester was subsequently dissolved in THF/MeOH/$H_2O$ (2:2:1, 5 mL), $LiOH.H_2O$ (50 mg, 2.0 mmol, 2 eq.) was added and the reaction mixture stirred at 40° C. for 4 h to hydrolyze the ester 20c back to the acid 20b. The reaction mixture was acidified with 0.5N HCl to pH=4–5, the THF and MeOH were evaporated to dryness and the remaining aqueous solution was extracted with EtOAc. The EtOAc layer was dried over anhydrous $MgSO_4$, and evaporated to dryness to give compound 20b, which was used in the subsequent synthesis of macrocyclic inhibitors without further purification.

Acyclic Dipeptide and Tripeptide Intermediates

The general procedure for coupling reactions done in solution and specific examples thereof are described in WO 00/09543 and WO 00/09558. These procedures have been used for the synthesis of the intermediate dipeptides 26c, 30a and tripeptides 23a, 24a, 31a, 32a, and 33a.

Example 21

Synthesis of Acyclic Tripeptide 21e

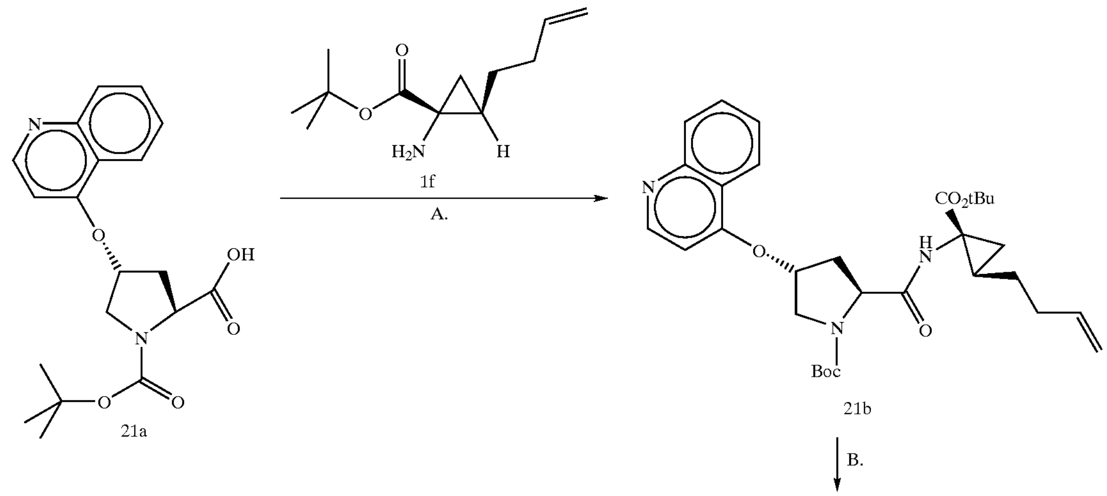

1f 21a 21b

-continued

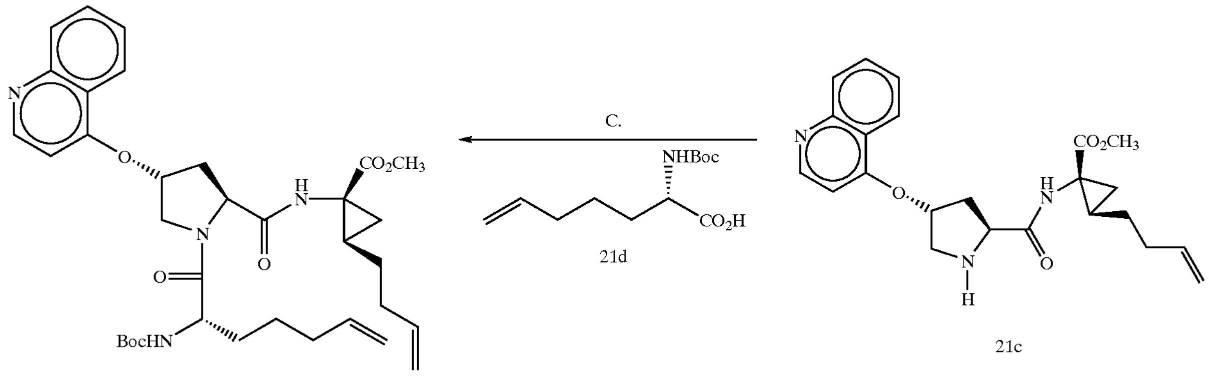

21e 21c

A. To a solution of the proline derivative 21a (prepared from commercially available Boc-4(R)-hydroxyproline and 4-chloro-quinoline as described in WO 00/05543 and WO 00/09558) (1.32 g, 3.68 mmol) and the crude homoallyl ACCA if (~3.35 mmol) in $CH_2Cl_2$ (10 mL), NMM (1.21 mL, 10.05 mmol) and HATU (1.53, 4.02 mmol) were added in succession and the suspension was stirred at RT for 18 h. After that period, the solvent was evaporated and the crude reaction mixture was redissolved in EtOAc (30 mL). The solution was washed with 5% aqueous $NaHCO_3$ (2–10 mL), brine (10 mL), dried over $MgSO_4$ and evaporated. The crude product was purified my chromatography on silica gel using 8% diethyl ether in EtOAc as the eluent to obtain the desired diastereomer of compound 21b in 20% yield (the absolute stereochemistry was not determined).

$^1H$ NMR ($CDCl_3$, 400 MHz): δ 0.93 & 1.01 (t, J=8.3 Hz, 1H, rotamers in ratio of 3:7), 1.14–1.35 (m, 2H), 1.44 (s, 9H), 1.45 (s, 9H), 1.50–1.82 (m, 4H), 2.08–2.24 (m, 2H), 2.32 (bs, 0.7H), 2.63 (bs, 0.75H), 2.93 (bs, 0.75H), 3.16 (m, 0.25H), 3.77 (bs, 1.5H), 3.88 (bs, 0.5H), 4.4–4.55 (m, 1H), 4.98 (d, J=10.2 Hz, 1H), 5.03 (dd, J=17.2 & 1.6 Hz, 1H), 5.24 (bs, 1H), 5.75–5.88 (m, 1H), 6.57 & 6.78 (2bs, 1H, 2 rotamers), 7.42–7.58 (m, 3H), 7.63–7.73 (m, 2H), 8.04 (d, J=8.3 Hz, 1H), 8.11 (d, J=8.3 Hz, 1H), 8.74 (d, J=5.1 Hz, 1H).

B. To a solution of the dipeptide 21b (137 mg, 0.248 mmol) in dry $CH_2Cl_2$, a solution of HCl in dioxane (4M, 4 mL) was added and the mixture was stirred at RT for 1.5 h. The solvent was then evaporated and the residue dried under high vacuum to give the free amino acid. The mixture was dissolved in diethyl ether MeOH (3 μL/2 μL) and treated with a slight excess of diazomethane dissolved in diethyl ether. After 30 min, the excess diazomethane was destroyed with the addition of HCl (4M in dioxane) and the mixture was evaporated to dryness to obtain the HCl salt of compound 21c which was used in the next step without any purification.

C. To a stirred suspension of the crude dipeptide 21c (0.23 g, 0.48 mmole) in $CH_2Cl_2$ (25 mL) was added in succession the (2S)-N-Boc-amino-hept-6-enoic acid 21d (0.151 g, 0.62 mmol), NMM (210 μL, 1.91 mmol) and HATU (0.236 g, 0.62 mmole) and the mixture was stirred at RT for 16 h (the pH was adjusted to ~8 with NNM after 1 h if needed). The $CH_2Cl_2$ was evaporated, the residue taken into EtOAc (50 mL) and the organic solution washed with 5% $NaHCO_3$ (2×20 mL), brine (2×20 mL), dried and evaporated. The crude compound obtained was chromatographed on silica gel (50 mL, 2% EtOH/EtOAc) to give compound 21e (0.139 g, yield 46%).

$^1H$ NMR ($CDCl_3$, 400 MHz, rotamers in 6:1 ratio) chemical shifts of major rotamer δ1.21–1.27 (m, 1H), 1.36 (s, 9H), 1.45–1.81 (4m, 7H), 2.20–2.22 (m, 4H), 2.28–2.37 (m, 1H), 2.90–2.99 (m, 1H), 3.66 (s, 3H), 3.94–3.98 (m, 1H), 4.29 (bd, J=9.9 Hz, 1H), 4.46–4.50 (m, 1H), 4.81 (dd, J=8.3 & 5.4 Hz, 1H), 4.92–5.06 (m, 4H), 5.16 (d, J=8.3 Hz 1H), 5.37 (m, 1H), 5.70–5.84 (m, 2H), 6.82 (d, J=5.1 Hz, 1H), 7.47–7.55 (m, 2H), 7.71 (dt, J=7.0 & 1.3 Hz, 1H), 8.03 (d, J=8.6 Hz, 1H), 8.17 (d, J=8.0 Hz, 1H), 8.78 (d, J=5.1 Hz, 1H).

Macrocyclic Peptides

Example 22

General Procedure for Macrocyclization via Olefin Metathesis

In all cases, the tri-peptide diene was dissolved in $CH_2Cl_2$ at a concentration of 0.01M and the solution was deoxygenated by the bubbling of argon (~1 h for a volume of 500 mL). A solution of catalyst (5–30 mol %, dissolved in a small amount of degassed $CH_2Cl_2$) is added and the reaction mixture is refluxed until all starting material was converted to product(s) as indicated by TLC and HPLC. The crude reaction mixtures were subsequently concentrated to near dryness and filtered through a short pad of silica gel, eluting first with $CH_2Cl_2$ to remove most of the catalyst and then with EtOAc in order to elute all of the macrocyclic product (s) (most of the time as a single diastereomer). The crude product(s) from each reaction is analyzed by chiral HPLC on a CHIRALCEL OJ-R column (purchased from Chiral Technologies Inc, 0.46 ϕ×15 cm), using an isocratic solvent mixture of 70% $H_2O$+0.06% TFA–30% $CH_3CN$+0.06% TFA at 205 nm. The major macrocyclic product(s) was fully characterized by: $^1H$, COSY, TOCSY, and ROESY NMR data in order to confirm its structure and stereochemistry.

Example 23

Synthesis of Macrocyclic Intermediate (23b)

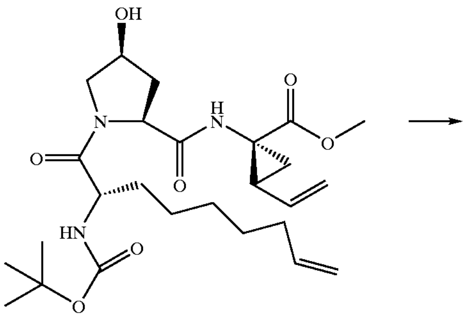

23a

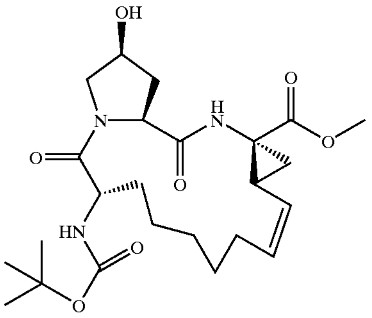

23b

A solution of diene 23a (4.0 g, 7.88 mmol) in dry $CH_2Cl_2$ (800 mL, Aldrich-anhydrous) was deoxygenated by bubbling Ar for 2 h. Hoveyda's catalyst (262 mg, 0.434 mmol, 5.5 mol %) was then added as a solid and the reaction was refluxed under an Ar balloon. After 28 h, the red-orange solution was evaporated to an amorphous solid and then purified by flash column chromatography over silica gel. The initial solvent system was 10% EtOAc in $CH_2Cl_2$. Once the catalyst was eluted from the column, the solvent was changed to pure EtOAc. Elution of the catalyst from the column was evident from its color. The macrocyclic product 23b was isolated as a colorless foam which was re-dissolved in $CH_2Cl_2$/hexane (~1:2). Evaporation of the solvent afforded a white powder (3.362 g, 89% yield).

$^1H$ NMR ($CDCl_3$, 400 MHz): δ 1.20–1.50 (m, 6H), 1.43 (s, 9H), 1.53 (dd, J=9.5 & 5.4, 1H), 1.61–1.70 (m, 1H), 1.76–1.90 (m, 2H), 2.05–2.26 (m, 4H), 2.45 (d, J=14.3, 1H), 3.67 (s, 3H), 3.71 (d, J=11.1, 1H), 3.90 (dd, J=11.1 & 4.3, 1H), 4.43–4.53 (m, 2H), 4.76 (d, J=8.6, 1H), 4.86 (bd, J=9.8, 1H), 5.20–5.23 (m, 2H), 5.57 (dt, J=7.0 & 9.8, 1H), 7.32 (bs, 1H).

Example 24

Synthesis of Macrocyclic Intermediate (24b)

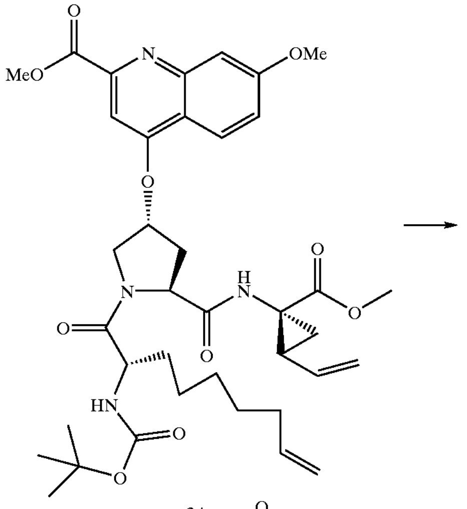

24a

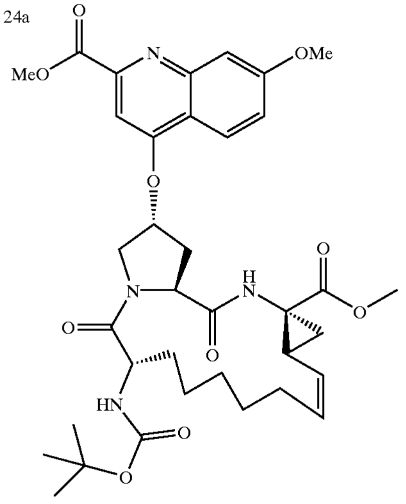

24b

A solution of diene 24a (2.76 g, 3.82 mmol) in anhydrous $CH_2Cl_2$ (600 mL, anhydrous) was deoxygenated by bubbling Ar for 1.5 h. A solution of Hoveyda's catalyst (117 mg, 0.19 mmol, 0.05 eq) in anhydrous and degassed $CH_2Cl_2$ (8 mL) was added via cannula and the reaction was stirred at reflux under an Ar balloon. After 20 h, the reaction mixture was approximately 50% completed, at which point a second portion of catalyst was added (117 mg) and the stirring was continued for an additional 16 h. The solution was then concentrated to ~100 mL, applied to the top of a pad of silica gel (6×10 cm) and the catalyst was first recovered by eluting with $CH_2Cl_2$. Compound 24b was washed off the pad of silica with 3% MeOH in EtOAc and re-purified by flash column chromatography using EtOAc/hexane (2:1) to obtain 70% yield of a slightly olive-tinted white solid (1.85 g, 94% pure by HPLC).

$^1H$ NMR (400 MHz, DMSO-$d_6$) δ 8.69 (s, 1H), 8.13 (d, J=9.2 Hz, 1H), 7.50–7.44 (m, 2H), 7.17 (dd, J=9.2, 2.2 Hz, 1H), 7.04 (d, J=6.4 Hz, 1H), 5.60–5.56 (m, 1H), 5.52 (dd, J=9.2 Hz, 1H), 5.25 (dd, J=9.2 Hz, 1H), 4.59 (d, J=11 Hz, 1H), 4.44 (dd, J=9.2 Hz, 1H), 4.05–3.98 (m, 1H), 3.94 (s, 3H), 3.92 (s, 3H), 3.89–3.82 (m, 1H), 3.55 (s, 3H), 2.64–2.53 (m, 1H), 2.46 (d, J=7.3 Hz, 1H), 2.40–2.31 (m, 1H), 2.21 (dd, J=8.9 Hz, 1H), 1.78–1.65 (m, 2H), 1.55 (dd, J=4.8 Hz, 1H), 1.485 (dd, J=4.8 Hz, 1H), 1.41–1.30 (m, 7H), 1.16 (s, 9H). MS; es$^+$: 795.4 $(M+H)^+$.

Example 25

Synthesis of Compound 202 & 203 (Table 2)

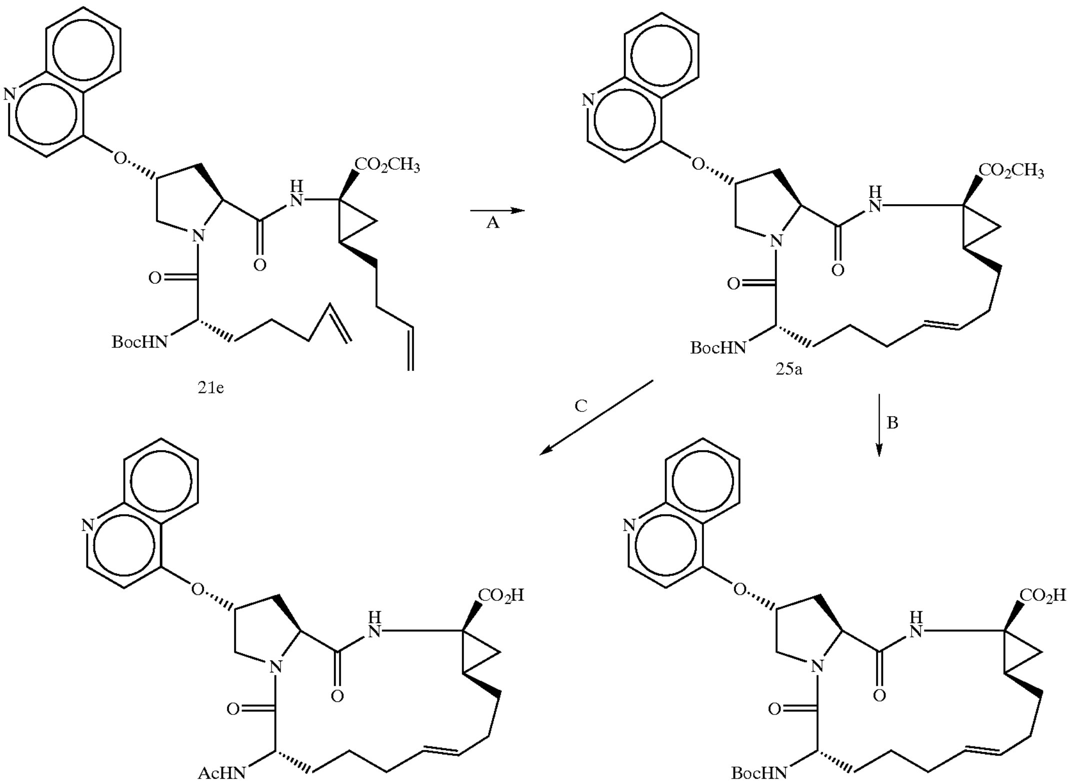

21e

25a compound 203 compound 202

A. The diene compound 21e (0.130 g, 0.205 mmol) was cyclized using catalytic amounts of bis-(tricyclohexylphosphine) benzylidene ruthenium IV dichloride (Grubb's catalyst, supra) (52 mg, 0.064 mmol) in $CH_2Cl_2$ (60 mL) under reflux for 2 h to give after chromatography on silica gel (50 mL, 3% EtOH/EtOAc) compound 25a (60.1 mg, yield 48%).

$^1$H NMR ($CDCl_3$, 400 MHz) δ 1.22–1.30 (m, 2H), 1.35 (s, 9H), 1.44–2.35 (m, 13H), 3.07–3.14 & 3.16–3.24 (2m, 1H, rotamers in 1:3 ratio), 3.69 (s, 3H), 3.96–4.04 (m, 1H0, 4.42–4.50 (m, 1H), 4.95–5.04 (m, 1H), 5.05–5.15 (m, 1H), 5.20–5.30 (m, 1H), 5.55–5.65 (m, 1H), 6.75–6.79 (2d, J=5.4 Hz, 1H, rotamers in 1:3 ratio), 7.36 (s, 1H), 7.46–7.50 (m, 1H), 8.03 (d, J=8.3 Hz, 1H), 8.13 & 8.17 (2d, J=8.0 Hz, 1H, rotamers in 1:3 ratio), 8.77 (d, J=5.1 Hz, 1H).

B. The ester moiety of the macrocyclic compound 25a (0.0156 g, 0.026 mmol) was hydrolyzed with $LiOH.H_2O$ (8.7 mg, 0.206 mmol) in THF/MeOH/$H_2O$ (4 mL/2 mL/2 mL). The crude product was purified by C18 reversed phase HPLC on a Whatman (Partisil 10,0DS3) 50/2.4 cm column using a solvent gradient from 5% aqueous $CH_3CN$ to 100% $CH_3CN$ to obtain pure compound 202 as an amorphous white solid (11.8 mg).

$^1$H NMR (DMSO, 400 MHz): δ 1.12 (s, 9H), 1.20–1.24 (m, 2H), 1.32–1.40 (m, 3H), 1.58–1.62 (m, 2H), 1.68–1.78 (m, 3H), 1.95–2.02 (m, 1H), 2.08–2.18 (m, 2H), 2.4–2.59 (m, 2H), 3.97–4.00 (bd, J=9.8 Hz, 2H), 4.47 (t, J=8.6 Hz, 1H), 4.58 (d, J=11.8 Hz, 1H), 5.22–5.29 (m, 1H), 5.46–5.54 (m, 1H), 5.66 (s, 1H), 7.12 (d, J=6.0 Hz, 1H), 7.49 (d, J=3.5 Hz, 1H), 7.68 (dd, J=7.3 Hz, 1H), 7.98 (dd, J=7.0 Hz, 1H), 8.08 (d, J=8.3 Hz, 1H), 8.21 (s, 1H), 8.35 (d, J=8.3 Hz, 1H), 9.08 (d, J=5 Hz, 1H).

C. The macrocyclic compound 25a (20 mg, 0.033 mmol) in dry $CH_2Cl_2$ (1 mL) was stirred in presence of 4M HCl/dioxane (5 mL) for 1 h. The mixture was evaporated and dried carefully. The residue was re-dissolved in $CH_2Cl_2$/DMF (3 mL /1 mL) and treated with NMM (14.5 μL, 0.132 mmol) and acetic anhydride (7.0 μL, 0.073 mmol) and stirred at RT for 14 h. The mixture was evaporated and dried under high vacuum. The residue was then dissolved in a mixture of THF/MeOH/$H_2O$ (4 mL/2 mL/2 mL) and stirred overnight with $LiOH.2H_2O$ (11 mg, 0.264 mmol). The residue isolated after acidification to pH=3 with 1N ice-cold HCl was purified by C18 reversed phase HPLC using a solvent gradient from 0–40% aqueous $CH_3CN$ (0.06% TFA) in order to isolated pure compound 203 as an amorphous white solid (12 mg).

$^1$H NMR (50 mM $Na_2PO_4$ buffer, pH=6.0, 600 MHz): δ 1.22–1.27 (m, 2H), 1.38–1.43 (m, 2H), 1.58–1.64 (m, 2H), 1.67–1.76 (m, 2H), 1.77–1.84 (m, 1H), 1.92–1.99 (m, 1H), 2.22–2.08 (m, 1H), 2.12–2.27 (m, 1H), 2.22–2.27 (m, 1H), 2.60–2.67 (m, 1H, Pro-β'), 2.83–2.89 (m, 1H, Pro-β), 4.32 (dd, J=12.1 & 3.5 Hz, 1H, Pro-δ'), 4.41 (dd, J=12.1 & 7.3 Hz, 1H), 4.56 (bd, J=8.0 Hz, 1H, Pro-δ), 4.62 (dd, J=8.9 Hz, 1H, Pro-α), 5.40–5.46 (m, 1H), 5.55–5.61 (m, 1H), 5.73 (bs, 1H, Pro-γ), 7.41 (d, J=6.3 Hz, 1H), 7.64 (bs, 1H, Acca-NH), 7.80 (dd, J=7.9 Hz, 1H), 8.03 (dd, J=8.0 Hz, 1H), 8.07 (d, J=9.5 Hz, 1H), 8.16 (d, J=7 Hz, 1H, AcNH), 8.36 (d, J=8.3 Hz, 1H), 8.90 (d, J=6.0 Hz, 1H).

Example 26

Synthesis of Compound 508 (Table 5)

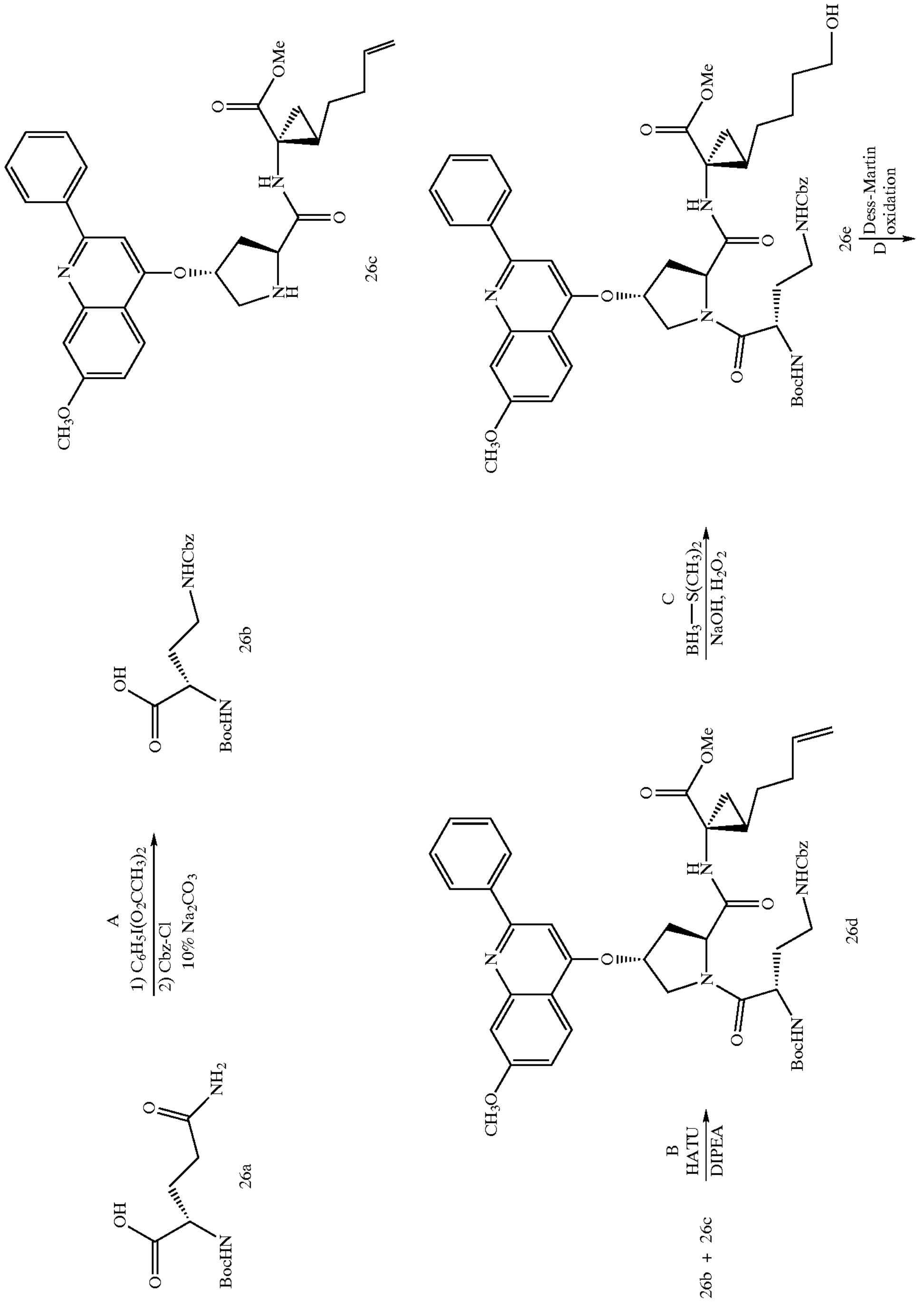
26a
26b
26c
26b + 26c
26d
26e

-continued
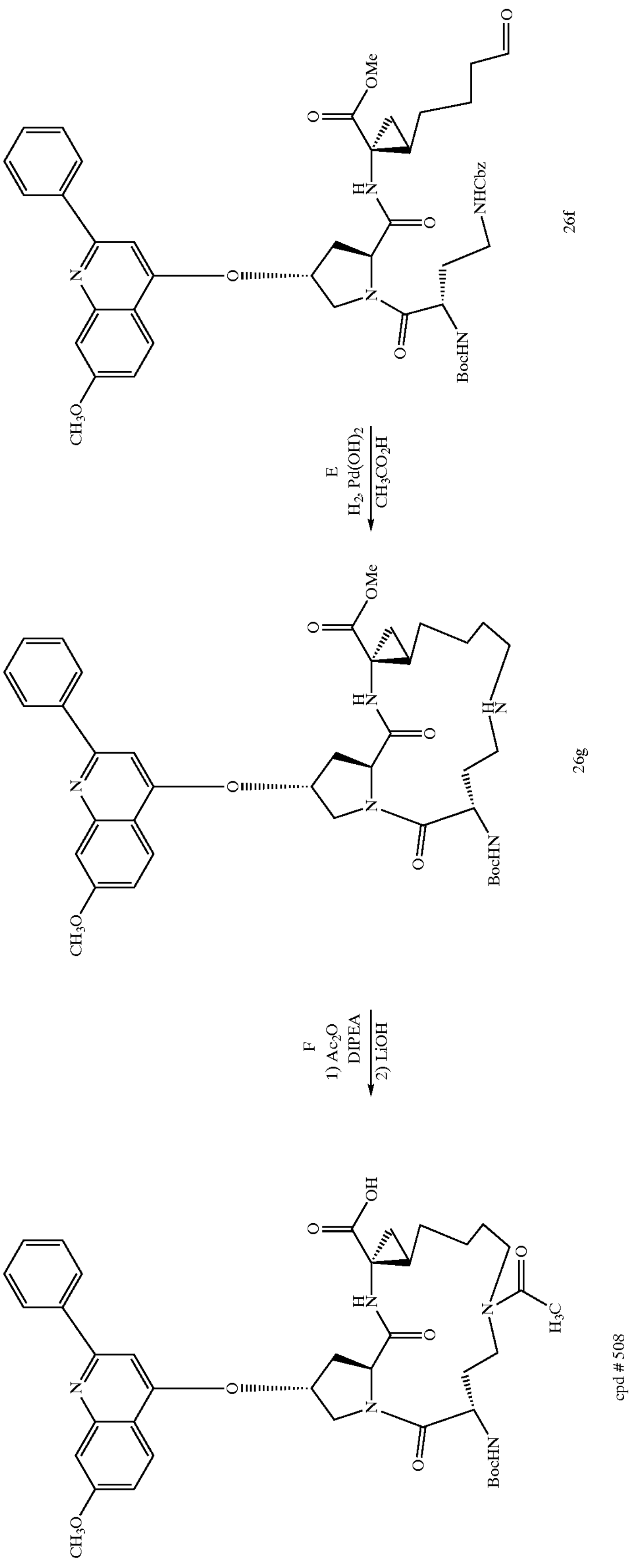
26f
26g
cpd # 508

A. A solution of Boc-protected L-glutamine 26a (4.93 g, 20 mmol) and iodobenzene diacetate (7.73 g, 24 mmol, 1.2 eq.) in EtOAc/$CH_3CN/H_2O$ (2:2:1, 60 mL), was stirred at 16° C. for 1 h and at 20° C. for 3 h. The reaction mixture was then diluted with $H_2O$ (20 mL), the EtOAc and $CH_3CN$ solvents were removed under vacuum and the remaining aqueous mixture was extracted with diethyl ether (3x50 mL) and EtOAc (50 mL) in order to remove most of the impurities. The aqueous layer (containing the amine intermediate) was then concentrated to dryness, the remaining material was re-dissolved in 10% $Na_2CO_3$ (30 mL), cooled to 0° C. in an ice bath and a solution of benzyl chloroformate (3.3 mL, 20.4 mmol, 1.02 eq.) dioxane (40 mL) was slowly added (~10 min). The reaction mixture was stirred at 0° C. for 1 h and at RT for 2 h. The mixture was then diluted with $H_2O$ (50 mL), extracted with cold (~5° C.) diethyl ether (3x50 mL), acidified with 4M HCl to pH=3–4 and extracted with EtOAc (3x50 mL). The combined organic layers were dried over anhydrous $MgSO_4$ and evaporated to dryness under vacuum. The crude material was purified by flash column chromatography, using EtOAc/Hexane/AcOH (7:2.9:0.1) to obtain compound 26b in 43% overall yield (3.04 g).

B. Dipeptide intermediate 26c (250 mg, 0.41 mmol), compound 26b (171 mg, 0.49 mmol, 1.2 eq.) and HATU (185 mg, 0.49 mmol, 1.2 eq.) were dissolved in $CH_2Cl_2$ (6 mL) and DIPEA (0.29 mL, 1.62 mmol, 4 eq.) was added. The reaction mixture was stirred at RT for 14 h, then the $CH_2Cl_2$ was evaporated under vacuum and the crude material re-dissolved in EtOAc. The EtOAc solution was washed with aqueous 5% $NaHCO_3$ and brine, dried over anhydrous $MgSO_4$ and evaporated to dryness. Compound 26d was obtained after purification of the crude material by flash column chromatography, using EtOAc/hexane (4:1) as the eluent, in 98% yield (338 mg).

C. A solution of compound 26d (335 mg, 0.394 mmol) in THF (5 mL) was cooled to 0° C. and a solution of $BH_3$ in dimethyl sulfide (0.12 mL of 10M solution, 1.2 mmol, 3 eq.) was added. The reaction mixture was allowed to warm-up to RT and stir for 1 h. Then it was cooled again to 0° C. before an aqueous solution of NaOH (0.8 mL of 2.5 M solution, 1.97 mmol, 5 eq) was added slowly over a period of 15 min, followed by the slow addition (~15 min) of an aqueous solution of $H_2O_2$ (0.8 mL of an 8.8 M solution, 6.9 mmol, 17.5 eq.). The reaction mixture was allowed to warm-up to RT and stir for 1 h. After that period, the reaction mixture was acidified to pH ~4 in order to quench the excess $BH_3$, then aqueous $NaHCO_3$ was added to adjust the pH=~9–10, the THF was removed under vacuum and the crude material was partitioned between $H_2O$ and EtOAc. The aqueous layer was re-extracted with EtOAc, the combined organic layers were washed with brine, dried over anhydrous $MgSO_4$ and evaporated to dryness under vacuum. The crude material was purified by flash column chromatography, using EtOAc/hexane/$NH_4OH$ (8:2:0.5) as the eluent, to obtain pure compound 26e in 57% yield (192 mg).

D. To a solution of compound 26e in $CH_2Cl_2$ (8 mL), Dess-Martin periodinate (195 mg, 97%, 0.33 mmol, 1.5 eq) was added and the reaction mixture was stirred at RT for 1.5 h. The reaction was quenched with the addition of aqueous $Na_2S_2O_3$ (3 mL of 5% solution), then saturated aqueous $NaHCO_3$ (5 mL) was added and the mixture was stirred at RT for 15 min. Finally, the reaction crude was extracted with EtOAc, the organic layer was washed with aqueous 5% $NaHCO_3$ and brine, dried over anhydrous $MgSO_4$ and evaporated under vacuum to give 188 mg of aldehyde 28f which was used in the next step without further purification.

E. A solution of compound 26f (188 mg, 0.22 mmol), $CH_3CO_2H$ (38 μL) and $Pd(OH)_2$ (25 mg) in ethanol (5 mL) was stirred to RT under $H_2$ at atmospheric pressure for 16 h. After that period, more $H_2$ gas, $Pd(OH)_2$ (180 mg) and $CH_3CO_2H$ (154 μL) and were added to the flask and stirring was continued for an additional 24 h. The mixture was then filtered and the solvent evaporated to dryness, the crude macrocyclic product was purified by flash column chromatography, using $CHCl_3$/MeOH/AcOH (10:2:1), to obtain compound 26g in ~30% yield (48 mg).

F. A mixture of compound 26g (22 mg, 0.031 mmol), DIPEA (27 μL, 0.155 mmol, 5 eq.) and acetic anhydride (8.7 μL, 0.093 mmol, 3 eq.) in $CH_2Cl_2$ (5 mL) was stirred at RT for 16 h. The $CH_2Cl_2$ was then removed under vacuum, a mixture of THF/MeOH/$H_2O$ (2:2:1, 5 mL) and $LiOH.2H_2O$ (13 mg, 0.31 mmol, 10 eq.) were added and the hydrolysis reaction was allowed to proceed for 68 h at RT and 2 h at 50° C. The reaction mixture was then acidified (pH=~4) and purified by reversed phase HPLC to obtain the final compound 508 (~6 mg, ~26% yield for the last 2 steps).

$^1H$ NMR (DMSO, 400 MHz) of 508 (mixture of rotamers confirmed by COSY, TOCSY and ROESY NMR data): δ 1.18 (s, 9H), 1.09–1.85 (overlapping m, 11H), 1.95 (s, 3H), 2.30 (m, 1H), 2.63 (m, 1H), 3.18–4.14 (overlapping m, 6H), 3.96 (s, 3H), 4.44 (m, 1H), 4.62 & 4.69 (2d, J=11.8 Hz, 1H, rotamers), 5.82 (bs, 1H), 7.20 (m, 2H), 7.53 (bs, 1H), 7.67 (bs, 4H), 8.19 (bs, 3H), 8.61 (s, 1H).

Example 27

Synthesis of the Saturated Macrocyclic Intermediate (27a)

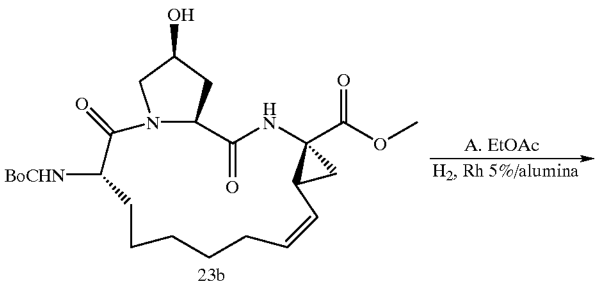

23b

-continued

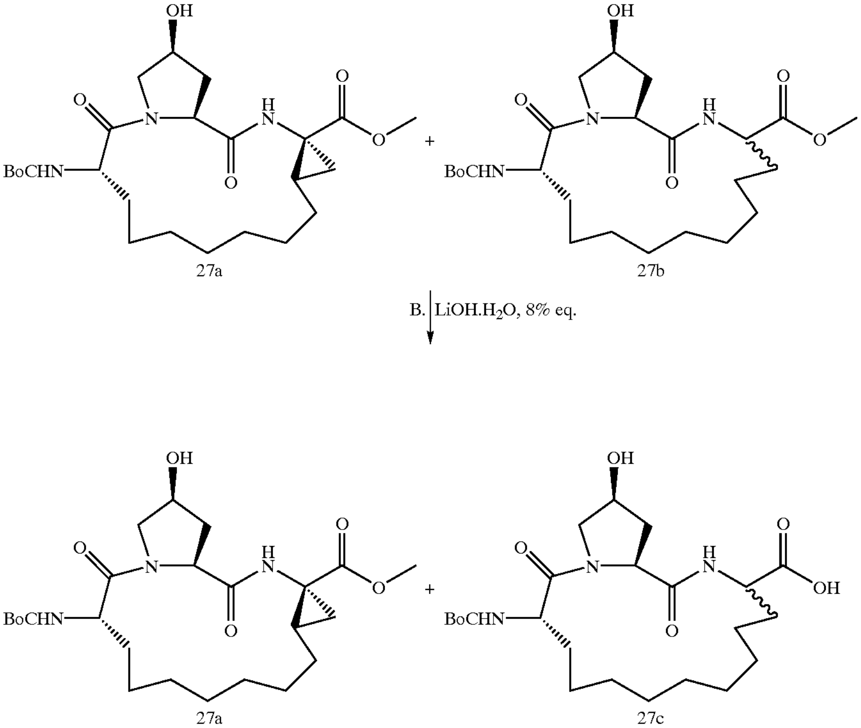

27a 27b 27a 27c

A. The unsaturated macrocyclic intermediate 23b (3.50 g, 7.30 mmol) was dissolved in EtOAc (30 mL) and 700 mg (20% w/w) of 5% Rh on alumina was added. The mixture was stirred under $H_2$ gas at atmospheric pressure and at RT for 1.5 h. After that period, HPLC analysis confirmed the complete conversion of starting material to two products, the desired product 27a and a minor product (8% of the total mass) which was later identified to be compound 27b, formed from opening of the cyclopropane ring. The reaction mixture was filtered and concentrated to give a light green color solid (3.47 g). The solid was co-evaporated twice with EtOH to remove all of the EtOAc (the presence of EtOAc interferes in the next step). Separation of compound 27a from 27b by chromatography proved to be very difficult, thus an alternative method was devised based on the relative rates of hydrolysis of their respective methyl ester moieties.

B. The crude mixture of compounds 27a and 27b (3.47 g) was dissolved in THF:MeOH (1:1, 20 mL), an aqueous solution of $LiOH.H_2O$ (24 mg in 5 mL $H_2O$, 8% eq) was added and the reaction mixture was stirred at RT for 16 h (complete hydrolysis of the side product 27b to its corresponding acid 27c was confirmed by HPLC). The reaction mixture was concentrated under vacuum in order to remove most of the THF and MeOH and partitioned between $H_2O$ (100 mL) and EtOAc (300 mL). The organic layer was washed with 0.5 N NaOH (3×100 m), brine (100 mL), 10% aqueous citric acid (2×100 mL), brine (100 mL), dried over anhydrous $MgSO_4$, filtered and concentrated to dryness. The desired product 27a was obtained in high purity (>90% by HPLC) as a light green foam and in 93% overall yield (3.28 g) for the two steps.

$^1$H NMR: (400 MHz, $CDCl_3$): δ 1.1–1.38 (m, 13 H), 1.42 (s, 9 H), 1.51–1.57 (m, 1 H), 1.63–1.67 (dd, J=8.0 & 5.1 Hz, 1 H), 1.81–1.87 (m, 1 H), 1.92–1.99 (m, 1 H), 2.02–2.08 (m, 1 H), 2.62 (d, J=14 Hz, 1 H), 3.4 (d, J=8.3, 1H), 3.65 (s, 3H), 4.01 (dd, J=10.8 & 4.1 Hz, 1 H), 4.42–4.48 (m, 1 H), 4.51–4.55 (m, 1 H), 4.87 (d, J=8.6 Hz, 1 H), 5.14 (d,J=8.6 Hz, 1 H), 7.97 (br s, 1 H).

Example 28

Synthesis of Compound #741 (Table 7)

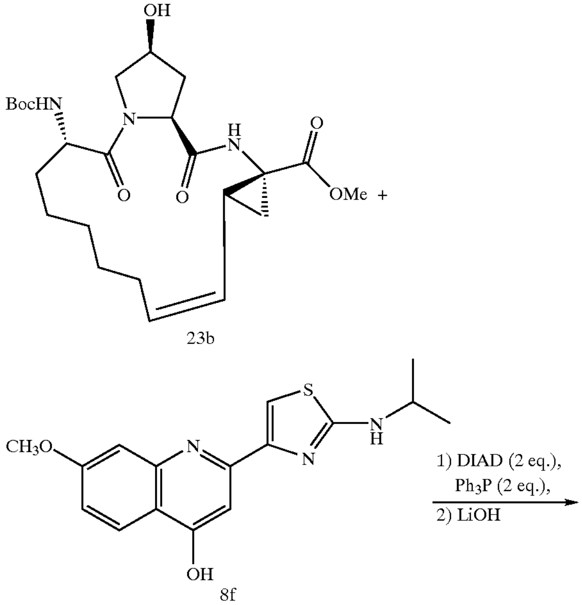

23b

8f

-continued

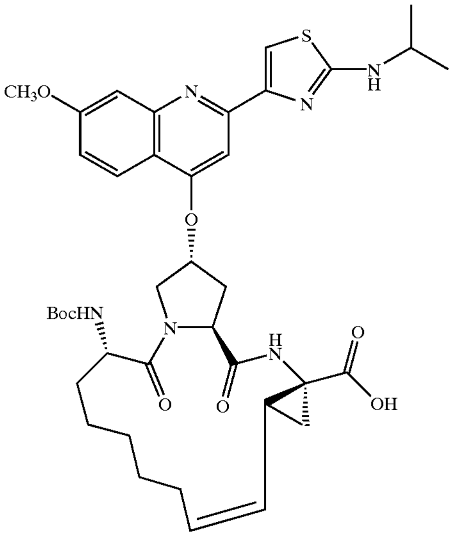

cpd # 741

Quinoline derivative 8f was attached to the pre-formed macrocyclic compound 23b via a Mitsunobu reaction. The quinoline derivative 8f (30 mg, 0.095 mmol) was dissolved in THF, then macrocycle 23b (45.6 mg, 1 eq.) and PPh3 (49.8 mg, 2 eq.) are then added. The resulting mixture is cooled to 0° C. DIAD (37.4 μl, 2 eq.) is then added dropwise. The solution is stirred 1 hour at 0 C. then stirred overnight at room temperature. The mixture was then diluted with EtOAc (15 ml), washed with a saturated solution of $NaHCO_3$ (15 ml), followed by brine. The solution was dried with $MgSO_4$, filtered and concentrated in vacuo. 202 mg of a yellow oil was obtained. The product was purified by flash chromatography on silica gel (100% EtOAc). The product still contained DIAD byproducts after the purification. The resulting product obtained contained 55% w/w of the desired product, so the yield was declared to be 62%.

The ester intermediate (46 mg, 0.06 mmol) was dissolved in a mixture of THF/MeOH/$H_2O$ (2:1:1 ratio, 2 mL), LiOH.$H_2O$ (20 mg, 0.48 mmol) was added and the solution was stirred at RT. After a period of 16 h, analysis of the reaction mixture by HPLC indicated that the hydrolysis was complete. The organic solvents were removed under vacuum and the remaining crude material dissolved in DMSO was purified by C18 reversed phase HPLC to give pure inhibitor 741.

$^1H$ NMR (400 MHz, DMSO-$d_6$) δ (ppm): 8.67 (s, 1H), 8.29–8.14 (m, 2H), 8.08–7.97 (m, 1H), 7.91–7.78 (m, 1H), 7.74 (s, 1H), 7.31–7.20 (m, 1H), 7.10 (d, J=5.7 Hz, 1), 5.82–5.71 (m, 1H), 5.58–5.47 (m, 1H), 5.32–5.23 (m, 1H), 4.74–4.64 (m, 1H), 4.55–4.47 (m, 1H), 4.23–4.06 (m, 1H), 4.04–3.94 (m, 1H), 3.97 (s, 3H), 3.92–3.85 (m, 1H), 2.70–2.55 (m, 2H), 2.53–2.36 (m, 2H), 2.20–2.09 (m, 1H), 1.80–1.62 (m, 2H), 1.56–1.43 (m, 2H), 1.42–1.29 (m, 6H), 1.27 (d, J=3.2 Hz, 3H), 1.25 (d, J=2.9 Hz, 3H), 1.12 (s, 9H).

MS: 763.1 (M+1), 761.1 (M−1).

Example 29

Synthesis of Compound 205 (Table 2)

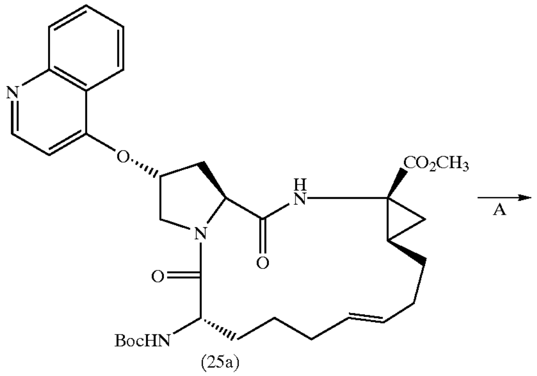

(25a)

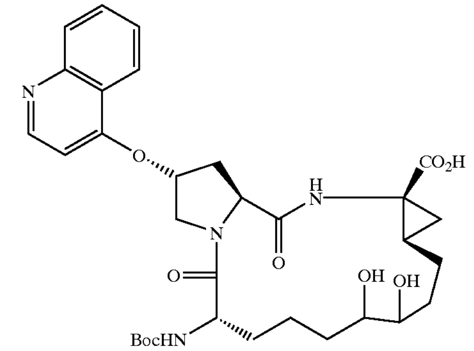

compounds 205

To a solution of the macrocyclic compound 25a (21 mg, 0.035 mmol) in t-butanol/$H_2O$) (1.5 mL/1.5 mL) at 0°, a solution of $O_5O_4$ in t-butanol (0.36 mL of a 35% w/v, 0.035 mmol) was added and the mixture was stirred at RT for 1 h. The mixture was diluted with EtOAc (20 mL) and the organic solution washed with 5% $NaHCO_3$ (2–10 mL), brine (2×10 mL), dried and evaporated to dryness. The crude compound was taken into THF/MeOH/$H_2O$ (3 mL/1.5 mL/1.5 mL) and stirred in presence of LiOH.$H_2O$ (13 mg, 0.28 mmol) for 16 h. The mixture was acidified to pH 4 with 0.5 N ice-cold HCl, evaporated and purified by C18 reversed phase HPLC using a solvent gradient from $H_2O$ (0.06% TFA) to 40% aqueous $CH_3CN$ (0.06% TFA). The syn diol 205 was isolated in high purity as amorphous white solid. compound #205: $^1H$ NMR (DMSO, 400 MHz): δ 1.01 (s, 9H), 1.06–1.30 (m, 9H), 1.48–1.68 (m, 3H), 1.78–1.88 (m, 1H), ≈2.2–2.5 (2m, 2H), 3.78–3.82 (m, 1H), 3.86–3.90 (m, 1H), 4.39 (t, J=8.9 Hz, 1H), 4.61 (d, J=11.4 Hz, 1H), 5.60 (bs, 1H, Pro-γ), 7.03 (d, J=6.0 Hz, 1H), 7.40 (bs, 1H), 7.58–7.62 (m, 1H), 7.87–7.91 (m, 1H), 8.00 (d, J=8.3 Hz, 1H), 8.24 (d, J=8.6 Hz, 1H), 8.60 (s, 1H), 8.99 (bs, 1H).

EMS (negative ionization mode): m/z 625 $(M-H)^-$.

Example 30
Synthesis of Compound 214 & 218 (Table 2)
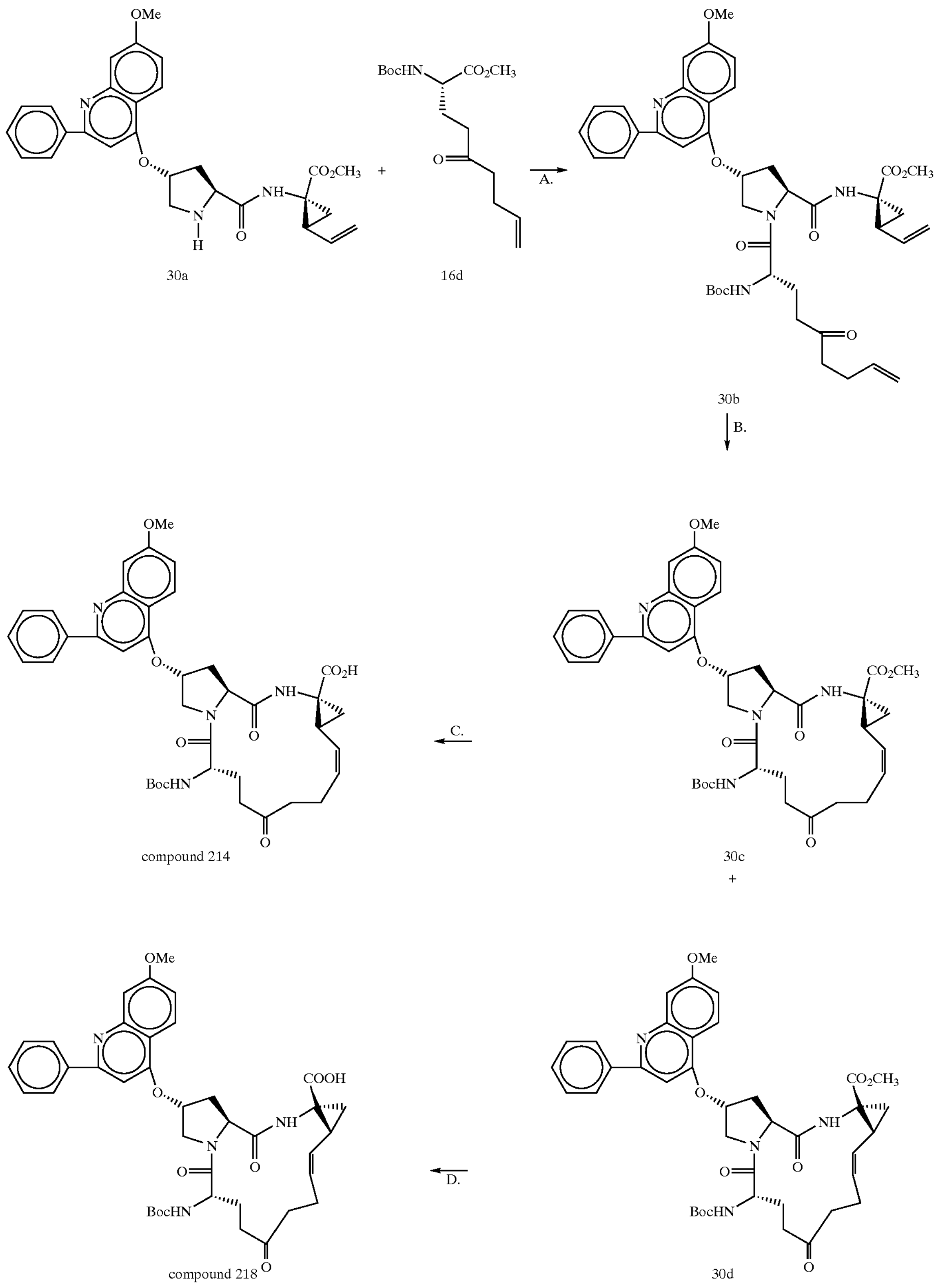
30a
16d
30b
30c
+
30d
compound 214
compound 218

A. A solution of the keto-nonenoate ester 16d (0.180 g, 0.6 mmol) in MeOH/$H_2O$ (5 mL/2 mL) was stirred at RT in presence of LiOH.$H_2O$ (50 mg, 1.2 mmol) for 1 h. The solution was acidified to pH 6 with 0.5 N ice-cold HCl and most of the MeOH was evaporated. The residue was then dissolved in EtOAc (30 mL) and the solution was washed with 0.5 N ice-cold HCl (10 mL), brined (10 mL), dried and evaporated. The crude residue was then re-dissolved in $CH_2Cl_2$ (10 mL) and reacted with the P1-P2 fragment 30a (0.337 g, 0.6 mmol) in the presence of HATU (233 mg, 0.612 mmol) and DIPEA (420 μL, 2.4 mmol) over a period of 16 h at RT. The reaction mixture was chromatographed on silica gel using EtOAc/hexane (1/1) as the eluent, to isolate the pure compound 30b (0.370 g, yield 83%, Purity >95% by HPLC).

$^1H$ NMR ($CDCl_3$, 400 MHz) δ 1.41 (s, 9H), 1.45–1.54 (m, 1H), 1.58–1.62 (m, 1H), 1.73–1.77 (m, 1H), 1.86–1.91 (m, 1H), 2.16 (dd, J=17.8 & 8.6 Hz, 1H), 2.26–2.43 (2m, 2H), 2.46–2.58 (m, 2H), 2.64–2.81 (m, 1H), 2.85–2.92 & 2.95–3.03 (2m, 1H, rotamers in 1:3 ratio), 3.67 (s, 3H), 3.95 (s, 3H), 4.10–4.18 (m, 1H), 4.20–4.30 (m, 1H), 4.40–4.55 (m, 1H), 4.80–4.88 (m, 1H), 4.92–5.10 (m, 2H), 5.14 (dd, J=10.2 & 1.6 Hz, 1H), 5.24–5.38 (m, 4H), 5.42–5.54 (m, 1H), 5.68–5.86 (m, 2H), 7.04–7.14 (m, 2H), 7.42–7.64 (m, 5H), 7.92–8.12 (m, 3H).

B. The diene 30b (0.370 g, 0.49 mmol) was cyclized in the presence of the bis-(tricyclohexylphosphine) benzylidene ruthenium IV dichloride catalyst (0.125 mg, 0.15 mmol) in $CH_2Cl_2$ (distilled from $CaH_2$ and degassed with argon for 30 min) over a period of 2 h at reflux. The compound was obtained as a mixture of stereoisomers (30c and 30d 1:1 ratio) after flash column chromatography on silica gel using EtOAc/Hexane (3/1) in 35% yield (0.124 g).

$^1H$ NMR of mixture 30c & 30d ($CDCl_3$, 400 MHz) δ 1.44 (s, 4H) & 1.37 (s, 4H), 1.60 (m, 2H), 1.83 (m, 0.5H), 2.01 (m, 1H), 2.09 (m, 1H), 2.42 (m, 5H), 2.73 (m, 2H, 3.26 (m, 0.5H), 3.69 (s, 1.5H), 3.76 (s, 1.5H), 3.96 (s, 3H), 4.10 (m, 1H), 4.24 (m, 0.5H), 4.10 (m, 0.5H), 4.58 (m, 1H), 4.73 (m, 1H), 4.89 (m, 0.5H), 4.97 (m, 0.5H), 5.30 (m, 0.5H), 5.44 (m, 2H), 5.64 (m, 1H), 7.1–7.0 (m, 3H), 7.47 (m, 4H), 8.08–7.98 (m, 3H).

C,D. Hydrolysis of the methyl esters 30c and 30d (24 mg, 0.033 mmol) was carried out in THF/MeOH/$H_2O$ (1 mL/0.5 mL/0.5 mL) with LiO.$H_2O$ (11 mg, 0.246 mmol) over a period of 16 h at RT. After that period the reaction mixture was acidified to pH 4–5 and chromatographed on a C18 reversed phase HPLC column using a solvent gradient from $H_2O$ (0.06% TFA) to 50% aqueous $CH_3CN$ (0.06% TFA). The desired compounds 214 and 218 were isolated from the mixture of the two compounds in high purity (94% pure by HPLC) in 15% yield (3 mg).

compound 214: $^1H$ NMR (DMSO, 400 MHz) δ 1.15 (s, 9H), 1.48–1.54 (m, 2H), 1.65–1.74 (m, 1H), 1.77–1.85 (m, 1H), 2.12–2.25 (m, 4H), 2.27–2.34 (m, 1H), 2.61–2.68 (m, 1H), 2.87 (bt, J=11.5 Hz, 1H), 3.92 (dd, J=9.2 & 1.5 Hz, 1H, Pro-δ), 3.97 (s, 3H, —$OCH_3$), 4.14–4.20 (m, 1H), 4.52 (t, J=7.8 Hz, 1H, Pro-α), 4.66 (d, J=11.8 Hz, 1H, Pro-δ), 5.45 (t, J=9.9 Hz, 1H), 5.51–5.58 (m, 1H), 5.82 (bs, 1H, Pro-γ), 7.09 (d, J=6.0 Hz, 1H, BocNH), 7.26 (bs, 1H), 7.53 (s, 1H), 7.67 (bs, 3H), 8.16 (d, J=2 Hz, 1H), 8.18 (s, 1H), 8.83 (s, 1H, ACCA-NH).

compound 218: $^1H$ NMR(DMSO, 400 MHz): δ 1.06–1.10 (m, 1H), 1.18 (s, 9H), 1.52–1.55 (m, 1H), 1.62–1.80 (m, 1H), 2.10–2.68 (overlapping, 9H), 3.90 (bd, J=8.3 Hz, 1H), 3.96 (s, 3H, $OCH_3$), 4.20–4.27 (m, 1H), 4.58–4.63 (m, 1H, Pro-δ), 4.66 (dd, J=8.3 Hz, 1H, Pro-α) 4.88 (dd, J=10.2 Hz, 1H), 5.18–5.26 (m, 1H), 5.73–5.79 (m, 1H, Pro-γ), 7.01 (d, J=6.4 Hz, 1H), 7.23 (bs, 1H), 7.50 (bs, 1H), 7.66 (bs, 3H), 8.20 (bs, 2H), 8.53 (s, 1H).

Example 31

Synthesis of compound 209 (Table 2)

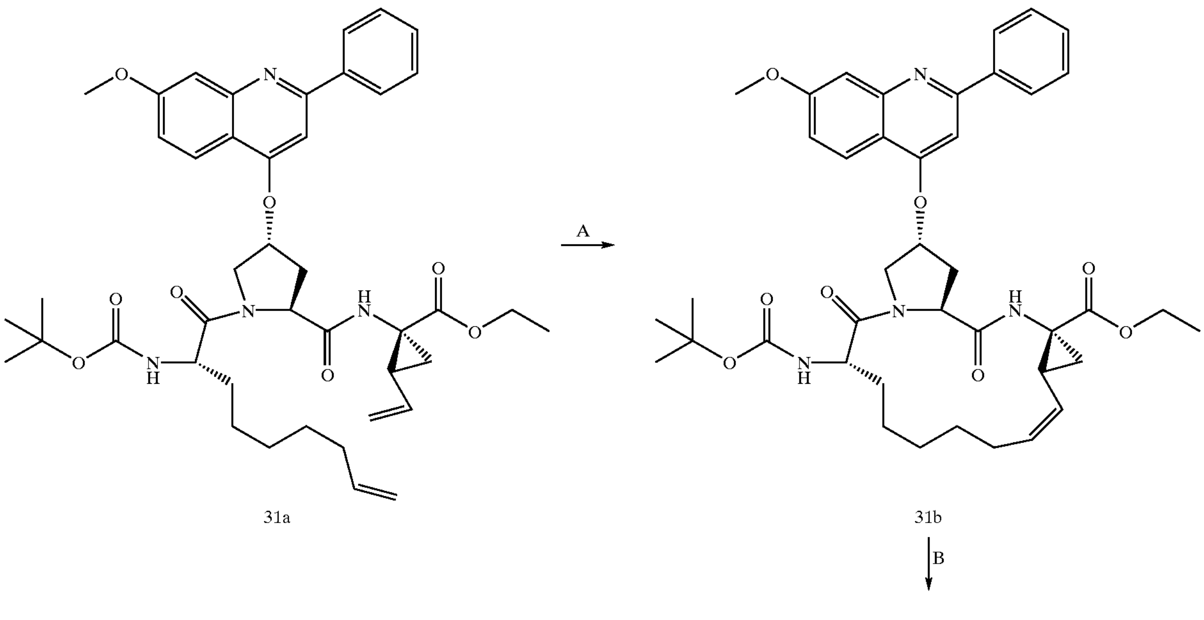

31a

31b

-continued

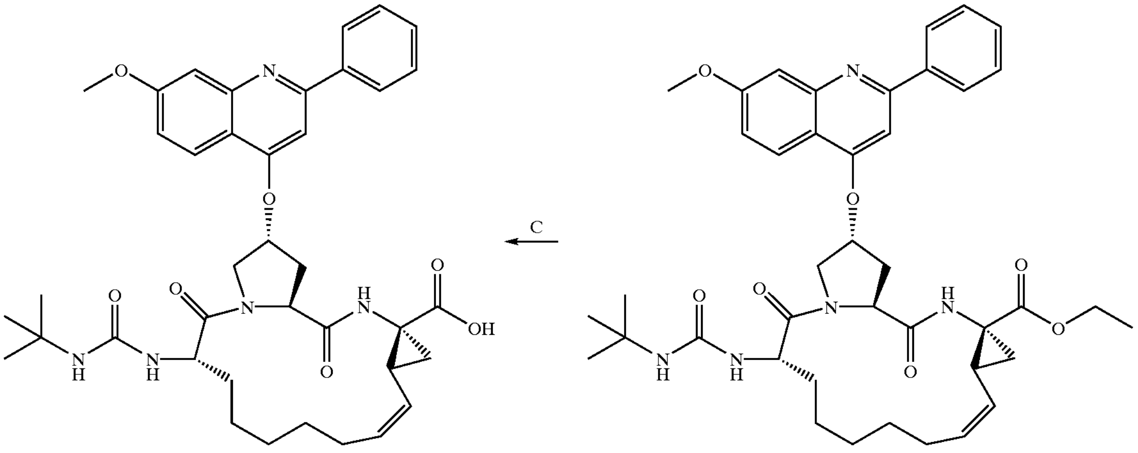

compound 209 31c

A. The diene 31a (249 mg, 0.330 mmol) was dissolved in 30 mL of anhydrous $CH_2Cl_2$ and the solution was degassed with argon for 15 min. The catalyst bis-(tricyclohexylphosphine) benzylidene ruthenium IV dichloride (82 mg, 0.100 mmol) was dissolved in 3 mL of anhydrous and degassed $CH_2Cl_2$ and added to the diene solution. The reaction mixture was refluxed for 2 h under $N_2$. The solution was concentrated and purified by flash column chromatography to obtain compound 31b as a brown solid in 71% yield (171 mg).

$^1$H NMR ($CDCl_3$, 400 MHz): δ 1.22–1.44 (m, 10H), 1.42 (s, 9H), 1.66–1.74 (m, 1H), 1.87–1.97 (m, 2H), 2.13–2.28 (m, 3H), 2.32–2.39 (m, 1H), 3.08–3.16 (m, 1H), 3.41 (s, 3H), 4.07–4.22 (m, 3H), 4.28–4.34 (m, 1H), 4.58–4.64 (m, 1H), 4.95–4.99 (m, 1H), 5.22–5.29 (m, 2H), 5.38–5.43 (m, 1H), 5.48–5.56 (m, 1H), 7.00–7.12 (m, 3H), 7.43–7.55 (m, 4H), 7.97–8.11 (m, 3H).

ES(+)MS: m/z 727.4 $(M+H)^+$.

B. Compound 31b (0.117 mmol) was stirred in a solution of HCl (1 mL of 4N in dioxane) for 30 min and concentrated to dryness. The solid was taken up in $CH_2Cl_2$ (2 mL), $Et_3N$ (82 μL, 0.585 mmol) and t-butylisocyanate (35 mg, 0.351 mmol) were successively added. After stirring at RT for 20 h, the mixture was concentrated to dryness and the crude compound 31c was used in the final hydrolysis step without further purification.

C. Compound 31c (85 mg, 0.117 mmol) was dissolved in THF/MeOH/$H_2O$ (2 mL/1 mL/1 mL), LiOH.$H_2O$ (39 mg, 0.936 mmol) was added and the solution was stirred for 20 h at RT. After that period, acetic acid (1 mL) was added and the solution was concentrated to remove the MeOH and THF. The pure compound 209 was isolated after purification of the crude by C18 reverse phase HPLC (25 mg, ~31% yield).

$^1$H NMR (DMSO, 400 MHz): δ 1.04 (s, 9H), 1.15–1.24 (m, 2H), 1.30–1.40 (m, 5H), 1.44–1.51 (m, 2H), 1.54–1.68 (m, 1H), 1.75–1.88 (m, 1H), 2.18 (dd, J 17.2 & 8.5 Hz, 1H), 2.32–2.45 (m, 1H, Pro-β), 2.54–2.62 (m, 1H), 2.65–2.68 (m, 1H, Pro-β), 3.91 (dd, J=11.1 & 3.5 Hz, 1H, Pro-δ), 3.96 (s, 3H, —$OCH_3$), 4.17–4.23 (m, 1H), 4.47 (dd, J=8.6, 1H, Pro-α), 4.67 (bd, J=7.9 Hz, 1H, Pro-δ), 5.30 (dd, J=9.5 Hz, 1H), 5.52 (bdd, J=19 & 8.3, 1H), 5.68 (s, 1H), 5.78 (bs, 1H, Pro-γ), 5.94 (bs, 1H), 7.21 (bs, 1H), 7.51 (bs, 1H), 7,66 (bs, 4H), 8.19 (s, 2H), 8.40 (d, J=7 Hz, 1H), 8.61 (s, 1H, ACCA-NH).

ES(+)MS: m/z 698.3 $(M+H)^+$.

Example 32

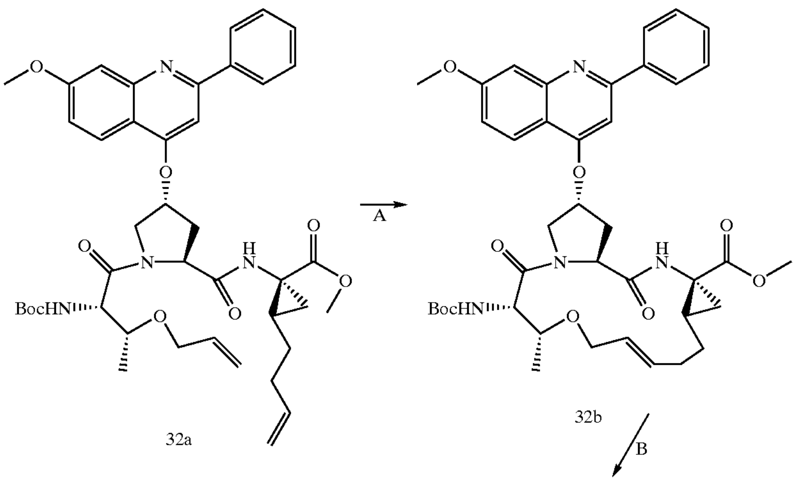

32a 32b

-continued

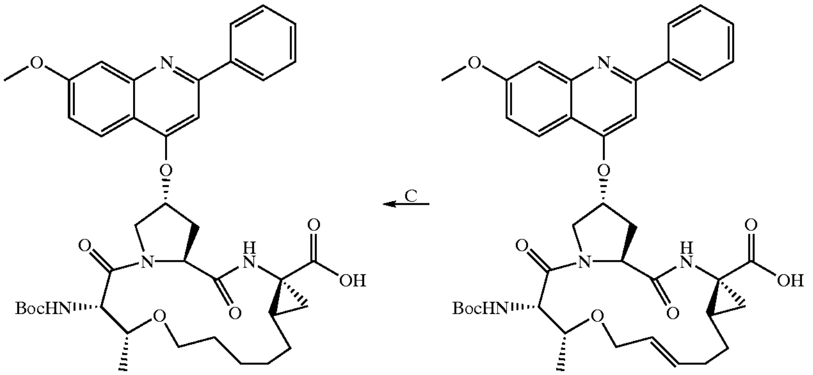

cpd # 407 cpd # 404

A. The diene 32a (84 mg, 0.11 mmol) was dissolved in anhydrous $CH_2Cl_2$ (11 mL) and the solution was degassed over a period of 15 min. with a flow of argon. The bis-(tricyclohexylphosphine) benzylidene ruthenium IV dichloride catalyst (19 mg, 0.023 mmol) was first dissolved in 1 mL of degassed $CH_2Cl_2$ and then it was transferred to the reaction flask via cannula. The reaction mixture was stirred for 2 h at reflux. The solvent was then removed under vacuum and the reaction mixture was purified by flash column chromatography on silica gel, using EtOAc/hexane (1:1) as the eluent, to give the macrocyclic compound 32b as a yellow oil (33 mg, 41% yield).

B. The ester intermediate 32b (33 mg, 0.045 mmol) was dissolved in a mixture of THF/MeOH/$H_2O$ (2:1:1 ratio, 2 mL), LiOH.$H_2O$ (8 mg, 0.18 mmol) was added and the solution was stirred at RT. After a period of 16 h, analysis of the reaction mixture by HPLC indicated that the hydrolysis was incomplete. Thus an additional amount of LiOH.$H_2O$ (4 mg, 0.09 mmol) was added and the solution was stirred at RT for a total of 36 h. Finally, the solution was acidified with a small aliquot of acetic acid, the organic solvents were removed under vacuum and the remaining crude material was purified by C18 reversed phase HPLC to give pure inhibitor 404.

$^1$H NMR (DMSO, 400 MHz): δ 1.21 (d, J=6.0 Hz, 3H, Me), 1.36 (s, 9H, Boc), 1.1–1.4 (3m, 3H), 1.66 (m, 1H), 1.80 (m, 1H), 2.10 (m, 2H), 2.57 (m, 2H), 3.90 (m, 4H), 4.47 (bd, J=12.7 Hz, 1H), 4.58 (bd, J=7.3, 1H), 4.66 (dd, J=8.0 Hz, 1H), 5.57 (m, 1H), 5.66 (m, 1H), 5.83 (bs, 1H), 6.18 (bd, J=6.9 Hz, 1H), 7.25 (bd, J=7.3 Hz, 1H), 7.56 (bs, 1H), 7.70 (m, 4H), 8.22 (bd, J=2.9 Hz, 2H), 8.29 (bs, J=9.2 Hz, 1H).

C. Inhibitor 404 (15 mg, 0.021 mmol) was dissolved in ethanol (2 mL) and Pd 10%/C (2 mg) was added. The mixture was stirred under hydrogen at RT for 16 h. After filtration, the mixture was purified by C18 reversed phase HPLC to give inhibitor 407 as a white solid (10 mg, 66% yield).

$^1$H NMR (DMSO, 400 MHz): δ 1.04 (m, 1H), 1.17 (d, J=6.0 Hz, 3 H), 1.35 (s, 9H), 1.25–1.75 (m, 12 H), 2.32–2.45 (m, 1 H), 3.40–3.50 (m, 2 H), 3.74–3.83 (m, 1H), 3.85–3.95 (m, 1H), 3.97 (s, 3H), 4.27–4.36 (dd, J=21.1 & 8.6 Hz, 1H), 4.54 (dd, J=7.95 & 7.95 Hz, 1H), 5.64 (d, J=8.3 Hz, 1H), 5.82 (br s, 1H), 7.27–7.33 (m, 1H), 7.53–7.57 (bs, 1 H), 7.60–7.74 (m, 4 H), 8.13–8.27 (m, 3 H), 8.30–8.35 (br s, 1H).

Example 33

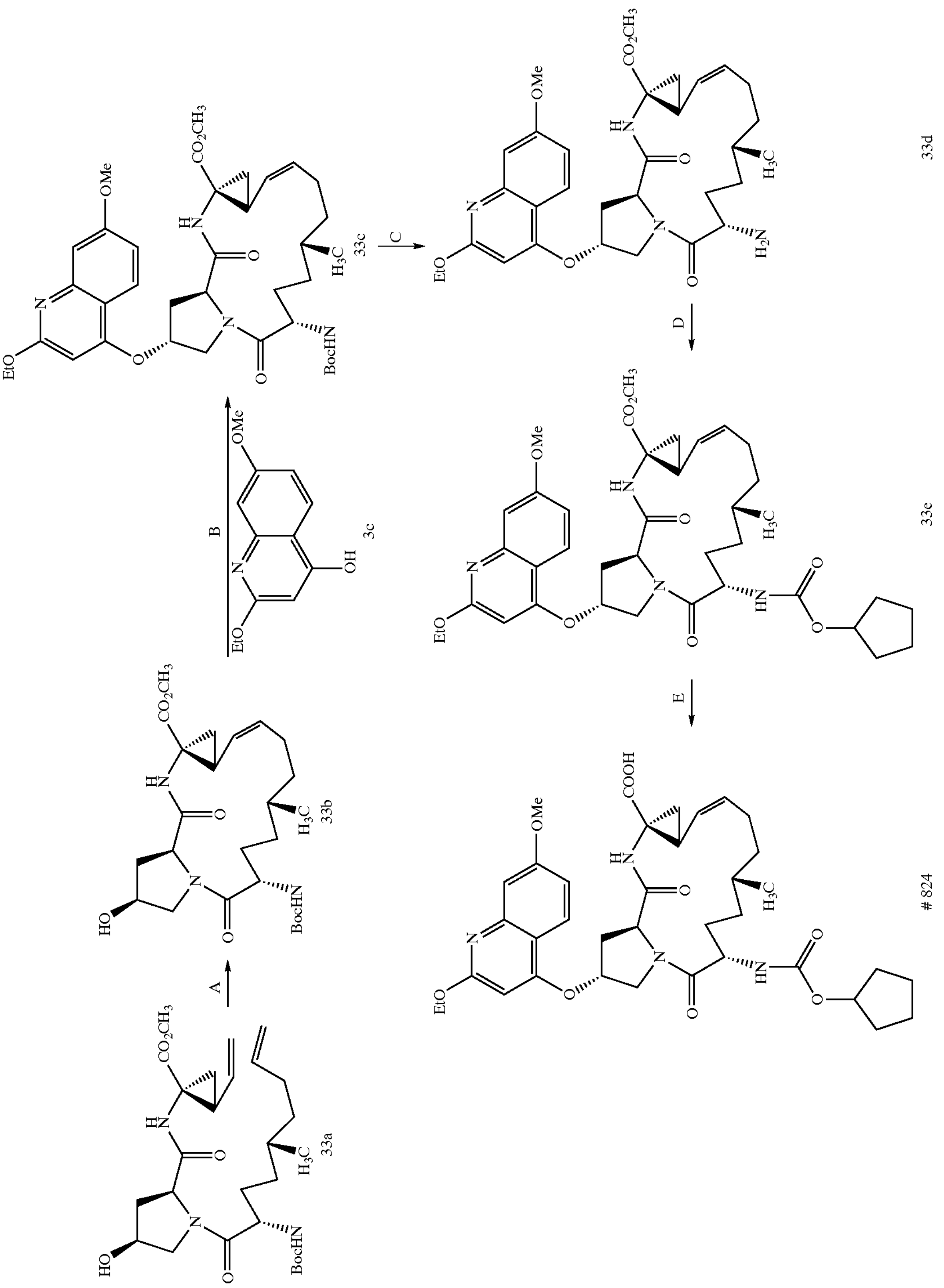
33a
33b
3c
33c
33d
33e
824

A. Compound 33a (~0.55 mmol) was dissolved in $CH_2Cl_2$ (100 mL) and the solution was degassed carefully before a sample of Hoveyda's catalyst (17 mg, 0.028 mmol, 0.05 eq.) was added. The solution was then stirred under reflux for 5 h. The reaction mixture was concentrated and purified by flash column chromatography, using a solvent gradient of $CH_2Cl_2$/EtOAc (from 3:2 to 2:3 ratio), to give compound 33b in 72% yield (194 mg).

B. To a solution of compound 33b (70 mg, 0.142 mmol), 2-ethoxy-4-hydroxy-7-methoxyquinoline 3c (63 mg, 0.284 mmol, 2 eq.) and $Ph_3P$ (186 mg, 0.71 mmol, 5 eq.) in anhydrous THF (15 mL) at 0° C., DIAD (140 $\mu$L, 0.71 mmol, 5 eq.) was added slowly over a period of 20 min. The reaction mixture was allowed to warm-up to RT and to stir at RT for 2.5 h. Subsequently, the THF was evaporated under vacuum and the crude product was purified by flash column chromatography, using a solvent gradient of hexane/EtOAc (from 7:3 to 1:1 ratio). Pure compound 33c was isolated in 73% yield (72 mg).

C. Compound 33c (72 mg, 0.104 mmol) was mixed with $CH_2Cl_2$ (5 mL) and 4M HCl in dioxane (5 mL) and the mixture was allowed to stir at RT for 1.5 h in order to cleave the Boc protecting group and obtain the HCl salt of intermediate 33d. The reaction crude reaction mixture was evaporated to dryness under vacuum, dried under vacuum to assure the removal of all HCl and used in the next step without purification.

D. To a solution of cyclopentanol (29 $\mu$L, 0.32 mmol) in THF (10 mL), a solution of phosgene in toluene (1.93 M, 274 $\mu$L, 0.528 mmol) was added dropwise and the mixture was stirred at R.T. for 2 h to form the cyclopentyl chloroformate reagent. After that period, approximately half of the solvent was removed by evaporation under vacuum, the remaining light yellow solution was diluted by the addition of $CH_2Cl_2$ (5 mL) and reconcentrated to half of its original volume, in order to assure the removal of all excess phosgene. The above solution of the cyclopentyl chloroformate reagent was further diluted with THF (10 mL), cooled to 0° C. and added to the solid compound 33d (0.104 mmol) at 0° C. $Et_3N$ (75 $\mu$L, 0.534 mmol, 5.2 eq.) was added to the reaction mixture and stirring was continued at 0° C. for 1.5 h. The solvents were removed under vacuum and the crude material purified by flash column chromatography, using EtOAc/hexane (1:1) as the eluent, to obtain compound 33e in almost quantitative yield (75 mg).

E. Hydrolysis of the methyl ester was achieved by reacting compound 33e (75 mg, 0.11 mmol) with $LiOH.H_2O$ (35 mg, 0.84 mmol, 8 eq.) in a solvent mixture of $THF/MeOH/H_2O$ (2:2:1 ratio, 7.5 mL) at 50° C. for 2.5 h. Upon completion of the hydrolysis, the mixture was acidified to pH=4.5 and the solvents were evaporated to dryness under vacuum. The crude product was purified by C18 reversed phase preparative HPLC, using a solvent gradient of $H_2O$ to 58% aqueous $CH_3CN$ (with 0.06% TFA), to obtain inhibitor #824 as a white amorphous solid (45 mg, 65% yield).

$^1H$ NMR of the $Na^+$ salt of #824 (DMSO, 400 MHz): δ 0.88 (d, J=6.7 Hz, 3H), 0.95–1.70 (overlapping resonances, 17H), 1.37 (t, J=7 Hz, 3H), 2.00–2.10 (m, 1H), 2.10–2.33 (m, 3H), 2.38–2.44 (m, 1H), 3.80–3.85 (m, 1H), 3.85 (s, 3H), 4.02–4.08 (m, 1H), 4.42 (q, J=7 Hz, 2H), 4.35–4.44 (m, 1H), 4.50 (d, J=10.8 Hz, 1H), 4.63 (bs, 1H), 5.28 (dd, J=9.5 Hz, 1H), 5.38 (bs, 1H), 5.42–5.49 (m, 1H), 6.37 (s, 1H), 6.87 (dd, J=8.9 & 2.2 Hz, 1H), 7.07 (d, J=2.2 Hz, 1H), 7.28 (d, J=7.0 Hz, 1H), 7.90 (d, J=8.9 Hz, 1H), 8.57 (s, 1H).

Example 34

Synthesis of compound #812 (Table 8)

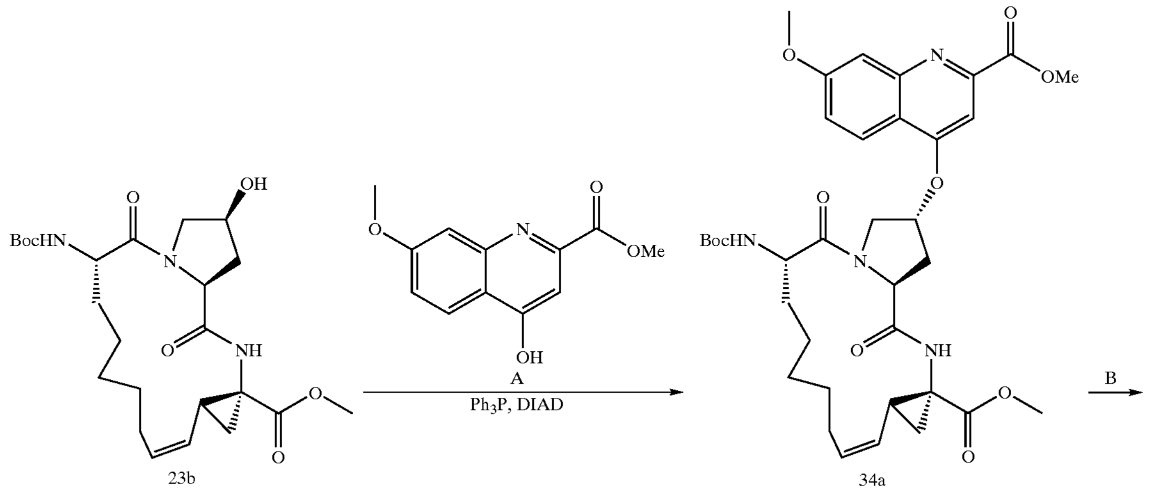

23b

34a

-continued
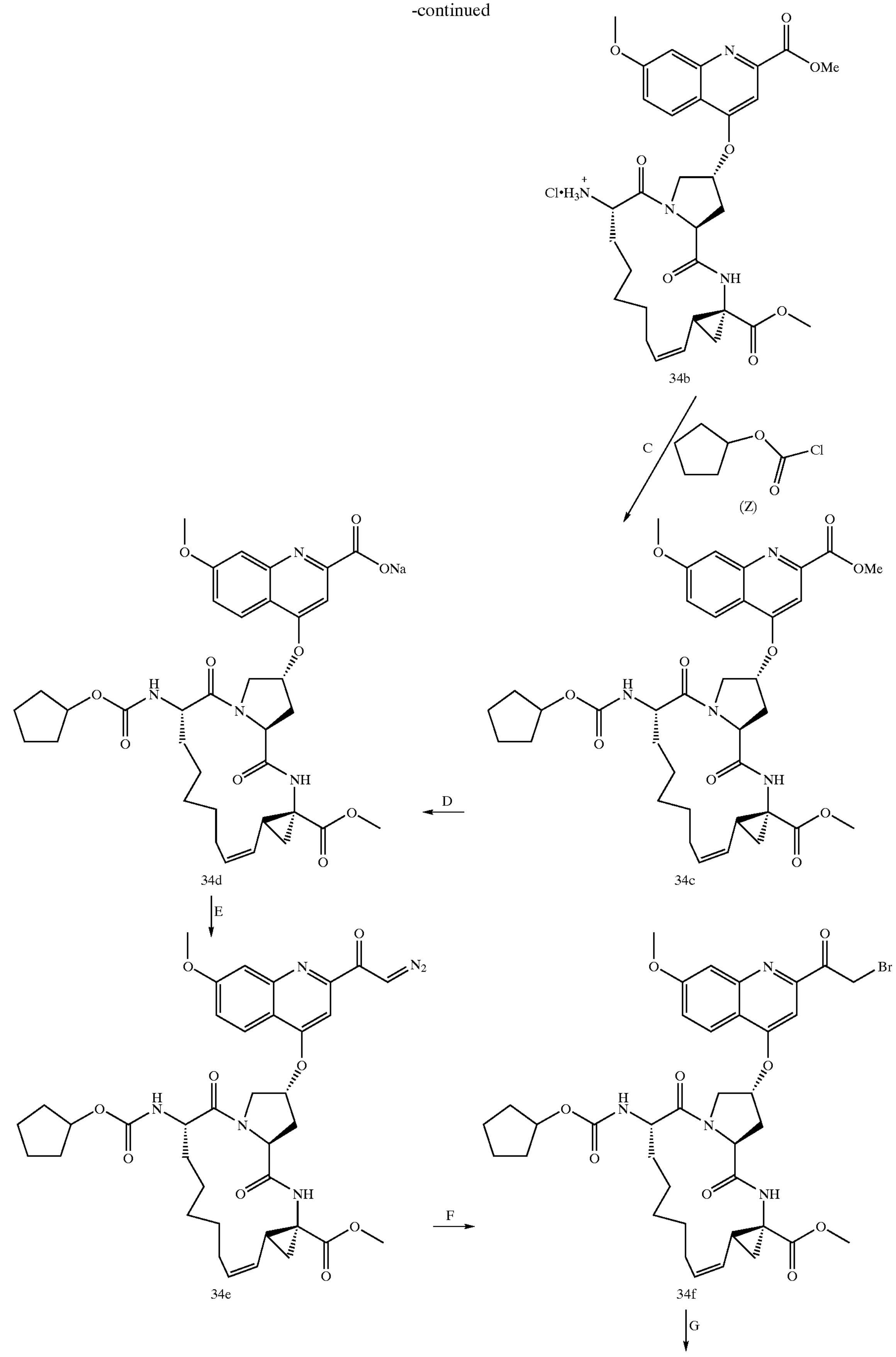
34b
34c
34d
34e
34f

-continued

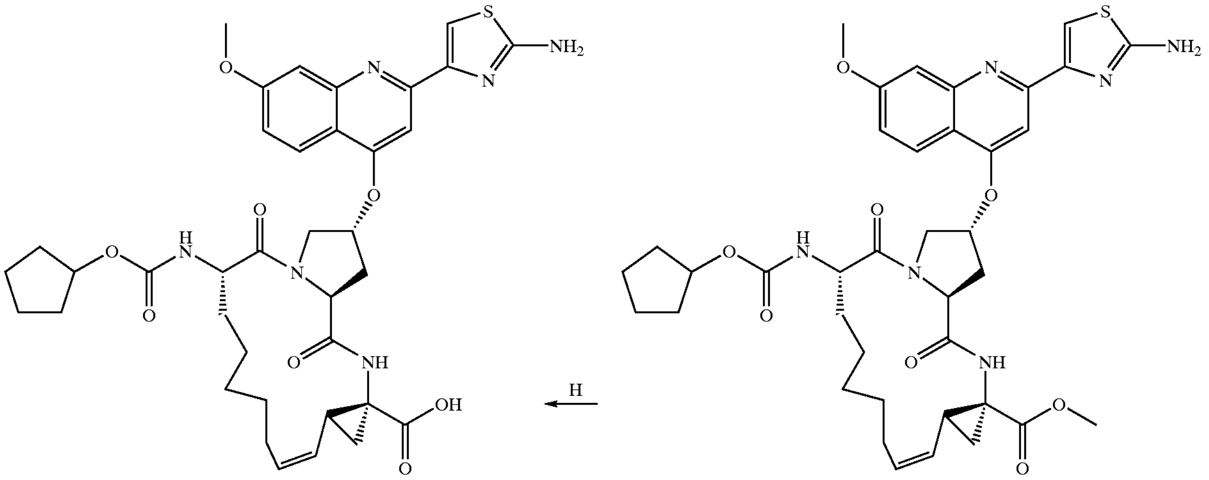

cpd # 812 34g

A. To a solution of the macrocyclic intermediate 23b (13.05 g 27.2 mmol, 1.0 eq.), $Ph_3P$ (14.28 g, 54.4 mmol, 2.0 eq) and 2-carboxymethoxy-4-hydroxy-7-methoxyquinoline (WO 00/09543 & WO 00/09558) (6.67 g, 28.6 mmol, 1.05 eq) in THF (450 mL) at 0° C., DIAD (10.75 mL, 54.6 mmol, 2.0 eq) was added dropwise over a period of 15 min. The ice bath was then removed and the reaction mixture was stirred at RT for 3 h. After the complete conversion of starting material to products, the solvent was evaporated under vacuum, the remaining mixture diluted with EtOAc, washed with saturated $NaHCO_3$ (2) and brine (1×), the organic layer was dried over anhydrous $MgSO_4$, filtered and evaporated to dryness. Pure compound 34a was obtained after flash column chromatography; the column was eluted first with hexane/EtOAc (50:50), followed by $CHCl_3$/EtOAc (95:5) to remove $Ph_3PO$ and DIAD byproducts and elution of the impurities was monitored by TLC. Finally, the desired product 34a was eluted from the column with $CHCl_3$/EtOAc (70:30). Usually, the chromatography step had to be repeated 2–3 times before compound 34a could be isolated in high purity as a white solid with an overall yield of 68% (12.8 g, 99.5% pure by HPLC).

B. To a solution of the Boc-protected intermediate 34a (1.567g) in $CH_2Cl_2$ (15 mL), 4N HCl in dioxane (12 mL) was added and the reaction mixture was stirred at RT for 1 h. [In the event that a thick gel would form half way through the reaction period, an additional 10 mL $CH_2Cl_2$ was added.] Upon completion of the deprotection the solvents were evaporate to dryness to obtain a yellow solid and a paste like material. The mixture was redissolved in approximately 5% MeOH in $CH_2Cl_2$ and re-evaporated to dryness under vacuum to obtain compound 34b as a yellow solid, which was used in the next step without any purification.

C. To a solution of cyclopentanol (614 μL, 6.76 mmol) in THF (15 mL), a solution of phosgene in toluene (1.93 M, 5.96 mL, 11.502 mmol) was added dropwise and the mixture was stirred at R.T. for 2 h to form the cyclopentyl chloroformate reagent (z). After that period, approximately half of the solvent was removed by evaporation under vacuum, the remaining light yellow solution was diluted by the addition of $CH_2Cl_2$ (5 mL) and concentrated to half of its original volume, in order to assure the removal of all excess phosgene. The above solution of the cyclopentyl chloroformate reagent was further diluted with THF (15 mL) and added to the amine-2HCl salt 34b. The mixture was cooled to 0° C. in an ice bath, the pH was adjusted to ~8.5–9 with the addition of $Et_3N$ (added dropwise) and the reaction mixture was stirred at 0° C. for 1 h. After that period, the mixture was diluted with EtOAc, washed with water (1×), saturated $NaHCO_3$ (2×), $H_2O$ (2×) and brine (1×). The organic layer was dried over anhydrous $MgSO_4$, filtered and evaporated under vacuum to obtain a yellow-amber foam. Compound 34c was obtained as a white foam after purification by flash column chromatography (using a solvent gradient from 30% hexane to 20% hexane in EtOAc as the eluent) in 80% yield (1.27 g) and >93% purity.

D. The dimethyl ester 34c (1.17g) was dissolved in a mixture of THF/MeOH/$H_2O$ (20 mL, 2:1:1 ratio), and an aqueous solution of NaOH (1.8 mL, 1N, 1 eq.) was added. The reaction mixture was stirred at RT for 1 h before it was evaporated to dryness to obtain the sodium salt 34d as a white solid (~1.66 mmol). Compound 34d was used in the next step without purification.

E. The crude sodium salt 34d (1.66 mmol) was dissolved in THF (17 mL), $Et_3N$ was added and the mixture was cooled to 0° C. in an ice bath. Isobutylchloroformate (322 μl, 2.5 mmol) was added dropwise and the mixture was stirred at 0° C. for 75 min. After that period, diazomethane (15 mL) was added and stirring was continued at 0° C. for 30 min and then at RT for an additional 1 h. Most of the solvent was evaporated to dryness under vacuum, the remaining mixture was diluted with EtOAc, washed with saturated $NaHCO_3$ (2×), $H_2O$ (2×) and brine (1×), dried over anhydrous $MgSO_4$, filtered and evaporated to dryness to obtain compound 34e as a light yellow foam (1.2g, ~1.66 mmol). The diazoketone intermediate 34e was used in the next step without purification.

F. The diazoketone 34e (1.2g, 1.66 mmol) dissolved in THF (17 mL) was cooled to 0° C. in an ice bath. A solution of aqueous HBr (48%, 1.24 mL) was added dropwise and the reaction mixture was stirred at 0° C. for 1 h. The mixture was then diluted with EtOAc, wash with saturated $NaHCO_3$ (2×), $H_2O$ (2×) and brine (1×), the organic layer was dried over anhydrous $MgSO_4$, filtered and evaporated to dryness to obtain the β-bromoketone intermediate 34f as a light yellow foam (~1.657 mmol).

G. To a solution of the bromoketone 34f (600 mg,0.779 mmol) in isopropanol (5 mL), thiourea (118 mg, 1.55 mmol) was added and the reaction mixture was placed in a pre-heated oil bath at 75° C. where it was allowed to stir for 1 hr. The isopropanol was then removed under vacuum and the product dissolved in EtOAc (100 mL). The solution was washed with saturated $NaHCO_3$ and brine, the organic layer was dried over anhydrous $Na_2SO_4$, filtered and evaporated to afford the crude product 34g (522 mg) as a red-brown solid. This material was used in the final step without any further purification.

H. The crude methyl ester 34g (122 mg, 0.163 mmol) was dissolved in a solution of $THF/MeOH/H_2O$ (2:1:1 ratio, 4 mL) and saponified using $LiOH.H_2O$ (89 mg, 2.14 mmol). The hydrolysis reaction was carried out over a 12–15 h period at RT. The solvents were then removed under vacuum and the crude product purified by C18 reversed phase HPLC, using a solvent gradient from 10% $CH_3CN$ in $H_2O$ to 100% $CH_3CN$, to afford the HCV protease inhibitor #812 as a yellow solid (24 mg, 20% overall yield for the conversion of intermediate 34f to inhibitor #812).

$^1H$ NMR (400 MHz, DMSO-$d_6$) δ 8.63 (s, 1H), 8.26–8.15 (m, 2H), 7.79 (bs, 1H), 7.72 (bs, 1H), 7.50 (bs, 2H), 7.33–7.25 (m, 2H), 5.77 (bs, 1H), 5.52 (dd, J=8.3 Hz, 1H), 5.27 (dd, J=9.2 Hz, 1H), 4.64 (d, J=10.8 Hz, 1H), 4.50 (dd, J=8.3 Hz, 1H), 4.39–4.31 (m, 1H), 4.08–3.99 (m, 2H), 3.94 (s, 3H), 3.87 (d, J=9.5 Hz, 2H), 2.65–2.53 (m, 2H), 2.46–2.36 (m, 2H), 2.20–2.12 (dd, J=8.6 Hz, 1H), 1.80–1.64 (m, 2H), 1.63–1.06 (m, 14H). MS; es$^+$: 733.2 $(M+H)^+$, es$^-$: 731.2 $(M-H)^-$.

Example 34A

Using the same procedure as described in example 34 but reacting bromoketone 34f with commercially available N-methylthiourea gave #811 (Table 8)

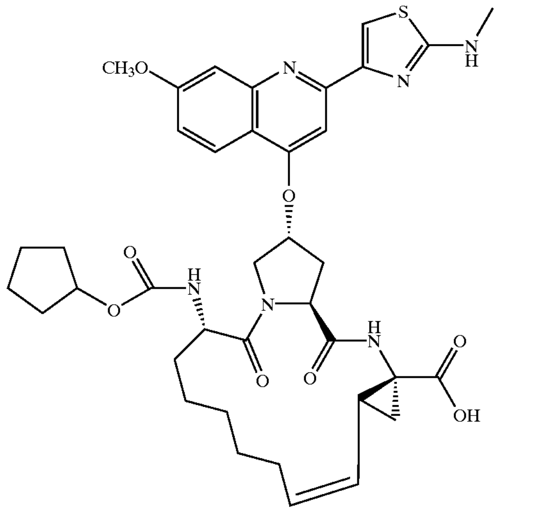

$^1H$ NMR (400 MHz, DMSO-$d_6$): δ 8.63 (s, 1H), 8.20 (s, 1H), 8.18 (s, 1H), 8.12–7.93 (m, 1H), 7.88–7.69 (m, 2H), 7.32–7.24 (m, 2H), 5.82–5.75 (m, 1H), 5.52 (ddd, J=8.1 Hz, 1H), 5.28 (dd, J=9.9 Hz, 1H), 4.67–4.61 (m, 1H), 4.51 (dd, J=8.8 Hz, 1H), 4.44–4.37 (m, 1H), 4.08–4.00 (m, 1H), 3.96 (s, 3H), 3.89 (m, 1H), 3.04 (d, J=4.1 Hz, 3H), 2.65–2.37 (m, 3H), 2.16 (m, 1H), 1.77–1.65 (m, 2H), 1.63–1.11 (m, 17H). MS; es$^+$: 747.2 $(M+H)^+$, es$^-$: 745.3 $(M-H)^-$.

Example 34B

Using the same procedure as described in example 34 but reacting bromoketone 34f with commercially available N-ethylthiourea gave #810 (Table 8)

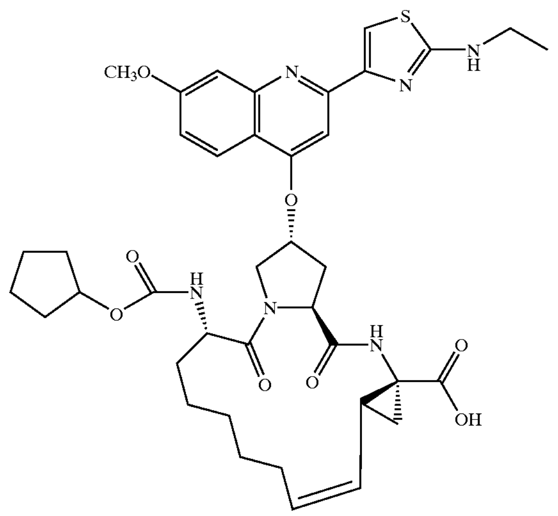

$^1H$ NMR (400 MHz, DMSO-$d_6$): δ 8.63 (s, 1H), 8.27 (bs, 1H), 8.20 (d, J=9.0 Hz, 1H), 8.13–8.07 (m, 1H), 7.86 (bs, 1H), 7.78 (s, 1H), 7.33–7.25 (m, 2H), 5.81 (bs, 1H), 5.54 (dd, J=8.8 Hz, 1H), 5.28 (dd, J=9.7 Hz, 1H), 4.65 (d, J=12.4 Hz, 1H), 4.51 (dd, J=8.8 Hz, 1H), 4.38 (bs, 1H), 4.03 (m, 1H), 3.97 (s, 3H), 3.92–3.87 (m, 1H), 3.54–3.46 (m, 2H), 2.68–2.65 (m, 2H), 2.47–2.38 (m, 1H), 2.15 (dd, J=8.6 Hz, 1H), 1.78–1.65 (m, 2H), 1.60–1.12 (m, 17H), 1.25 (t, J=7.3Hz, 3H). MS; es$^+$: 783.2 $(M+Na)^+$, es$^-$: 761.2 $(M+H)^+$.

Example 34C

Using the same procedure as described in example 34 but reacting bromoketone 34f with commercially available N-iso-propylthiourea gave #822

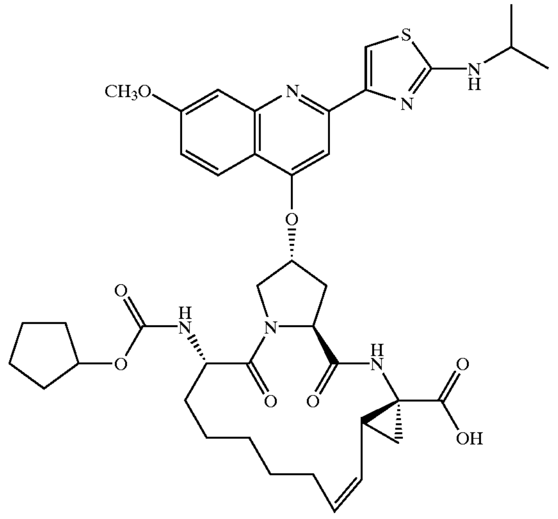

$^1H$ NMR (400 MHz, DMSO-$d_6$) δ 8.63 (s, 1H), 8.33–8.23 (bs, 1H), 8.21 (d, J=9.2 Hz, 1H), 8.04 (d, J=8.3 Hz, 1H), 7.86 (bs, 1H), 7.77 (s, 1H), 7.35–7.23 (m, 2H), 5.81 (bs, 1H), 5.52 (dd, J=8.5 Hz, 1H), 5.27 (dd, J=9.2 Hz, 1H), 4.65 (d, J=11.8

Hz, 1H), 4.51 (dd, J=7.6 Hz, 1H), 4.37 (bs, 1H), 4.15 (bs, 1H), 4.07–3.98 (m, 2H), 3.97 (s, 3H), 3.88 (d, J=8.9 Hz, 1H), 2.60–2.53 (m, 2H), 2.47–2.37 (m, 2H), 2.19–2.10 (dd, J=9.2 Hz, 1H), 180–1.64 (m, 2H), 1.63–1.29 (m, 13H), 1.27 and 1.25 (2×d, J=6.5 Hz, 6H), 1.23–1.09 (m, 2H). MS; es$^{30}$ : 775.0 $(M+H)^+$, $es^-$: 772.9 $(M-H)^-$.

Example 34E

To a stirred solution of the 2-amino-4-thiazolyl intermediate 34g (0.24 g, 0.32 mmol) in $CH_2Cl_2$ (5 mL) at RT was added DIPEA (0.55 mL, 3.18 mmol, 10 eq) and methyl chloroformate (0.13 mL, 1.6 mmol, 5 eq). The reaction mixture was stirred for 6.5 h before being concentrated under vacuum. The crude isolated material was then hydrolyzed to the desired carboxylic acid as described in Example 34 to yield compound #818

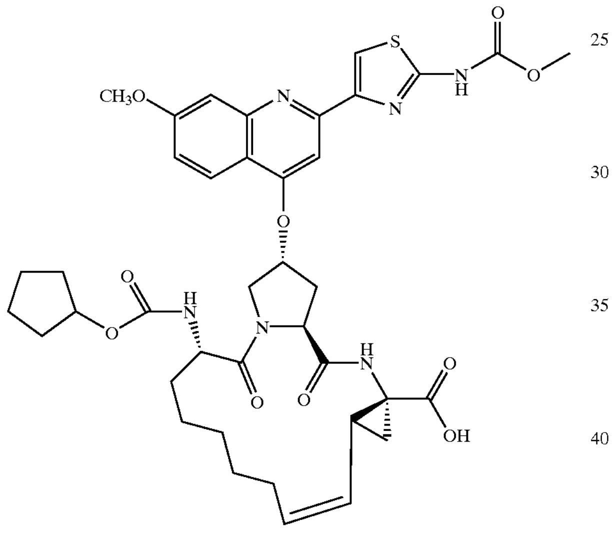

$^1H$ NMR (400 MHz, DMSO-$d_6$): δ 8.61 (s, 1H), 8.21–8.07 (m, 2H), 7.61–7.38 (m, 2H), 7.26 (d, J=6.4 Hz, 1H), 7.19–7.10 (m, 1H), 5.60–5.47 (m, 2H), 5.27 (dd, J=9.2 Hz, 1H), 4.63–4.53 (m, 1H), 4.47 (d, J=7.9 Hz, 1H), 4.13–4.04 (m, 1H), 3.93 (s, 3H), 3.92–3.87 (m, 2H), 3.79 (s, 3H), 2.42–2.30 (m, 2H), 2.17 (dd, J=9.2 Hz, 1H), 1.81–1.68 (m, 2H), 1.63–1.29 (m, 16H), 1.23–1.10 (m, 2H). MS; $es^+$: 791.1 $(M+H)^+$, $es^-$: 789.1 $(M-H)^-$.

Example 34F

Following the conditions described above in example 34E, but using isobutyl chloroformate, gave the analogous substituted carbamate intermediate. The crude isolated material was then hydrolyzed to the desired compound #819

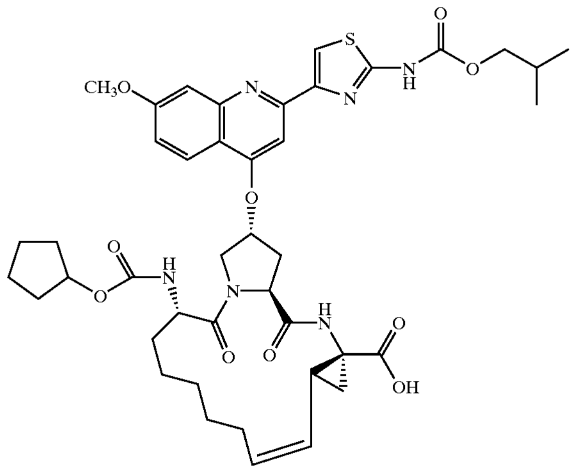

1H NMR (400 MHz, DMSO-$d_6$): δ 8.62 (s, 1H), 8.47–8.27 (bs, 1H), 8.18 (d, J=8.6 Hz, 1H), 7.69–7.60 (m, 1H), 7.60–7.51 (m, 1H), 7.28 (d, J=6.7 Hz, 1H), 7.28–7.19 (m, 1H), 5.70–5.60 (m, 1H), 5.52 (dd, J=8.3 Hz, 1H), 5.27 (dd, J=9.8 Hz, 1H), 4.63 9d, J=11.8 Hz, 1H), 4.53–4.44 (m, 2H), 4.10–3.99 (m, 1H), 4.04 (d, J=6.7 Hz, 2H), 3.95 (s, 3H), 3.94–3.87 (m, 1H), 2.65–2.53 (m, 1H), 2.46–2.34 (m, 1H), 2.16 (dd, J=8.1 Hz, 1H), 2.03–1.91 (m, 1H), 1.79–1.09 (m, 20H), 0.95 (d, J=6.7 Hz, 6H). MS; $es^+$: 833.2 $(M+H)^+$, $es^-$: 831.2 $(M-H)^-$.

Example 35

Synthesis of Compound #908

Starting with derivative 27a and using the same chemistry as described in example 34, the following saturated macrocycle, compound #908 (Table 9) was obtained.

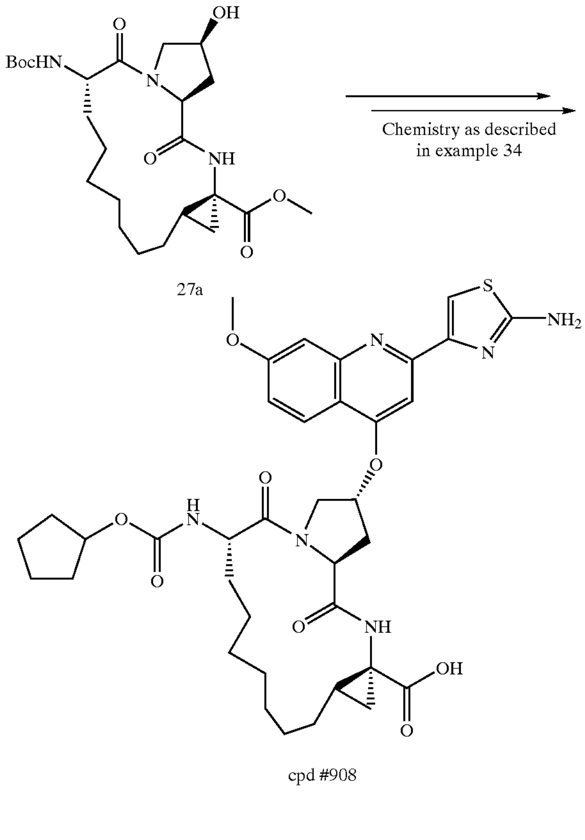

27a cpd #908

$^1$H NMR (400 MHz, DMSO-$d_6$): δ 8.47 (s, 1H), 8.16 (d, J=10 Hz, 1H), 8.15–8.07 (m, 1H), 7.82–7.63 (m, 2H), 7.53–7.43 (m, 2H), 7.33–7.22 (m, 1H), 7.13 (d, J=7 Hz, 1H), 5.77–5.65 (m, 1H), 4.62–4.52 (m, 2H), 4.50–4.4 (m, 1H), 4.20–4.10 (m, 1H), 3.94 (s, 3H), 3.89–3.83 (m, 1H), 2.59–2.53 (m, 1H), 2.48–2.40 (m, 1H), 1.79–1.0 (m, 25H);). MS; es$^+$: 735.2 $(M+H)^+$, es$^-$: 733.2 $(M-H)^-$.

Example 35A

Synthesis of Compound #909

Using the same procedure as described in example 35 but using available N-acetylthiourea gave compound #909 (Table 9).

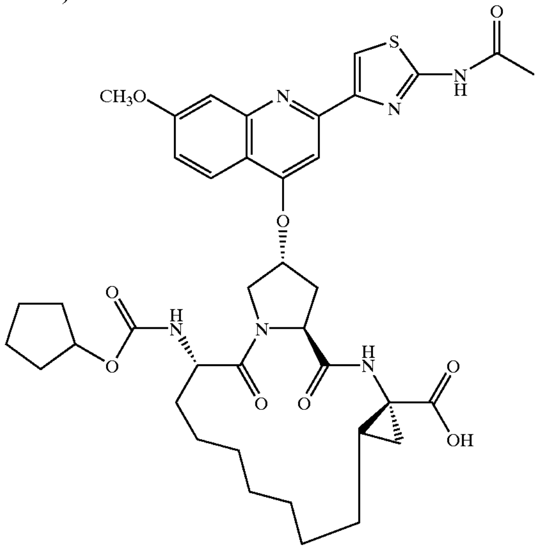

$^1$H NMR (400 MHz, DMSO-$d_6$): δ 8.53–8.41 (m, 2H), 8.20 (d, J=9.2 Hz, 1H), 7.68 (bs, 1H), 7.68 (bs, 1H), 7.27 (dd, J=9.2 Hz, 1H), 7.15 (d, J=6.4 Hz,1H), 5.67 (bs, 1H), 4.65–4.50 (m, 3H), 4.44–4.37 (m, 1H), 4.21–4.13 (m, 1H), 3.96 (s, 3H), 3.99–3.86 (m, 1H), 2.62–2.39 (m, 2H), 2.24 (s, 3H), 1.78–1.67 (m, 3H), 1.67–1.01 (m, 22H). MS; es$^+$: 798.0 $(M+Na)^+$, es$^-$: 777.0 $(M+H)^+$.

Example 35B

Synthesis of Compound #910

Using the same procedure as described in example 35 but using available N-ethylthiourea gave compound #910 (Table 9).

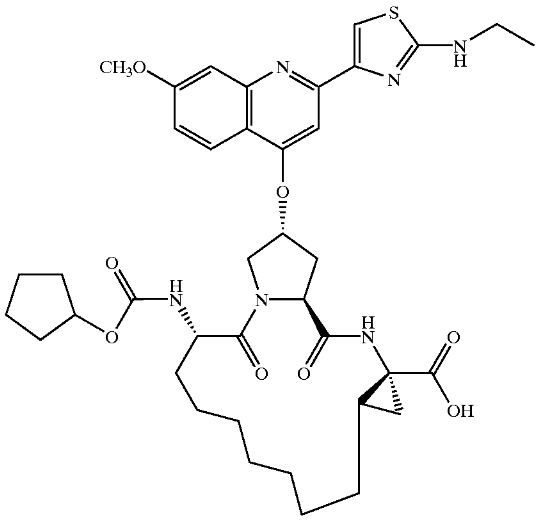

$^1$H NMR (400 MHz, DMSO-$d_6$): δ 8.47 (s, 1H), 8.29 (bs, 1H), 8.20 (d, J=9.2 Hz, 1H), 8.09 (bs, 1H), 7.87 (s, 1H), 7.77 (s, 1H), 7.32 (dd, J=9.2 Hz, 1H), 7.14 (dd, J=6.7 Hz, 1H), 5.78 (bs, 1H), 4.58 (dd, J=8.1 Hz, 2H), 4.43 (bs, 1H), 4.18–4.12 (m, 1H), 3.97 (s, 3H), 3.87 (d, J=8.9 Hz, 1H), 3.55–3.46 (m, 2H), 2.63–2.53 (m, 1H), 2.47–2.41 (m, 1H), 1.78–1.00 (m, 25H), 1.25 (t, J=7.3 Hz, 3H).). MS; es$^+$: 763.1 $(M+H)^+$, es$^-$: 761.1 $(M-H)^-$.

Example 35C

Synthesis of Compound #911

Using the same procedure as described in example 35 but using available N-iso-propylthiourea gave compound #911 (Table 9).

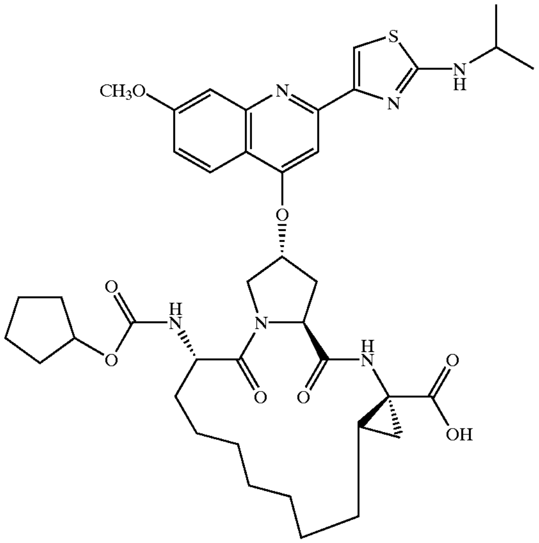

$^1$H NMR (400 MHz, DMSO-$d_6$): δ 8.47 (s, 1H), 8.29–8.19 (m, 1H), 8.19 (d, J=9.2 Hz, 1H), 8.09–8.0 (m, 1H), 7.83 (bs, 1H), 7.74 (bs, 1H), 7.31 (d, J=8 Hz, 1H), 7.14 (d, J=6.4 Hz, 1H), 5.76 (bs, 1H), 4.64–4.53 (m, 2H), 4.44 (bs, 1H), 4.22–4.09 (m, 3H), 3.97 (s, 3H), 3.87 (d, J=8.6 Hz, 1H), 2.63–2.58 (m, 1H), 2.46–2.41 (m, 1H), 1.79–1.10 (m, 24H), 1.27 and 1.26 (2×d, J=6.5 Hz, 6H). MS; es$^+$: 777.0 $(M+H)^+$, es$^-$: 775.0 $(M-H)^-$.

Example 36

Synthesis of compound #716

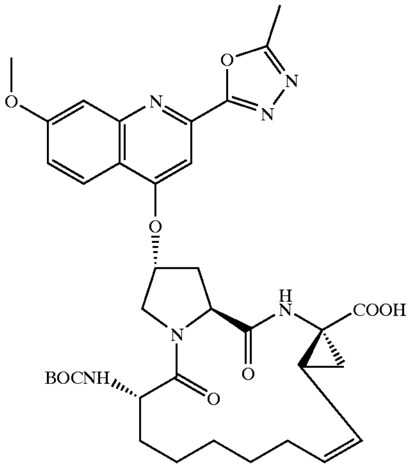

$^1$H NMR (400 MHz, DMSO-$d_6$): δ (ppm): 8.62 (s, 1H), 8.13 (d, J=9.2 Hz, 1H), 7.64–7.54 (m, 2H), 7.47 (d, J=2.6 Hz, 1H), 7.16 (dd, J=9.2, 2.2 Hz, 1H), 7.03 (d, J=6.0 Hz, 1H), 5.63 (s, 1H), 5.52 (q, J=9.9 Hz, 1H), 5.26 (t, J=8.9 Hz, 1H),4.62 (d, J=11.45, 1H), 4.45 (dd, J=9.2, 8.27 Hz, 1H), 4.02 (m, 1H) 3.93 (s, 3H), 3.7 (dd, J=7.6, 1.0 Hz, 1H), 2.66 (s, 3H), 2.55–2.65 (m, 1H), 2.35–2.45 (m, 1H), 2.17 (q, J=8.6 Hz, 1H), 1.65–1.75 (m, 2H), 1.5–1.35 (m, 7H), 1.15 (s, 9H).

MS: 705. (M+1), 703 (M−1)

Example 37

Synthesis of Compound #717

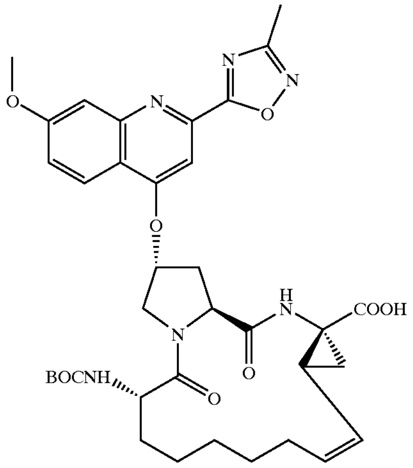

$^1$H NMR (400 MHz, DMSO-$d_6$): δ (ppm): 8.62 (s, 1H), 8.15 (d, J=8.9 Hz, 1H), 7.62 (s, 1H), 7.49 (s, 1H), 7.19 (dd, J=9.2, 2.2 Hz, 1H), 7.02 (d, J=5.4 Hz, 1H), 5.64 (s, 1H), 5.52 (q, J=9.9 Hz, 1H), 5.26 (t, J=9.2 Hz, 1H),4.63 (d, J=11.44, 1H), 4.45 (t, J=9.2 Hz, 1H), 3.94 (s, 3H), 3.9–3.8 (m, 1H),2.7–2.55 (m, 1H), 2.4–2.3 (m, 1H), 2.18 (q, J=8.9 Hz, 1H), 1.75–1.65 (m, 2H), 1.5–1.2 (m, 7H), 1.14 (s, 9H).

MS: 705. (M+1), 703 (M−1).

Example 38

Synthesis of Compound #718

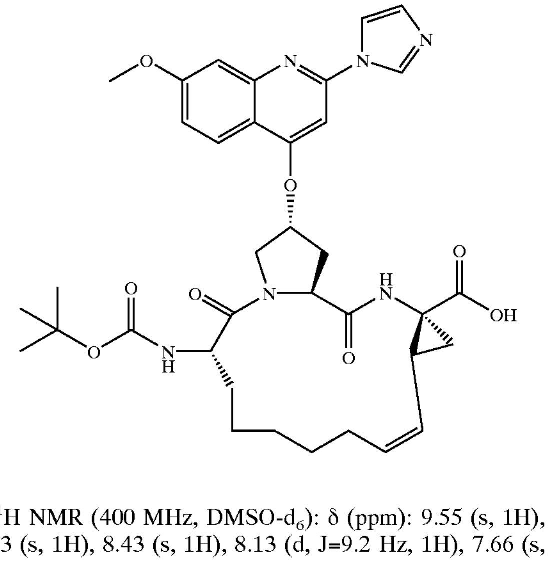

$^1$H NMR (400 MHz, DMSO-$d_6$): δ (ppm): 9.55 (s, 1H), 8.63 (s, 1H), 8.43 (s, 1H), 8.13 (d, J=9.2 Hz, 1H), 7.66 (s, 1H), 7.46 (s, 1H), 7.32 (d, J=2.6 Hz, 1H), 7.10–7.07 (m, 2H), 5.64–5.54 (m, 1H), 5.59–5.48 (m, 1H), 5.33–5.23 (m, 1H), 4.73–4.61 (m, 1H), 4.45 (dd, J=7.5, 9.1 Hz, 1H), 4.09–4.00 (m, 1H), 3.92 (s, 3H), 3.93–3.83 (m, 1H), 2.67–2.55 (m, 2H), 2.53–2.43 (m, 1H), 2.42–2.31 (m, 1H), 2.23–2.12 (m,1H), 1.81–1.66 (m, 2H), 1.52–1.42 (m, 2H), 1.42–1.25 (m, 6H), 1.21 (s, 9H).

MS: 689.3 (M+1), 687.3 (M−1)

Example 39

Synthesis of Compound #722

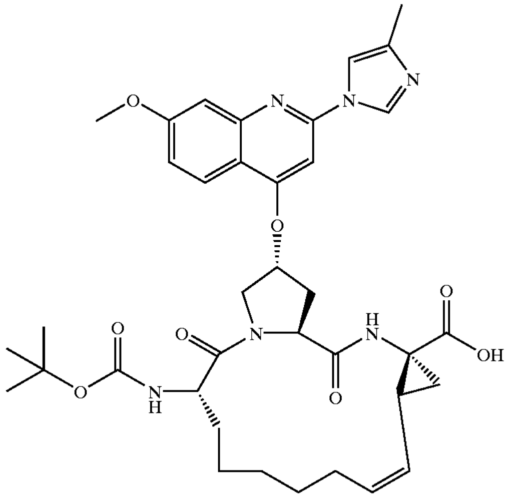

$^1$H NMR (400 MHz, DMSO-$d_6$): δ (ppm): 9.70 (s, 1H), 8.64 (s, 1H), 8.26 (s, 1H), 8.14 (d, J=9.2 Hz, 1H), 7.45 (s, 1H), 7.30 (d, J=2.5 Hz, 1H), 7.14–7.06 (m, 2H), 5.60–5.54 (m, 1H), 5.58–5.48 (m, 1H), 5.31–5.23 (m, 1H), 4.71–4.62 (m, 1H), 4.49–4.40 (m, 1H), 4.08–3.99 (m, 1H), 3.92 (s, 3H), 3.92–3.84 (m, 1H), 2.69–2.54 (m, 2H), 2.53–2.46 (m, 1H), 2.42–2.31 (m, 1H), 2.37 (s, 3H), 2.22–2.13 (m, 1H), 1.81–1.64 (m, 2H), 1.54–1.42 (m, 2H), 1.42–1.27 (m, 6H), 1.22 (s, 9H).

MS: 703.3 (M+1), 701.3 (M−1)

Example 40

Synthesis of Compound #733

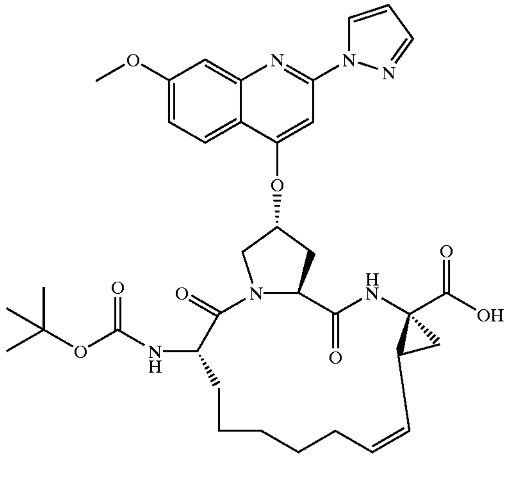

$^1$H NMR (400 MHz, DMSO-$d_6$): δ (ppm): 8.75 (m, 1H), 8.62 (s, 1H), 8.06 (d, J=9.2 Hz, 1H), 7.88–7.87 (m, 1H), 7.48 (s, 1H), 7.28 (d, J=2.6Hz, 1H), 7.05–7.00 (m, 2H), 6.64–6.63 (m, 1H), 5.62–5.58 (m, 1H), 5.55–5.49 (m, 1H), 5.28–5.24 (m, 1H), 4.64–4.61 (m, 1H), 4.48–4.44 (m, 1H), 4.07–4.03 (m, 1H), 3.91 (s, 3H), 3.92–3.85 (m, 1H), 2.67–2.54 (m, 2H),2.53–2.45 (m, 1H), 2.41–2.34 (m, 1H), 2.20–2.14 (m, 1H), 1.75–1.69 (m, 2H), 1.50–1.43 (m, 2H), 1.41–1.32 (m, 6H), 1.17 (s, 9H).

MS: 689.3 (M+1), 687.2 (M−1)

Example 41

Synthesis of Compound #703

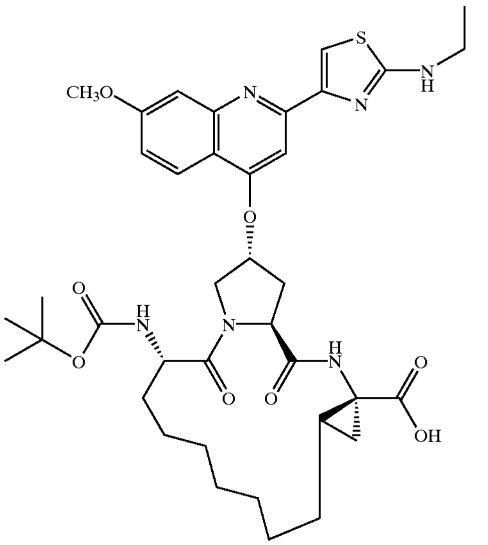

$^1$H NMR (400 MHz, DMSO-$d_6$): δ 8.50 (s, 1H), 8.19 (s, 1H), 8.17 (s, 1H), 8.11–8.00 (m, 1H), 7.88–7.77 (m, 1H), 7.73 (s, 1H), 7.25 (d, J=8.6 Hz, 1H), 6.93 (d, J=6 Hz, 1H), 5.89–5.68 (m, 1H), 4.62 (d, J=11 Hz, 1H), 4.53 (dd, J=8.3 Hz, 1H), 4.16–4.07 (m, 1H), 3.96 (s, 3H), 3.88 (bd, J=9.5 Hz, 1H), 3.53–3.43 (m, 2H), 2.63–2.51 (m, 1H), 2.46–2.36 (m, 1H), 1.81–1.62 (m, 2H), 1.60–1.01 (m, 15H), 1.24 (t, J=7.4 Hz, 3H), 1.17 (s, 9H),

MS; $es^+$: 751.1$(M+H)^+$, $es^-$: 749.1–$(M-H)^-$.

Example 42

Synthesis of Compound #734

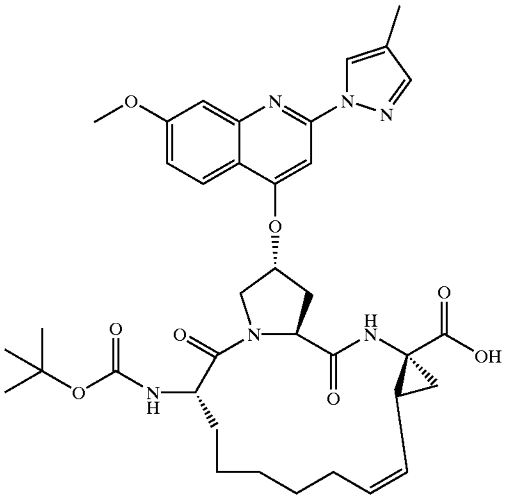

$^1$H NMR (400 MHz, DMSO-$d_6$): δ (ppm): 8.62 (s, 1H), 8.54 (s, 1H), 8.04 (d, J=9.2 Hz, 1H), 7.70 (s, 1H), 7.43 (s, 1H), 7.24 (d, J=2.6Hz, 1H), 7.05–6.98 (m, 2H), 5.57–5.54 (m, 1H), 5.55–5.48 (m, 1H), 5.28–5.24 (m, 1H), 4.63–4.59 (m, 1H), 4.47–4.43 (m, 1H), 4.13–3.99 (m, 1H), 3.90 (s, 3H), 3.92–3.83 (m, 1H), 2.67–2.55 (m, 2H), 2.53–2.46 (m, 1H), 2.43–2.31 (m, 1H), 2.22–2.15 (m, 1H), 2.15 (3H), 1.75–1.70 (m, 2H), 1.51–1.42 (m, 2H), 1.41–1.28 (m, 6H), 1.17 (s, 9H).

MS: 703.2 (M+1), 701.3 (M−1)

Example 43

Synthesis of Compound #738

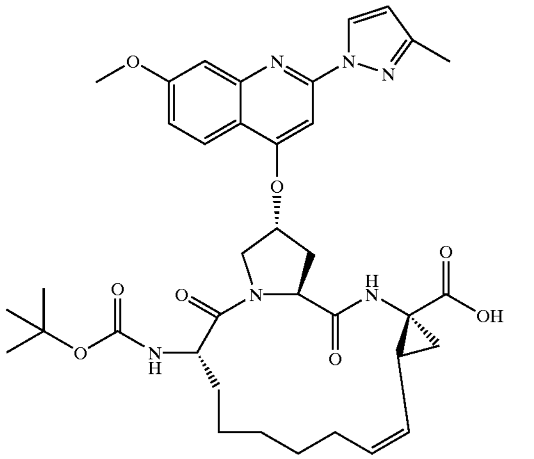

$^1$H NMR (400 MHz, DMSO-$d_6$): δ (ppm): 8.64 (d, J=2.5 Hz, 1H), 8.62 (s, 1H), 8.04 (d, J=9.2 Hz, 1H), 7.39 (s, 1H), 7.24 (d, J=2.5 Hz, 1H), 7.04 (d, J=6.0 Hz, 1H), 6.99 (dd, J=2.2, 9.2 Hz, 1H), 6.43 (d, J=2.2 Hz, 1H), 5.62–5.57 (m, 1H), 5.56–5.47 (m, 1H), 5.31–5.22 (m, 1H), 4.65–4.56 (m, 1H), 4.45 (dd, J=7.6, 8.9 Hz, 1H), 4.07–4.00 (m, 1H), 3.90 (s, 3H), 3.88–3.84 (m, 1H), 2.68–2.56 (m, 2H), 2.54–2.43 (m, 1H), 2.42–2.31 (m, 1H), 2.34 (s, 3H), 2.24–2.14 (m, 1H), 1.80–1.64 (m, 2H), 1.52–1.43 (m, 2H), 1.43–1.27 (m, 6H), 1.18 (s, 9H).

MS: 703.2 (M+1), 701.2 (M−1)

Example 44

Synthesis of Compound #725

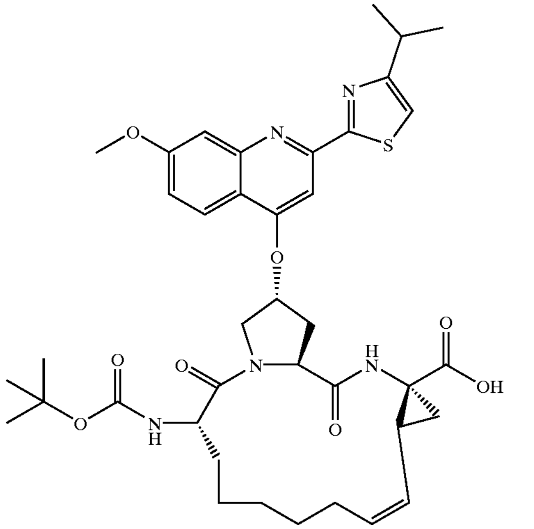

$^1$H NMR (400 MHz, DMSO-$d_6$): δ (ppm): 8.62 (s, 1H), 8.10 (d, J=9.2 Hz, 1H), 7.57 (s, 1H), 7.49 (s, 1H), 7.35 (d, J=2.2 Hz, 1H), 7.09–7.03 (m, 2H), 5.65–5.61 (m, 1H), 5.55–5.49 (m, 1H), 5.28–5.24 (m, 1H), 4.62–4.57 (m, 1H), 4.49–4.45 (m, 1H), 4.08–4.01 (m, 1H), 3.93 (s, 3H), 3.92–3.86 (m, 1H), 3.20–3.14 (m, 1H), 2.65–2.56 (s, 1H), 2.53–2.47 (m, 1H) 2.42–2.35 (m, 1H), 2.22–2.15 (m, 1H), 1.79–1.68 (m, 2H), 1.50–1.43 (m, 2H), 1.41–1.28 (m, 12H), 1.18 (s, 9H).

MS: 748.2 (M+1), 746.2 (M−1)

Example 45

Synthesis of Compound #726

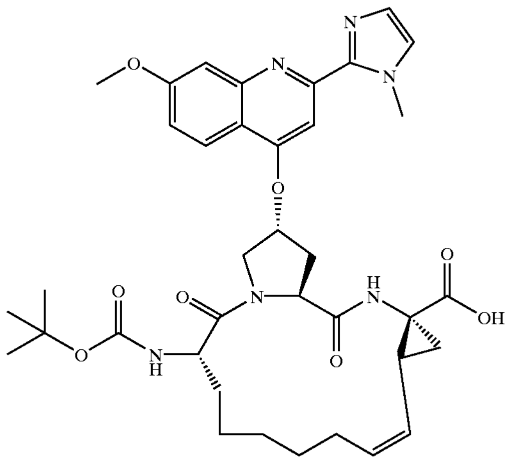

$^1$H N MR (400 M Hz, DMSO-$d_6$): δ (ppm): 8.64 (s, 1H), 8.10 (d, J=9.5 Hz, 1H), 7.83–7.76 (m, 2H), 7.60 (s, 1H), 7.44–7.42 (m, 1H), 7.18–7.01 (m, 2H), 5.56–5.49 (m, 2H), 5.29–5.24 (m, 1H), 4.66–4.63 (m, 1H), 4.47–4.42 (m, 1H), 4.28 (s, 3H), 4.06–4.02 (m, 2H), 3.94 (s, 3H), 3.93–3.86 (m, 1H), 2.66–2.55 (m, 2H), 2.42–2.31 (m,2H), 2.22–2.14 (m, 1H), 1.79–1.65 (m, 2H), 1.52–1.27 (m, 7H), 1.22 (s, 9H).

MS: 703.2 (M+1), 701.3 (M−1)

Example 46

Synthesis of Compound #906

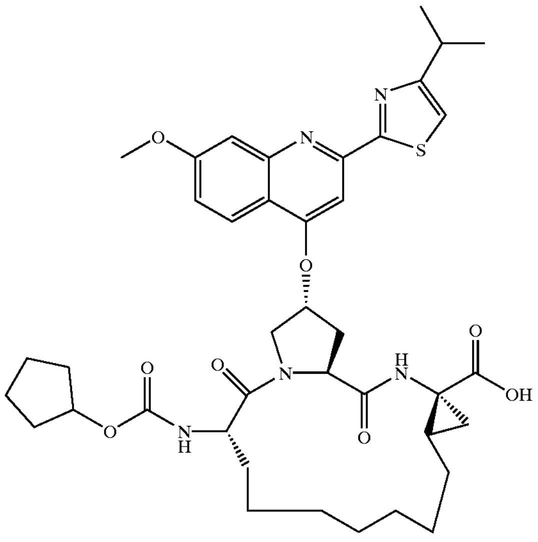

$^1$H NMR (400 MHz, DMSO-$d_6$): δ (ppm): 8.46 (s, 1H), 8.06 (d, J=9.2 Hz, 1H), 7.57 (s, 1H), 7.49 (s, 1H), 7.34 (m, 1H), 7.14–7.05 (m, 2H), 5.63–5.58 (m, 1H), 4.66–4.61 (m, 1H), 4.54–4.44 (m, 2H),4.23–4.18 (m, 1H) 3.93 (s, 3H), 3.92–3.88 (m, 1H), 3.21–3.14 (m, 1H), 2.44–2.33 (m, 1H), 1.35 (d, J=7Hz, 6H), 1.73–1.01 (m, 26H)

MS: 762.0 (M+1), 759.9 (M−1)

Example 47

Synthesis of Compound #907

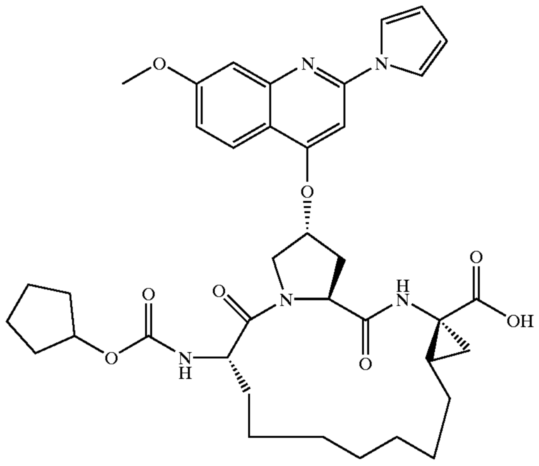

$^1$H NMR (400 MHz, DMSO-$d_6$): δ (ppm): 8.46 (s, 1H), 7.98 (d, J=8.9 Hz, 1H), 7.91–7.89 (m, 2H), 7.23–7.21 (m, 2H), 7.07–7.00 (m, 2H), 6.35–6.32 (m, 2H), 5.64–5.58 (m, 1H), 4.65–4.61 (m, 1H), 4.53–4.47 (m, 2H),4.24–4.19 (m, 1H) 3.90 (s, 3H), 3.86–3.84 (m, 1H), 2.40–2.33 (m, 1H), 1.73–1.01 (m, 26H).

MS: 702.0 (M+1), 699.9 (M−1)

Example 47A

Compound #825

Using the same procedure as described in Example 34 but, in step G, using N-cyclopropylthiourea gave compound #825.

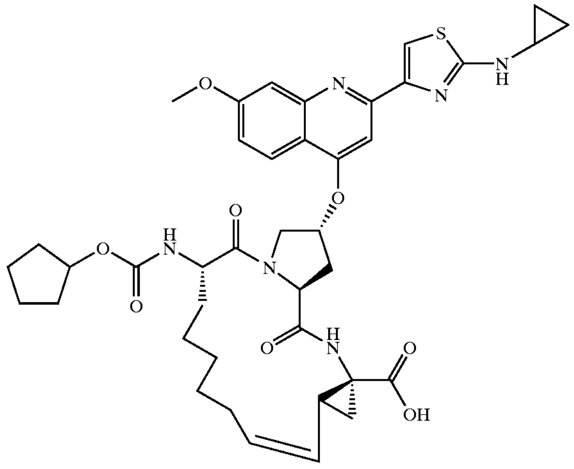

$^1$H NMR (400 MHz,DMSO-$d_6$): δ 8.55 (bs, 1H), 8.38 (bs, 1H), 8.02 (d, J=8.9 Hz, 1H), 7.53 (s, 1H), 7.42 (s, 1H), 7.28 (d, J=1.6 Hz, 1H), 7.12 (bs, 1H), 7.04 (d, J=8.3 Hz, 1H), 5.52–5.37 (m, 2H), 5.34 –5.13 (m, 1H), 4.75–4.64 (m, 1H), 4.41 (d, J=15.9, 8.9 Hz, 1H), 4.33–4.18 (m, 1H), 4.09–3.98 (m, 1H), 3.98–3.83 (m, 1H), 3.91 (s, 3H), 2.57–2.43 (m, 1H), 2.06 (s, 3H), 1.78–1.18 (m, 19H), 1.16–1.12 (m, 1H), 0.78–0.72 (m, 2H), 0.61–0.54 (m, 2H). MS; $es^+$: 773.4$(M+H)^+$, $es^-$: 771.5 $(M-H)^-$.

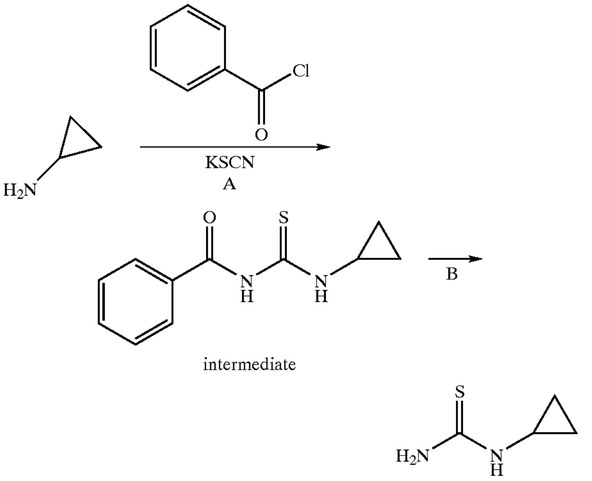

A: The KSCN was first pumped overnight under high vacuum prior to use. Then, to a solution of the KSCN (4.60 g; 47.33mmol) in acetone (35 mL), at 0 C., was added dropwise the benzoylchloride (5.0 mL; 43.03 mmol). The milky solution was stirred in an ice bath for 1.5 h, then, the cyclopropylamine (3.2 mL; 46.04 mmol) was added dropwise to the light yellow opaque mixture. The reaction mixture was stirred for 1.5 h at 0 C., then, another 500 μL cyclopropylamine (7.22 mmol) was added and the reaction mixture stirred at RT for 30 min. at which time the reaction was determined to be complete by HPLC. The reaction mixture was poured into ice/$H_2O$ (300 mL), stirred for 5 min. and the light yellow solid was filtered, washed several times with $H_2O$ and dried under vacuum to provide the intermediate (6.62 g).

B: The intermediate (6.62 g) was suspended in 2N NaOH (50 mL) and heated to reflux for 15 min. HPLC indicated the complete conversion of the intermediate to the product. The solution was cooled to RT, saturated with solid NaCl and extracted into EtOAc (3×). The combined EtOAc extracts were washed with $H_2O$ (2×) and brine (1×), dried ($MgSO_4$), filtered and evaporated to obtain the crude product as an off-white solid. The crude product was triturated in hexane/EtOAc 95/5 to provide the N-cyclopropyl thiourea as a white crystalline-like solid (2.5 g; 50% yield over 2 steps).

$^1$H NMR (400 MHz,DMSO-$d_6$): 7.92 (bs, 1H), 7.61 (bs, 1H), 7.13 (bs, 1H), 2.39 (bs, 1H), 0.67–0.63 (m, 2H), 0.51–0.44 (m, 2H). MS; $es^+$116.9 $(M+H)^+$, $es^-$: 114.8 $(M-H)^-$.

Example 47B

Synthesis of Compound #827

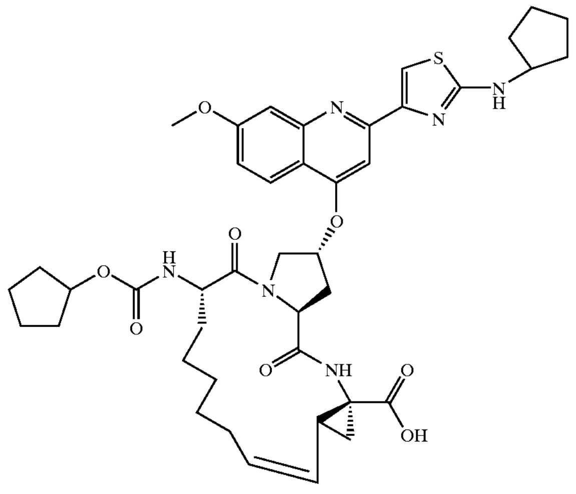

Using the same procedure as described in Example 34 up to and including step H, but in step G, using N-cyclopentylthiourea gave compound #827.

Synthesis of N-cyclopentylthiourea

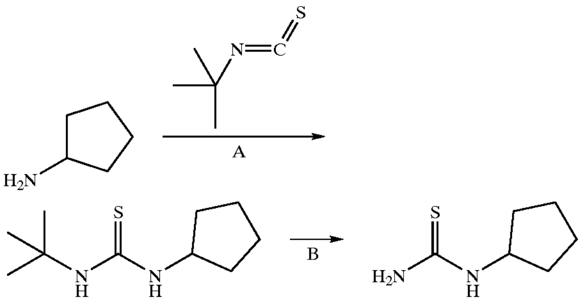

A: To a solution of t-butyl isothiocyanate (5.0 mL; 39.41 mmol) in $CH_2Cl_2$ (200 mL) was added cyclopentylamine (4.67 mL; 47.29 mmol) followed by DIEA and the reaction mixture was stirred at RT for 2 h. The mixture was diluted with EtOAc, washed with 10% citric acid (2×), saturated $NaHCO_3$ (2×), $H_2O$ (2×) and brine (1×). The organic layer was dried over anhydrous $MgSO_4$, filtered and evaporated to dryness to obtain the t-butyl-cyclopentylthiourea as a white solid (3.70 g; 47% yield).

B: The t-butyl-cyclopentylthiourea (3.70 g) was dissolved in concentrated HCl (46 mL). The dark yellow solution was set to a gentle reflux. After 40 min, the reaction mixture was allowed to cool. The volume was concentrated to approx. half under reduced pressure, cooled in ice and basified to pH 9.5 with solid and saturated $NaHCO_3$. The product was extracted into EtOAc (3×), the combined EtOAc extracts were washed with $H_2O$ (2×) and brine (1×). The organic layer was dried over anhydrous $MgSO_4$, filtered and evaporated to dryness to obtain the crude N-cyclopentylthiourea as a beige solid (2.46 g crude). Trituration of the crude material in hexane/EtOAc 95/5 provided, after filtration, the N-cyclopentylthiourea as a white solid (2.38; 90% yield).

$^1$H NMR (400 MHz,DMSO-$d_6$): 7.58 (bs, 1H), 7.19 (bs, 1H), 6.76 (bs, 1H), 4.34 (bs, 1H), 1.92–1.79 (m,2H), 1.66–1.55 (m, 2H), 1.55–1.30 (m,4H). MS; es$^+$144.9(M+H$^+$, es$^-$: 142.8 (M−H)$^-$.

(Na salt) $^1$H NMR (400 MHz,DMSO-$d_6$): δ 8.02 (d, J=9.2 Hz, 1H), 7.90 (d, J=6.4 Hz, 1H), 7.76 (s, 1H), 7.44 (bs, 2H), 7.27 (d, J=1.9 Hz, 1H), 7.11 (d, J=7.0 Hz, 1H), 7.03 (d, J=9.2 Hz, 1H), 5.48 (dd, J=18.4, 9.9 Hz, 1H), 5.43 (bs, 1H), 5.15 (dt, J=17.8, 7.63 Hz, 1H), 4.70 (bs, 1H), 4.49–4.34 (m, 2H), 4.34–4.25 (m, 1H), 4.13–4.03 (m, 1H), 3.99–3.86 (m,1H), 3.90 (s, 3H), 2.58–2.44 (m, 1H), 2.42–2.32 (m, 1H), 2.15–1.93 (m, 4H), 1.83–1.14 (m, 24H), 1.14–1.12 (m, 1H). MS; es$^+$: 801.4(M+H)$^+$, es$^-$: 799.3 (M−H)$^-$.

Example 47C

Compound #826

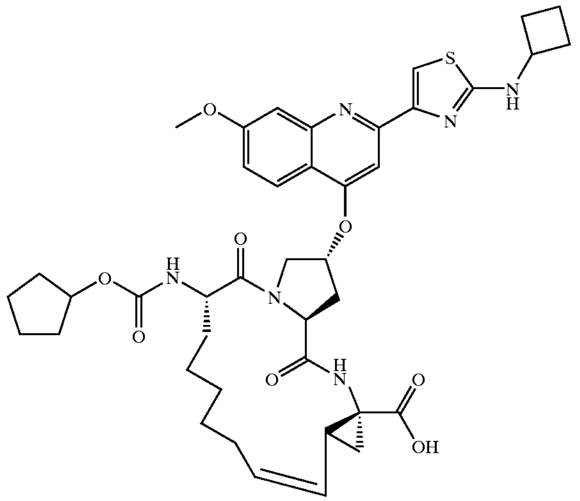

$^1$H NMR (400 MHz,DMSO-$d_6$): δ 8.22 (d, J=6.0 Hz, 1H), 8.02 (d, J 9.2 Hz, 1H), 7.75 (s, 1H), 7.46 (s, 1H), 7.44 (s, 1H), 7.27 (d, J=1.9 Hz, 1H), 7.11 (d, J=6.7 Hz,1H), 7.02 (dd, J=9.5, 1.9 Hz,1H), 5.54–5.41 (m, 1H), 5.44 (s, 1H), 5.14 (dd, J=15.9, 9.9 Hz, 1H), 4.75–4.66 (m, 1H), 4.48–4.34 (m, 2H), 4.34–4.26 (m, 1H), 4.12–4.02 (m, 2H), 3.90 (s, 3H), 2.57–2.46 (m, 1H), 2.42–2.31 (m, 3H), 2.12–1.95 (m, 4H), 1.82–1.20 (m, 20H), 1.13–1.02 (m, 1H). MS; es$^+$: 787.4(M+H)$^+$, es$^-$: 785.4 (M−H)$^-$.

Example 47D

Compound #828

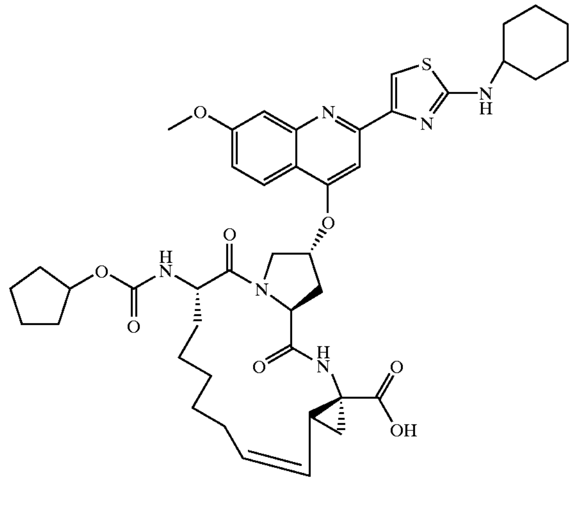

$^1$H NMR (400 MHz,DMSO-$d_6$): δ 8.02 (d, J=9.2 Hz, 1H), 7.86 (bs, 1H), 7.78 (d, J=7.3 Hz, 1H), 7.43 (s, 2H), 7.27 (d, J=2.2 Hz, 1H), 7.12 (d, J=6.9 Hz,1H), 7.03 (dd, J=9.2, 1.9 Hz, 1H), 5.57–5.40 (m, 1H), 5.40 (s, 1H), 5.26–5.17 (m, 1H), 4.70 (bs, 1H), 4.52–4.35 (m, 2H), 4.29–4.23 (m, 1H), 4.18–4.00 (m, 1H), 3.90 (s, 3H), 3.87–3.65 (m,1H), 2.42–2.32 (m, 1H), 2.19–2.10 (m, 1H), 2.07–1.96 (m, 3H), 1.82–0.95 (m, 28H).

MS; es$^+$: 815.4(M+H)$^+$, es$^-$: 813.4 (M−H)$^-$.

Example 48

Full-length NS3–NS4A Heterodimer Protein Fluorogenic Assay

The NS2–NS5B-3'non coding region was cloned by RT-PCR into the pCR®3 vector (Invitrogen) using RNA extracted from the serum of an HCV genotype 1b infected individual (provided by Dr. Bernard Willems, Hôpital St-Luc, Montréal, Québec, Canada). The NS3–NS4A region (NS3–NS4AFL) was then subcloned by PCR into the pFastBac™ HTa baculovirus expression vector (Gibco/BRL). The vector sequence includes a region encoding a 28-residue N-terminal sequence which contains a hexahistidine tag. The Bac-to-Bac™ baculovirus expression system (Gibco/BRL) was used to produce the recombinant baculovirus. His-NS3–NS4AFL was expressed by infecting $10^6$ Sf21 cells/mL with the recombinant baculovirus at a multiplicity of infection of 0.1–0.2 at 27°. Authentic auto-proteolysis occurs during expression to produce a non covalent and stable NS3–NS4A protein complex (referred to as full-length "FL"). The infected culture was harvested 48 to 64 h later by centrifugation at 4°. The cell pellet was homogenized in 50 mM $NaPO_4$, pH 7.5, 40% glycerol (w/v), 2 mM β-mercaptoethanol, in presence of a cocktail of protease inhibitors. His-NS3–NS4AFL was then extracted from the cell lysate with 1.5% NP-40, 0.5% Triton X-100, 0.5M NaCl, and a DNase treatment. After ultracentrifugation, the soluble extract was diluted 4-fold and bound on a Pharmacia Hi-Trap Ni-chelating column. The His-NS3–NS4AFL was eluted in a >90% pure form (as judged by SDS-PAGE), using a 50 to 400 mM imidazole gradient. The His-NS3–NS4AFL was stored at −80° in 50 mM sodium phosphate, pH 7.5, 10% (w/v) glycerol, 0.5 M NaCl, 0.25 M imidazole, 0.1% NP-40. It was thawed on ice and diluted just prior to use.

The protease activity of His-NS3–NS4AFL was assayed in 50 mM Tris-HCl, pH 8.0, 0.25 M sodium citrate, 0.01% (w/v) n-dodecyl-β-D-maltoside, 1 mM TCEP. Five (5) μM of the internally quenched substrate anthranilyl-DDIVPAbu [C(O)—O]-AMY(3-$NO_2$)TW-OH (SEQ. ID NO.: 1) in presence of various concentrations of inhibitor were incubated with 1.5 nM of His-NS3–NS4AFL for 45 min at 23°. The final DMSO concentration did not exceed 5.25%. The reaction was terminated with the addition of 1M MES, pH 5.8. Fluorescence of the N-terminal product was monitored on a Perkin-Elmer LS-50B fluorometer equipped with a 96-well plate reader (excitation wavelength: 325 nm, emission wavelength: 423 nm).

The % inhibition was calculated with the following equation:

$$100-[(fluo_{inh}-fluo_{blank})/(fluo_{ctl}-fluo_{blank})\times 100]$$

A non-linear curve fit with the Hill model was applied to the inhibition-concentration data, and the 50% effective concentration ($IC_{50}$) was calculated by the use of SAS software (Statistical Software System; SAS Institute, Inc. Cary, N.C.).

Example 49

Recombinant HCV NS3 Protease Radiometric Assay

The substrate used for the HCV NS3 protease radiometric assay, DDIVPC-SMSYTW (SEQ. ID NO.: 2), is cleaved between the cysteine and the serine residues by the enzyme. The sequence DDIVPC-SMSYTW (SEQ. ID NO.: 2) corresponds to the NS5A/NS5B natural cleavage site in which the cysteine residue in P2 has been substituted for a proline. The peptide substrate DDIVPC-SMSYTW (SEQ. ID NO.: 2) and the tracer biotin-DDIVPC-SMS[$^{125}$I-Y]TW (SEQ. ID NO.: 3) were incubated with the recombinant NS3 protease in the absence or in the presence of inhibitors. The separation of substrate from products was performed by adding avidin-coated agarose beads to the assay mixture followed by filtration. The amount of SMS[$^{125}$I-Y]TW (SEQ. ID NO.: 4) product found in the filtrate (with or without inhibitor) allowed for the calculation of the percentage of substrate conversion and of the percentage of inhibition.

A. Reagents

Tris and Tris-HCl (UltraPure) were obtained from Life Technologies. Glycerol (UltraPure), MES and BSA were purchased from Sigma®. TCEP was obtained from Pierce, DMSO from Aldrich® and NaOH from Anachemia®.

Assay buffer: 50 mM Tris-HCl, pH 7.5, 30% (w/v) glycerol, 2% (w/ v) CHAPS, 1 mg/mL BSA, 1 mM TCEP (TCEP added just prior to use from a 1 M stock solution in water).

Substrate: DDIVPC-SMSYTW (SEQ. ID NO.: 2), 25 $\mu$M final concentration (from a 2 mM stock solution in DMSO stored at −20° C. to avoid oxidation).

Tracer: reduced mono-iodinated substrate(biotin-DDIVPC-SMS[$^{125}$I-Y]TW (SEQ. ID NO.: 3)) (≈1 nM final concentration).

HCV NS3 protease type 1b, 25 nM final concentration (from a stock solution in 50 mM sodium phosphate, pH 7.5, 10% glycerol, 300 mM NaCl, 5 mM DTT, 0.01% NP-40).

B. Protocol

The assay was performed in a 96-well polypropylene plate. Each well contained:

20 $\mu$L substrate/tracer in assay buffer;

10 $\mu$L±inhibitor in 20% DMSO/assay buffer;

10 $\mu$L NS3 protease 1b.

Blank (no inhibitor and no enzyme) and control (no inhibitor) were also prepared on the same assay plate.

The enzymatic reaction was initiated by the addition of the enzyme solution and the assay mixture was incubated for 60 min at 23° C. under gentle agitation. Twenty (20) $\mu$L of 0.025 N NaOH were added to quench the enzymatic reaction.

Twenty (20) $\mu$L of avidin-coated agarose beads (purchased from Pierce®) were added in a Millipore® MADP N65 filtration plate. The quenched assay mixture was transferred to the filtration plate, and incubated for 60 min at 23° C. under gentle agitation.

The plates were filtered using a Millipore® MultiScreen Vacuum Manifold Filtration apparatus, and 40 $\mu$L of the filtrate was transferred to an opaque 96-well plate containing 60 $\mu$L of scintillation fluid per well.

The filtrates were counted on a Packard® TopCount instrument using a $^{125}$I-liquid protocol for 1 minute. The %inhibition was calculated with the following equation:

$$100-[(\text{counts}_{inh}-\text{counts}_{blank})/(\text{counts}_{ctl}-\text{counts}_{blank})\times100]$$

A non-linear curve fit with the Hill model was applied to the inhibition-concentration data, and the 50% effective concentration ($IC_{50}$) was calculated by the use of SAS software (Statistical Software System; SAS Institute, Inc., Cary, N.C.).

Example 50

Specificity Assays

The specificity of the compounds was determined against a variety of serine proteases: human leukocyte elastase, porcine pancreatic elastase and bovine pancreatic α-chymotrypsin and one cysteine protease: human liver cathepsin B. In all cases a 96-well plate format protocol using a chromogenic substrate specific for each enzyme was used. Each assay included a 1 h enzyme-inhibitor pre-incubation at RT followed by addition of substrate and hydrolysis to ≈30% conversion as measured on a UV Thermomax® microplate reader or a fluorescence Perkin-Elmer® LS50B plate reader. Substrate concentrations were kept as low as possible compared to $K_M$ to reduce substrate competition. Compound concentrations varied from 300 to 0.06 $\mu$M depending on their potency.

The final conditions for each assay were as follows:

50 mM Tris-HCl pH 8, 0.5 M $Na_2SO_4$, 50 mM NaCl, 0.1 mM EDTA, 3% DMSO, 0.01% Tween-20 with;

[100 $\mu$M Succ-AAPF-pNA (SEQ. ID NO.: 5) and 250 pM α-chymotrypsin], [133 $\mu$M Succ-AAA-pNA and 8 mM porcine elastase], [133 $\mu$M Succ-AAV-pNA and 8 nM leukocyte elastase];

[100 mM $NaHPO_4$ pH 6, 1 mM EDTA, 3% DMSO, 1 mM TCEP, 0.01% Tween-20, 4 $\mu$M Z-FR-AMC (7-amino-4-methylcoumarin) and 0.5 nM cathepsin B (the stock enzyme was activated in buffer containing 20 mM TCEP before use)].

A representative example is summarized below for porcine pancreatic elastase: In a polystyrene flat-bottom 96-well plate (Cellwells, Corning) were added using a Biomek liquid handler (Beckman):

40 $\mu$L of assay buffer (50 mM Tris-HCl pH 8, 1 M $Na_2SO_4$, 50 mM NaCl, 0.1 mM EDTA);

20 $\mu$L of enzyme solution (50 mM Tris-HCl pH 8, 50 mM NaCl, 0.1 mM EDTA, 0.02% Tween-20, 40 nM porcine pancreatic elastase); and 20 $\mu$L of inhibitor solution (50 mM Tris-HCl, pH 8, 50 mM NaCl, 0.1 mM EDTA, 0.02% Tween-20, 1.5 mM-0.3 $\mu$M inhibitor, 15% v/v DMSO).

After 60 min pre-incubation at RT, 20 $\mu$L of substrate solution (50 mM Tris-HCl, pH 8,0.5 M $Na_2SO_4$, 50 mM NaCl, 0.1 mM EDTA, 665 $\mu$M Succ-AAA-pNA) were added to each well and the reaction was further incubated at RT for 60 min after which time the absorbance was read on the UV Thermomax® plate reader. Rows of wells were allocated for controls (no inhibitor) and for blanks (no inhibitor and no enzyme).

The sequential 2-fold dilutions of the inhibitor solution were performed on a separate plate by the liquid handler using 50 mM Tris-HCl pH 8, 50 mM NaCl, 0.1 mM EDTA, 0.02% Tween-20, 15% (v/v) DMSO. All other specificity assays were performed in a similar fashion. The percentage of inhibition was calculated using the formula:

$[1-((UV_{inh}-UV_{blank})/(UV_{ctl}-UV_{blank}))]\times 100$

A non-linear curve fit with the Hill model was applied to the inhibition-concentration data, and the 50% effective concentration ($IC_{50}$) was calculated by the use of SAS software (Statistical Software System; SAS Institute, Inc., Cary, N.C.).

Example 51

NS3 Protease Cell-based Assay

This assay is done with Huh-7 cells, a human cell line derived from a hepatoma, co-transfected with 2 DNA constructs: one (called NS3) expressing part of the HCV non-structural polyprotein fused to the tTA protein through an NS5A–NS5B cleavage site in the following order: NS3-NS4A-NS4B-NS5A-(NS5B)tTA where (NS5B) represents the 6 first amino acids of NS5

B. This polyprotein is expressed under the control of the CMV promoter, the other (called SEAP) expressing the reporter protein, secreted alkaline phosphatase (SEAP), under the regulation of a tTA-responsive promoter. The first construct leads to the expression of a polyprotein from which the different mature proteins are released through cleavage by the NS3 protease. It is believed that the mature viral proteins forms a complex at the membrane of the endoplasmic reticulum. tTA is a fusion protein, described by Gossen and Bujard (Proc. Natl. Acad. Sci. USA 89 (1992): 5547–5551), which contains a DNA-binding domain and a transcriptional activator. Release of the tTA protein requires an NS3-dependent cleavage at the NS5A–NS5B cleavage site between NS5A and itself. This last cleavage allows tTA to migrate to the nucleus and transactivate the SEAP gene. Therefore, reduction of NS3 proteolytic activity leads to confinement of tTA to the cytoplasm and concomitant decrease in SEAP activity.

To control for cellular activities other than inhibition of NS3 protease which are due to the compound, a parallel co-transfection is done with a construct expressing tTA alone and the same reporter construct such that SEAP activity is independent of the NS3 protease.

Protocol of the assay: Huh-7 cells, grown in CHO-SFMII (Life Technologies)+10% FCS (fetal calf serum) were co-transfected with the two DNA constructs in the following proportions: 7 μg NS3+500 ng SEAP+800 μl FuGENE (Boehringer Mannheim) per $4\times10^6$ Huh-7 cells. After 5 hours at 37° C., the cells were washed, trypsinized and plated (at 80 000 cells/well) in 96-well plates containing a range of concentrations of the compounds to be tested. After a 24-hour incubation period, the SEAP activity in the medium was measured with the Phospha-Light kit (Tropix).

Analysis of the percent inhibition of SEAP activity with respect to compound concentration was performed with the SAS software to obtain the $EC_{50}$.

Tables of Compounds

The following tables list compounds representative of the invention. All compounds listed in Tables 1 to 9 were found to be active in the enzymatic assay presented in Example 48. A number accompanied by an asterisk (*) represents enzymatic activity obtained with the radiometric assay presented in Example 49 with $IC_{50}$'s under 50 μM. In these enzymatic assays, the following grading was used: A≧1 μM; 1 μM>B>0.1 μM; and C≦0.1 μM.

Several compounds were tested in the specificity assays presented in Example 50 and were found to be specific for the NS3 protease. In general, the results from the different specificity assays are the following: HLE>300 μM; PPE>300 μM; α-Chym.>300 μM; Cat. B>300 μM; indicating that these compounds are highly specific toward the HCV NS3 protease and are not expected to exhibit serious side-effects. In addition, certain of these compounds were tested in the cell-based assay described in Example 51 and were found to have activity with an $EC_{50}$ below 10 μM, strongly indicating that these compounds can cross the cell membrane. Particularly, compounds of Tables 7, 8 and 9 have been assessed in the cellular assay and the result indicated in the last column. In this cellular assay, the following coding was used: A>1 μM; B≦1 μM.

The following abbreviations are used within the following tables:

MS: Electrospray mass spectral data; m/z $MH^+$ except when otherwise indicated by an asterisk*=m/z $MH^-$; Ac: acetyl; Bn: benzyl; Boc: tert-butyloxycarbonyl; Ph: phenyl; Pr: propyl.

TABLE 1

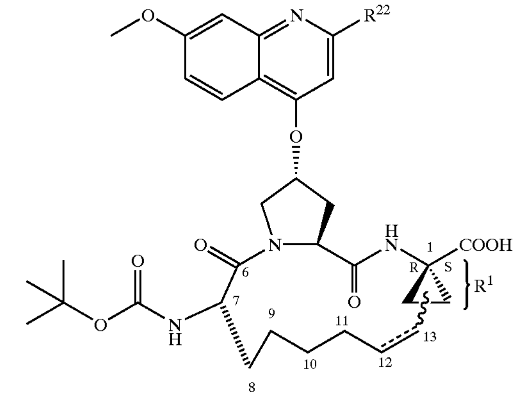

single stereoisomer at $R^1$

| Cpd. # | Double bond between 12 and 13 | position 13-$R^1$ bond stereochem | $R^{22}$ | MS | enzyme activity. |
|---|---|---|---|---|---|
| 101 | 12, 13-trans | 1R, position 13 syn to amide | phenyl | 685.8 | A* |
| 102 | none | 1R, position 13 syn to acid | phenyl | 687.2 | C |
| 103 | none | 1R position 13 syn to amide | phenyl | 687.2 | A* |

TABLE 2

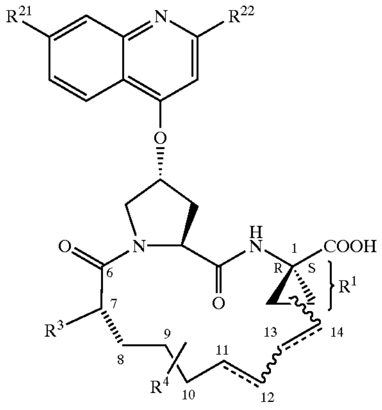

| Cpd # | $R^3$ | $R^4$ | double bond | single stereoisomer at $R^1$ position 14-$R^1$ bond stereochem | $R^{21}$ | $R^{22}$ | MS | enz. act. |
|---|---|---|---|---|---|---|---|---|
| 202 | NH—Boc | H | 11, 12-trans | 1R or 1S, position 14 syn to acid | H | H | 593.7 | B |
| 203 | NH—acetyl | H | 11, 12-trans | 1R or 1S, position 14 syn to acid | H | H | 535.6 | A |
| 205 | NH—Boc | 11-OH 12-OH cis | none | 1R or 1S, position 14 syn to acid | H | H | 627.7 | B |
| 206 | NH—Boc | H | 13, 14-cis | 1R, position 14 syn to acid | H | H | 593.7 | C |
| 207 | NH—Boc | H | 13, 14-cis | 1R, position 14 syn to acid | OMe | H | 623.7 | C |
| 208 | NH—Boc | H | 13, 14-cis | 1R, position 14 syn to acid | OMe | phenyl | 699.8 | C |
| 209 | NH—C(O)—NH-tBu | H | 13, 14-cis | 1R, position 14 syn to acid | OMe | phenyl | 698.8 | C |
| 210 | NH—Boc | H | 13, 14-cis | 1S, position 14 syn to acid | OMe | phenyl | 699.8 | A* |
| 211 | $NH_2$ | H | 13, 14-cis | 1R, position 14 syn to acid | OMe | phenyl | 599.7 | C |
| 213 | OH (one isomer) | H | 13, 14-cis | 1R, position 14 syn to acid | OMe | H | 524.6 | B |
| 214 | NH—Boc | 10-oxo | 13, 14-cis | 1R, position 14 syn to acid | OMe | phenyl | 713.8 | C |
| 215 | NH—Boc | H | none | 1R, position 14 syn to acid | OMe | phenyl | 701.8 | C |
| 217 | NH—Boc | 10-OH (mixt dia stereo) | 13, 14-cis | 1R, position 14 syn to acid | OMe | phenyl | 715.8 | C |
| 218 | NH—Boc | 10-oxo | 13, 14-cis | 1R, position 14 syn to amide | OMe | phenyl | 713.8 | C |
| 219 | NH—Ac | H | none | 1R, position 14 syn to acid | OMe | phenyl | 643.2 | C |
| 220 | NH—Boc | H | 13, 14-cis | 1R, position 14 syn to amide | OMe | 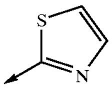 | 706.2 | C |

TABLE 3
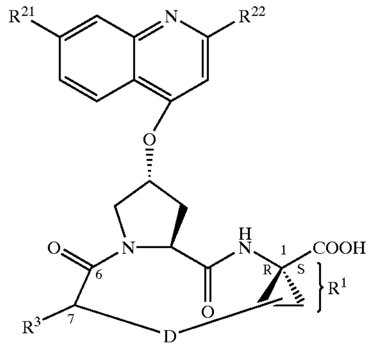
single stereoisomer at $R^1$
| Cpd. # | $R^3$ | —D— | D—$R^1$ bond stereochem | $R^{21}$ | $R^{22}$ | MS | enz act. |
|---|---|---|---|---|---|---|---|
| 301 | NH—Boc | 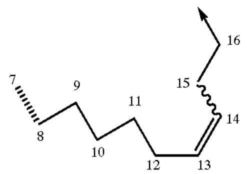 | 1R or 1S, D syn to acid | H | H | 621.7 | B |
| 302 | NH—Boc | 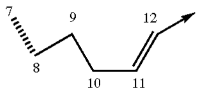 | 1R, D syn to amide | OMe | Ph | 671 | A |
| 303 | NH—Boc | 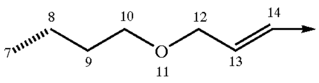 | 1R, D syn to amide | OMe | Ph | 701.3 | B |
| 304 | NH—Boc | 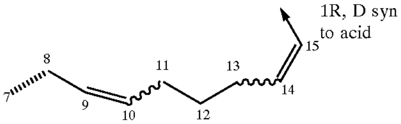 | 1R, D syn to acid | OMe | Ph | 711.1 | C |
| 305 | HO | 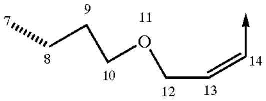 | 1R, D syn to acid | OMe | Ph | 602.2 | B |
| 306 | NH—Boc | 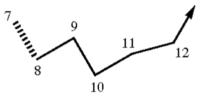 | 1R, D syn to amide | OMe | Ph | 673.2 | A* |
| 307 | NH—Boc | 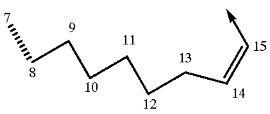 | 1R, D syn to acid | OMe | 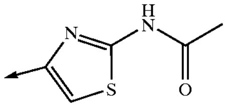 | 777 | C |
| 308 | NH—Ac | 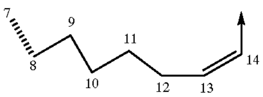 | 1R, D syn to acid | OMe | OEt | 609.2 | C |

TABLE 4

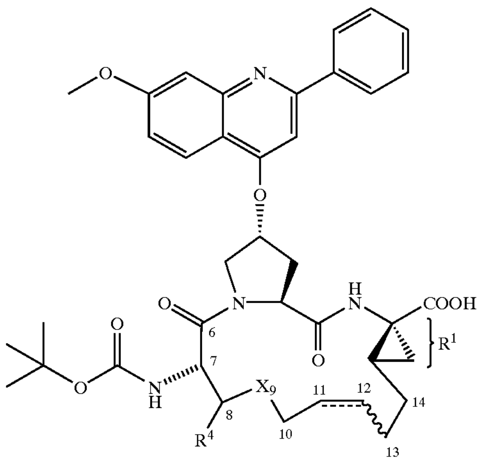

position 14-$R^1$ bond syn to the acid

| Cpd # | $R^4$ | 9-X | 11, 12 double bond | MS | enzyme activity. |
|---|---|---|---|---|---|
| 401 | H | $CH_2$ | trans | 699.3 | C |
| 402 | H | $CH_2$ | cis | 699.4 | B |
| 403 | H | O | trans | 701.3 | C |
| 404 | 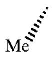 | O | trans | 715.3 | B |
| 405 | 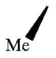 | O | trans | 715.2 | C |
| 406 | H | O | none | 703.3 | C |
| 407 | 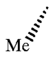 | O | none | 717.3 | B |
| 408 | 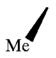 | O | none | 717.3 | C |
| 409 | 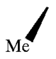 | O | cis | 715.2 | B |
| 410 | 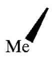 | S | trans | 731.3 | C |
| 411 | 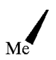 | S | cis | 731.3 | A* |
| 412 | 8-$(Me)_2$ | 9-S | cis | 745.3 | A |

TABLE 5

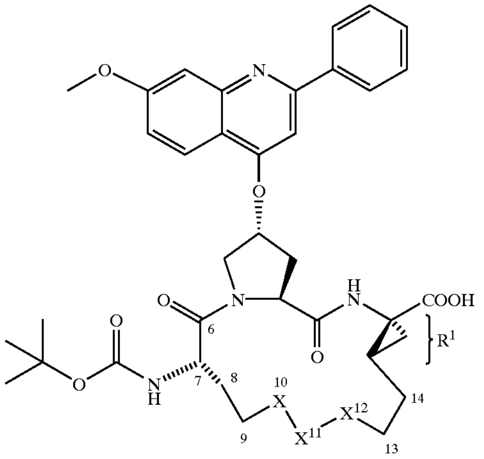

position 14-$R^1$ bond syn to the acid

| Cpd # | 10-X | 11-X | 12-X | MS | enzyme activity. |
|---|---|---|---|---|---|
| 501 | $CH_2$ | O | $CH_2$ | 703.2 | C |
| 502 | $CH_2$ | $CH_2$ | $CH_2$ | 701 | C |
| 503 | $CH_2$ | $CH_2$ | NH | 702.3 | A |
| 504 | $CH_2$ | $CH_2$ | N(Me) | 716.3 | A* |
| 505 | $CH_2$ | $CH_2$ | N(CO)Me | 744.3 | B |
| 506 | $CH_2$ | $CH_2$ | N(CO)Ph | 806.3 | B |
| 507 | NH | $CH_2$ | $CH_2$ | 702.3 | C |
| 508 | N(CO) Me | $CH_2$ | $CH_2$ | 744.3 | C |

TABLE 6

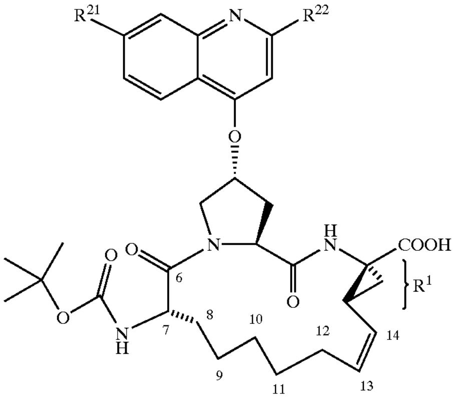

position 14-$R^1$ bond syn to the acid
| Cpd # | $R^{21}$ | $R^{22}$ | MS | enzyme activity. |
|---|---|---|---|---|
| 601 | $N(Me)_2$ | 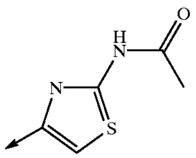 | 776.2 | C |
| 602 | OH | $(CF_3)$ | 675.2* | C |
| 603 | OMe | 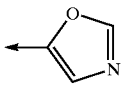 | 690.1 | C |
TABLE 7
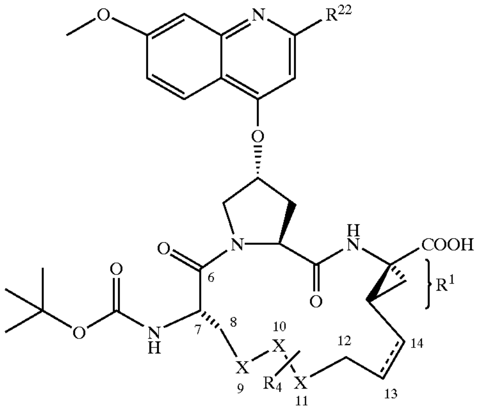
position 14-$R^1$ bond syn to the acid
| Cpd # | $R^4$ | $X_9$; $X_{10}$; and $X_{11}$ | 13, 14 double bond | $R^{22}$ | MS | cell. act. |
|---|---|---|---|---|---|---|
| 701 | H | $X_9 = CH_2$ $X_{10} = CH_2$ $X_{11} = O$ | Cis | phenyl | 701.3 | A |
| 702 | H | $CH_2$(All) | Cis | 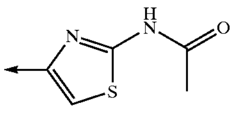 | 763.1 | B |
| 703 | H | $CH_2$(All) | None | 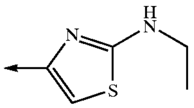 | 751.4 | B |
| 704 | H | $CH_2$(All) | Cis | 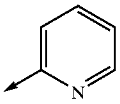 | 700.3 | B |
| 705 | H | $CH_2$(All) | Cis | 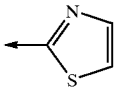 | 706.2 | B |
| 707 | H | $CH_2$(All) | Cis | 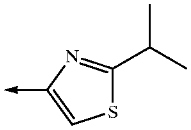 | 748.2 | B |
| 708 | H | $CH_2$(All) | Cis | 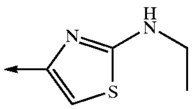 | 749.2 | B |

-continued
| Cpd # | $R^4$ | $X_9$; $X_{10}$; and $X_{11}$ | 13, 14 double bond | $R^{22}$ | MS | cell. act. |
|---|---|---|---|---|---|---|
| 709 | H | $CH_2$(All) | None | 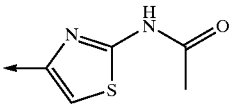 | 765.2 | B |
| 710 | H | $CH_2$(All) | None | 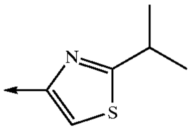 | 750.1 | B |
| 711 | H | $CH_2$(All) | None | 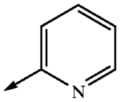 | 702.2 | B |
| 712 | H | $CH_2$(All) | Cis | —OEt | 667.3 | B |
| 713 | H | $CH_2$(All) | None | 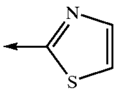 | 708.1 | B |
| 714 | H | $CH_2$(All) | None | —OEt | 669.3 | B |
| 715 | H | $CH_2$(All) | Cis | 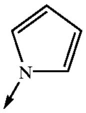 | 688.3 | B |
| 716 | H | $CH_2$(All) | Cis | 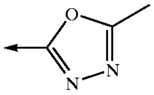 | 705.3 | A |
| 717 | H | $CH_2$(All) | Cis | 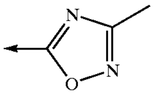 | 705.2 | B |
| 718 | H | $CH_2$(All) | Cis | 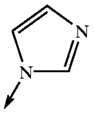 | 689.3 | B |
| 719 | H | $CH_2$(All) | Cis | 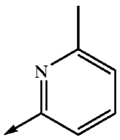 | 714.2 | B |
| 720 | H | $CH_2$(All) | None | 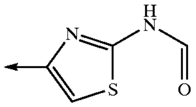 | 751.2 | B |
| 721 | H | $CH_2$(All) | None | 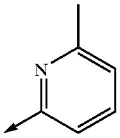 | 716.3 | B |

-continued
| Cpd # | $R^4$ | $X_9$; $X_{10}$; and $X_{11}$ | 13, 14 double bond | $R^{22}$ | MS | cell. act. |
|---|---|---|---|---|---|---|
| 722 | H | $CH_2$(All) | Cis | 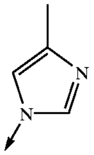 | 703.3 | B |
| 723 | H | $CH_2$(All) | None | 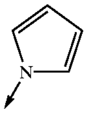 | 690.3 | B |
| 724 | H | $CH_2$(All) | None | 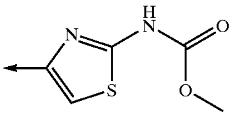 | 781.1 | B |
| 725 | H | $CH_2$(All) | Cis | 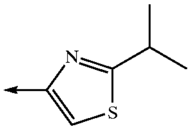 | 748.2 | B |
| 726 | H | $CH_2$(All) | Cis | 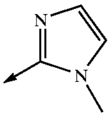 | 703.2 | B |
| 727 | H | $CH_2$(All) | Cis | $—CH_2—OMe$ | 667.3 | A |
| 728 | H | $CH_2$(All) | Cis | Me | 637.3 | A |
| 729 | H | $CH_2$(All) | Cis | 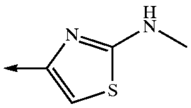 | 735.2 | B |
| 730 | H | $CH_2$(All) | None | 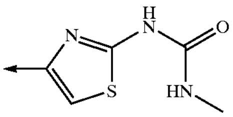 | 780.1 | B |
| 731 | H | $CH_2$(All) | Cis | 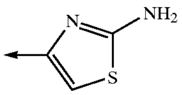 | 721.1 | B |
| 732 | H | $CH_2$(All) | Cis | 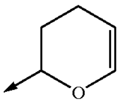 | 705.3 | A |
| 733 | H | $CH_2$(All) | Cis | 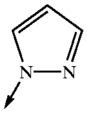 | 689.3 | B |

-continued
| Cpd # | $R^4$ | $X_9$; $X_{10}$; and $X_{11}$ | 13, 14 double bond | $R^{22}$ | MS | cell. act. |
|---|---|---|---|---|---|---|
| 734 | H | $CH_2$(All) | Cis | 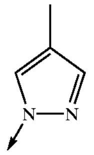 | 703.2 | B |
| 735 | H | $CH_2$(All) | Cis | 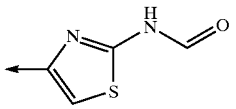 | 749.2 | B |
| 736 | H | $CH_2$(All) | Cis | 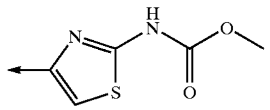 | 779.2 | B |
| 737 | H | $CH_2$(All) | Cis | 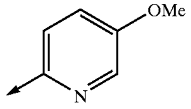 | 730.2 | B |
| 738 | H | $CH_2$(All) | Cis | 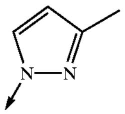 | 703.2 | B |
| 739 | 10-(R) Me | $CH_2$(All) | None | Ph | 715.2 | B |
| 740 | 10-(S) Me | $CH_2$(All) | none | Ph | 715.3 | B |
| 741 | H | $CH_2$(All) | Cis | 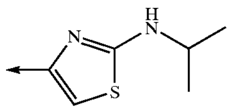 | 763.1 | B |
TABLE 8
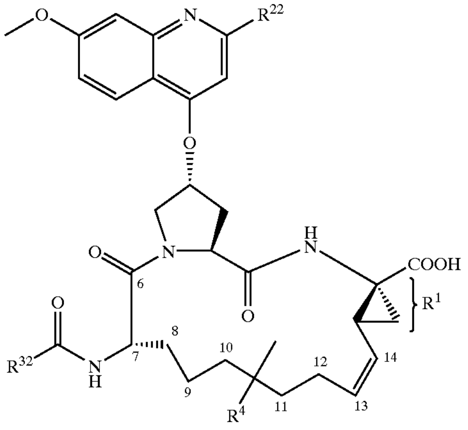

position 14-$R^1$ bond syn to the acid, double bond 13, 14: cis
| Cpd # | $R^{32}$ | $R^4$ | $R^{22}$ | MS | cell. act. |
|---|---|---|---|---|---|
| 801 | 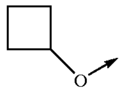 | H | 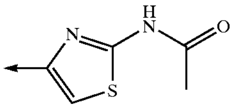 | 761.2 | B |
| 803 | n-Pr | H | OEt | 637.3 | A |
| 804 | 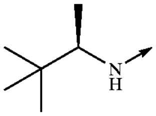 | H | 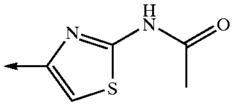 | 790.3 | B |
| 805 | 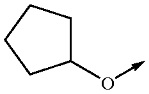 | H | 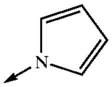 | 700.1 | B |
| 806 | 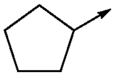 | H | OEt | 663.2 | A |
| 807 | 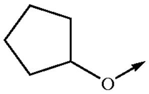 | H | OEt | 679.3 | B |
| 808 | 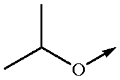 | H | OEt | 653.2 | A |
| 809 | 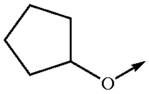 | H | 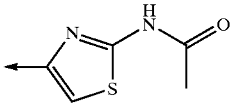 | 775.1 | B |
| 810 | 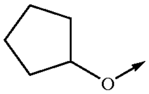 | H | 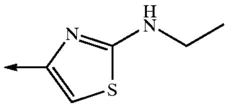 | 761.2 | B |
| 811 | 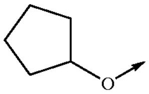 | H | 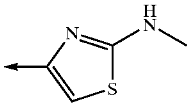 | 747.2 | B |
| 812 | 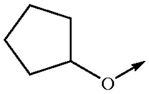 | H | 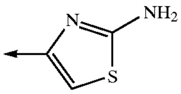 | 733.2 | B |
| 813 | 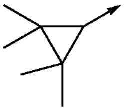 | H | OEt | 691.3 | B |
| 814 | 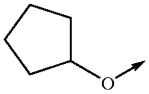 | H | 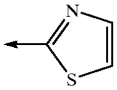 | 718.3 | B |

-continued
| Cpd # | $R^{32}$ | $R^4$ | $R^{22}$ | MS | cell. act. |
|---|---|---|---|---|---|
| 815 | 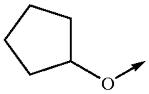 | H | 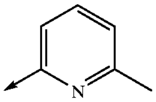 | 726.3 | B |
| 816 | 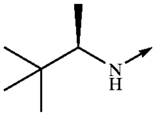 | H | 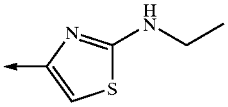 | 776.3 | B |
| 817 | 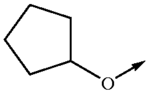 | H | 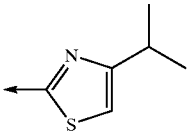 | 760.2 | B |
| 818 | 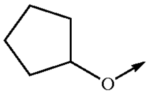 | H | 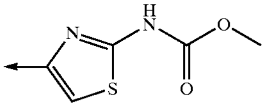 | 791.1 | B |
| 819 | 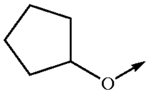 | H | 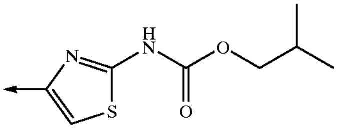 | 833.2 | B |
| 820 | 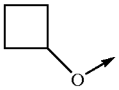 | H | 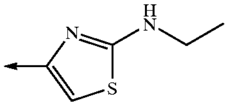 | 747.2 | B |
| 821 | 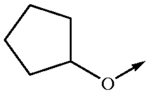 | H | 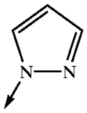 | 700.9 | B |
| 822 | 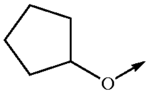 | H | 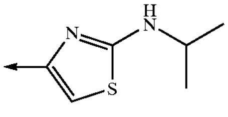 | 775.4 | B |
| 823 | 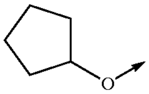 | H | 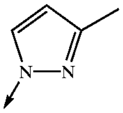 | 715.2 | B |
| 824 | 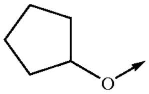 | 10-(R) Me | OEt | 693.0 | B |
| 825 | 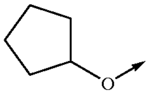 | H | 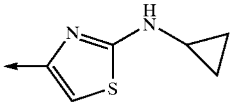 | 773.4 | B |
| 826 | 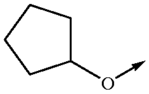 | H | 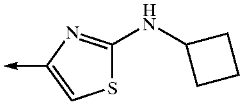 | 787.4 | B |

-continued
| Cpd # | $R^{32}$ | $R^4$ | $R^{22}$ | MS | cell. act. |
|---|---|---|---|---|---|
| 827 | 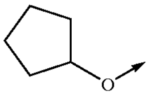 | H | 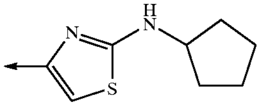 | 801.4 | B |
| 828 | 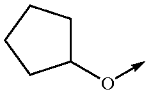 | H | 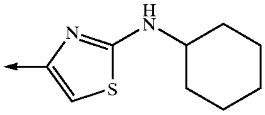 | 815.4 | B |
TABLE 9
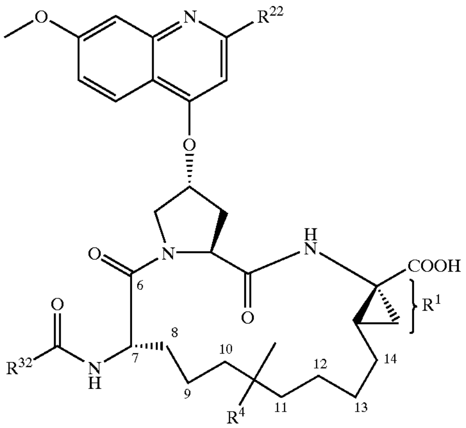
position 14-$R^1$ bond syn to the acid
| Cpd # | $R^{32}$ | $R^4$ | $R^{22}$ | MS | cell. act. |
|---|---|---|---|---|---|
| 901 | 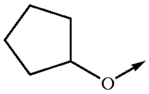 | H | OEt | 681.3 | B |
| 902 | 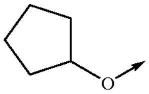 | H | 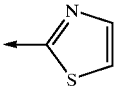 | 719.9 | B |
| 903 | 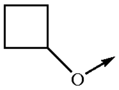 | H | 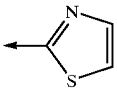 | 705.9 | B |
| 904 | 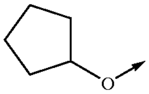 | H | 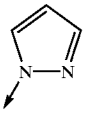 | 703.0 | B |
| 905 | 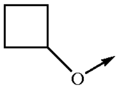 | H | 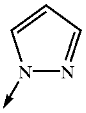 | 689.0 | B |

-continued
| Cpd # | $R^{32}$ | $R^4$ | $R^{22}$ | MS | cell. act. |
| --- | --- | --- | --- | --- | --- |
| 906 | 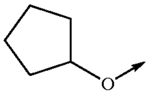 | H | 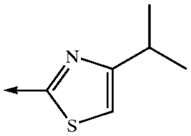 | 762.0 | B |
| 907 | 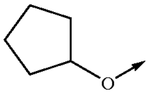 | H | 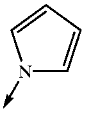 | 702.0 | B |
| 908 | 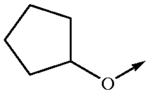 | H | 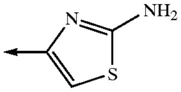 | 735.2 | B |
| 909 | 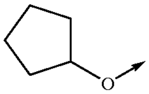 | H | 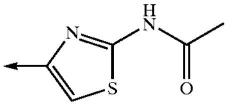 | 777.0 | B |
| 910 | 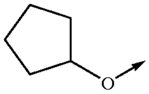 | H | 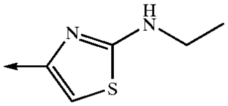 | 763.1 | B |
| 911 | 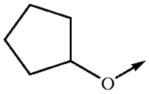 | H | 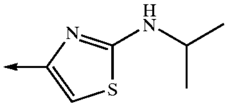 | 777.0 | B |
| 912 | 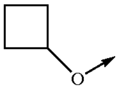 | H | 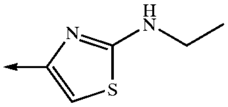 | 748.9 | B |
| 913 | 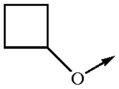 | H | 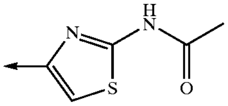 | 762.9 | B |
| 914 | 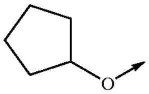 | H | 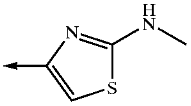 | 749.0 | B |
| 915 | 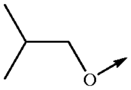 | H | 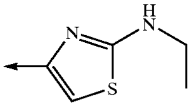 | 751.1 | B |
| 916 | 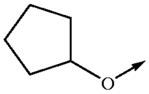 | 10 (R) Me | OEt | 695.2 | B |

What is claimed is:

1. A compound of formula (I):

(I)

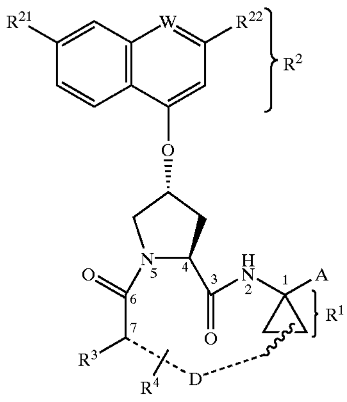

wherein

W is CH or N, $R^{21}$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^{23})_2$, wherein each $R^{23}$ is independently H, $C_{1-6}$ alkyl or $C_{3-6}$ cycloalkyl;

$R^{22}$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{3-6}$ cycloalkyl, $C_{6\ or\ 10}$ aryl or Het, wherein Het is a five-, six-, or seven-membered saturated or unsaturated heterocycle containing from one to four heteroatoms selected from nitrogen, oxygen and sulfur;

said cycloalkyl, aryl or Het being substituted with $R^{24}$, wherein $R^{24}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{25})_2$, NH—C(O)—$R^{25}$ or NH—C(O)—NH—$R^{25}$, wherein each $R^{25}$ is independently: H, $C_{1-6}$ alkyl or $C_{3-6}$ cycloalkyl;

or $R^{24}$ is NH—C(O)—$OR^{26}$ wherein $R^{26}$ is $C_{1-6}$ alkyl or $C_{3-6}$ cycloalkyl;

$R^3$ is hydroxy, $NH_2$, or a group of formula —NH—$R^{31}$, wherein $R^{31}$ is $C_{6\ or\ 10}$ aryl, heteroaryl, —C(O)—$R^{32}$, —C(O)—$NHR^{32}$ or —C(O)—$OR^{32}$, wherein $R^{32}$ is $C_{1-6}$ alkyl or $C_{3-6}$ cycloalkyl;

D is a 5 to 10-atom saturated or unsaturated alkylene chain optionally containing one to three heteroatoms independently selected from: O, S, or N—$R^{41}$, wherein $R^{41}$ is H, $C_{1-6}$ alkyl, $C_{3-6}$ cycloalkyl or —C(O)—$R^{42}$, wherein $R^{42}$ is $C_{1-6}$ alkyl, $C_{3-6}$ cycloalkyl or $C_{6\ or\ 10}$ aryl;

$R^4$ is H or from one to three substituents at any carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio and $C_{1-6}$ thioalkyl, and A is an amide of formula —C(O)—NH—$R^5$, wherein $R^5$ is selected from the group consisting of: $C_{1-8}$ alkyl, $C_{3-6}$ cycloalkyl, $C_{6\ or\ 10}$ aryl and $C_{7-16}$ aralkyl;

or A is a carboxylic acid or a pharmaceutically acceptable salt or ester thereof.

2. A compound of formula I according to claim 1, wherein said $R^1$ moiety is selected from the 2 different diastereoisomers represented by structures (i) and (ii):

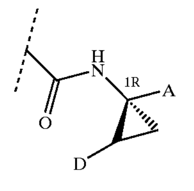

D syn to the amide (i), or

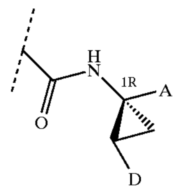

D syn to A (ii).

3. The compound of formula I according to claim 2, wherein D is linked syn to A as represented by formula (ii).

4. The compound of formula I according to claim 1, wherein W is N;

$R^{21}$ is H, $C_{1-6}$ alkyl, $C_{1-6}$ alkoxy, hydroxy, chloro, or $N(R^{23})_2$, wherein $R^{23}$ is H or $C_{1-6}$ alkyl;

$R^{22}$ is H, $C_{1-6}$ thioalkyl, $C_{1-6}$ alkoxy, phenyl or Het selected from the group consisting of:

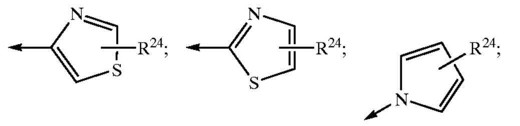

-continued

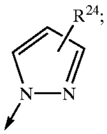
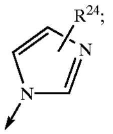
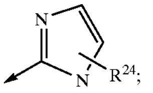
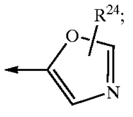
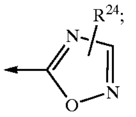
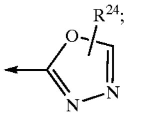
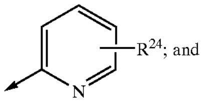 and 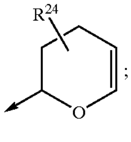

wherein $R^{24}$ is H, $C_{1-6}$ alkyl, NH—$R^{25}$, NH—C(O)—$R^{25}$ or NH—C(O)—NH—$R^{25}$, wherein each $R^{25}$ is independently: H, $C_{1-6}$ alkyl, or $C_{3-6}$ cycloalkyl;

or NH—C(O)—$OR^{26}$, wherein $R^{26}$ is $C_{1-6}$ alkyl.

5. A compound of formula I according to claim 4, wherein $R^{21}$ is H or $C_{1-6}$ alkoxy.

6. The compound of formula I according to claim 4, wherein $R^{22}$ is $C_{1-4}$ alkoxy, phenyl or Het selected from the group consisting of:

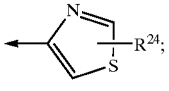
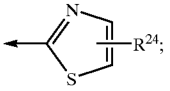
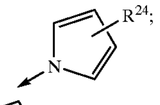
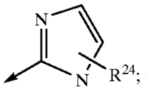 and
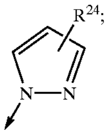
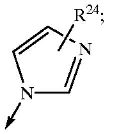
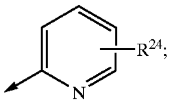

wherein $R^{24}$ is H, $C_{1-6}$ alkyl, NH—$R^{25}$, or NH—C(O)—$R^{25}$;

wherein each $R^{25}$ is $C_{1-6}$ alkyl or $C_{3-6}$ cycloalkyl, or NH—C(O)—$OR^{26}$, wherein $R^{26}$ is as defined in claim 4.

7. A compound of formula I according to claim 6, wherein $R^{21}$ is methoxy.

8. The compound of formula I according to claim 7, wherein $R^{22}$ is ethoxy, or Het selected from the group consisting of:

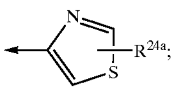
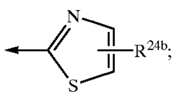 and

-continued

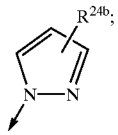

wherein $R^{24a}$ is NH—$R^{25}$ or NH—C(O)—$R^{25}$, wherein $R^{25}$ is $C_{1-6}$ alkyl or $C_{3-6}$ cycloalkyl;

or $R^{24a}$ is NH—C(O)—$OR^{26}$, wherein $R^{26}$ is $C_{1-6}$ alkyl, and $R^{24b}$ is H or $C_{1-6}$ alkyl.

9. The compound of formula I according to claim 1, wherein $R^3$ is an amide of formula NH—C(O)$R^{32}$ or a urea of formula NH—C(O)—NH—$R^{32}$ or a carbamate of formula NH—C(O)—$OR^{32}$, wherein $R^{32}$ is $C_{1-6}$ alkyl or $C_{3-6}$ cycloalkyl.

10. The compound of formula I according to claim 9, wherein $R^3$ is a urea or a carbamate, wherein $R^{32}$ is $C_{1-6}$ alkyl or $C_{4-6}$ cycloalkyl.

11. The compound of formula I according to claim 10, wherein $R^3$ is a carbamate and $R^{32}$ is tert-butyl, cyclobutyl or cyclopentyl.

12. The compound of formula I according to claim 1, wherein D is a 6 to 8 atom saturated or unsaturated alkylene chain optionally containing one or two heteroatoms independently selected from: O, S or N—$R^{41}$, wherein $R^{41}$ is H, $C_{1-6}$ alkyl, or $C_{2-7}$ acyl.

13. The compound of formula I according to claim 12, wherein D optionally contains one heteroatom selected from: NH, or N—$C_{2-7}$ acyl.

14. The compound according to claim 13, wherein said heteroatom is selected from: NH or N(Ac).

15. The compound according to claim 13, wherein said D chain contains 7 atoms.

16. The compound according to claim 15, wherein said heteroatom is at position 10 of said D chain.

17. The compound according to claim 13, wherein said D chain is saturated.

18. The compound of formula I according to claim 12, wherein D is a 6 to 8 atom saturated or unsaturated alkylene chain optionally containing one heteroatom selected from: O, or S.

19. The compound according to claim 18, wherein said D chain contains 7 atoms.

20. The compound according to claim 19, wherein said heteroatom is at position 9 of said D chain.

21. The compound according to claim 20, wherein said D chain is substituted at position 8 with $R^4$, wherein $R^4$ is H or $C_{1-6}$ alkyl.

22. The compound according to claim 21, wherein said $R^4$ is H or methyl.

23. The compound according to claim 22, wherein said $R^4$ is H or 8-(S)—Me.

24. The compound according to claim 23, wherein said D chain is saturated.

25. The compound according to claim 19, wherein said D chain contains one double bond at position 11,12.

26. The compound according to claim 25, wherein said double bond is trans.

27. The compound of formula I according to claim 12, wherein D is a 6 to 8 atom, saturated or unsaturated, all carbon alkylene chain.

28. The compound of formula I according to claim 27, wherein D is a 7 atom chain.

29. The compound of formula I according to claim 28, wherein D is saturated.

30. The compound according to claim 29, wherein said D chain is substituted with $R^4$, wherein $R^4$ is H, oxo, hydroxy, alkoxy or alkyl.

31. The compound according to claim 30, wherein said $R^4$ is H or $C_{1-6}$ alkyl.

32. The compound according to claim 31, wherein said $R^4$ is H or methyl.

33. The compound according to claim 32, wherein said $R^4$ is H or 10-(S)—Me.

34. The compound of formula I according to claim 28, wherein D contains one double bond.

35. The compound of formula I according to claim 34, wherein said double bond is at position 13,14 of said D chain.

36. The compound of formula I according to claim 35, wherein said double bond is cis.

37. The compound according to claim 36, wherein said D chain is substituted with $R^4$, wherein $R^4$ is H, oxo, hydroxy, $C_{1-6}$ alkoxy or $C_{1-6}$ alkyl.

38. The compound according to claim 37, wherein said $R^4$ is H or $C_{1-6}$ alkyl.

39. The compound according to claim 38, wherein said $R^4$ is H or methyl.

40. The compound according to claim 39, wherein said $R^4$ is H or 10-(S)—Me.

41. The compound of formula I according to claim 1, wherein A is a carboxylic acid.

42. A compound according to claim 1, wherein W is N;

$R^3$ is a group of formula —NH—C(O)—$NHR^{32}$ or —NH—C(O)—$OR^{32}$, wherein $R^{32}$ is $C_{1-4}$ alkyl or $C_{4-6}$ cycloalkyl;

D is a 6 to 8 atom saturated or unsaturated alkylene chain linked to $R^1$ syn to A, optionally containing one or two heteroatoms independently selected from: O, S or N—$R^{41}$, wherein $R^{41}$ is H or $C_{2-7}$ acyl;

$R^4$ is H or from one to three substituents independently selected from hydroxy or $C_{1-6}$ alkyl; and A is a carboxylic acid, or a pharmaceutically acceptable salt or ester thereof.

43. The compound of formula I according to claim 42, wherein $R^{21}$ is H or methoxy;

$R^{22}$ is $C_{1-6}$ alkoxy, or Het selected from the group consisting of:

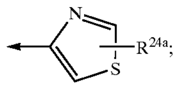 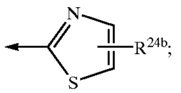 and

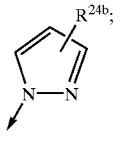

wherein $R^{24a}$ is H, $C_{1-6}$ alkyl, NH—$R^{25}$, NH—C(O)—$R^{25}$ or NH—C(O)—NH—$R^{25}$, wherein $R^{25}$ is: H, $C_{1-6}$ alkyl or $C_{3-6}$ cycloalkyl;

or $R^{24a}$ is NH—C(O)—$OR^{26}$, wherein $R^{26}$ is $C_{1-6}$ alkyl or $C_{3-6}$ cycloalkyl;

and $R^{24b}$ is H or $C_{1-6}$ alkyl;

$R^3$ is urea of the formula NH—C(O)—$NHR^{32}$ or a carbamate of the formula NH—C(O)—$OR^{32}$, wherein $R^{32}$ is $C_{1-6}$ alkyl or $C_{3-6}$ cycloalkyl;

D is a 7-atom alkylene chain optionally containing one double bond at position 11,12 or 13,14; said D chain optionally containing one heteroatom independently selected from: O, S, NH, N(Me), and N(Ac); and $R^4$ is $C_{1-6}$ alkyl.

44. The compound of formula I according to claim 43, wherein $R^{21}$ is methoxy, and $R^{22}$ is ethoxy or

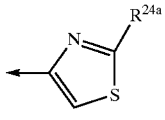

wherein $R^{24a}$ is NH—($C_{1-4}$ alkyl); NH—($C_{3-6}$ cycloalkyl); NH—C(O)—($C_{1-4}$ alkyl); NH—C(O)—(O)—($C_{1-4}$ alkyl); or NH—C(O)—NH—($C_{1-4}$ alkyl);

D is a C7 all carbon chain, saturated or containing one cis double bond at position 13,14.

45. A compound of formula:

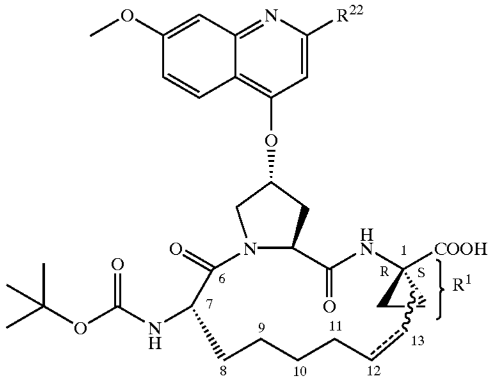

comprising a single stereoisomer at $R^1$, wherein the optional double bond between 12 and 13, the position 13-$R^1$ group bond stereochemistry and $R^{22}$ are defined as follows:

| Cpd. # | double bond between 12 and 13: | position 13 - $R^1$ bond stereochem: | $R^{22}$: |
|---|---|---|---|
| 101 | 12,13-trans | 1R, position 13 syn to amide | phenyl; |
| 102 | none | 1R, position 13 syn to acid | phenyl; |
| and 103 | none | 1R position 13 syn to amide. | phenyl |

46. A compound of formula:

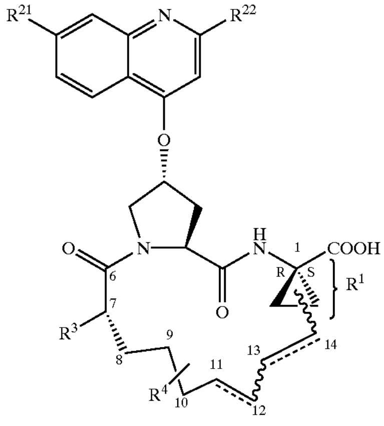

comprising a single stereoisomer at $R^1$, wherein $R^3$, $R^4$, the optional 11, 12 or 13, 14 double bond position 14-$R^1$ bond stereochemistry, $R^{21}$ and $R^{22}$ are defined as follows:

| Cpd # | $R^3$: | $R^4$: | double bond: | position 14-$R^1$ bond stereo-chemistry: | $R^{21}$: | $R^{22}$: |
|---|---|---|---|---|---|---|
| 202 | NH-Boc | H | 11,12-trans | 1R or 1S, position 14 syn to acid | H | H; |
| 203 | NH-acetyl | H | 11,12-trans | 1R or 1S, position 14 syn to acid | H | H; |
| 205 | NH-Boc | 11-OH 12-OH cis | none | 1R or 1S, position 14 syn to acid | H | H; |
| 206 | NH-Boc | H | 13,14-cis | 1R, position 14 syn to acid | H | H; |
| 207 | NH-Boc | H | 13,14-cis | 1R, position 14 syn to acid | OMe | H; |
| 208 | NH-Boc | H | 13,14-cis | 1R, position 14 syn to acid | OMe | phenyl; |
| 209 | NH-C(O)-NH-tBu | H | 13,14-cis | 1R, position 14 syn to acid | OMe | phenyl; |
| 210 | NH-Boc | H | 13,14-cis | 1S, position 14 syn to acid | OMe | phenyl; |
| 211 | $NH_2$ | H | 13,14- | 1R, | OMe | phenyl; |

-continued

| Cpd # | $R^3$: | $R^4$: | double bond: | position 14-$R^1$ bond stereo-chemistry: | $R^{21}$: | $R^{22}$: |
|---|---|---|---|---|---|---|
| | | | cis | position 14 syn to acid | | |
| 213 | OH (one isomer) | H | 13,14-cis | 1R, position 14 syn to acid | OMe | H; |
| 214 | NH-Boc | 10-oxo | 13,14-cis | 1R, position 14 syn to acid | OMe | phenyl; |
| 215 | NH-Boc | H | none | 1R, position 14 syn to acid | OMe | phenyl; |
| 217 | NH-Boc | 10-OH (mixt dia stereo) | 13,14-cis | 1R, position 14 syn to acid | OMe | phenyl; |
| 218 | NH-Boc | 10-oxo | 13,14-cis | 1R, position 14 syn to amide | OMe | phenyl; |
| 219 | NH-Ac | H | none | 1R, position 14 syn to acid | OMe | phenyl; |
| and 220 | NH-Boc | H | 13,14-cis | 1R, position 14 syn to amide | OMe | 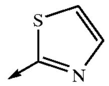 . |

47. A compound of formula:

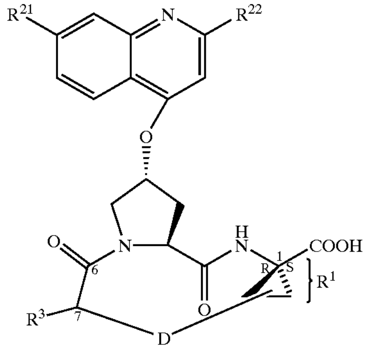

comprising a single stereoisomer at $R^1$, wherein $R^3$, D, D—$R^1$ bond stereochemistry, $R^{21}$ and $R^{22}$ are defined as follows:

| Cpd. # | $R^3$: | —D—: | D—$R^1$ bond stereochemistry: | $R^{21}$: | $R^{22}$: |
|---|---|---|---|---|---|
| 301 | NH—Boc | 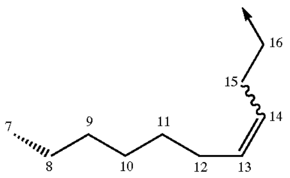 | 1R or 1S, D syn to acid | H | H; |

-continued

| Cpd. # | $R^3$: | —D—: | D—$R^1$ bond stereochemistry: | $R^{21}$: | $R^{22}$: |
|---|---|---|---|---|---|
| 302 | NH—Boc | 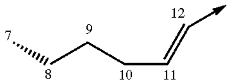 | 1R, D syn to amide | OMe | Ph; |
| 303 | NH—Boc | 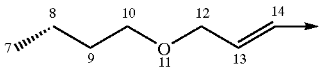 | 1R, D syn to amide | OMe | Ph; |
| 304 | NH—Boc | 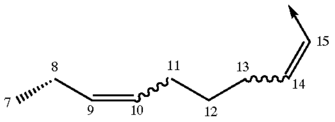 | 1R, D syn to acid | OMe | Ph; |
| 305 | HO | 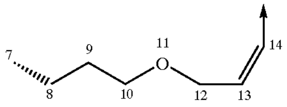 | 1R, D syn to acid | OMe | Ph; |
| 306 | NH—Boc | 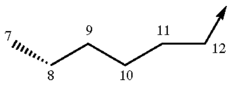 | 1R, D syn to amide | OMe | Ph; |
| 307 | NH—Boc | 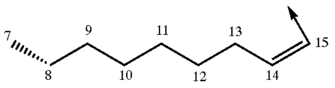 | 1R, D syn to acid | OMe | 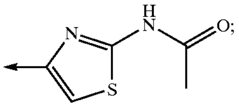; |
| and 308 | NH—Ac | 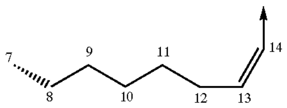 | 1R, D syn to acid | OMe | OEt. |

48. A compound of formula:

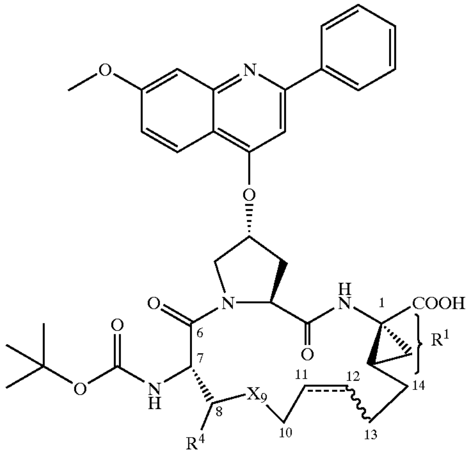

wherein the position 14-$R^1$ bond is syn to acid, $R^4$, $X_9$, and the optional 11,12 double bond are defined as follows:

| Cpd # | $R^4$: | $X_9$: | 11, 12 double bond: |
|---|---|---|---|
| 401 | H | $CH_2$ | trans; |
| 402 | H | $CH_2$ | cis; |
| 403 | H | O | trans; |
| 404 | 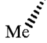 | O | trans; |
| 405 | 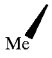 | O | trans; |
| 406 | H | O | none; |
| 407 | 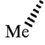 | O | none; |
| 408 | 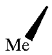 | O | none; |

-continued

| Cpd # | $R^4$: | $X_9$: | 11, 12 double bond: |
|---|---|---|---|
| 409 | 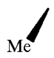 | O | cis; |
| 410 | 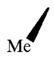 | S | trans; |
| 411 | 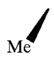 | S | cis; |
| and 412 | 8-$(Me)_2$ | 9-S | Cis. |

49. A compound of formula:

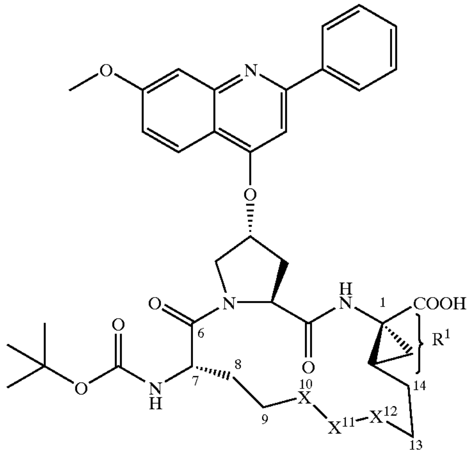

wherein the position 14-$R^1$ bond is syn to acid, $X_{10}$, $X_{11}$, and $X_{12}$ are defined as follows:

| Cpd # | $X_{10}$: | $X_{11}$: | $X_{12}$: |
|---|---|---|---|
| 501 | $CH_2$ | O | $CH_2$; |
| 502 | $CH_2$ | $CH_2$ | $CH_2$; |
| 503 | $CH_2$ | $CH_2$ | NH; |
| 504 | $CH_2$ | $CH_2$ | N(Me); |
| 505 | $CH_2$ | $CH_2$ | N(CO)Me; |
| 506 | $CH_2$ | $CH_2$ | N(CO)Ph; |
| 507 | NH | $CH_2$ | $CH_2$; |
| and 508. | N(CO)Me | $CH_2$ | $CH_2$ |

50. A compound of formula:

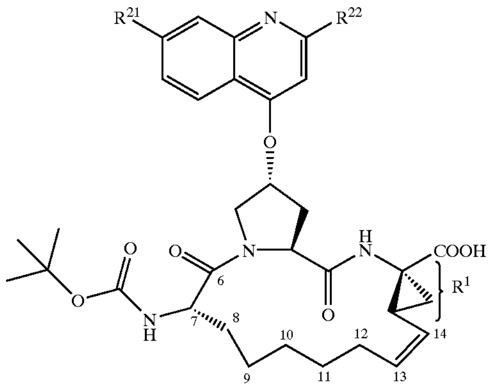

wherein the position 14-$R^1$ bond is syn to acid, $R^{21}$ and $R^{22}$ are defined as follows:

| Cpd # | $R^{21}$: | $R^{22}$: |
|---|---|---|
| 601 | $N(Me)_2$ | 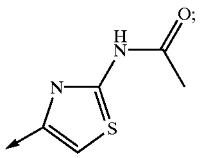 ; |
| 602 | OH | $(CF_3)$; |
| and 603 | OMe | 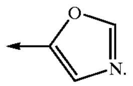 . |

51. A compound of formula:

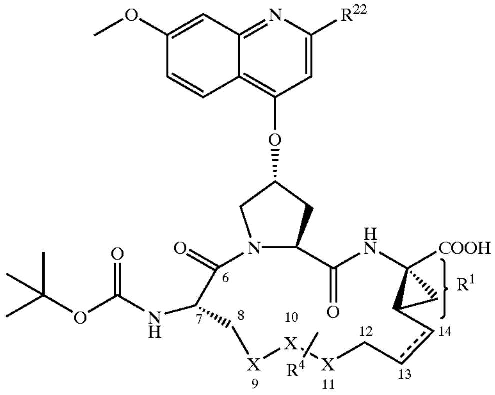

wherein the position 14-$R^1$ bond is syn to acid, $R^4$, $X_9$, $X_{10}$, $X_{11}$, the optional 13,14 double bond and $R^{22}$ are defined as follows:

| Cpd # | $R^4$: | $X_9$; $X_{10}$; and $X_{11}$: | 13,14 double bond: | $R^{22}$: |
|---|---|---|---|---|
| 701 | H | $X_9 = CH_2$ $X_{10} = CH_2$ $X_{11} = O$ | Cis | phenyl; |
| 702 | H | $CH_2$ (All) | Cis | 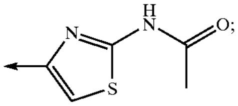 |
| 703 | H | $CH_2$ (All) | None | 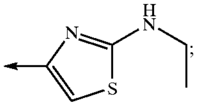 |
| 704 | H | $CH_2$ (All) | Cis | 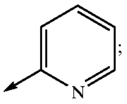 |
| 705 | H | $CH_2$ (All) | Cis | 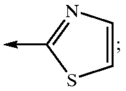 |
| 707 | H | $CH_2$ (All) | Cis | 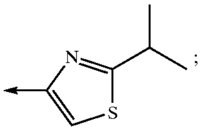 |
| 708 | H | $CH_2$ (All) | Cis | 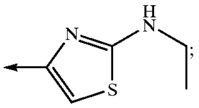 |
| 709 | H | $CH_2$ (All) | None | 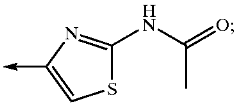 |
| 710 | H | $CH_2$ (All) | None | 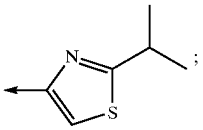 |
| 711 | H | $CH_2$ (All) | None | 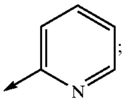 |
| 712 | H | $CH_2$ (All) | Cis | —OEt; |
| 713 | H | $CH_2$ (All) | None | 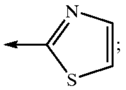 |
| 714 | H | $CH_2$ (All) | None | —OEt; |
| 715 | H | $CH_2$ (All) | Cis | 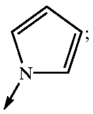 |

-continued
| Cpd # | $R^4$: | $X_9$; $X_{10}$; and $X_{11}$: | 13,14 double bond: | $R^{22}$: |
|---|---|---|---|---|
| 716 | H | $CH_2$ (All) | Cis | 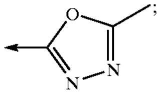 |
| 717 | H | $CH_2$ (All) | Cis | 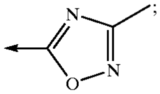 |
| 718 | H | $CH_2$ (All) | Cis | 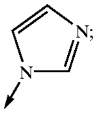 |
| 719 | H | $CH_2$ (All) | Cis | 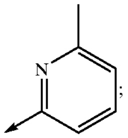 |
| 720 | H | $CH_2$ (All) | None | 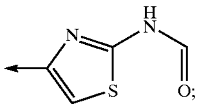 |
| 721 | H | $CH_2$ (All) | None | 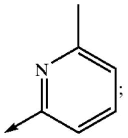 |
| 722 | H | $CH_2$ (All) | Cis | 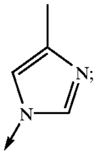 |
| 723 | H | $CH_2$ (All) | None | 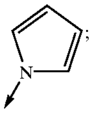 |
| 724 | H | $CH_2$ (All) | None | 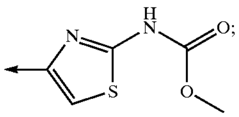 |
| 725 | H | $CH_2$ (All) | Cis | 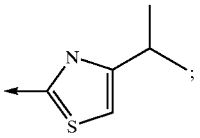 |
| 726 | H | $CH_2$ (All) | Cis | 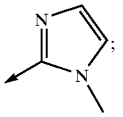 |
| 727 | H | $CH_2$ (All) | Cis | $—CH_2—OMe$; |
| 728 | H | $CH_2$ (All) | Cis | Me; |

-continued
| Cpd # | $R^4$: | $X_9$; $X_{10}$; and $X_{11}$: | 13,14 double bond: | $R^{22}$: |
|---|---|---|---|---|
| 729 | H | $CH_2$ (All) | Cis | 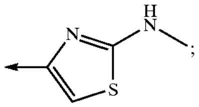 |
| 730 | H | $CH_2$ (All) | None | 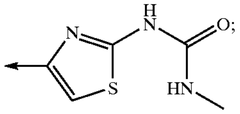 |
| 731 | H | $CH_2$ (All) | Cis | 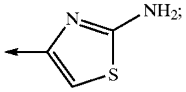 |
| 732 | H | $CH_2$ (All) | Cis | 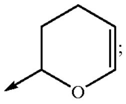 |
| 733 | H | $CH_2$ (All) | Cis | 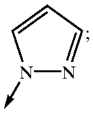 |
| 734 | H | $CH_2$ (All) | Cis | 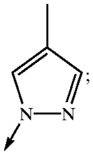 |
| 735 | H | $CH_2$ (All) | Cis | 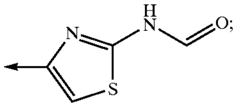 |
| 736 | H | $CH_2$ (All) | Cis | 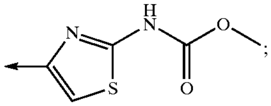 |
| 737 | H | $CH_2$ (All) | Cis | 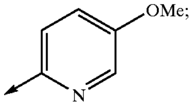 |
| 738 | H | $CH_2$ (All) | Cis | 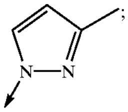 |
| 739 | 10-(R) Me | $CH_2$ (All) | none | Ph; |
| 740 | 10-(S) Me | $CH_2$ (All) | none | Ph; |
| and 741 | H | $CH_2$ (All) | Cis | 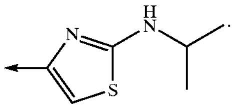 |

52. A compound of formula:
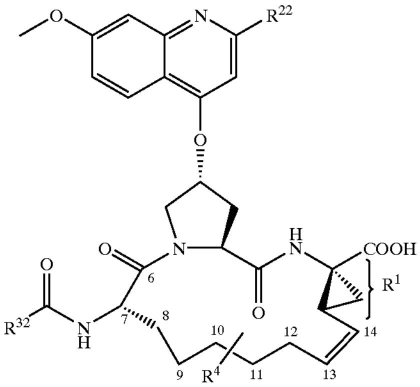
wherein the position 14-$R^1$ bond is syn to acid, said 13,14 double bond is cis, $R^{32}$, $R^4$ and $R^{22}$ are defined as follows:
| Cpd # | $R^{32}$: | $R^4$: | $R^{22}$: |
|---|---|---|---|
| 801 | 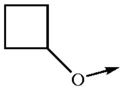 | H | 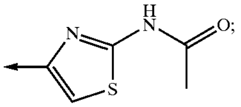 |
| 803 | n-Pr | H | OEt; |
| 804 | 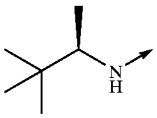 | H | 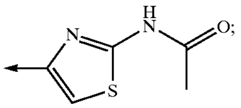 |
| 805 | 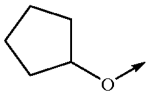 | H | 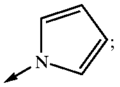 |
| 806 | 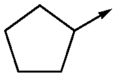 | H | OEt; |
| 807 | 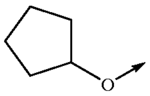 | H | OEt; |
| 808 | 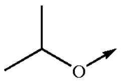 | H | OEt; |
| 809 | 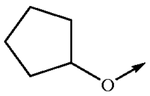 | H | 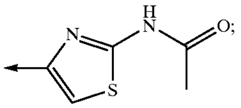 |
| 810 | 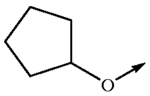 | H | 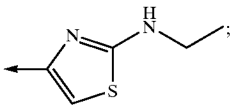 |
| 811 | 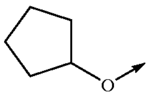 | H | 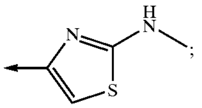 |

-continued
| Cpd # | $R^{32}$: | $R^4$: | $R^{22}$: |
|---|---|---|---|
| 812 | 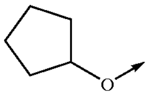 | H | 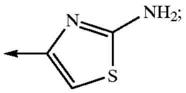 |
| 813 | 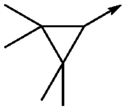 | H | OEt; |
| 814 | 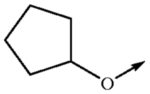 | H | 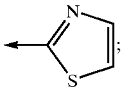 |
| 815 | 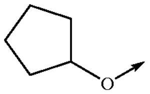 | H | 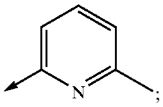 |
| 816 | 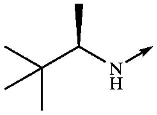 | H | 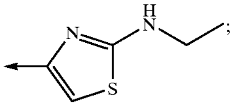 |
| 817 | 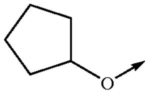 | H | 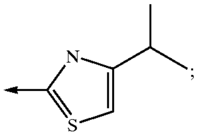 |
| 818 | 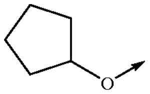 | H | 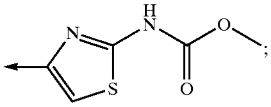 |
| 819 | 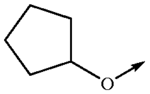 | H | 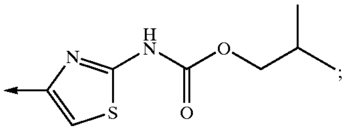 |
| 820 | 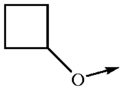 | H | 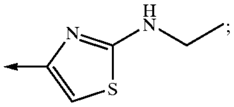 |
| 821 | 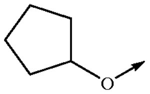 | H | 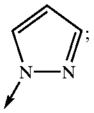 |
| 822 | 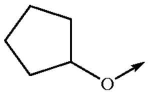 | H | 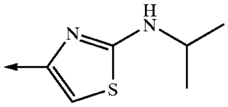 |
| 823 | 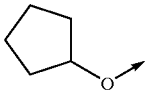 | H | 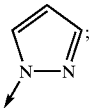 |

-continued
| Cpd # | $R^{32}$: | $R^4$: | $R^{22}$: |
|---|---|---|---|
| and 824 | 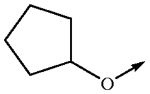 | 10-(R) Me | OEt. |
53. A compound of formula:
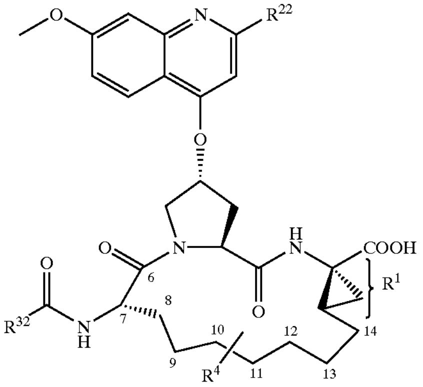
wherein the position 14-$R^1$ bond is syn to acid, $R^{32}$, $R^4$ and $R^{22}$ are defined as follows:
| Cpd # | $R^{32}$: | $R^4$: | $R^{22}$: |
|---|---|---|---|
| 901 | 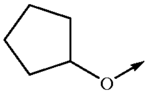 | H | OEt; |
| 902 | 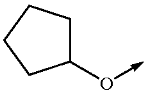 | H | 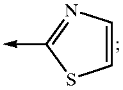 ; |
| 903 | 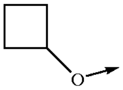 | H | 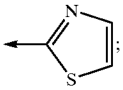 ; |
| 904 | 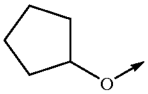 | H | 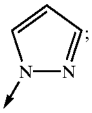 ; |
| 905 | 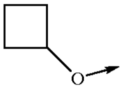 | H | 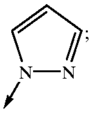 ; |
| 906 | 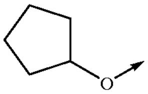 | H | 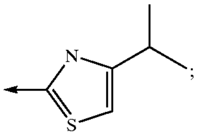 ; |
-continued
| Cpd # | $R^{32}$: | $R^4$: | $R^{22}$: |
|---|---|---|---|
| 907 | 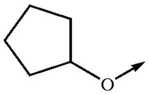 | H | 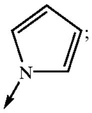 ; |
| 908 | 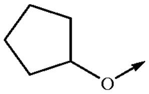 | H | 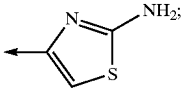 ; |
| 909 | 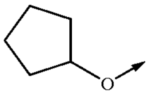 | H | 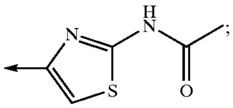 ; |
| 910 | 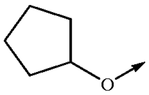 | H | 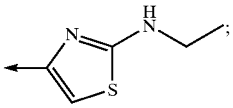 ; |
| 911 | 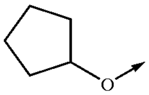 | H | 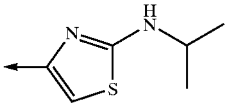 |
| 912 | 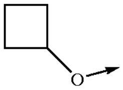 | H | 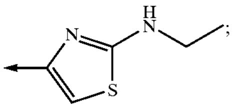 ; |
| 913 | 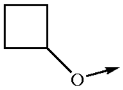 | H | 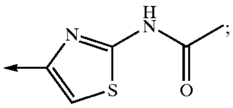 ; |
| 914 | 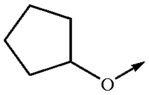 | H | 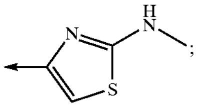 ; |
| 915 | 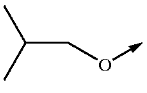 | H | 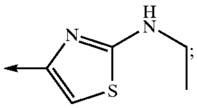 ; |
| and 916 | 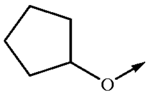 | 10 (R) Me | OEt. |
54. A method of inhibiting the replication of hepatitis C virus by exposing the virus to a hepatitis C viral NS3 protease inhibiting amount of the compound of formula I according to claim 1.

55. A pharmaceutical composition comprising an anti-hepatitis C virally effective amount of a compound of formula I according to claim 1, or a therapeutically acceptable salt or ester thereof, in admixture with a pharmaceutically acceptable carrier medium or auxiliary agent.

56. The pharmaceutical composition according to claim 55, further comprising an immunomodulatory agent.

57. The pharmaceutical composition according to claim 56, wherein said immunomodulatory agent is selected from the group consisting of: α-, β-, and γ-interferons.

58. The pharmaceutical composition according to claim 55, further comprising an antiviral agent.

59. The pharmaceutical composition according to claim 58, wherein said antiviral agent is selected from the group consisting of: ribavirin and amantadine.

60. The pharmaceutical composition according to claim 55, further comprising another inhibitor of HCV NS3 protease.

61. The pharmaceutical composition according to claim 55, further comprising an inhibitor of other targets in the HCV life cycle.

62. A method for treating or preventing the contamination of a material by the hepatits C virus comprising contacting said material with an effective amount of a compound of formula I according to claim 1.

63. A method of treating a hepatitis C viral infection in a mammal by administering to the mammal an anti-hepatitis C virally effective amount of the compound of formula I according to claim 1, or a therapeutically acceptable salt or ester thereof.

64. A method of treating a hepatitis C viral infection in a human by administering thereto an anti-hepatitis C virally effective amount of a pharmaceutical composition according to claim 55.

65. The pharmaceutical composition according to claim 61, wherein said inhibitor inhibits a target selected from the group consisting of: helicase, polymerase, and metalloprotease.

66. The pharmaceutical composition according to claim 57, wherein the immunomodulatory agent is α-interferon.

67. The pharmaceutical composition according to claim 57, further comprising an antiviral agent.

68. The pharmaceutical composition according to claim 67, wherein the antiviral agent is ribavirin.

69. The pharmaceutical composition according to claim 66, further comprising an antiviral agent.

70. The pharmaceutical composition according to claim 69, wherein the antiviral agent is ribavirin.

71. A method of treating a hepatitis C viral infection in a human by administering thereto an anti-hepatitis C virally effective amount of a pharmaceutical composition according to claim 57.

72. A method of treating a hepatitis C viral infection in a human by administering thereto an anti-hepatitis C virally effective amount of a pharmaceutical composition according to claim 59.

73. A method of treating a hepatitis C viral infection in a human by administering thereto an anti-hepatitis C virally effective amount of a pharmaceutical composition according to claim 60.

74. A method of treating a hepatitis C viral infection in a human by administering thereto an anti-hepatitis C virally effective amount of a pharmaceutical composition according to claim 61.

75. A method of treating a hepatitis C viral infection in a human by administering thereto an anti-hepatitis C virally effective amount of a pharmaceutical composition according to claim 66.

76. A method of treating a hepatitis C viral infection in a human by administering thereto an anti-hepatitis C virally effective amount of a pharmaceutical composition according to claim 67.

77. A method of treating a hepatitis C viral infection in a human by administering thereto an anti-hepatitis C virally effective amount of a pharmaceutical composition according to claim 68.

78. A method of treating a hepatitis C viral infection in a human by administering thereto an anti-hepatitis C virally effective amount of a pharmaceutical composition according to claim 69.

79. A method of treating a hepatitis C viral infection in a human by administering thereto an anti-hepatitis C virally effective amount of a pharmaceutical composition according to claim 70.

80. A compound according to claim 44, wherein $R^3$ is —NH—C(O)—$OR^{32}$, wherein $R^{32}$ is $C_{1-4}$ alkyl or $C_{4-6}$ cycloalkyl; D is a C7 all carbon chain, saturated or containing one cis double bond at position 13,14; and $R^{22}$ is

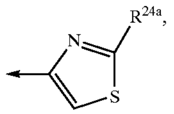

wherein $R^{24a}$ is NH—($C_{1-4}$ alkyl); NH—($C_{3-6}$ cycloalkyl); NH—C(O)—($C_{1-4}$ alkyl); NH—C(O)—O—($C_{1-4}$ alkyl); or NH—C(O)—NH—($C_{1-4}$ alkyl).

81. A compound of formula:

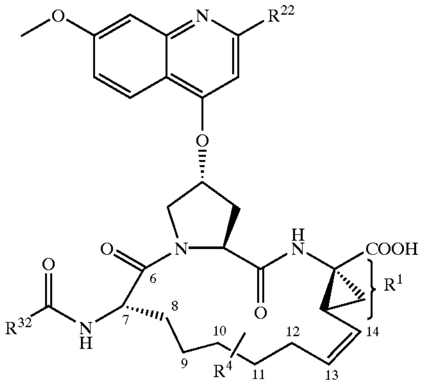

wherein said position 14-$R^1$ bond is syn to acid, said 13,14 double bond is cis, $R^{32}$, $R^4$ and $R^{22}$ are defined as follows:

| Cpd # | $R^{32}$: | $R^4$: | $R^{22}$: |
|---|---|---|---|
| 825 | 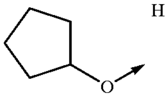 | H | 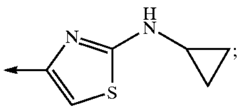 |
| 826 | 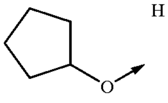 | H | 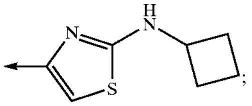 |

-continued

| Cpd # | $R^{32}$: | $R^4$: | $R^{22}$: |
|---|---|---|---|
| 827 | 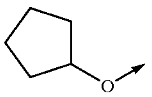 | H | 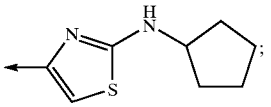; |
| and 828 | 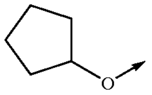 | H | 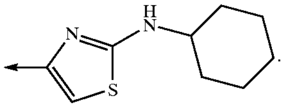. |

82. The compound 208 according to claim 46.
83. The compound 209 according to claim 46.
84. The compound 214 according to claim 46.
85. The compound 217 according to claim 46.
86. The compound 408 according to claim 48.
87. The compound 508 according to claim 49.
88. The compound 601 according to claim 50.
89. The compound 603 according to claim 50.
90. The compound 702 according to claim 51.
91. The compound 703 according to claim 51.
92. The compound 709 according to claim 51.
93. The compound 714 according to claim 51.
94. The compound 715 according to claim 51.
95. The compound 719 according to claim 51.
96. The compound 725 according to claim 51.
97. The compound 736 according to claim 51.
98. The compound 738 according to claim 51.
99. The compound 801 according to claim 52.
100. The compound 809 according to claim 52.
101. The compound 810 according to claim 52.
102. The compound 811 according to claim 52.
103. The compound 812 according to claim 52.
104. The compound 814 according to claim 52.
105. The compound 818 according to claim 52.
106. The compound 819 according to claim 52.
107. The compound 821 according to claim 52.
108. The compound 822 according to claim 52.
109. The compound 823 according to claim 52.
110. The compound 827 according to claim 81.
111. The compound 904 according to claim 53.
112. The compound 909 according to claim 53.
113. The compound 914 according to claim 53.
114. The compound 916 according to claim 53.

115. A pharmaceutical composition comprising an anti-hepatitis C virally effective amount of a compound of formula I according to any one of claims 82 to 114, or a therapeutically acceptable salt or ester thereof, in admixture with a pharmaceutically acceptable carrier medium or auxiliary agent.

116. The pharmaceutical composition according to claim 115, further comprising an immunomodulatory agent.

117. The pharmaceutical composition according to claim 116, wherein said immunomodulatory agent is selected from the group consisting of: α-, β-, and γ-interferons.

118. The pharmaceutical composition according to claim 117, wherein said immunomodulatory agent is α-interferon.

119. The pharmaceutical composition according to claim 115, further comprising an antiviral agent.

120. The pharmaceutical composition according to claim 119, wherein said antiviral agent is ribavirin.

121. The pharmaceutical composition according to claim 117, further comprising an antiviral agent.

122. The pharmaceutical composition according to claim 121, wherein said antiviral agent is ribavirin.

123. The pharmaceutical composition according to claim 118, further comprising an antiviral agent.

124. The pharmaceutical composition according to claim 123, wherein said antiviral agent is ribavirin.

125. The pharmaceutical composition according to claim 115, further comprising another inhibitor of HCV NS3 protease.

126. The pharmaceutical composition according to claim 115, further comprising an inhibitor of other targets in the HCV life cycle.

127. The pharmaceutical composition according to claim 126, wherein said inhibitor inhibits a target selected from the group consisting of: a helicase, a polymerase, and a metalloprotease.

128. A compound having the following formula (A):

(A)

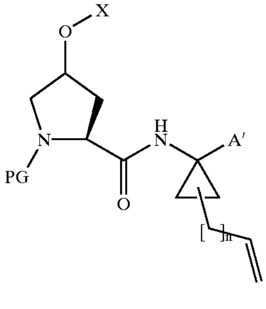

wherein

X is PG or $R^2$;

each PG is independently a protecting group;

$R^2$ is as defined in claim 1;

A' is a protected carboxylic acid;

and n is 2.

129. A process for preparing a compound of formula (A) according to claim 128, said process comprising reacting a compound of formula (B) with a compound of formula (C):

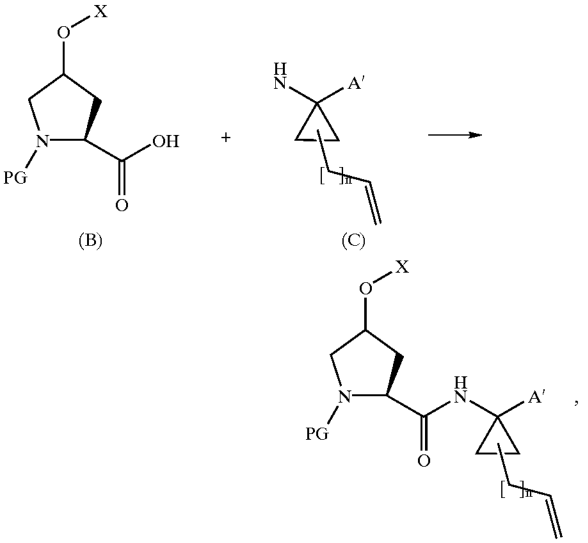

(B) (C) (A)

wherein PG, X, A' and n are as defined in claim 128.

130. A compound having the following formula (D):

(D)

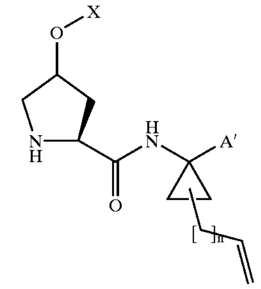

wherein

X is PG or $R^2$;

PG is a protecting group;

$R^2$ is as defined in claim 1;

A' is a protected carboxylic acid;

and n is 2.

131. A process for preparing a compound of the formula (D) according to claim 130, said process comprising cleaving the protecting group PG on the pyrrolidine ring in the compound of formula (A):

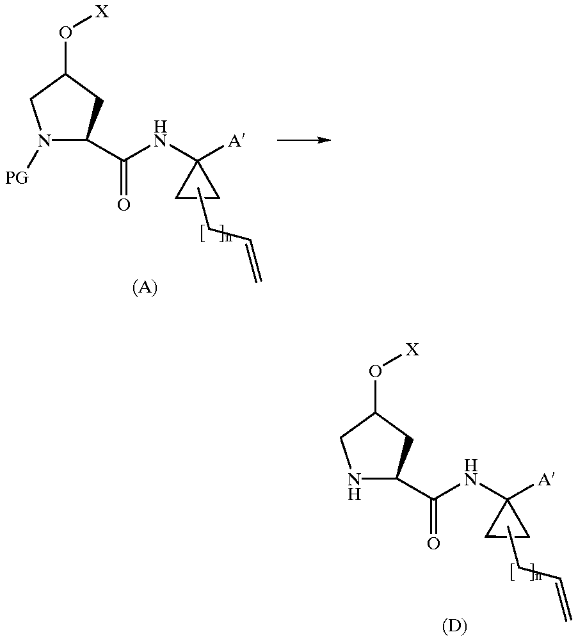

(A) (D)

wherein

X is PG or $R^2$;

each PG is independently a protecting group;

$R^2$, A' and n are as defined in claim 130.

132. A compound having the following formula (E):

(E)

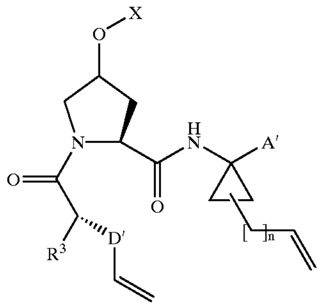

wherein

X is PG or $R^2$;

PG is a protecting group;

$R^2$ is as defined in claim 1;

A' is a protected carboxylic acid;

$R^3$is as defined in claim 1;

n is 0 or 2; and:

(1) when n is 0, D' is a 5-atom saturated alkylene chain optionally containing one to three heteroatoms independently selected from: O, S, or N—$R^{41}$, or (2) when n is 2, D' is a 3-atom saturated alkylene chain optionally containing one to three heteroatoms independently selected from: O, S, or N—$R^{41}$;

and $R^{41}$ is as defined in claim 1.

133. A process for preparing a compound of formula (E) according to claim 132, said process comprising reacting a compound of formula (D) with a compound of formula (F):

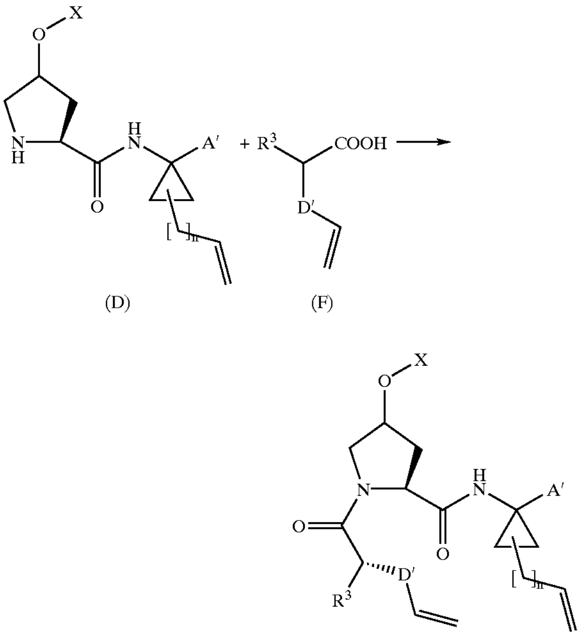

(D) (F) (E)

wherein X, A', n, $R^3$, and D' are as defined in claim 132.

134. A compound having the following formula (G):

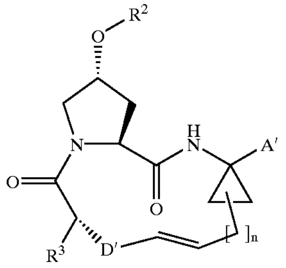

(G)

wherein $R^2$ and $R^3$ are as defined in claim 1;

A' is a protected carboxylic acid;

n is 0 or 2; and (1) when n is 0, D' is a 5-atom saturated alkylene chain optionally containing one to three heteroatoms independently selected from: O, S, or N—$R^{41}$, or (2) when n is 2, D' is a 3-atom saturated alkylene chain optionally containing one to three heteroatoms independently selected from: O, S, or N—$R^{41}$;

and $R^{41}$ is as defined in claim 1.

135. A process for preparing a compound of formula (G) according to claim 134, said process comprising causing a ring-closure of the compound of formula (E) by reacting the compound of formula (E) in the presence of a transition metal-based catalyst to obtain a compound of formula (G'):

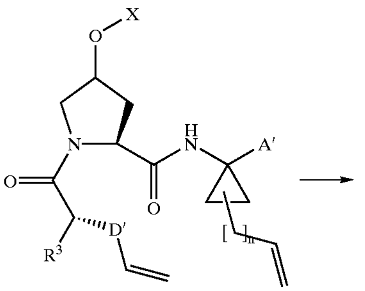

(E)

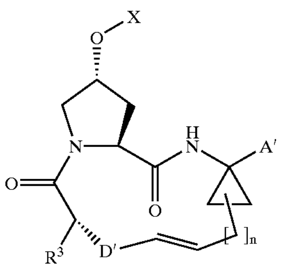

(G')

wherein

X is PG or $R^2$;

PG is a protecting group;

and $R^2$, $R^3$, D', n and A' are as defined in claim 134;

and when X is PG, the compound of formula (G') is deprotected and further reacted with a compound $R^2$—OH to obtain a compound of formula (G):

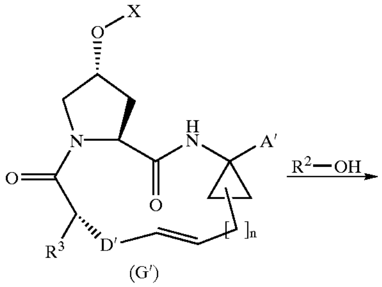

(G')

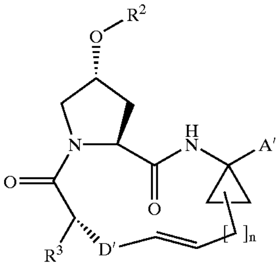

(G)

wherein $R^2$, $R^3$, D', n and A' are as defined in claim 134.

136. A compound having the following formula (H):

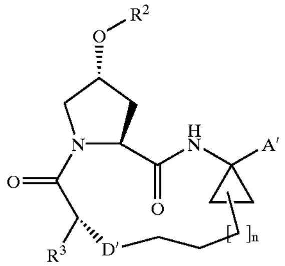

(H)

wherein $R^2$ and $R^3$ are as defined in claim 1;

A' is a protected carboxylic acid;

n is 0 or 2; and (1) when n is 0, D' is a 5-atom saturated alkylene chain optionally containing one to three heteroatoms independently selected from: O, S, or N—$R^{41}$, or (2) when n is 2, D' is a 3-atom saturated alkylene chain optionally containing one to three heteroatoms independently selected from: O, S, or N—$R^{41}$;

and $R^{41}$ is as defined in claim 1.

137. A process for preparing a compound of the formula (H) according to claim 136, said process comprising subjecting the compound of formula (G) to hydrogenation:

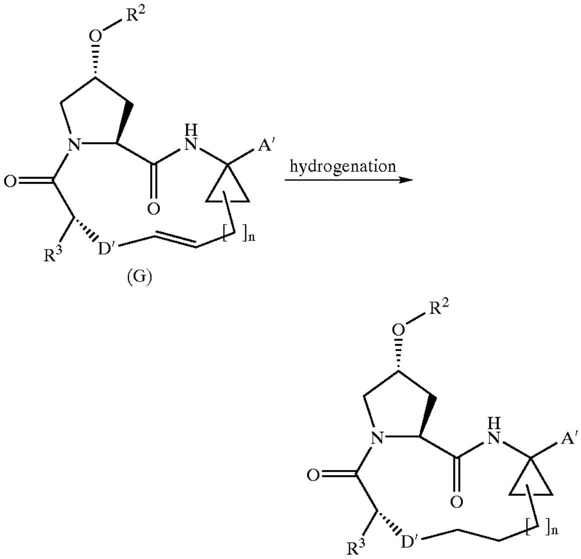

(G)

(H)

wherein $R^2$, $R^3$, D', n, and A' are as defined in claim 136.

138. A compound having the following formula (J):

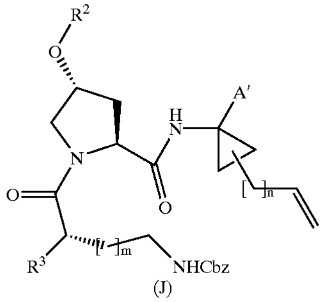

(J)

wherein $R^2$ and $R^3$ are as defined in claim 1;

m is 1 to 5;

n is 1 to 5;

A' is a protected carboxylic acid;

and Cbz is benzyloxycarbonyl.

139. A compound of the following formula (K):

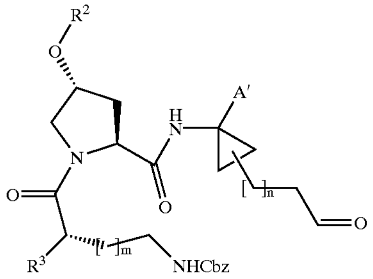

(K)

wherein $R^2$ and $R^3$ are defined in claim 1;

m is 1 to 5;

n is 1 to 5;

A' is a protected carboxylic acid;

and Cbz is benzyloxycarbonyl.

140. A process for preparing a compound of formula (K) according to claim 139, said process comprising subjecting the compound of formula (J) to hydroboration and then oxidation:

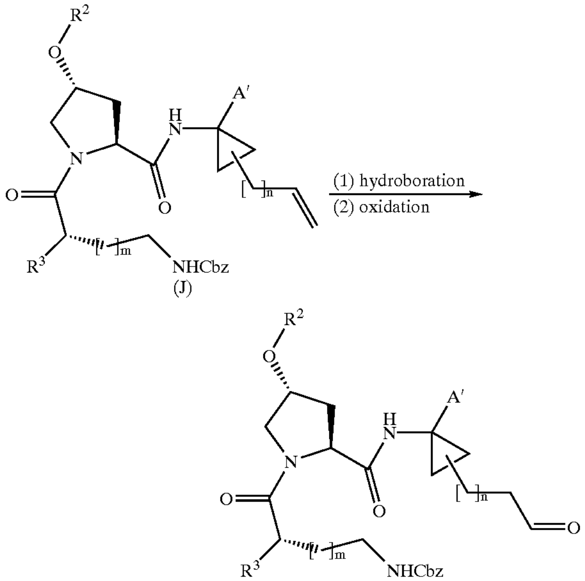

(J)

(K)

wherein $R^2$, $R^3$, m, n, A' and Cbz are as defined in claim 139.

141. A compound having the following formula (L):

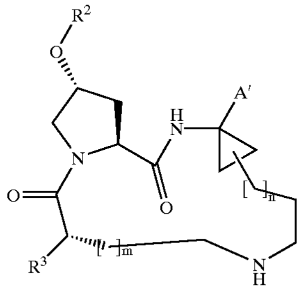

(L)

wherein $R^2$ and $R^3$ are as defined in claim 1;

m is 1 to 5;

n is 1 to 5;

and A' is a protected carboxylic acid.

142. A process for preparing a compound of formula (L) according to claim 141, said process comprising subjecting the compound of formula (K) to hydrogenation in the presence of acid:

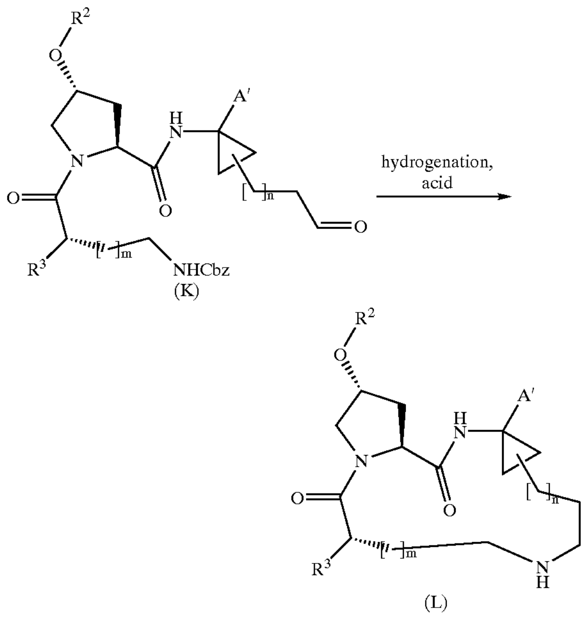

wherein $R^2$ and $R^3$, m, n and A' are as defined in claim 141;

and Cbz is benzyloxycarbonyl.

143. A method of preventing a hepatitis C viral infection in a mammal comprising administering to the mammal an anti-hepatitis C virally effective amount of the compound of formula I according to claim 1, or a therapeutically acceptable salt or ester thereof.

144. A method of treating a hepatitis C viral infection in a mammal comprising administering to the mammal an anti-hepatitis C virally effective amount of a combination of the compound of formula I according to claim 1, or a therapeutically acceptable salt or ester thereof, and at least one additional agent selected from an immunomodulatory agent, an antiviral agent, another inhibitor of HCV NS3 protease, and an inhibitor of another target in the HCV life cycle, wherein said at least one additional agent is administered prior to, concurrently with, or following the administration of the compound of formula I according to claim 1, or a therapeutically acceptable salt or ester thereof.

145. A method of preventing a hepatitis C viral infection in a mammal comprising administering to the mammal an anti-hepatitis C virally effective amount of a combination of the compound of formula I according to claim 1, or a therapeutically acceptable salt or ester thereof, and at least one additional agent selected from an immunomodulatory agent, an antiviral agent, another inhibitor of HCV NS3 protease, and an inhibitor of another target in the HCV life cycle, wherein said at least one additional agent is administered prior to, concurrently with, or following the administration of the compound of formula I according to claim 1, or a therapeutically acceptable salt or ester thereof.

* * * * *